United States Patent
Garcia da Rocha et al.

(10) Patent No.: US 9,314,449 B2
(45) Date of Patent: *Apr. 19, 2016

(54) METHODS OF TREATING PEDIATRIC PATIENTS USING DEXMEDETOMIDINE

(71) Applicant: HOSPIRA, INC., Lake Forest, IL (US)

(72) Inventors: Marcelo Garcia da Rocha, Buffalo Grove, IL (US); Wayne Wisemandle, Gurnee, IL (US); Dennis Stalker, Vernon Hills, IL (US); Edward Koo, Vernon Hills, IL (US)

(73) Assignee: HOSPIRA, INC., Lake Forest, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/726,496

(22) Filed: Dec. 24, 2012

(65) Prior Publication Data

US 2013/0096172 A1 Apr. 18, 2013

Related U.S. Application Data

(63) Continuation of application No. 13/343,693, filed on Jan. 4, 2012.

(60) Provisional application No. 61/547,626, filed on Oct. 14, 2011.

(51) Int. Cl.
| | | |
|---|---|---|
| A01N 43/50 | (2006.01) | |
| A61K 31/415 | (2006.01) | |
| A01N 33/02 | (2006.01) | |
| A61K 31/135 | (2006.01) | |
| A61K 31/4174 | (2006.01) | |

(52) U.S. Cl.
CPC .................................. *A61K 31/4174* (2013.01)

(58) Field of Classification Search
USPC ........................................................ 514/649
See application file for complete search history.

(56) References Cited

U.S. PATENT DOCUMENTS

| | | |
|---|---|---|
| 4,407,957 A | 10/1983 | Lim |
| 4,544,604 A | 10/1985 | Usui et al. |
| 4,670,455 A | 6/1987 | Virtanen et al. |
| 4,910,214 A | 3/1990 | Karjalainen et al. |
| 5,091,402 A | 2/1992 | Kalso et al. |
| 5,124,157 A | 6/1992 | Colley et al. |
| 5,217,718 A | 6/1993 | Colley et al. |
| 5,304,569 A | 4/1994 | Lammintausta et al. |
| 5,344,840 A | 9/1994 | Maze et al. |
| 5,520,639 A | 5/1996 | Peterson et al. |
| 5,654,007 A | 8/1997 | Johnson et al. |
| 5,704,911 A | 1/1998 | Parsons |
| 5,712,301 A | 1/1998 | Jaatinen et al. |
| 5,716,988 A | 2/1998 | Ibrahim et al. |
| 5,780,014 A | 7/1998 | Eljamal et al. |
| 5,798,113 A | 8/1998 | Dionne et al. |
| 5,814,607 A | 9/1998 | Patton |
| 5,846,233 A | 12/1998 | Lilley et al. |
| 5,879,327 A | 3/1999 | Moreau Defarges et al. |
| 6,562,855 B1 | 5/2003 | Franks et al. |
| 6,716,867 B1 | 4/2004 | Aantaa et al. |
| 6,806,291 B1 | 10/2004 | Sunkel et al. |
| 8,242,158 B1 | 8/2012 | Roychowdhury et al. |
| 8,324,260 B1 | 12/2012 | Garcia da Rocha et al. |
| 8,338,470 B1 | 12/2012 | Roychowdhury et al. |
| 8,436,033 B1 | 5/2013 | Roychowdhury et al. |
| 8,455,527 B1 | 6/2013 | Roychowdhury et al. |
| 8,507,542 B2 | 8/2013 | Garcia da Rocha et al. |
| 8,648,106 B2 | 2/2014 | Roychowdhury et al. |
| 2002/0044966 A1 | 4/2002 | Bartholomaeus et al. |
| 2010/0094219 A1 | 4/2010 | Kriesel et al. |
| 2010/0197694 A1 | 8/2010 | Horn |
| 2010/0305160 A1 | 12/2010 | Brummett |
| 2010/0326868 A1 | 12/2010 | McClain et al. |
| 2011/0152271 A1 | 6/2011 | Horn |
| 2011/0230534 A1 | 9/2011 | Miyawaki et al. |
| 2011/0269666 A1 | 11/2011 | Quintin |
| 2013/0096170 A1 | 4/2013 | Garcia da Rocha et al. |
| 2014/0005243 A1 | 1/2014 | Garcia da Rocha et al. |
| 2014/0155446 A1 | 6/2014 | Roychowdhury et al. |

FOREIGN PATENT DOCUMENTS

| | | |
|---|---|---|
| DE | 19749724 A1 | 6/1999 |
| WO | WO 99/24023 A2 | 5/1999 |
| WO | WO 2010/031819 | 3/2010 |
| WO | WO 2010/132882 A2 | 11/2010 |
| ZA | 9810272 A | 5/1999 |

OTHER PUBLICATIONS

Berkenbosch et al. (Prospective evaluation of dexmedetomidine for noninvasive procedural sedation in children. Pediatr Crit Care Med. Jul. 2005;6(4):435-9.*
Tobias et al. (Additional Experience with Dexmedetomidine in Pediatric Patients. South Med J. Sep. 2003;96(9):871-5).*
Nichols et al. (Rescue sedation with dexmedetomidine for Diagnositic imaging: a preliminary report. Paediatr Anaesth. Mar. 2005;15(3):199-203).*
Khasawinah et al. (Preliminary Experience with Dexmedetomidine in the Treatment of Cyclic Vomiting Syndrome. Am J Ther. Jul.-Aug. 2003;10(4):303-7).*
Koroglu et al. (Sedative, haemodynamic and respiratory effects of dexmedetomidine in children undergoing magnetic resonance imaging examination: preliminary results. Br J Anaesth. Jun. 2005;94(6):821-4. Epub Mar. 11, 2005).*
Tobias et al. (Initial experience with dexmedetomidine in paediatric-aged patients. Paediatric Anaesthesia 2002 12: 171±175).*

(Continued)

*Primary Examiner* — Layla Soroush
(74) *Attorney, Agent, or Firm* — Baker Botts L.L.P.

(57) ABSTRACT

The presently disclosed subject matter relates to methods of administering an effective amount of dexmedetomidine to a pediatric patient in order to reduce the incidence of neurological damage. More particularly, the presently disclosed subject matter relates to methods of providing sedation or analgesia to a pediatric patient by administering a dexmedetomidine infusion and optionally a loading dose. The dexmedetomidine can be administered before, during, or after surgery.

7 Claims, 76 Drawing Sheets

(56) References Cited

OTHER PUBLICATIONS

Oschman et al. (Dexmedetomidine for Opioid and benzodiazepine withdrawal in pediatric patients.Am J Health Syst Pharm. Jul. 1, 2011;68(13):1233-8.).*
Kemp et al ("PRECEDEX: Is it the future of cooperative sedation?." OR Nurse 2014 1.1 (2007): 17-20.*
Martens et al. ("Sorption of various drugs in polyvinyl chloride, glass, and polyethylene-lined infusion containers." American Journal of Health-System Pharmacy 47.2 (1990): 369-373).*
U.S. Appl. No. 13/343,693, filed Jan. 4, 2012.
U.S. Appl. No. 13/471,403, filed May 14, 2012.
U.S. Appl. No. 13/343,693, Dec. 21, 2012 Response to Non-Final Office Action.
U.S. Appl. No. 13/343,693, Non-Final Rejection issued Jul. 3, 2012.
U.S. Appl. No. 13/471,403, Sep. 26, 2012 Notice of Allowance.
U.S. Appl. No. 13/471,403, Aug. 6, 2012 Response to Non-Final Office Action.
U.S. Appl. No. 13/471,403, Jul. 5, 2012 Non-Final Office Action.
Chrysostomou et al., "Use of dexmedetomidine in children after cardiac and thoracic surgery." *Pediatr Crit Care Med.* 2006, 7(2):126-131.
Deutsch et al., "Hemodynamic and respiratory changes following dexmedetomidine administration during general anesthesia: sevoflurane vs. desflurane." *Pediatric Anesthesia.* 2007, 17:438-444.
Berkenbosch et al., "Development of bradycardia during sedation with dexmedetomidine in an infant concurrently receiving digoxin." *Pediatr Crit Care Med.* 2003, 4(2):203-205.
Easley et al., "Dexmedetomidine for the treatment of postanesthesia shivering in children." *Pediatric Anesthesia.* 2007, 17:341-346.
Enomoto et al., "Prolonged use of dexmedetomidine in an infant with respiratory failure following living donor liver transplantation." *Pediatric Anesthesia.* 2006, 16:1285-1288.
Finkel et al., "The use of dexmedetomidine to facilitate acute discontinuation of opioids after cardiac transplantation in children." *Crit Care Med.* 2005, 33(9):2110-2112.
Finkel et al., "Hypothermia-induced bradycardia in a neonate receiving dexmedetomidine." *Journal of Clinical Anesthesia.* 2007, 19:290-292.
Mason et al., "Dexmedetomidine for pediatric sedation for computed tomography imaging studies." *Anesthesia & Analgesia.* 2006, 103(1):57-62.
Petroz et al., "A phase I, two-center study of the pharmacokinetics and pharmacodynamics of dexmedetomidine in children." *Anesthesiology.* 2006, 105:1098-110.
Shehabi et al., "Dexmedetomidine infusion for more than 24 hours in critically ill patients: sedative and cardiovascular effects." *Intensive Care Med.* 2004, 30:2188-2196.
Laudenbach et al. "Effects of alpha(2)-adrenoceptor agonists on perinatal excitotoxic brain injury: comparison of clonidine and dexmedetomidine." Anesthesiol. 2002, 96:134-41.
Sanders et al. "Dexmedetomidine provides cortical neuroprotection: impact on anaesthetic-induced neuroapoptosis in the rat developing brain." Acta Anaesthesiol Scand. 2010 , 54(6): 710-6.
Davidson. "Anesthesia and neurotoxicity to the developing brain: the clinical relevance." Paediatr. Anaesth. 2011, 21(7):716-721.
International Search Report and Written Opinion in International Application No. PCT/US12/057652, mailed Oct. 26, 2012.
U.S. Appl. No. 13/726,479, filed Dec. 24, 2012.
U.S. Appl. No. 13/726,479, Notice of Allowance mailed Mar. 6, 2013.
Tobias et al., "Sedation during mechanical ventilation in infants and children: dexmedetomidine versus midazolam." South Med J. May 2004;97(5):451-5.
Baddigarn et al., "Dexmedetomidine in the treatment of withdrawal syndromes in cardiothoracic surgery patients." J Intensive Care Med. Mar.-Apr. 2005;20(2):118-23.
Berkenbosch et al., "Prospective evaluation of dexmedetomidine for noninvasive procedural sedation in children." Pediatr Crit Care Med. Jul. 2005;6(4):435-9; quiz 440.

U.S. Appl. No. 13/343,693, Apr. 11, 2013 Final Office Action.
Abulhasan, et al., "Perioperative use of dexmedetomidine in an infant with familial dysautonomia", *British Journal of Anaesthesia,* 103(3):413-415 (2009).
U.S. Appl. No. 13/343,693, Sep. 11, 2013 Amendment and Request for Continued Examination (RCE).
Chrysostomou et al. "Dexmedetomidine: sedation, analgesia and beyond." Exp. Op. Drug Metabol. & Tox. 2008, 4(5): 619-27.
Chrysostomou et al. "Dexmedetomidine Use in a Pediatric Cardiac Intensive Care Unit: Can We Safely Use It in Infants After Cardiac Surgery?" Pediatr. Crit. Care Med. 2007, 8 (Suppl 3): A308.
Chrysostomou, et al., "Dexmedetomidine: Therapeutic Use for the Termination of reentrant Supraventricular Tachycardia", *Congenit Heart Dis.,* 8:48-56 (2013).
Chrysostomou, et al., "Dexmedetomidine: A Novel Drug for the treatment of Atrial and Junctional Tachyarrhythmias During the Perioperative Period for Congenital Cardiac Surgery: A Preliminary Study", *Anesthesia & Analgesia,* 107(5):1514-1522 (2008).
Diaz et al., "Pharmacokinetics of dexmedetomidine in postsurgical pediatric intensive care unit patients: Preliminary study." *Pediatr Crit Care Med.* 2007, 8(5):419-424.
Hammer et al., "The effects of dexmedetomidine on cardiac electrophysiology in children." *Anesthesia & Analgesia.* 2008, 106(1):79-83.
Parent, et al., Use of dexmedetomidine in sustained ventricular tachycardia, *Anaesthesia and Intensive Care,* 38(4):781-782 (2010).
Tobias, et al. "Bradycardia during dexmedetomidine and therapeutic hypothermia." J Intensive Care Med. Nov.-Dec. 2008 , 23(6): 403-8.
Tobias, et al., "Dexmedetomidine: Antiarrhythmic Effects in the Pediatric Cardiac Patient", *Pediatr Cardiol,* 34:779-785 (2013).
Walker et al., "Sedation using dexmedetomidine in pediatric burn patients." *Journal of Burn Care & Research.* 2006, 27(2):206-210.
"Dexmedetomidine HCL Draft Labeling: Precedex™ Dexmedetomidine Hydrochloride Injection," FDA approved label, dated Dec. 17, 1999, and available online Jul. 26, 2001, pp. 1-13. Downloaded from <http://www.accessdata.fda.gov/drugsatfda_docs/nda/99/21-038_Precedex_prntlbl.pdf> on Jan. 4, 2012.
FDA Memorandum from Cynthia G. McCormick, M.D., Director, Division of Anesthetics, Critical Care and Addiction Drug Products, dated Nov. 30, 1999, in connection with the Medical Reviews of the Precedex (dexmedetomidine hydrochloride injection) Application No. 21-038 submitted to the FDA by Abbott Laboratories on Dec. 18, 1998, and available on the FDA website Jul. 26, 2001. Downloaded on Mar. 7, 2012 from <http://www.accessdata.fda.gov/drugsatfda_docs/nda/99/21-038_Precedex.cfm>.
Petersen, "Trends in Pharmaceutical Primary Packaging for Injectables—Solutions for New Challenges," *Drug Development and Delivery,* Issue Date: Sep. 2012, Posted on: Sep. 5, 2012. Downloaded on Sep. 14, 2012 from < http://www.drug-dev.com/ME2/dirmod.asp?sid=4306B1E9C3CC4E07A4D64E23FBDB232C&nm=Back+Issues&type=Publishing&mod=Publications%3A%3AArticle&mid=8F3A7027421841978F18BE895F87F791&tier=4&id=C2347A2CEAE1422DAA7E592E47648D77 >.
Precedex® Package Insert, Document EN-2680, Hospira, Inc., Sep. 2010, downloaded on Aug. 10, 2012 from <URL:http://www.precedex.com/wp-content/uploads/2010/11/Precedex_PI.pdf>, pp. 1-24.
Short, "Use of dexmedetomidine for primary sedation in a general intensive care unit." Critical Care Nurse (online), Epub Oct. 29, 2009 [Retrieved on Aug. 13, 2012], vol. 30, No. 1, pp. 29-38, Feb. 2010, Retrieved from the internet: <URL:http://ccn.aacnjournals.org/content/30/1/29>.
Unger, et al., "Adsorption of xenobiotics to plastic tubing incorporated into dynamic in vitro systems used in pharmacological research-limits and progress", *Biomaterials,* 22:2031-2037 (2001).
Venn, et al., "Pharmacokinetics of dexmedetomidine infusions for sedation of postoperative patients requiring intensive care", *British Journal of Anaesthesia,* 88(5):669-675 (2002).
Xylocaine® Package Insert, AstraZeneca LP, 2001 and 2007, downloaded on Aug. 10, 2012 from <URL:http://www.pdr3d.com/print.php?c=4818>, pp. 1-30.
International Search Report and Written Opinion in International Application No. PCT/US2012/042940, dated Aug. 24, 2012.

(56) References Cited

OTHER PUBLICATIONS

"Product Monograph: PRECEDEX, Dexmedetomidine Hydrochloride for Injection, 100mcg/mL in a 2 mL glass vial", *Hospira HealthCare Corporation*, pp. 1-29 (Aug. 12, 2009) http://www.gisoura.ca/english_docs/Precedex_Eng_PM-pdf.
Petrick, et al., "Review of current knowledge of plastic intravenous fluid containers", *Am J. Hosp. Pharm.*, 34:357-362 (2007).
Nedich, "Selection of containers and closure systems for injectable products", *Am J. Hosp. Pharma*, 40:1924-1927 (1983).
Kobo, Bunji, *Medicine and Drug Journal*, 24(10):2257-2265 (1988)—(In Japanese—cited in Japanese Application No. 2013-273409).
Office Action from Japanese Application No. 2013-273409 (English translation).
"Saikin no Shinyaku 2005" (New Drugs 2005 in Japan), *Yakuji Nippo Co., Ltd.*, pp. 1-8 (May 27, 2005)—(In Japanese—cited in Japanese Application No. 2014-011233).
Namaki, Noriyuki, "Premixed Parenteral Solution and Safety Management", *Journal of Pharmaceutical Science and Technology*, 65(5):289-296 (2005)—(In Japanese—cited in Japanese Application No. 2014-011233). (English translation is enclosed).
Office Action from Japanese Application No. 2014-011233 (English translation).
Anonymous, "Assessment report Dexdor Dexmedetomidine Procedure No. EMEA/H/C/002268", *European Medicines Agency*, pp. 1-79 (2011) retrieved from internet: URL:http://www.ema.europa.eu/docs/en_GB/document_library/EPAR_-_Public_assessment_report/human/002268/WC500115632.pdf. retrieved online Mar. 31, 2014. XP-002722522.
Extended European Search Report for EP Application No. 12823234, dated Mar. 31, 2014.
Trissel et al., "Compatibility Screening of Precedex During Simulated Y-Site Administration with Other Drugs", International Journal of Pharmaceutical Compounding, 6(3):230-233 (2002).
"Summary Basis of Decision (SBD) Precedex, Dexmedetomidine Hydrochloride, 100 ug/mL, solution, Hospira Healthcare Corporation", Submission Control No. 126931, Health Products and Food Branch of Canada (20 pages) (Sep. 23, 2010).
"Dexdomitor: EPAR-Product Information, Annex, 1, Summary of Product Characteristics", European Medicines Agency, (43 pages) (Nov. 19, 2009).
"Dexdor: EPAR-Product Information, Annex 1, Summary of Product Characteristics", European Medicines Agency, (25 pages) (Oct. 4, 2011).
Carollo et al., "Dexmedetomidine: A review of clinical applications", Current Opinion in Anesthesiology, 21:457-461 (2008).
Szumita et al., "Sedation and analgesia in the intensive care unit: Evaluating the role of dexmedetomidine", Am. J. Health-System Pharm., 64:37-44 (2007).
Ard et al., "Awake craniotomy with dexmedetomidine in pediatric patients", Journal of Neurological Anesthesiology, 15(3):263-266 (2003).
U.S. Appl. No. 13/963,885, Nov. 19, 2015 Final Office Action.
U.S. Appl. No. 13/343,693, Oct. 1, 2015 Non-Final Office Action.
Jooste, et al., "Acute hemodynamic changes after rapid intravenous bolus dosing of dexmedetomidine in pediatric heart transplant patients undergoing routine cardiac catheterization" Anesth Analg. Dec. 2010; 111(6):1490-6. Epub Nov. 8, 2010.
Mansour, Bis-guided evaluation of dexmedetomidine vs. midazolam as anaesthetic adjuncts in off-pump coronary artery bypass surgery (OPCAB). Saudi Journal of Anaesthesia, 2009. vol. 3:1, pp. 7-14.
U.S. Appl. No. 13/343,693, Oct. 2, 2014 Non-Final Office Action.
U.S. Appl. No. 13/343,693, Dec. 31, 2014 Response to Non-Final Office Action.
U.S. Appl. No. 13/343,693, Mar. 5, 2015 Final Office Action.
U.S. Appl. No. 13/343,693, Aug. 4, 2015 Amendment and Request for Continued Examination (RCE).
U.S. Appl. No. 13/963,885, Apr. 9, 2015 Non-Final Office Action.
U.S. Appl. No. 13/963,885, Aug. 4, 2015 Response to Non-Final Office Action.
U.S. Appl. No. 13/471,403, Oct. 24, 2012 Issue Fee Payment.
U.S. Appl. No. 13/726,479, Jun. 6, 2013 Issue Fee Payment.
U.S. Appl. No. 13/867,861, Oct. 2, 2013 Notice of Allowance.
U.S. Appl. No. 13/867,861, Jan. 2, 2014 Issue Fee Payment.
U.S. Appl. No. 13/343,672, Feb. 13, 2012 Non-Final Office Action.
U.S. Appl. No. 13/343,672, Mar. 6, 2012 Applicant Initiated Interview Summary.
U.S. Appl. No. 13/343,672, Apr. 18, 2012 Notice of Allowance.
U.S. Appl. No. 13/343,672, Jul. 18, 2012 Issue Fee Payment.
U.S. Appl. No. 13/541,524, Aug. 17, 2012 Non-Final Office Action.
U.S. Appl. No. 13/541,524, Sep. 17, 2012 Response to Non-Final Office Action.
U.S. Appl. No. 13/541,524, Oct. 22, 2012 Notice of Allowance.
U.S. Appl. No. 13/541,524, Nov. 20, 2012 Issue Fee Payment.
U.S. Appl. No. 13/678,148, Jan. 11, 2013 Notice of Allowance.
U.S. Appl. No. 13/678,148, Feb. 22, 2013 Applicant Initiated Interview Summary.
U.S. Appl. No. 13/678,148, Apr. 8, 2013 Issue Fee Payment.
U.S. Appl. No. 13/678,148, May 9, 2013 Issue Fee Payment.
U.S. Appl. No. 13/678,260, Jan. 8, 2013 Notice of Allowance.
U.S. Appl. No. 13/678,260, Feb. 21, 2013 Applicant Initiated Interview Summary.
U.S. Appl. No. 13/678,260, Apr. 8, 2013 Issue Fee Payment.
U.S. Appl. No. 14/177,008, Jun. 19, 2015 Non-Final Office Action.
U.S. Appl. No. 14/177,008, Sep. 21, 2015 Response to Non-Final Office Action.
Al-Zaben, et al.: "Intraoperative administration of dexmedetomidine reduces the analgesic requirements for children undergoing hypospadius surgery", *European Journal of Anaesthesiology*, vol. 27, No. 3, Mar. 2010, pp. 247-252, XP009183967.
Buck, et al. "Use of dexmedetomidine in the pediatric intensive care unit", *Pharmacotherapy*, vol. 28, No. 1, Jan. 2008, pp. 51-57, XP055185593.
Carroll, et al.: "Use of dexmedetomidine for sedation of children hospitalized in the intensive care unit", *Journal of Hospital Medicine*, vol. 3, No. 2, Mar. 2008 pp. 142-147, XP002738968.
Chrysostomous, C. et al., "Dexmedetomidine use in a pediatric cardiac intensive care unit: Can we use it in infants after cardiac surgery?", Pediatric Critical Care Medicine, Dec. 31, 2009, vol. 10, No. 6.
CN Office Action dated Jul. 24, 2015 in CN Application No. 201280058634.1.
Database MedLine [Online]; US National Library of Medicine (NLM), Bethesda, MD, US; Jan. 2011, Lin Hsin, et al.: "Use of dexmedetomidine for sedation in critically ill mechanically ventilated pediatric burn patients"; Database accession No. NLM21088616; & Lin Hsin, et al. *Journal of Burn Care & Research: Official Publication of the American Burn Association* Jan.-Feb. 2011, vol. 32, No. 1, Jan. 2011, pp. 98-103, ISSN: 1559-0488; XP002738969.
Easley, et al.: "Pro: Dexmedetomidine should be used for infants and children undergoing cardiac surgery", *Journal of Cardiothoracic and Vascular Anesthesia*, vol. 22, No. 1, Feb. 1, 2008, pp. 147-151, XP055185516.
EP Extended Search Report dated May 26, 2015 in EP Patent Application No. 12840033.0.
Kawaai, et al. (A Comparison of Intravenous Sedation with Two Doses of Dexmedetomidine: 0.2 µg/kg/hr Versus 0.4 µg/kg/hr. *Anesthesia Progress* 2010;57(3):96-103).
Tobias, J.D.: "Dexmedetomidine: applications in pediatric critical care and pediatric anesthesiology", *Pediatric Critical Care Medicine: A Journal of the Society of Critical Care Medicine and the World Federation of Pediatric Intensive and Critical Care Societies*, vol. 8, No. 2, Mar. 2007, pp. 115-131, XP009183962.
Center for Drug Evaluation, China Food and Drug Administration edited, "Corpus of Drug Technological Evaluation, Part I", Dec. 31, 2006, pp. 281-283.
Center for Drug Evaluation, China Food and Drug Administration edited, "Corpus of Drug Technological Evaluation, Part I", Dec. 31, 2006, pp. 156-158.
Meng Shengnan, "Pharmaceutics", Shanghai Science and Technology Press, Sep. 31, 2011, pp. 41-43.
Zhu Zhaojing, "Pharmaceutics", Science Press, Beijing, pp. 82-87, the section "Infusion", Jun. 30, 2010.
Chinese Office Action dated Feb. 6, 2016 in Chinese Application No. 201280003734.4 (with English Translation).

\* cited by examiner

Plasma Clearance versus Age-Full Evaluable Population

Plasma Clearance versus Weight-Full Evaluable Population

Weight-adjusted Plasma Clearance vs. Age – Full Evaluable Population

Weight-Adjusted Volume of Distribution Versus Age — Full Evaluable Population

Predicted Mean Curve for $C_{ss}$ — Full Evaluable Population

RSS$_{avg}$ Versus AUC$_{0-\infty}$ — Full Evaluable Population

AUC$_{0-\infty}$ = area under the concentration-time curve from zero to the time infinity; RSS=Ramsay Sedation Scale;

RSS avg = Average of RSS calculated from Hour 2 to end of infusion

RSS$_{avg}$ Versus C$_{ss}$ — Full Evaluable Population

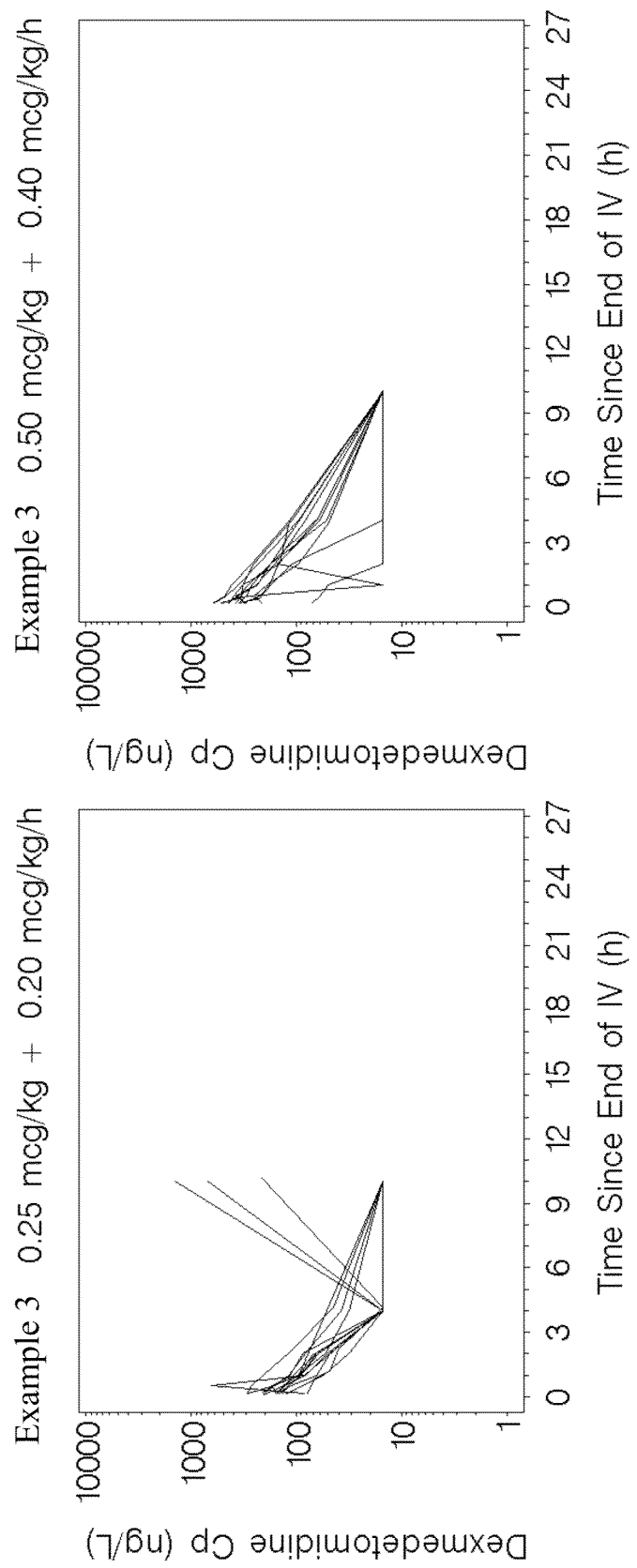

Original Report - 95% Confidence Intervals of Dexmedetomidine Weight-Adjusted Clearance Expressed as Percent of the Geometric Mean Original Report - 95% Confidence Intervals of Dexmedetomidine Weight-Adjusted Volume of Distribution Expressed as Percent of the Geometric Mean Predicted Mean Curve for AUC$_{0\text{-inf}}$: Power Model Fit Predicted Mean Curve for $C_{max}$: Power Model Fit Mean Plasma Dexmedetomidine over Time (Observed Cases)

METHODS OF TREATING PEDIATRIC PATIENTS USING DEXMEDETOMIDINE

1. CROSS-REFERENCE TO RELATED APPLICATIONS

This application is a continuation of U.S. application Ser. No. 13/343,693 filed Jan. 4, 2012, which claims priority under 35 U.S.C. §119 to U.S. Provisional Application Ser. No. 61/547,626 filed Oct. 14, 2011, both of which are hereby incorporated by reference in their entireties, and to both of which priority is claimed.

2. FIELD OF THE INVENTION

The presently disclosed subject matter relates to a method of providing a safe and effective sedative and/or analgesic agent for pediatric patients. More particularly, the presently disclosed subject matter relates to reducing, preventing, and/or ameliorating neurological damage in a pediatric patient by administering dexmedetomidine.

3. BACKGROUND OF THE INVENTION

Sedation is an important component of care for pediatric patients in the intensive care unit (ICU) not only for their physiologic well being, but also for patient safety and the safety of the caregivers.

Benzodiazepines and opioids, such as fentanyl or morphine, are frequently administered to provide sedation and analgesia in the pediatric intensive care unit (PICU). Propofol has been shown to cause severe, life-threatening metabolic alterations in children including circulatory failure, and is not indicated in the pediatric population for continuous intensive care sedation. (See Propofol Injectable Emulsion [package insert]. Lake Forest Ill.: Hospira, Inc.: 2008). With prolonged administration of benzodiazepines and opioids, tolerance and physical dependence may develop. Midazolam sedation in some pediatric patients causes oversedation alternating with under sedation and paradoxical agitation. (See Midazolam hydrochloride [Package Insert]. Lake Forest, Ill.: Hospira, Inc.: 2005).

Recent reports of apoptosis and neurodevelopment abnormalities in neonatal and infant animal models from gamma-amino butyric acid (GABA)-agonist drugs have heightened the concern of sedating neonates and infants with benzodiazepines. (See Young et al. Brit J Pharma 2005; 146:189-197; and Sander et al. Brit J Anaesth 2008; 101 (5): 597-609). The concomitant administration of opioids further complicates pediatric patient management because of respiratory depression. Therefore, there is a significant unmet need for safe and effective sedation and analgesia in pediatric patients.

Dexmedetomidine (Precedex®) is a highly selective alpha-2 adrenergic agonist with significant sedative, analgesic, and anxiolytic effects. Dexmedetomidine is currently approved by the FDA for sedation of initially intubated and mechanically ventilated adult patients in an intensive care setting, and is also approved for sedation of non-intubated adult patients as a component of monitored anesthesia care during surgical or diagnostic procedures. Dexmedetomidine is the only sedative approved in the United Sates for administration as a continuous infusion in non-intubated ICU patients because it does not significantly affect respiratory drive.

Sedation with dexmedetomidine for adult patients in the ICU has been widely studied. When used in combination with opioids or benzodiazepines, dexmedetomidine often allows for a reduction in the doses of the other agents, reducing the risk of respiratory depression.

4. SUMMARY OF THE INVENTION

The present invention is directed to methods of sedation or analgesia in a pediatric patient in need thereof comprising administering dexmedetomidine to the patient, wherein the dexmedetomidine is administered in an amount effective to reduce the incidence of neurological damage.

In one embodiment, the dexmedetomidine is administered at a concentration of between about 0.01 to about 2.5 µg/kg/hr, the pediatric is about 17 years of age or younger, the dexmedetomidine is administered as a continuous infusion for a period of time of less than about 36 hours, and the dexmedetomidine is administered in an amount effective to reduce the incidence of neurological damage.

In a particular embodiment, the pediatric patient is a pre-term neonate. In one embodiment, the pediatric patient's gestational age ranges from about 7 months to about 11 months.

In certain embodiments, the pediatric patient is intubated prior to, during, or after administration of the dexmedetomidine. In one embodiment, the pediatric patient is critically ill.

In particular embodiments, the dexmedetomidine is parenterally administered. In certain embodiments, the dexmedetomidine is administered by an intravenous infusion.

In particular embodiments, the neurological damage is cellular degeneration or neuroapoptosis. In one embodiment, the neurological damage occurs in a cortex lamina layer selected from the group consisting of layer I and layer II.

In certain embodiments, the dexmedetomidine is administered before surgery. In particular embodiments, the dexmedetomidine is administered after surgery. In a specific embodiment, the dexmedetomidine is administered after cardiopulmonary bypass. In one embodiment, the pediatric patient has an age selected from the group consisting of between about 12 to about 17 years of age and about 2 years of age or younger.

In particular embodiments, the administration of dexmedetomidine reduces a need for rescue medication. In one embodiment, the rescue medication is a sedative. In a specific embodiment, the rescue medication is an analgesic.

In certain embodiments, the administration of dexmedetomidine further comprises a first loading dose prior to a maintenance dose and wherein the loading dose ranges from about 0 to about 0.4 µg/kg. In one embodiment, no loading dose is administered.

5. DESCRIPTION OF THE FIGURES

Figure 16A:
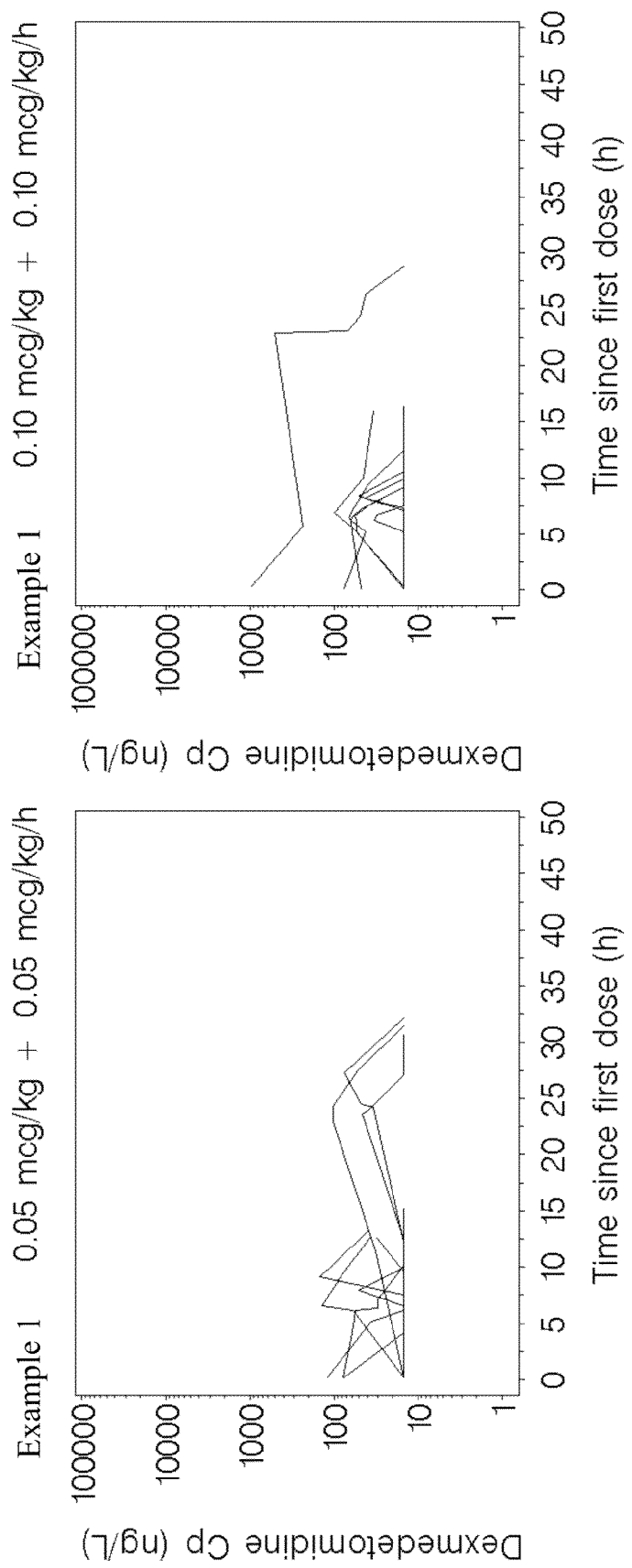
Figure 16A:
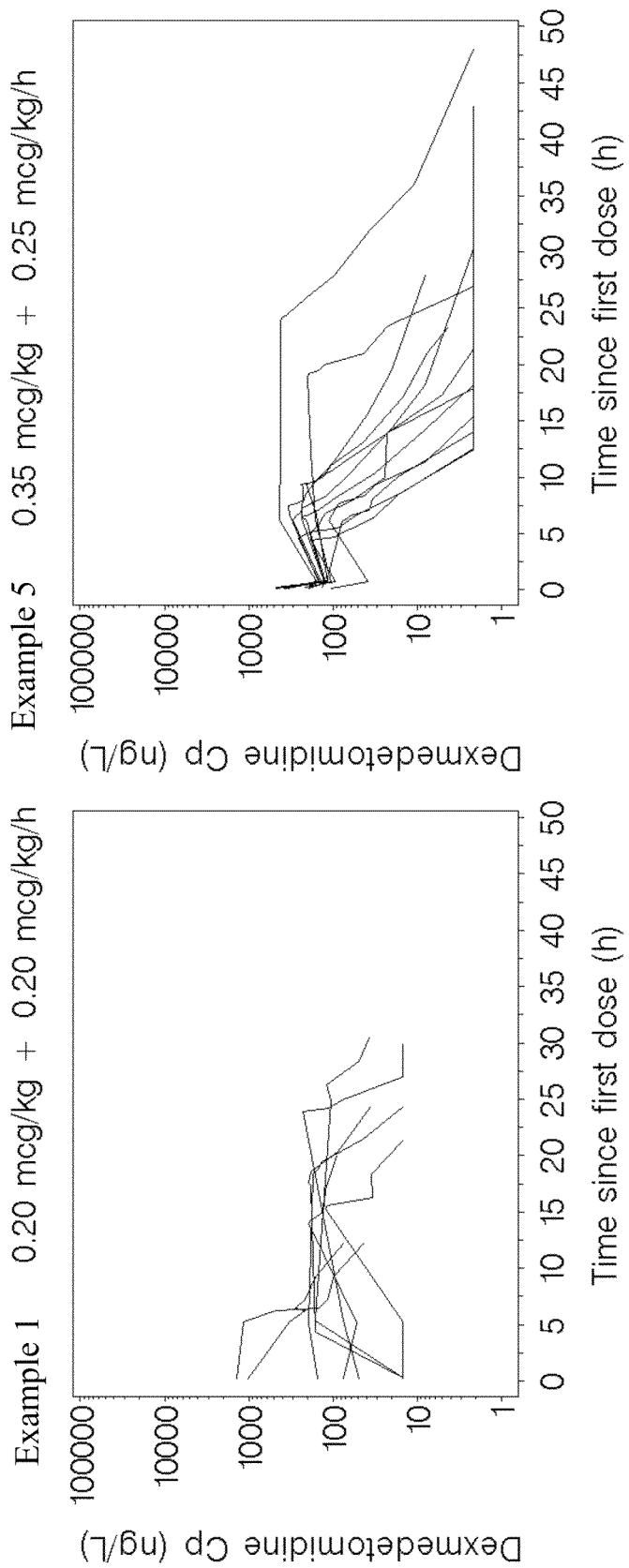
Figure 16B:
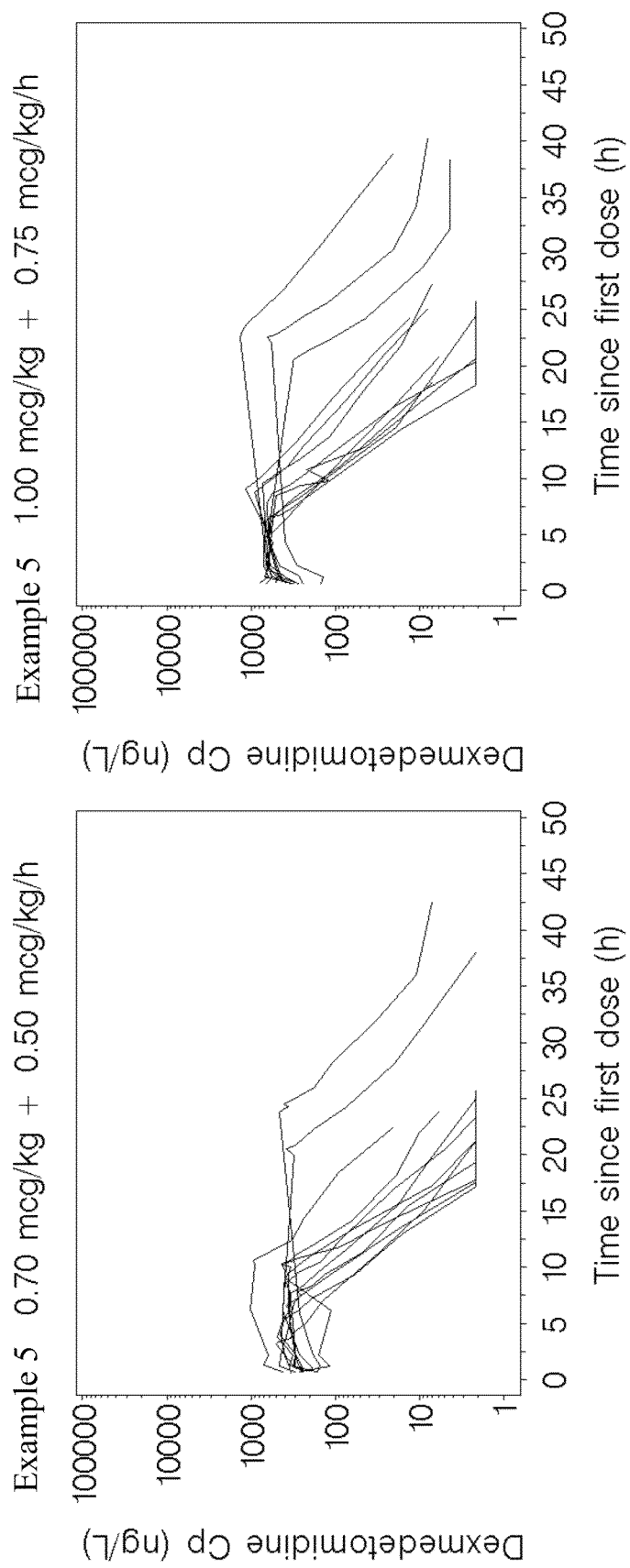
Figure 16B:
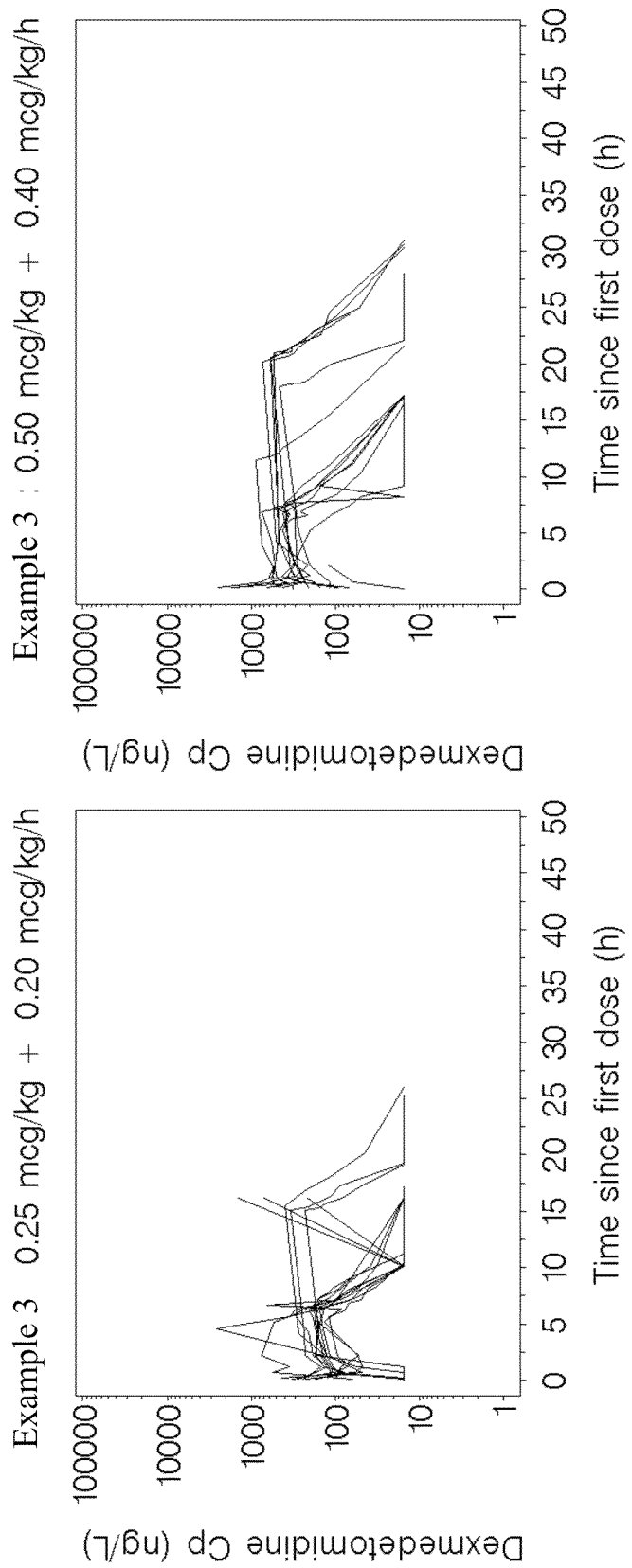
Figure 16C:
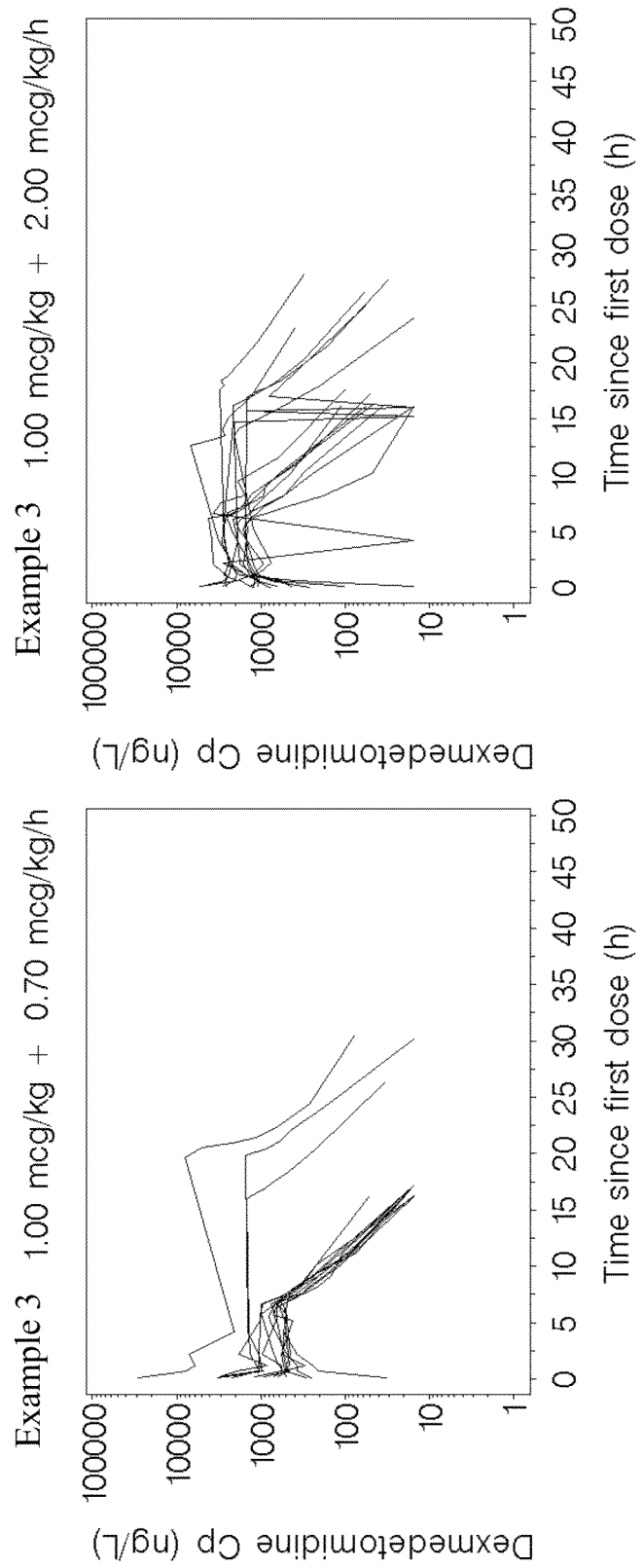

FIGS. 16A-C depict lineplots of plasma dexmedetomidine concentrations versus time since the start of the loading dose infusion for each treatment group for the treatment groups in the studies of Examples 1, 3, and 5.

Figure 17A:
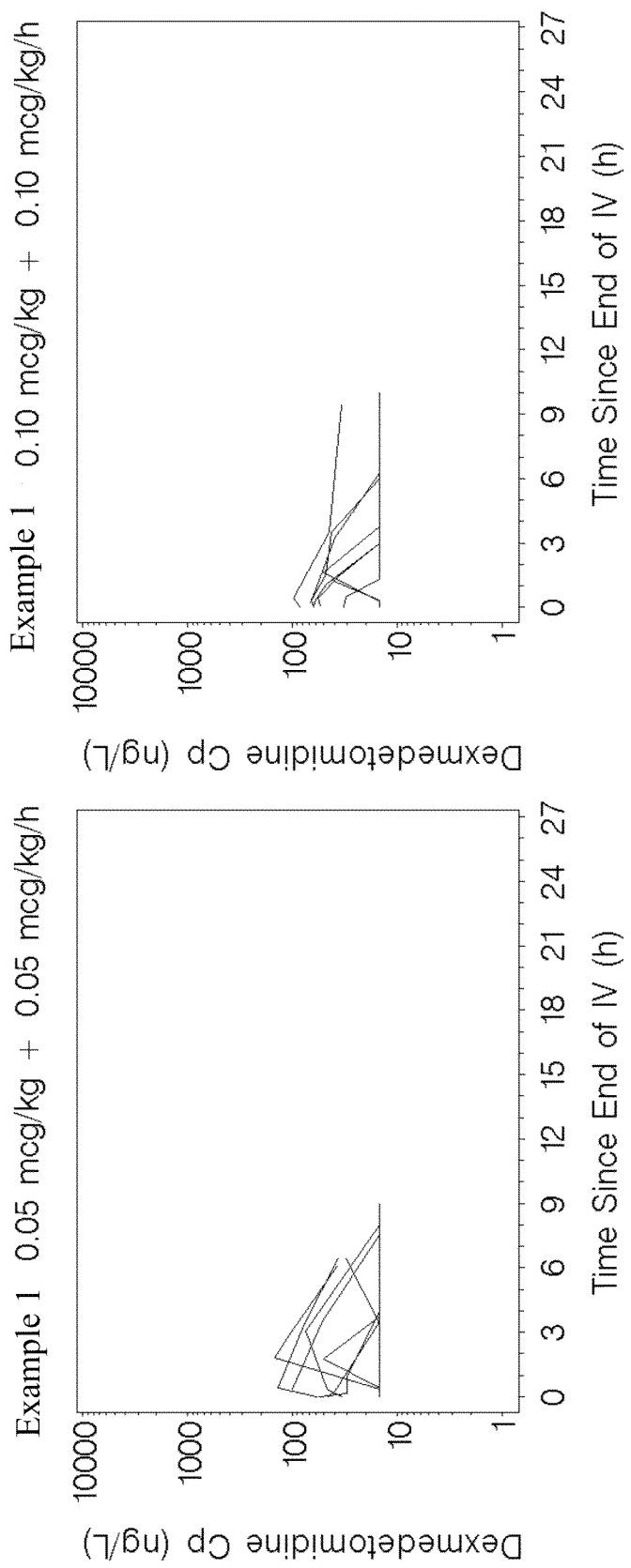
Figure 17A:
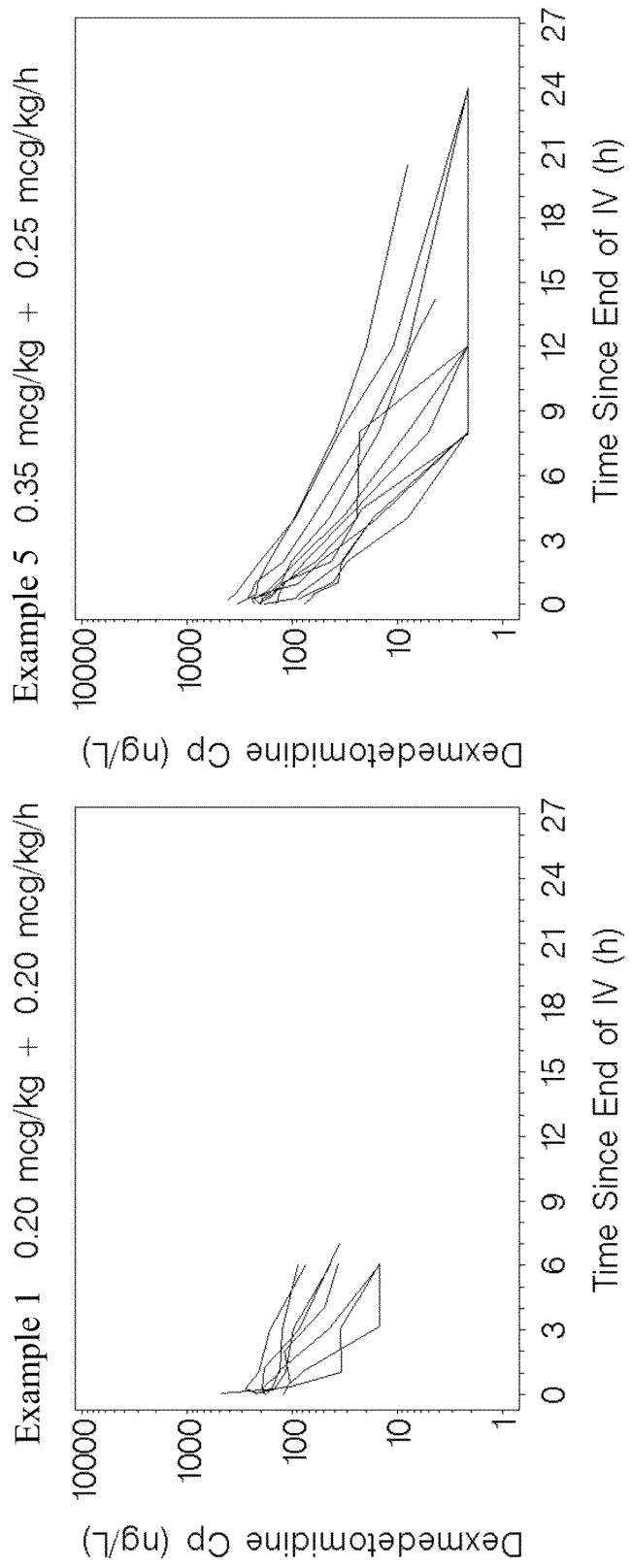
Figure 17B:
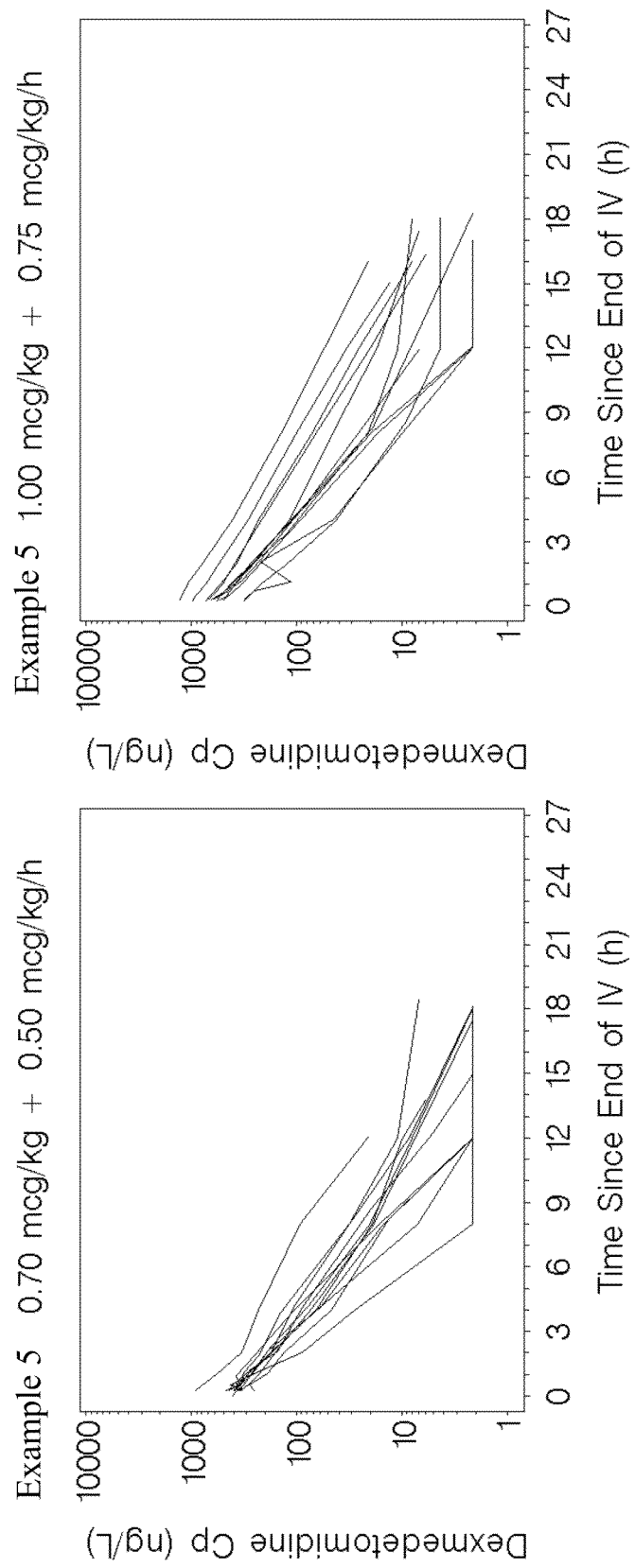
Figure 17C:
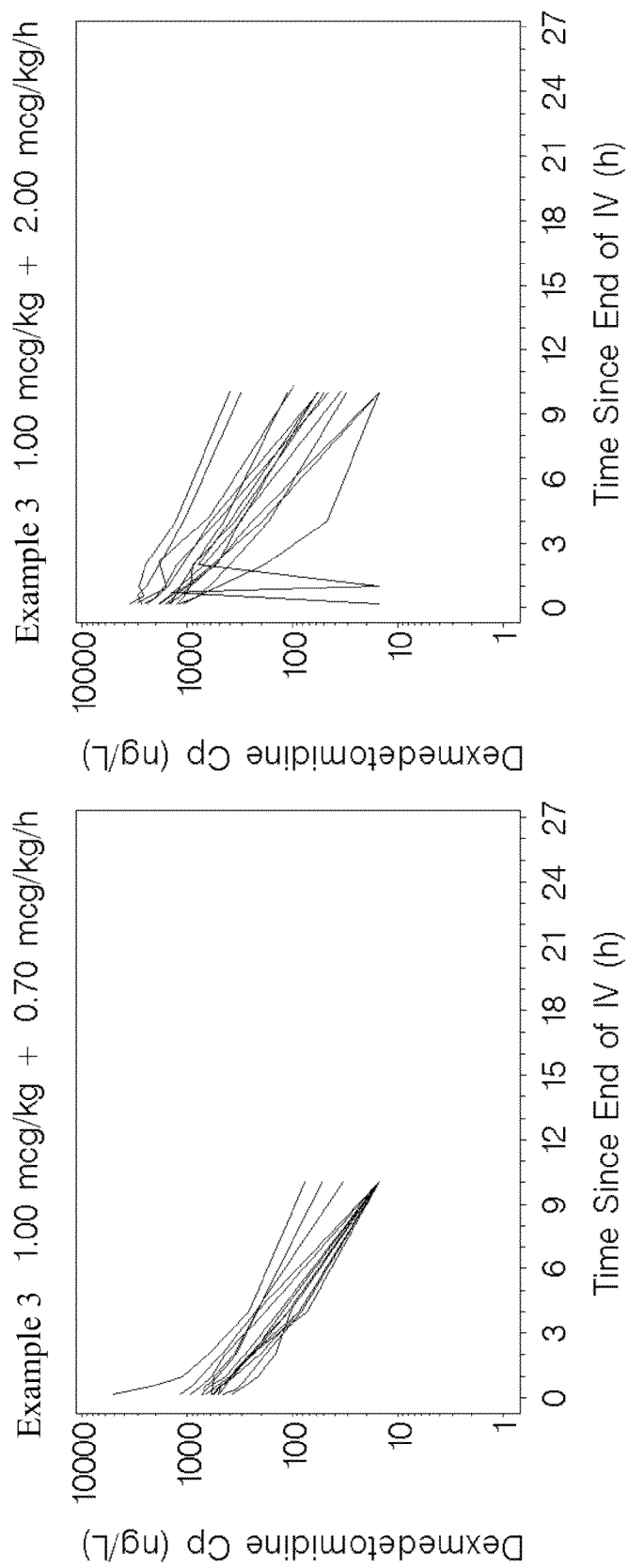

FIGS. 17A-C depicts lineplots of dexmedetomidine concentrations versus time since the end of the maintenance infusion are shown for each treatment group for the treatment groups in the studies of Examples 1, 3, and 5.

Figure 18A:
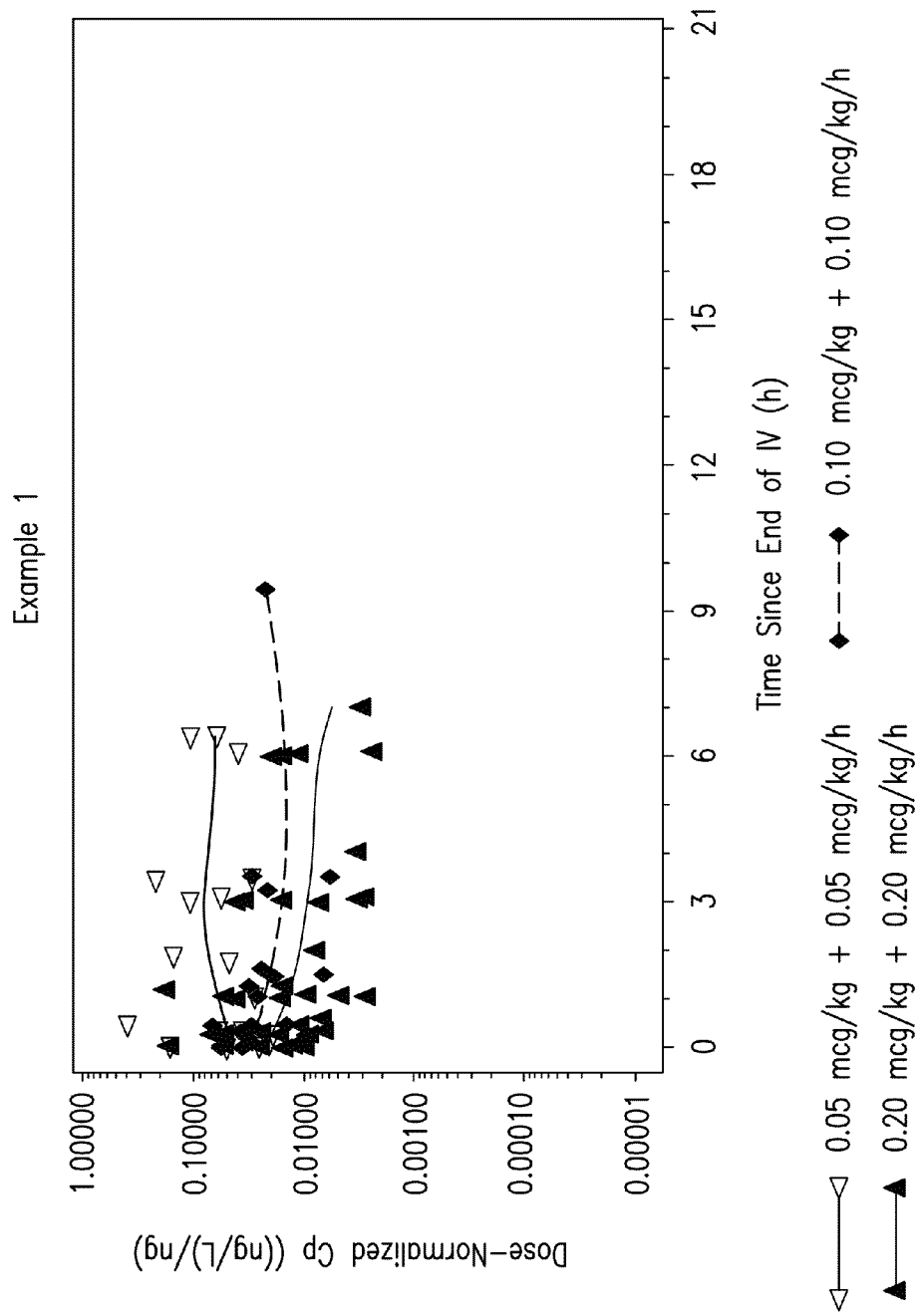
Figure 18A:
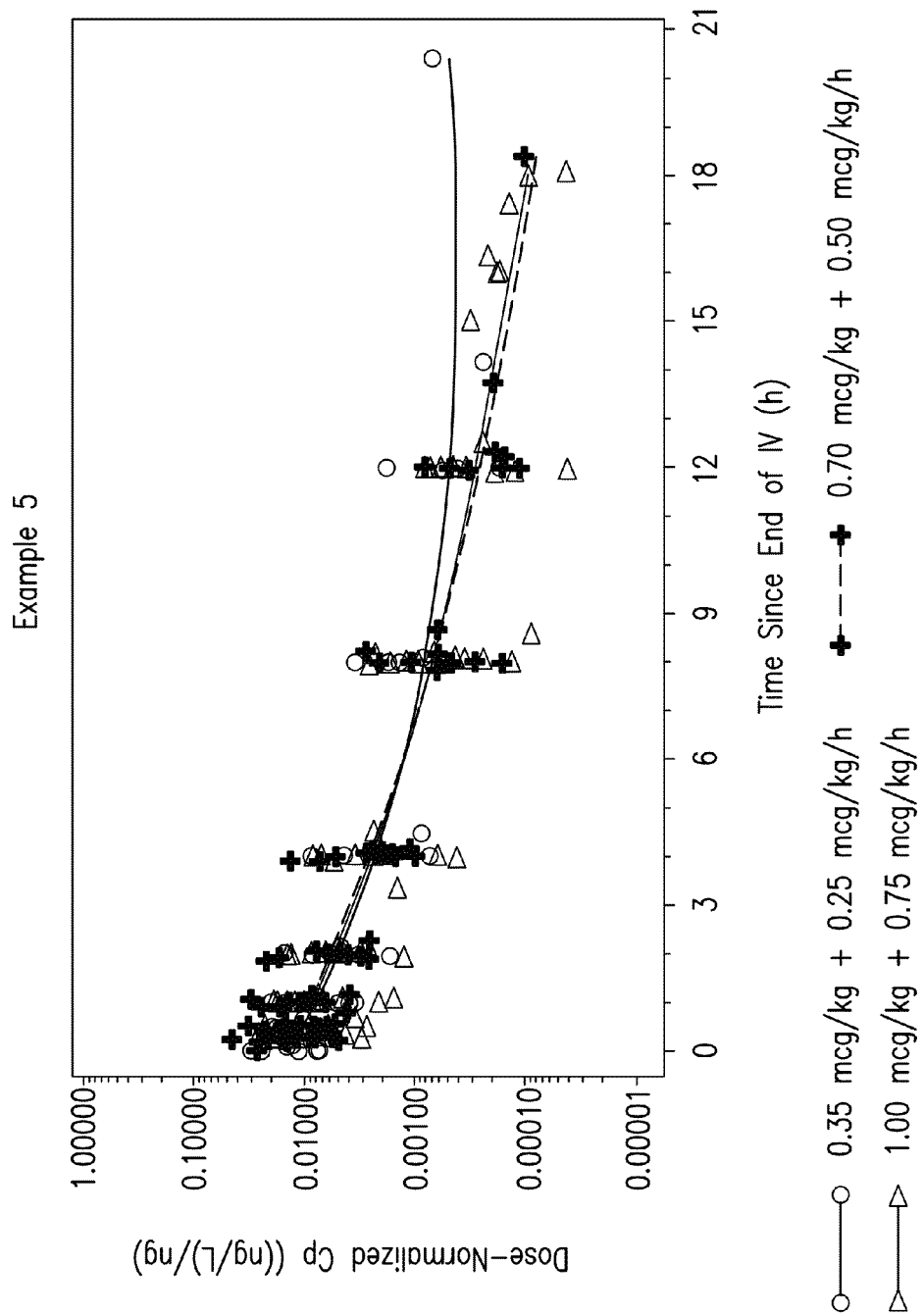
Figure 18B:
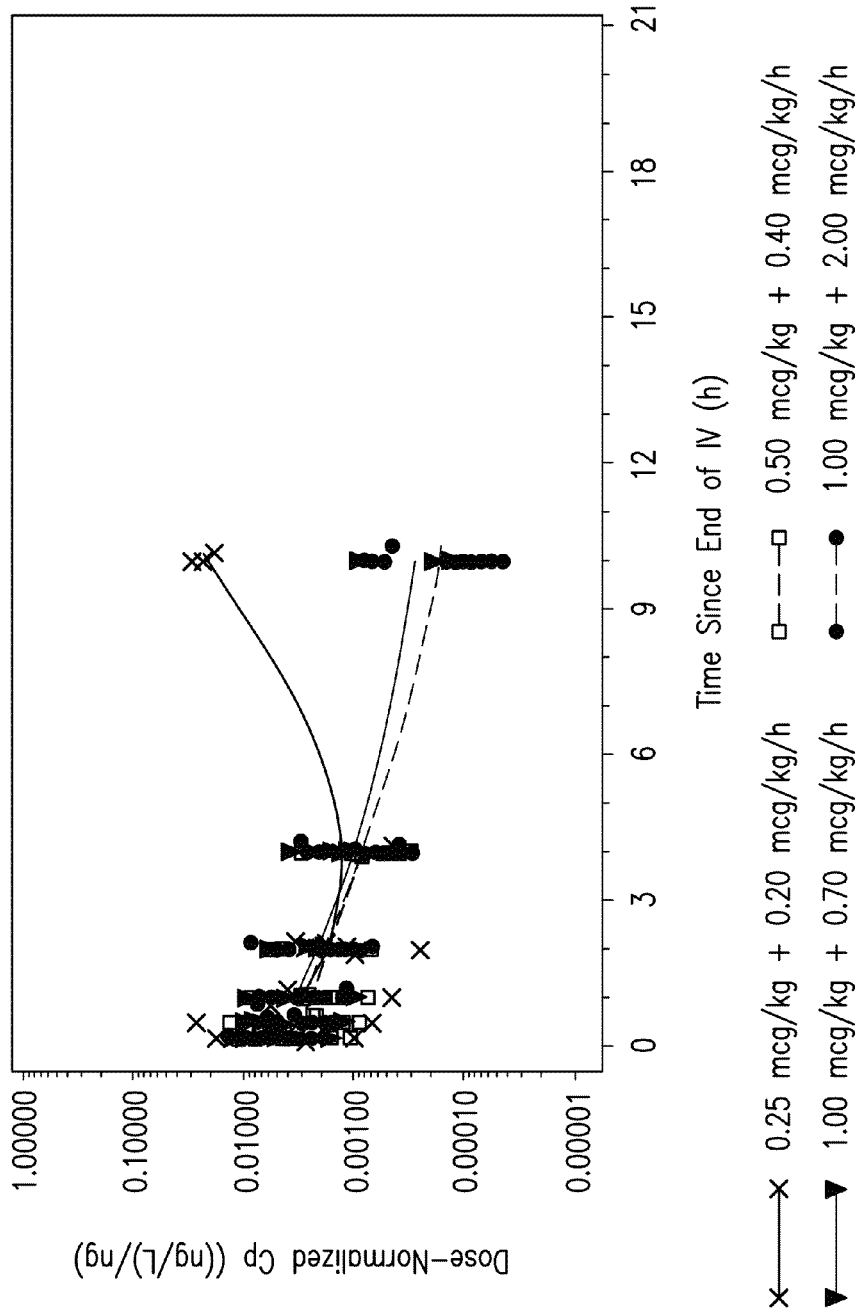

FIGS. 18A-B depict a semilogarithmic scatterplot of dose-normalized dexmedetomidine plasma concentrations versus time since the end of the maintenance infusion for the studies of Examples 1, 3, and 5.

Figure 19A:
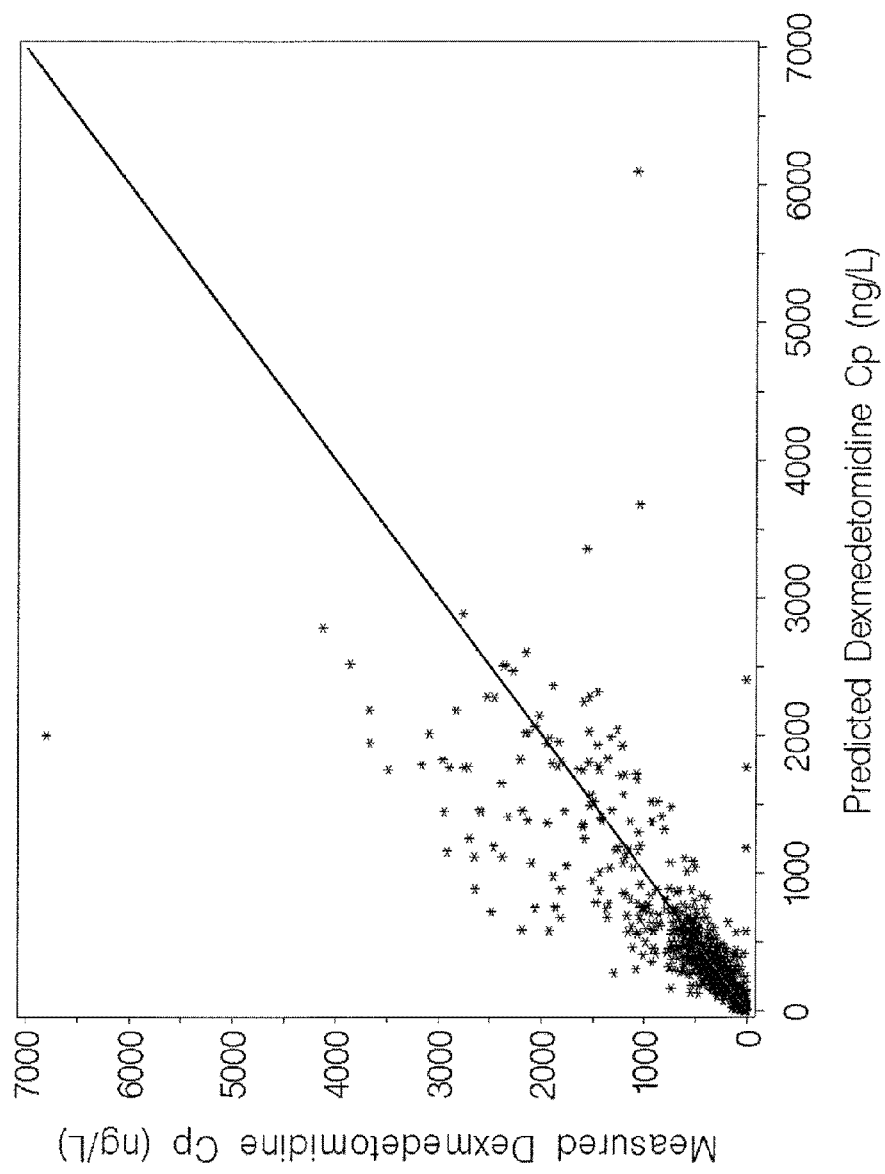
Figure 19A:
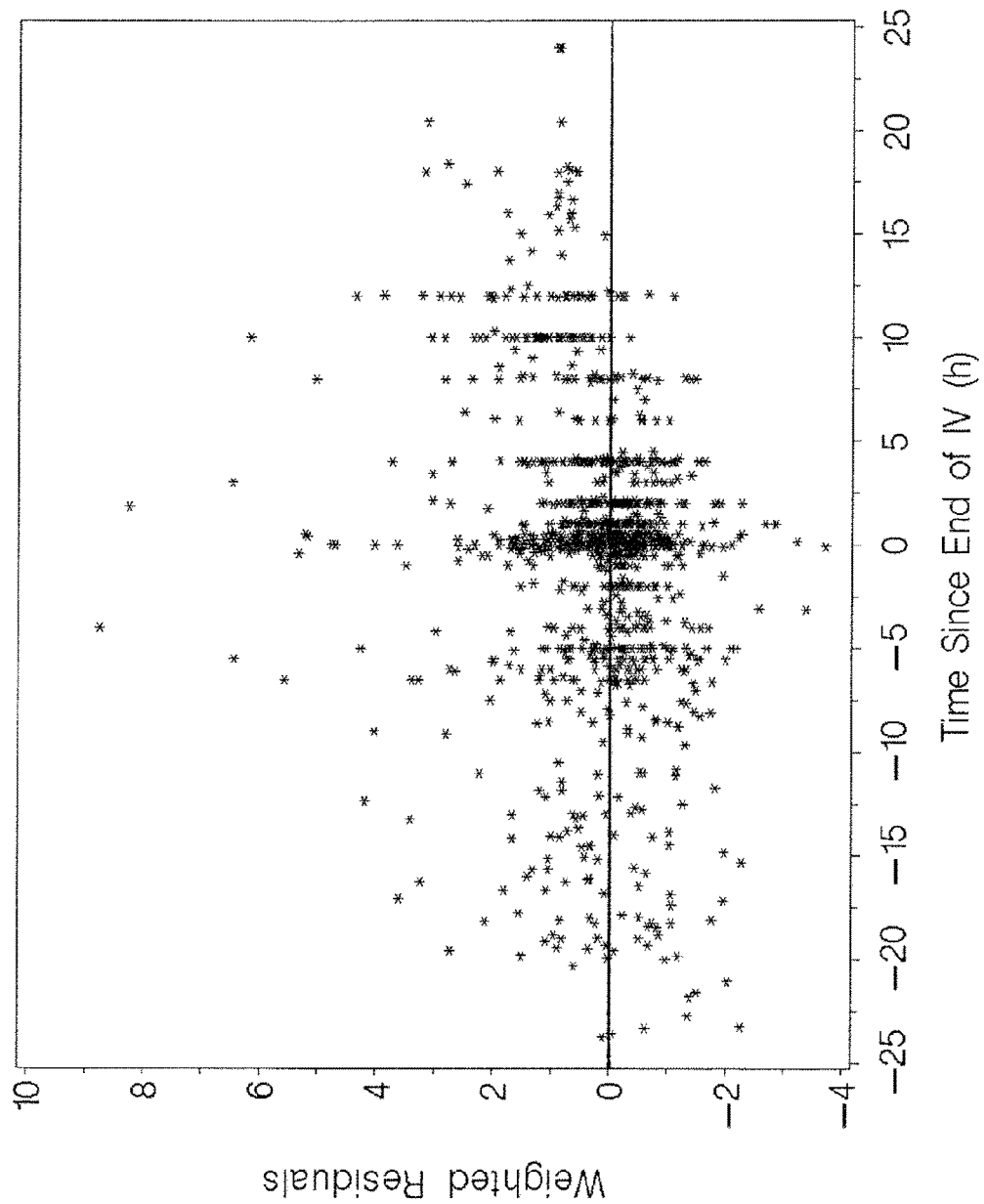
Figure 19B:
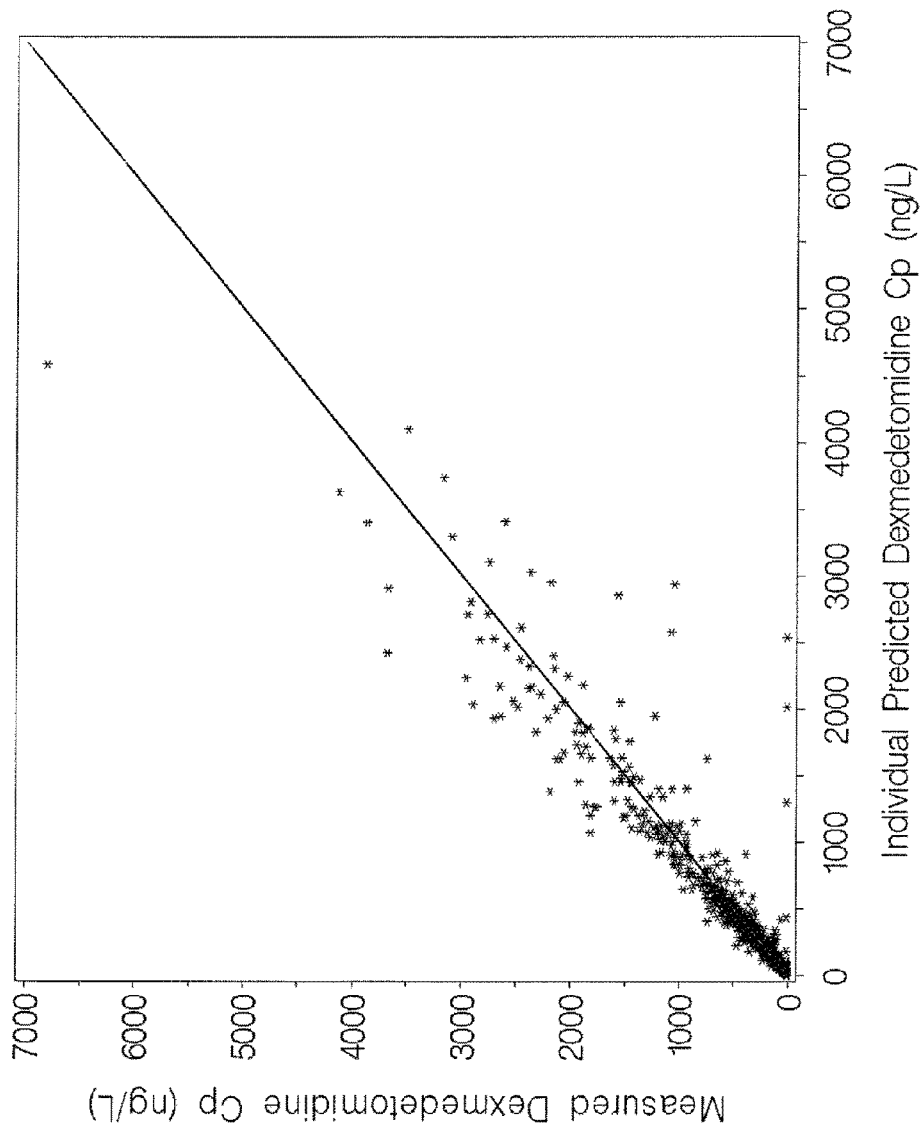
Figure 19B:
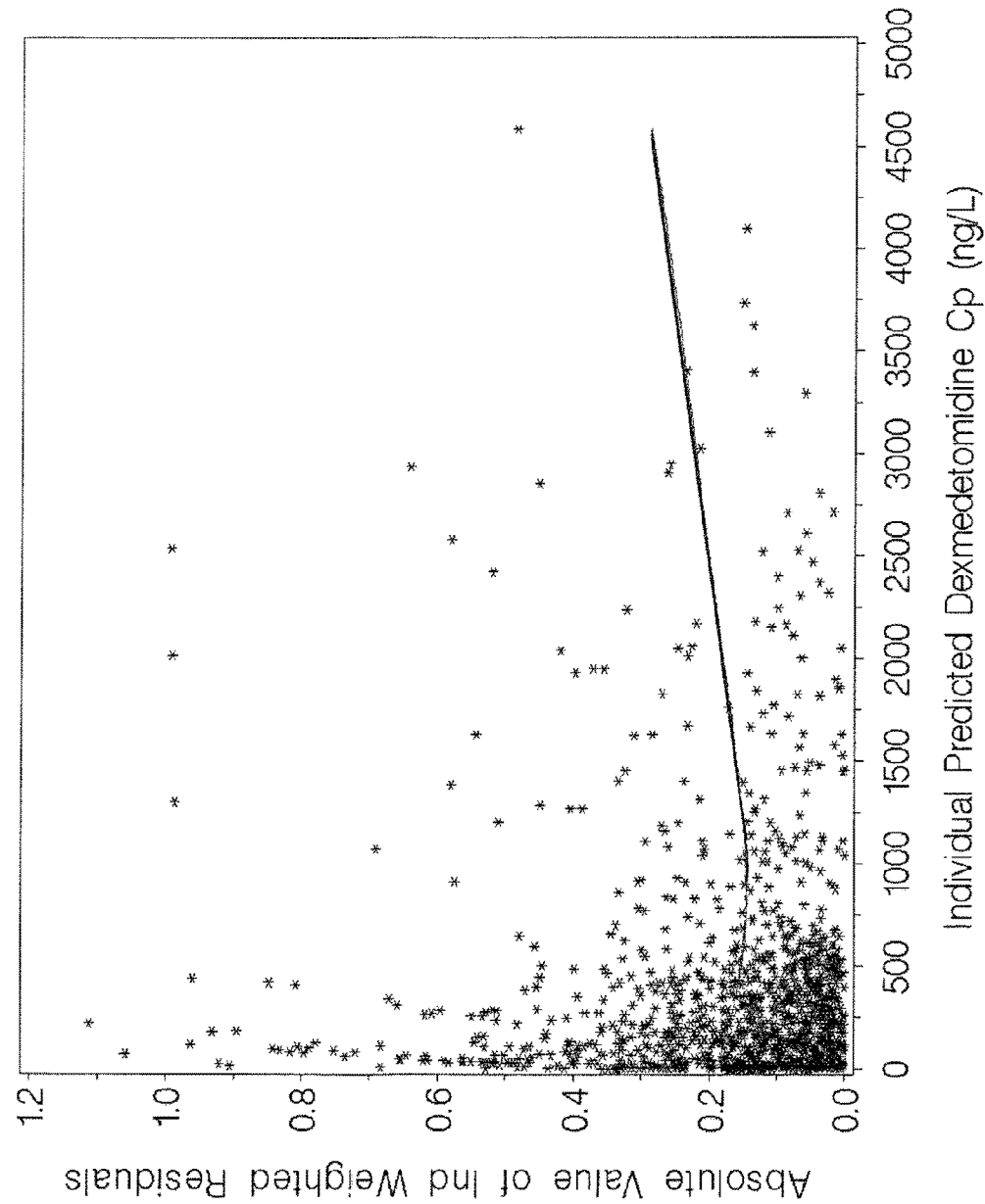

FIGS. 19A-B depict goodness-of-fit plots for the individual predicted dexmedetomidine Cp base structural model for the pooled dataset of Examples 1, 3, and 5.

Figure 20:
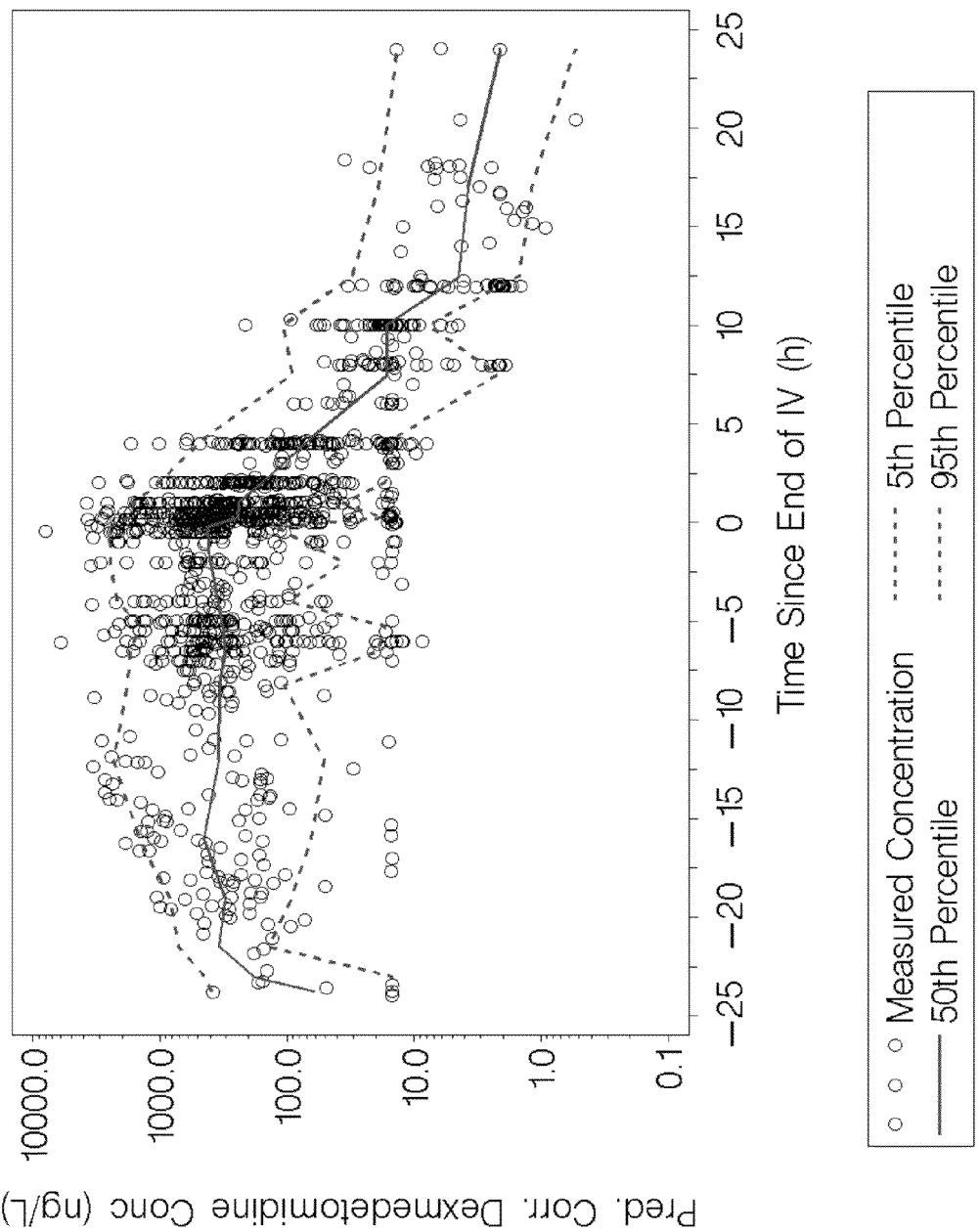

FIG. 20 depicts the 90% prediction interval, derived from the 1000 simulated datasets, overlaid on the observed dexmedetomidine concentrations versus time since the end of the maintenance infusion of Examples 1, 3, and 5.

Figure 21:
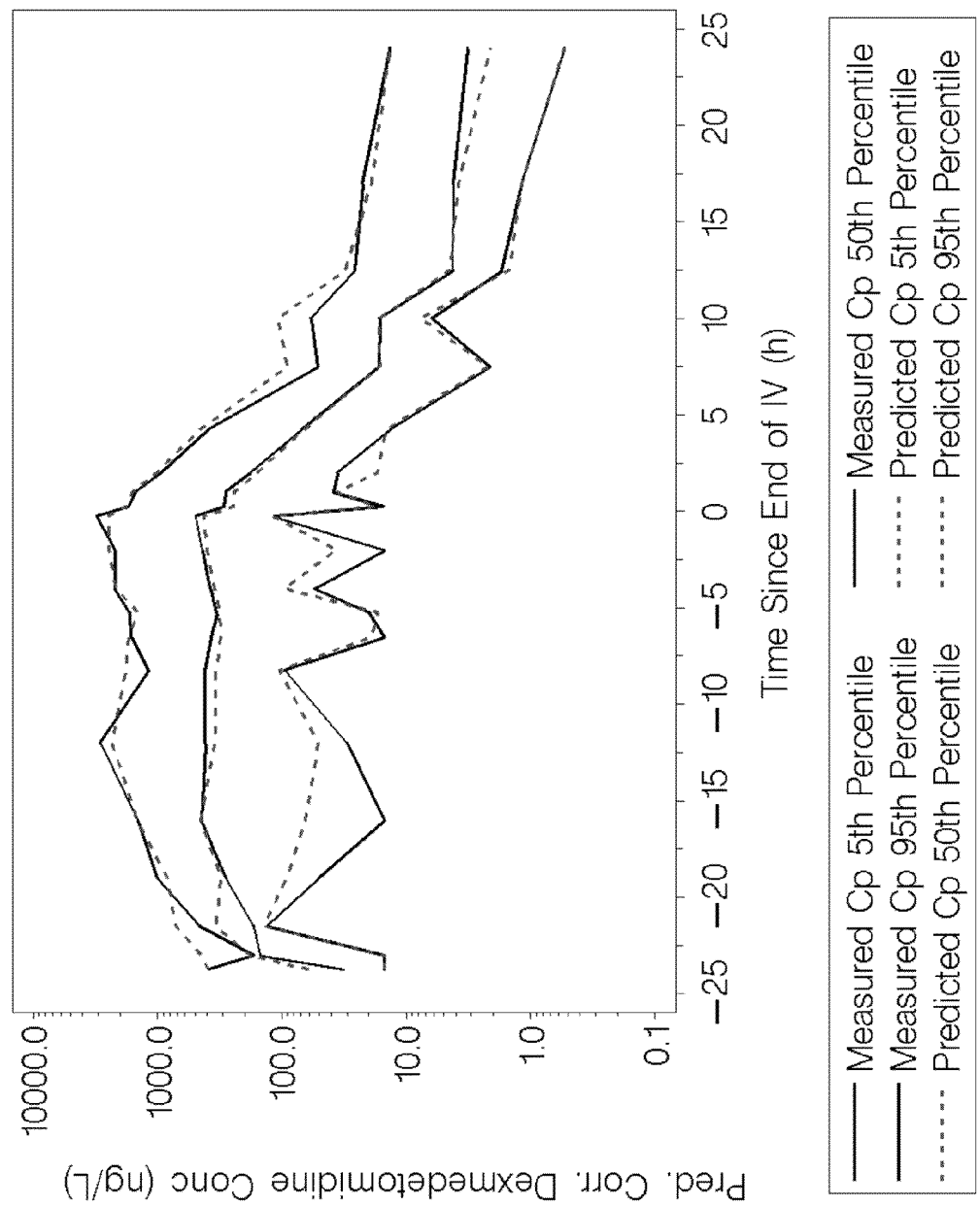
Figure 22A:
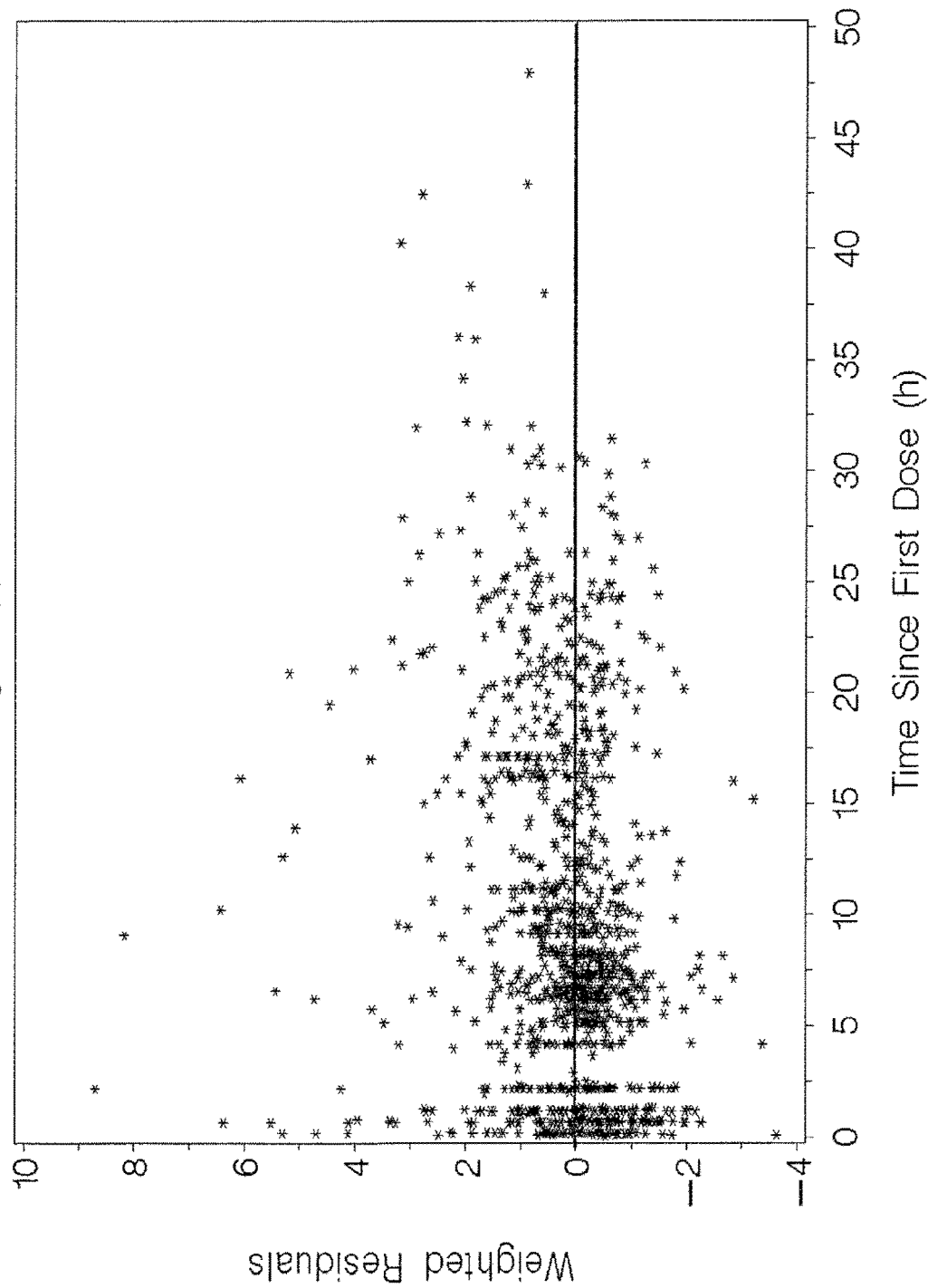
Figure 22A:
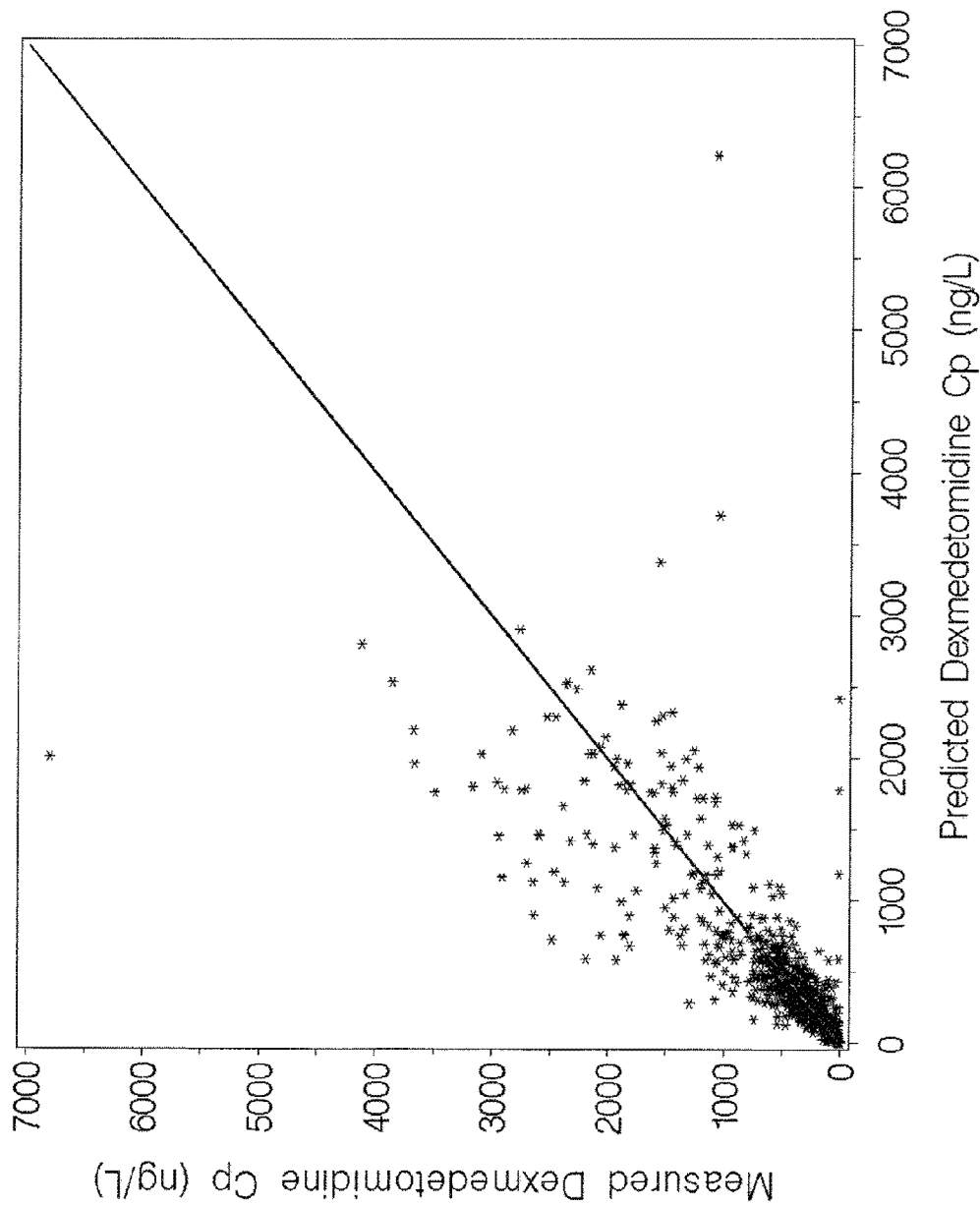
Figure 22B:
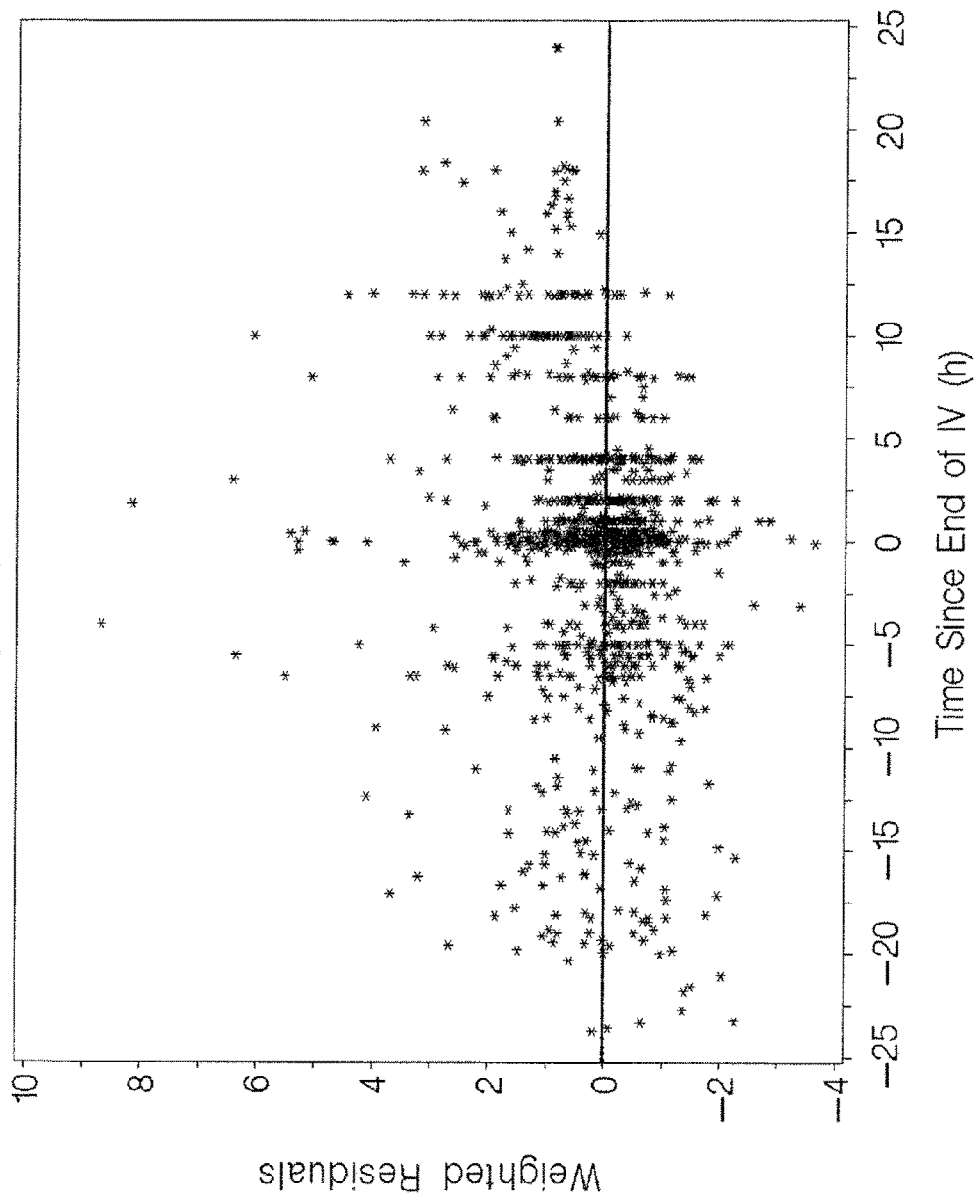
Figure 22B:
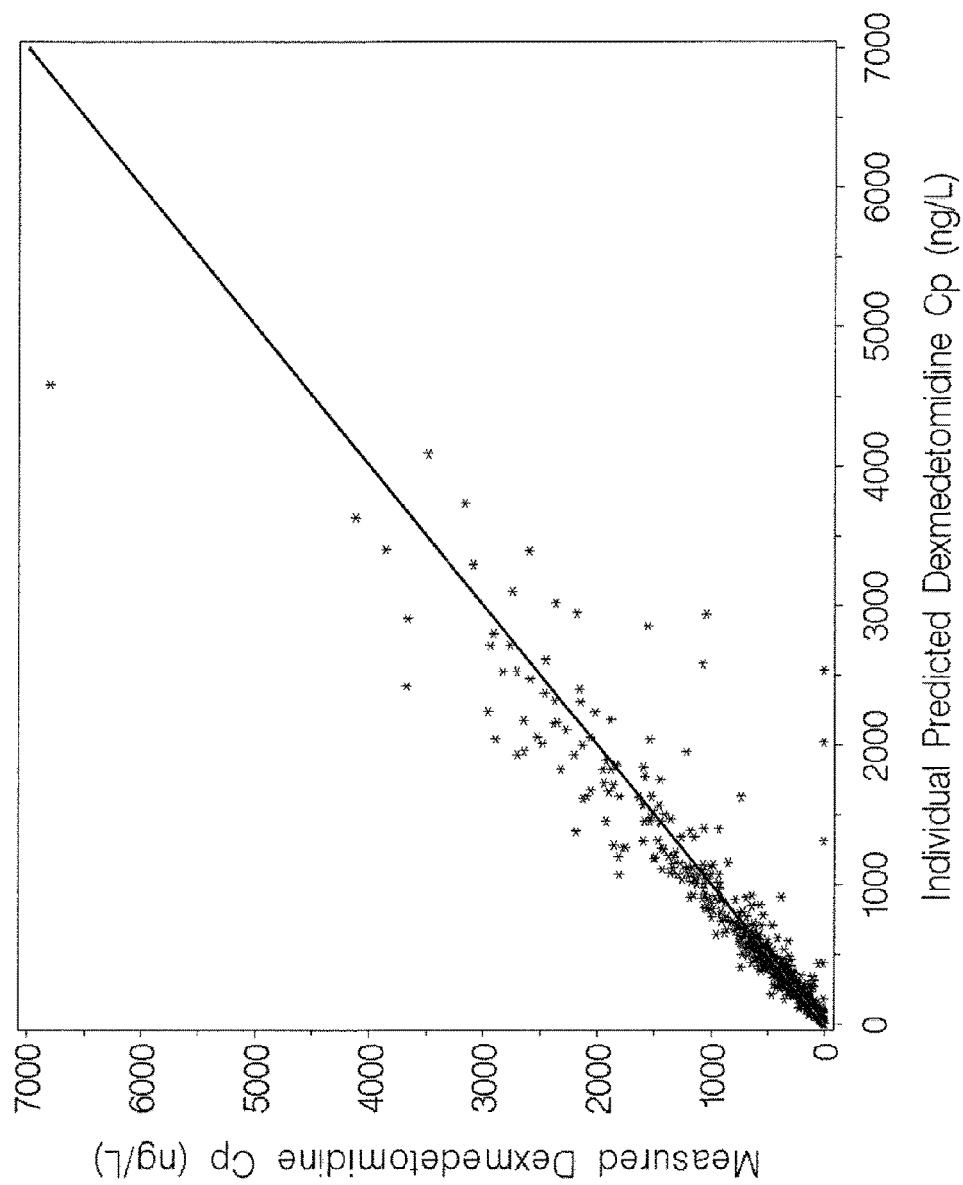
Figure 22C:
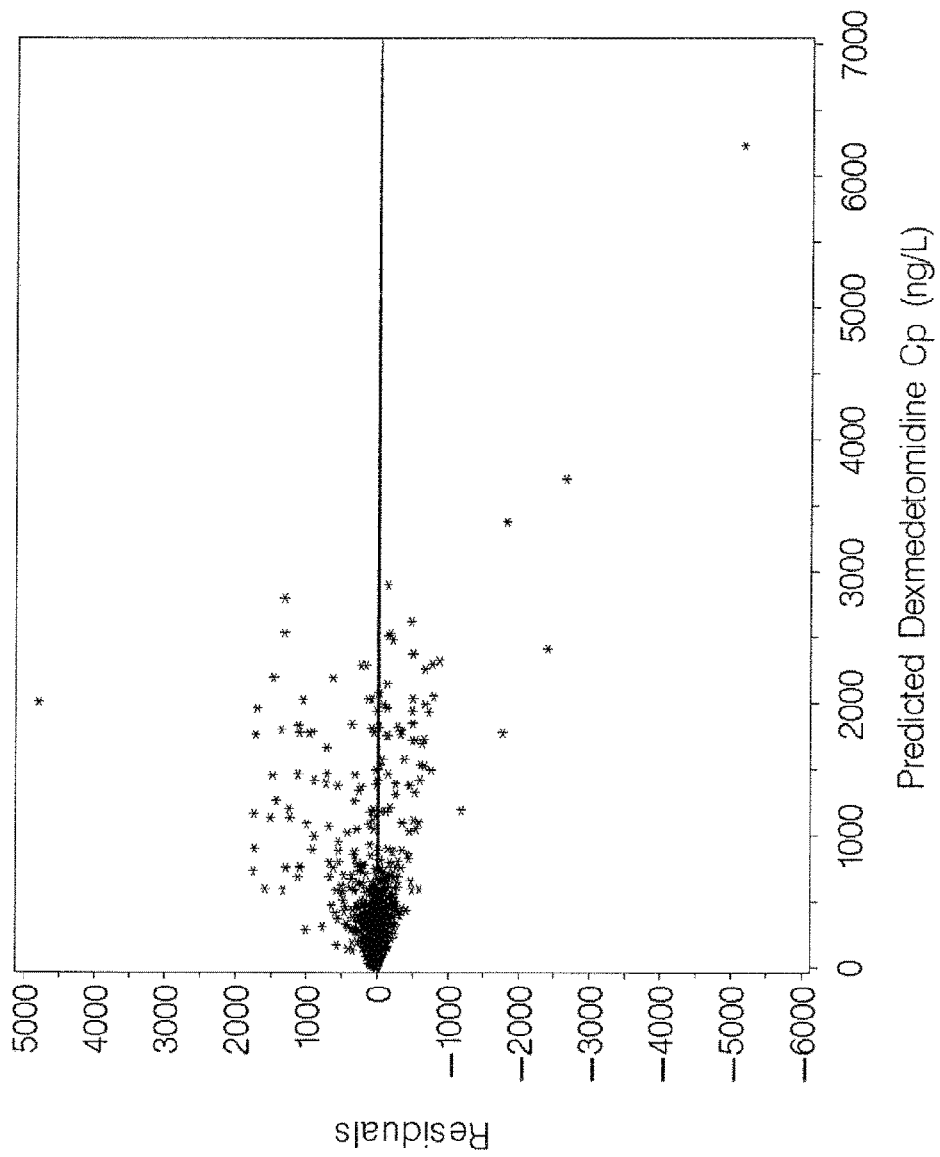
Figure 22C:
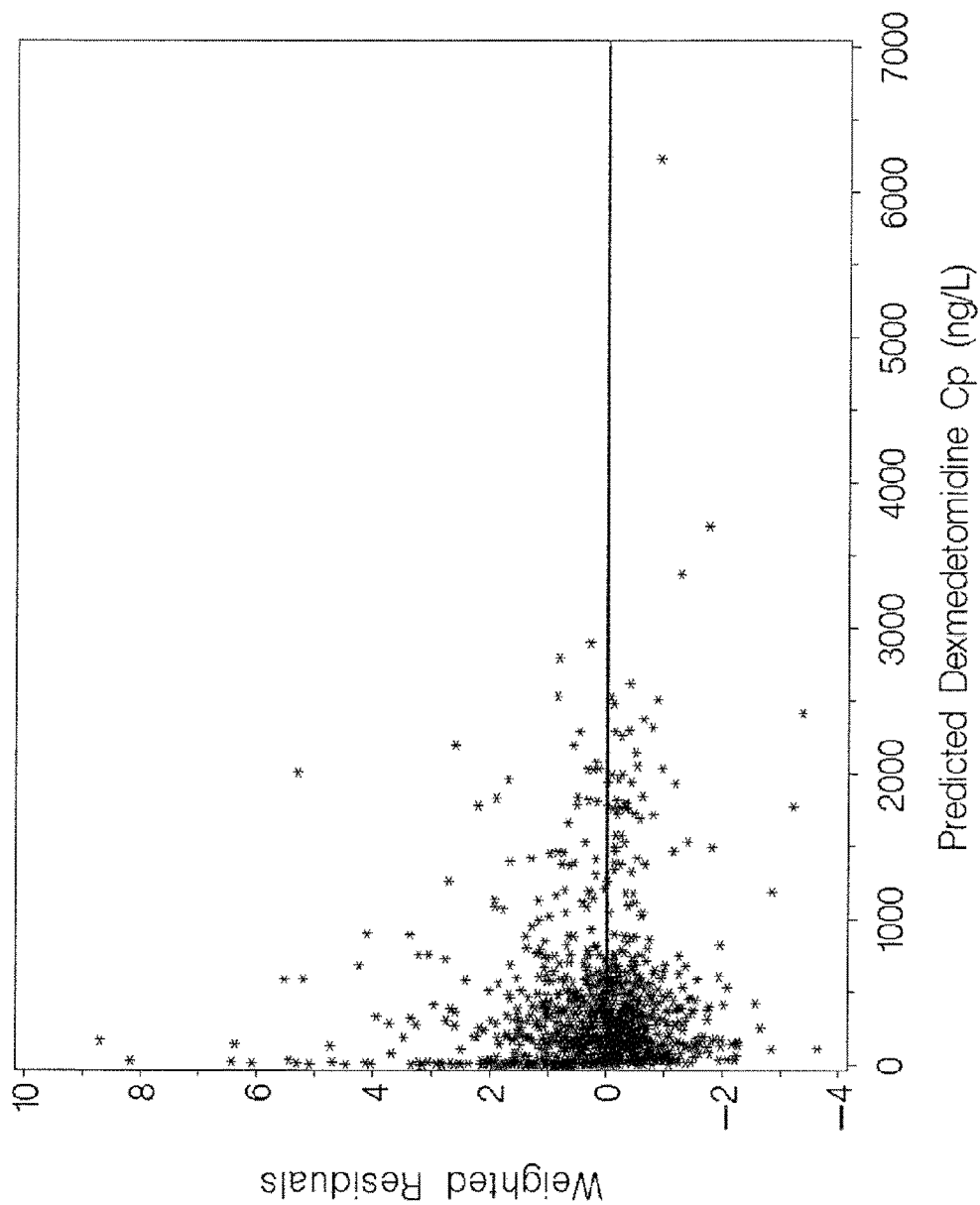
Figure 22D:
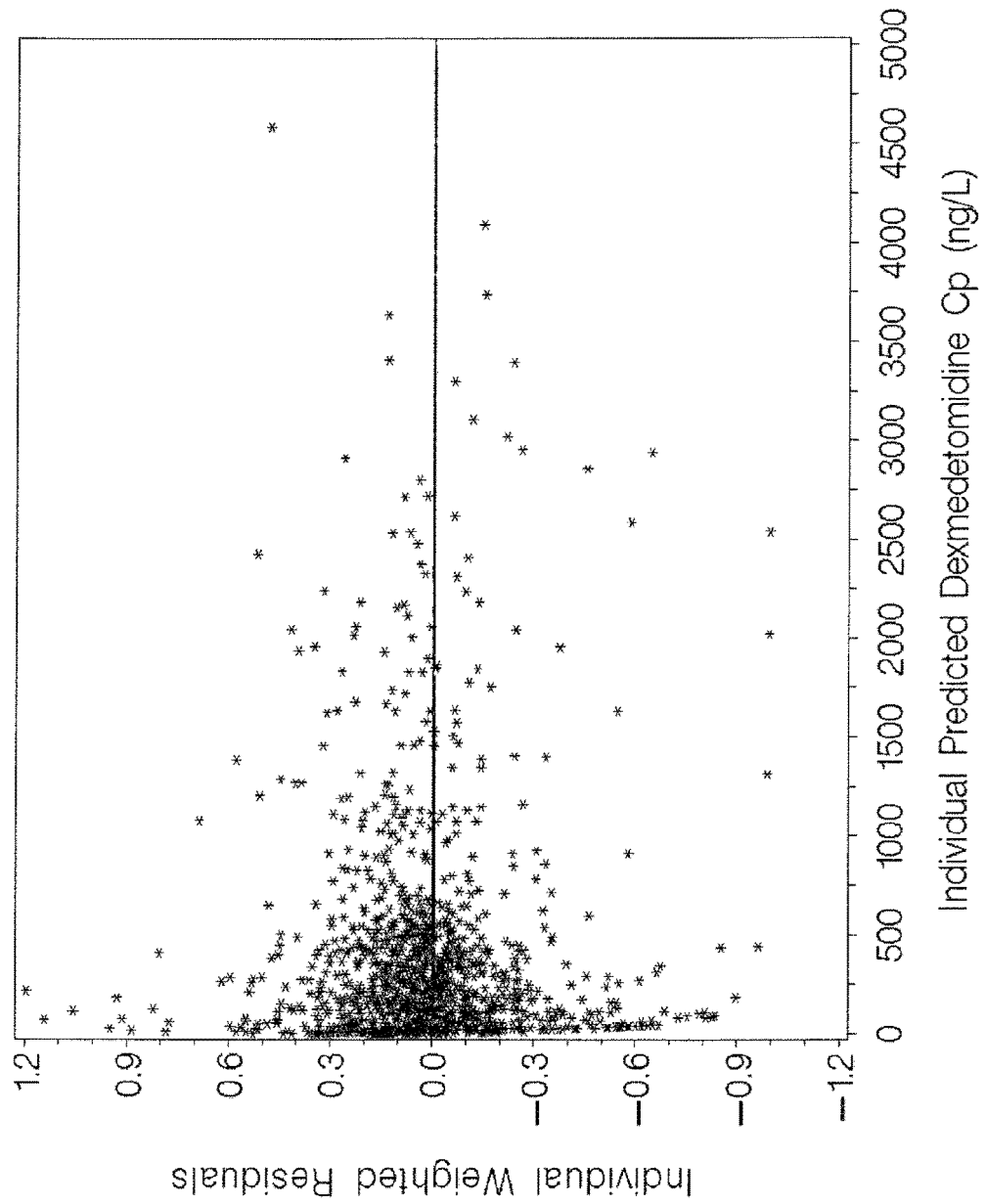
Figure 22D:
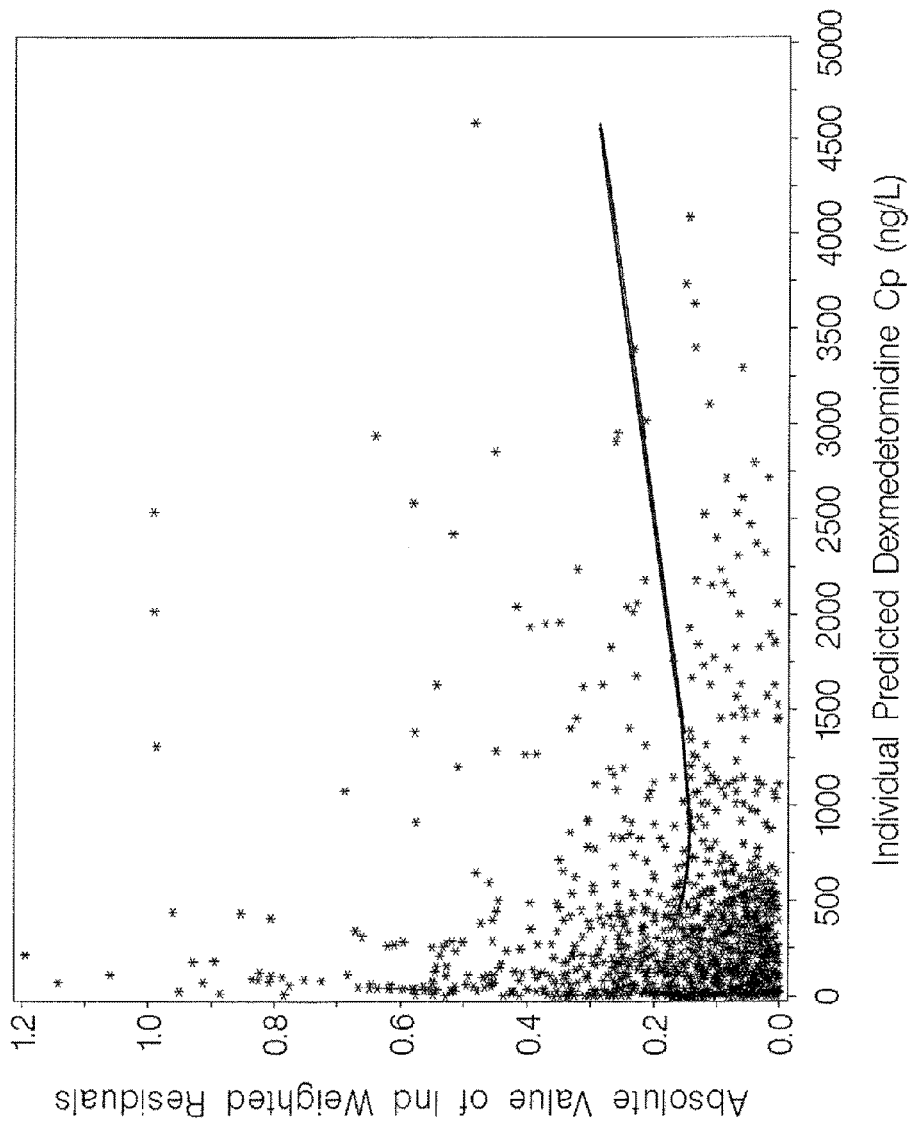

FIG. 21 depicts a comparison of the 5th, 50th, and 95th percentile of the prediction-corrected observed and model-based simulated data of Examples 1, 3, and 5.

FIGS. 22A-D depicts goodness-of-fit plots for the final population pharmacokinetics model for the entire population for the data of Examples 1, 3, and 5.

Figure 23:
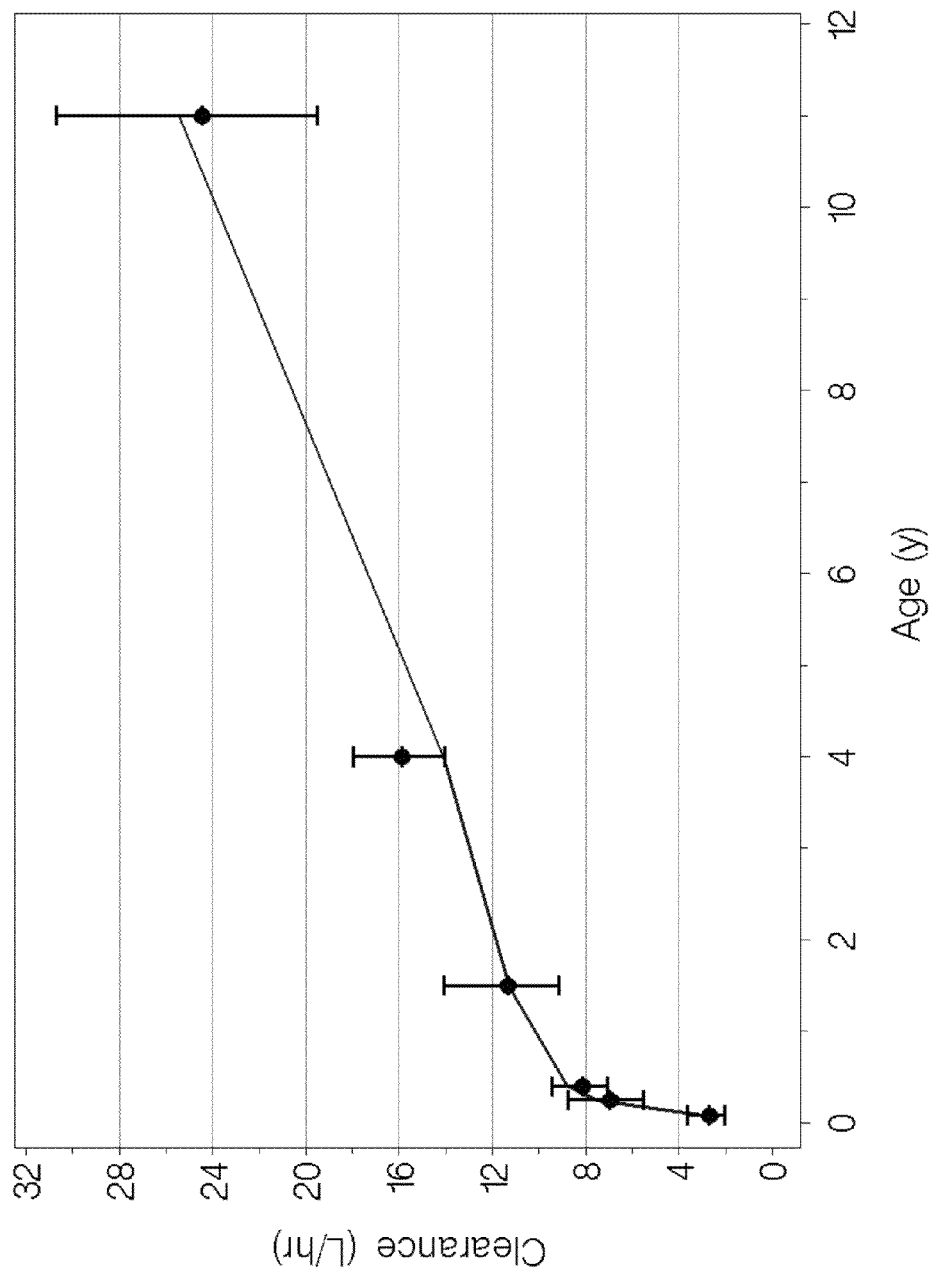
Figure 23:
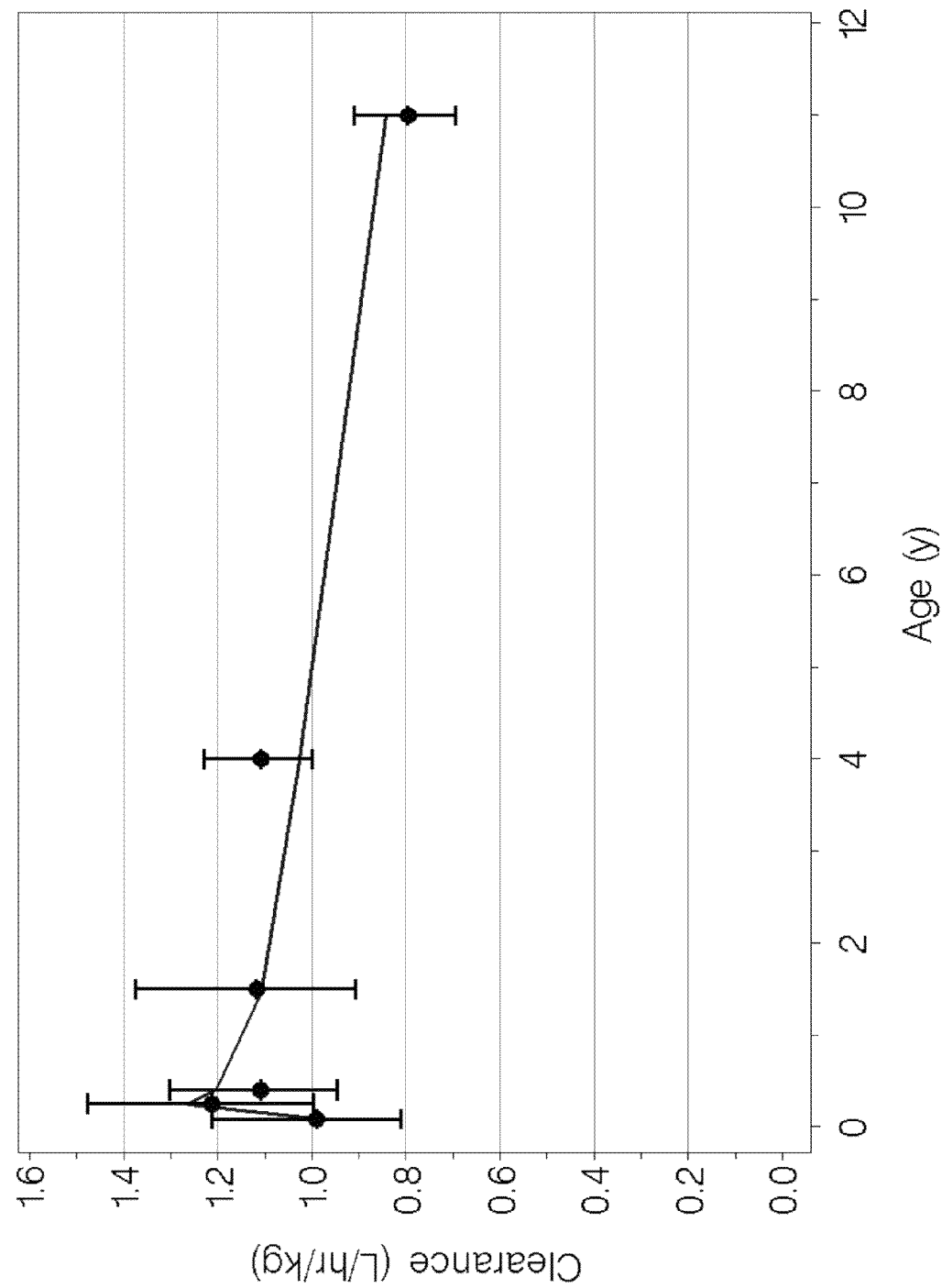

FIG. 23 in the upper panel depicts the geometric means and 95% confidence intervals for the individual Bayesian estimates of dexmedetomidine clearance plotted at the midpoint of each age group. The lower panels depict the corresponding weight-adjusted estimates for dexmedetomidine clearance. A line for the population model-based typical value of each parameter versus age is overlaid in each plot.

Figure 24:
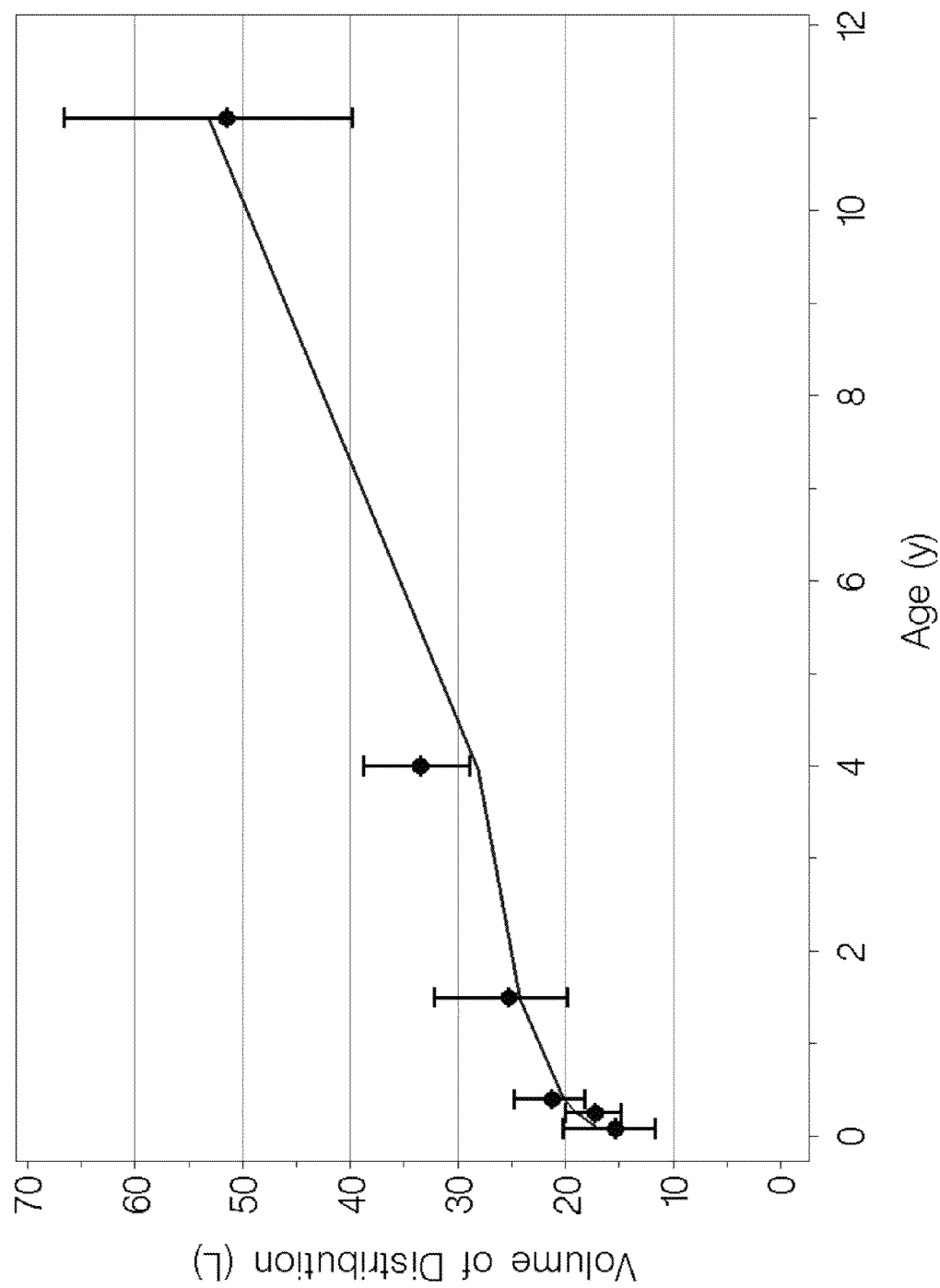
Figure 24:
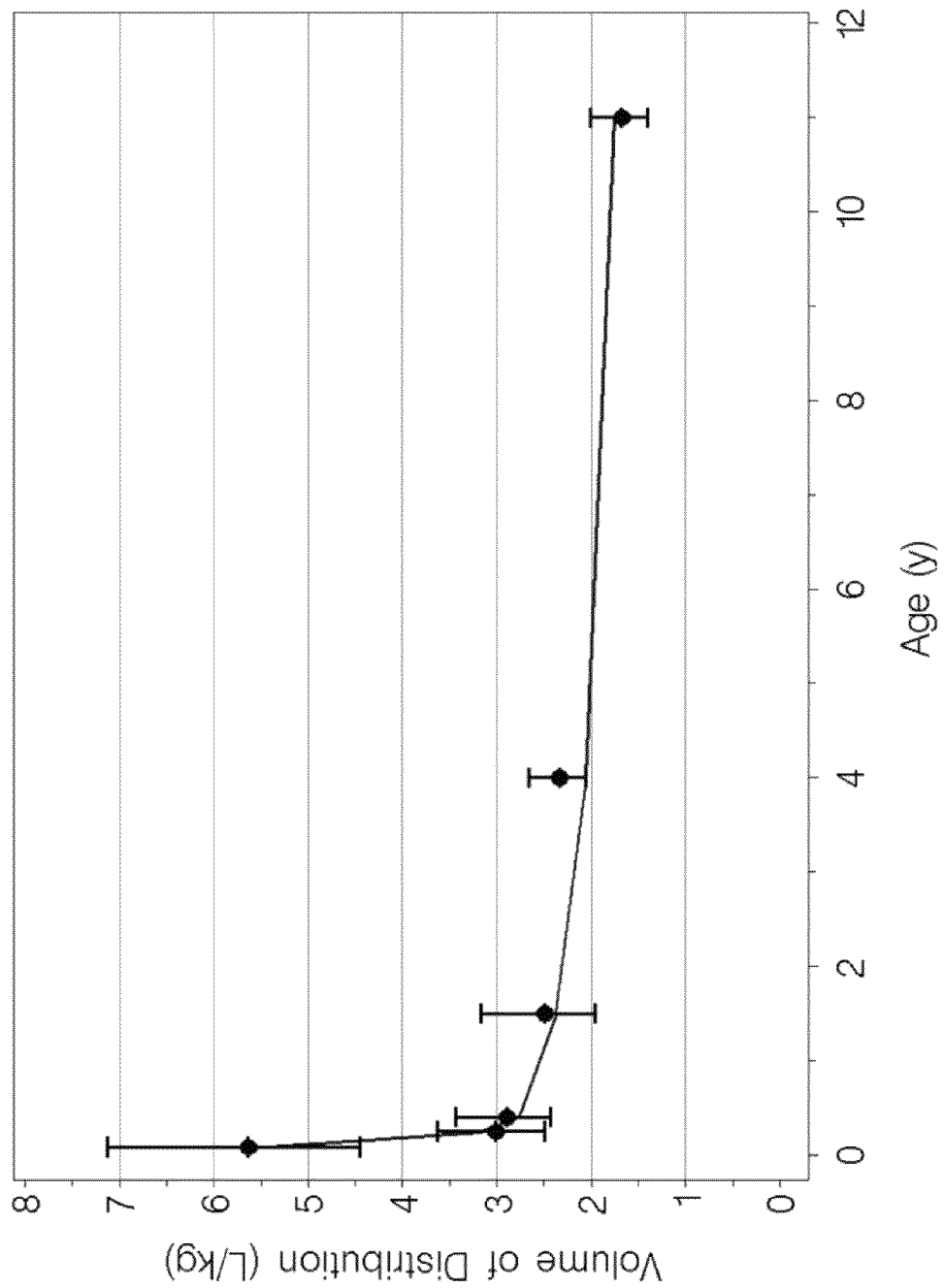

FIG. 24 in the upper panel depicts the geometric means and 95% confidence intervals for the individual Bayesian estimates of dexmedetomidine volume of distribution plotted at the midpoint of each age group. The lower panels depict the corresponding weight-adjusted estimates for dexmedetomidine volume of distribution. A line for the population model-based typical value of each parameter versus age is overlaid in each plot.

Figure 25:
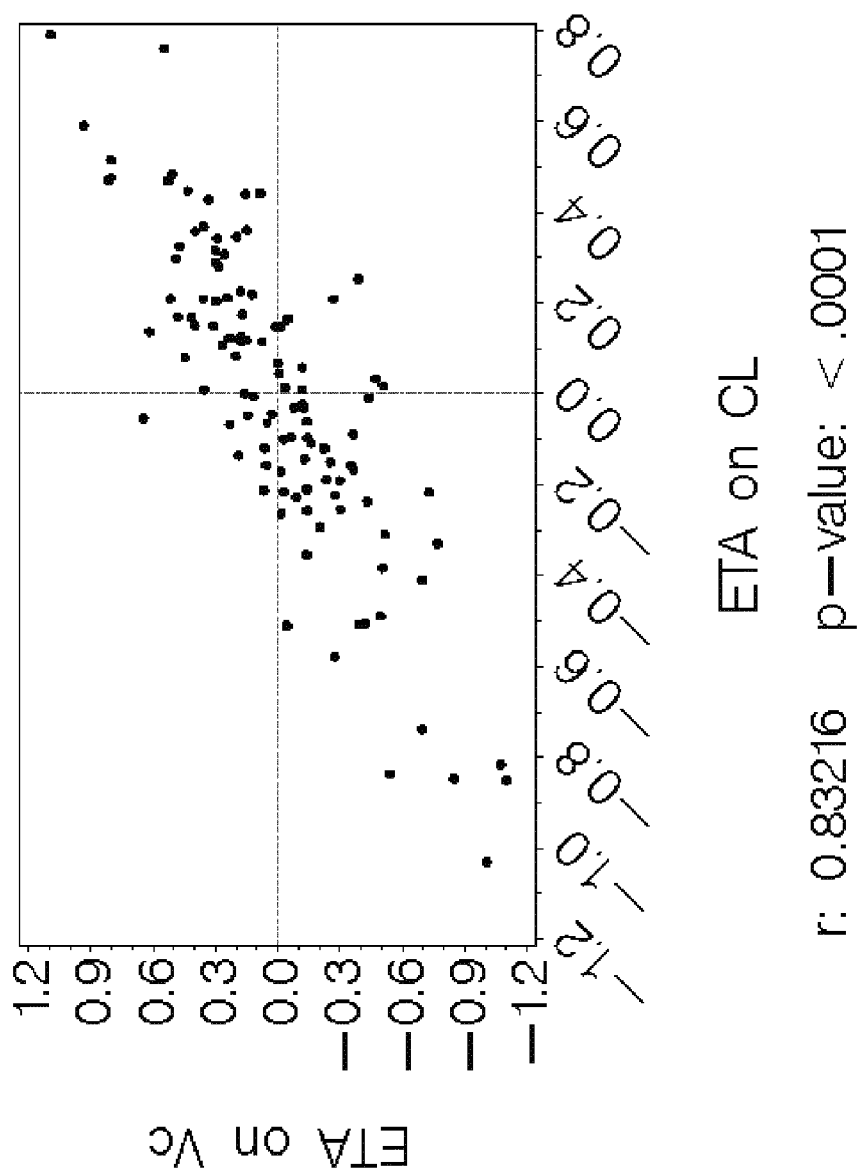
Figure 25:
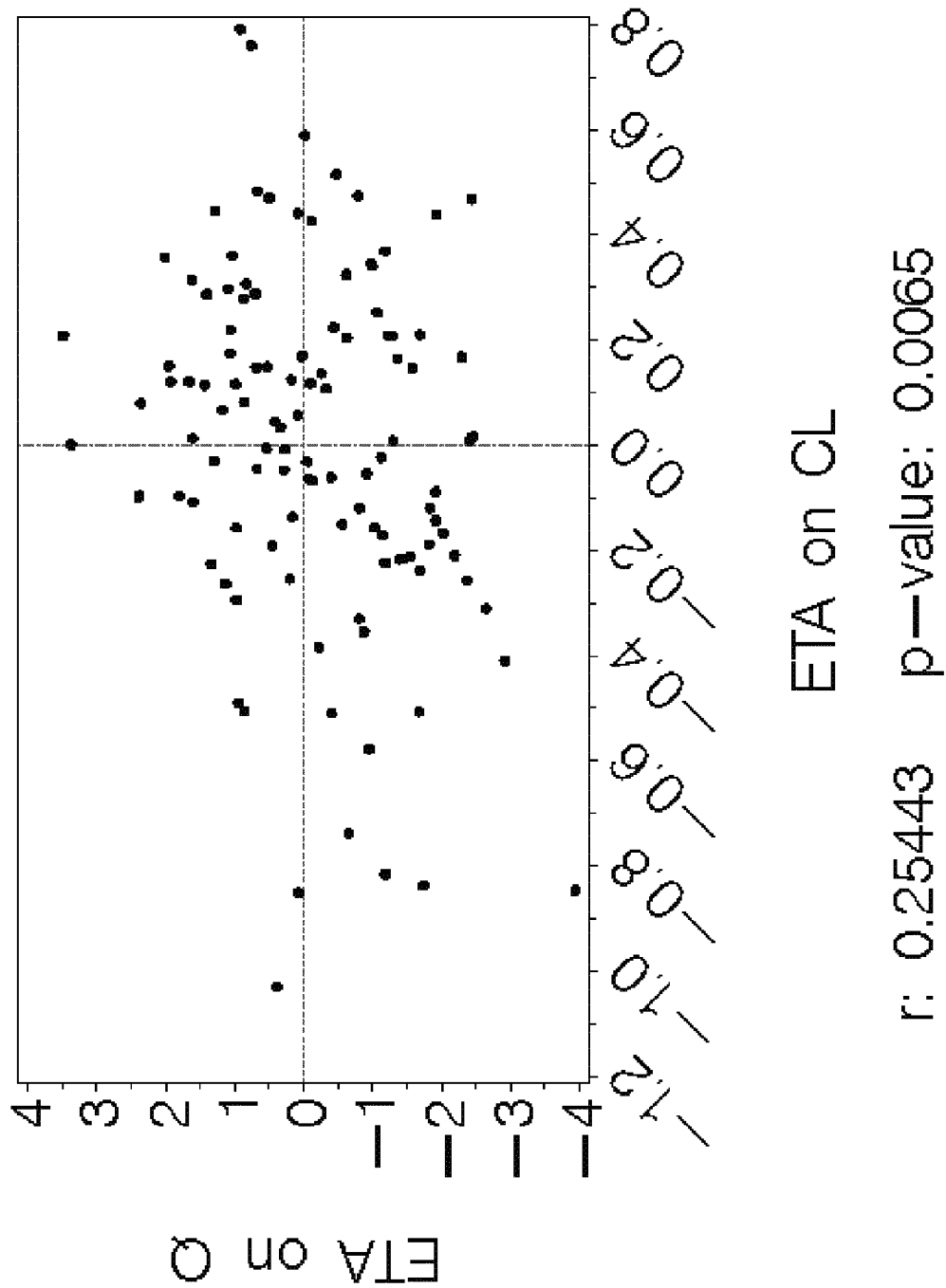
Figure 25:
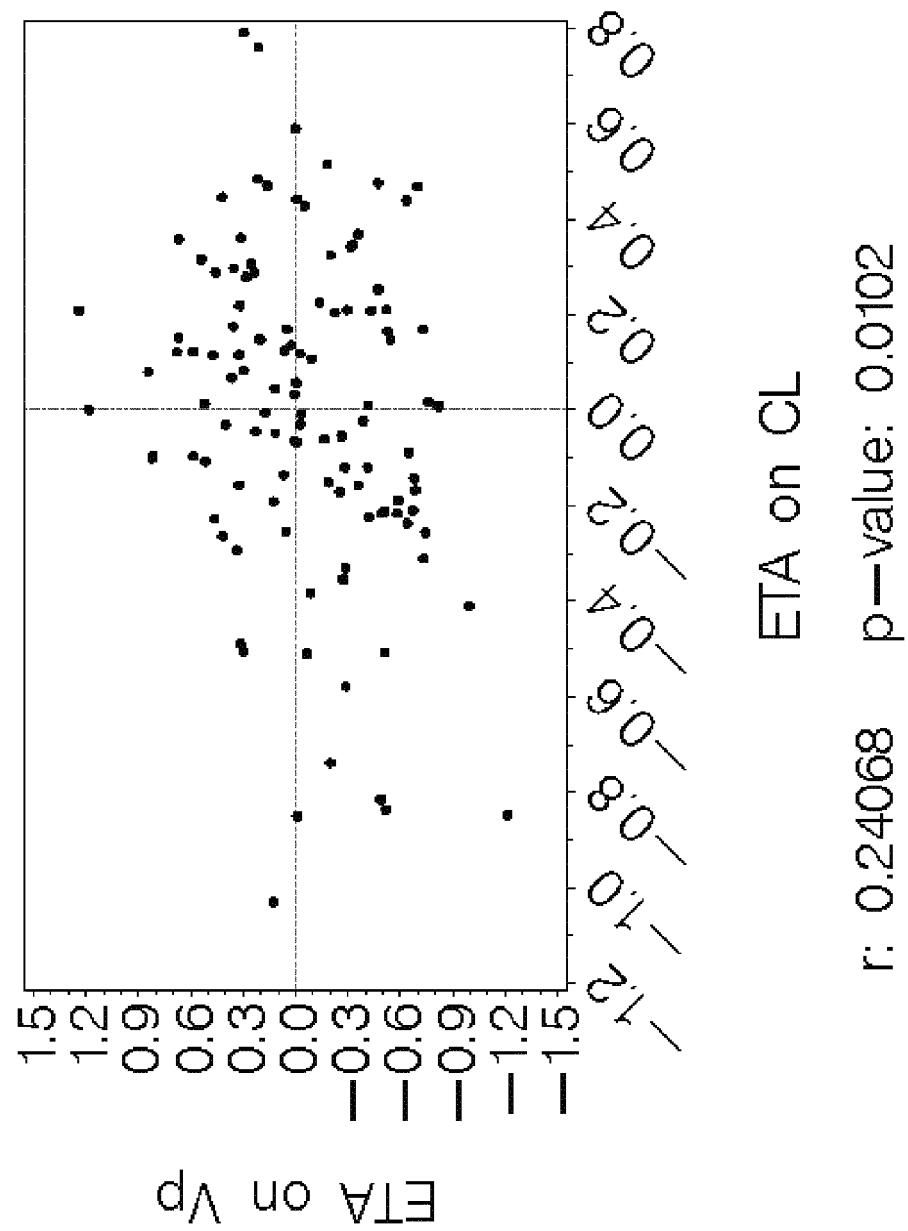
Figure 25:
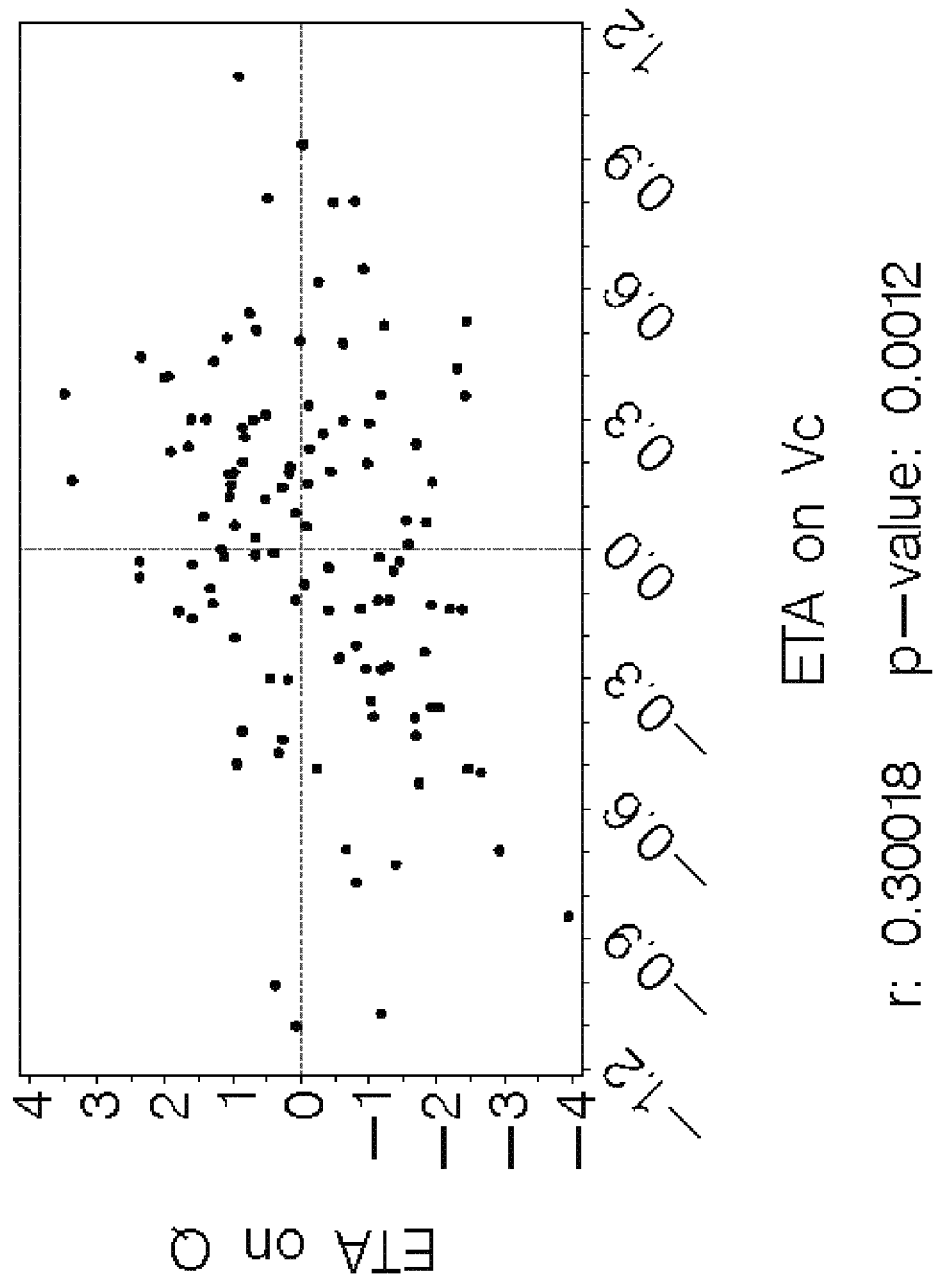
Figure 25:
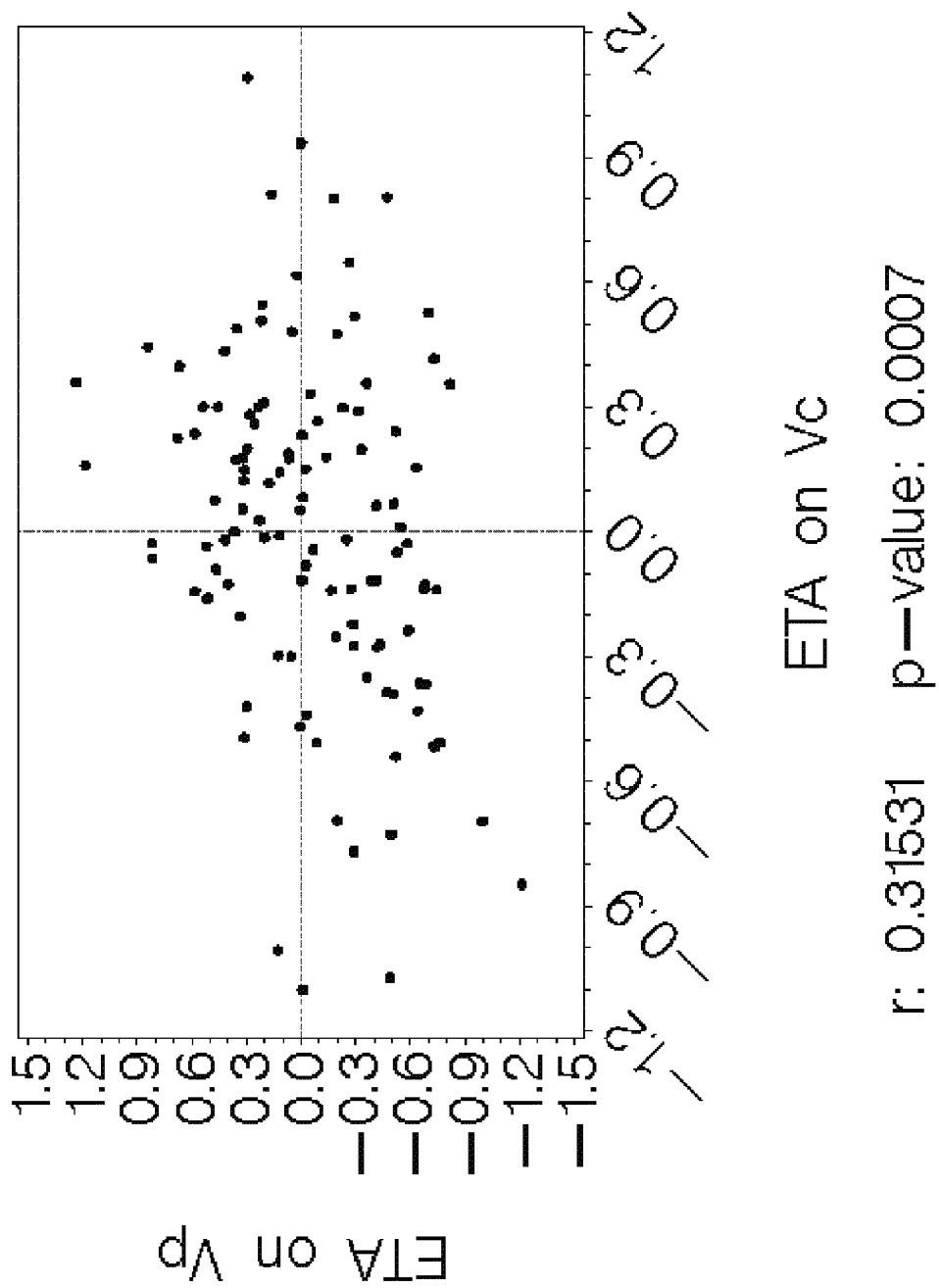
Figure 25:
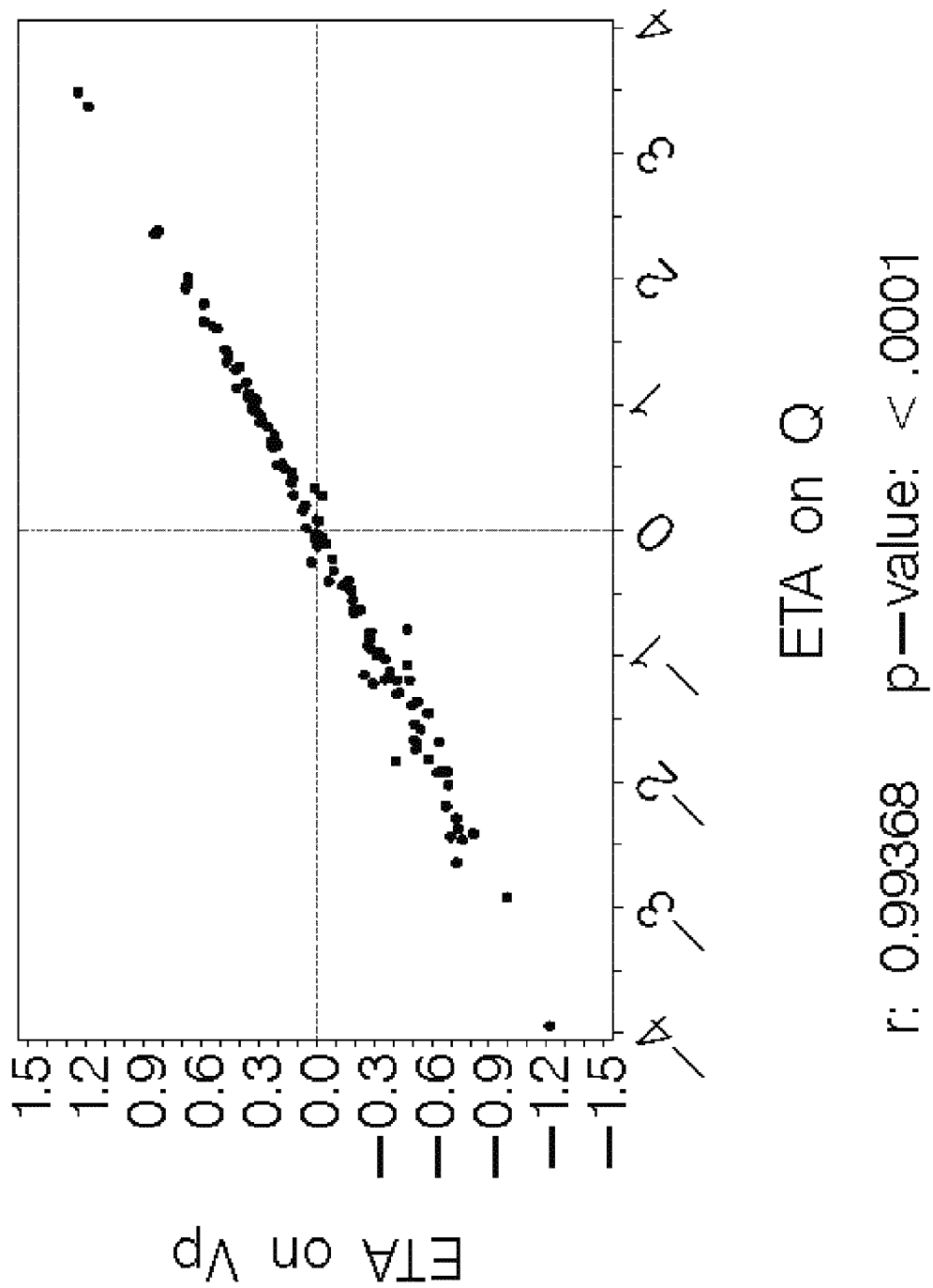

FIG. 25 depicts the pairwise scatterplots of interindividual variance terms from the final model in Example 6.

Figure 26:
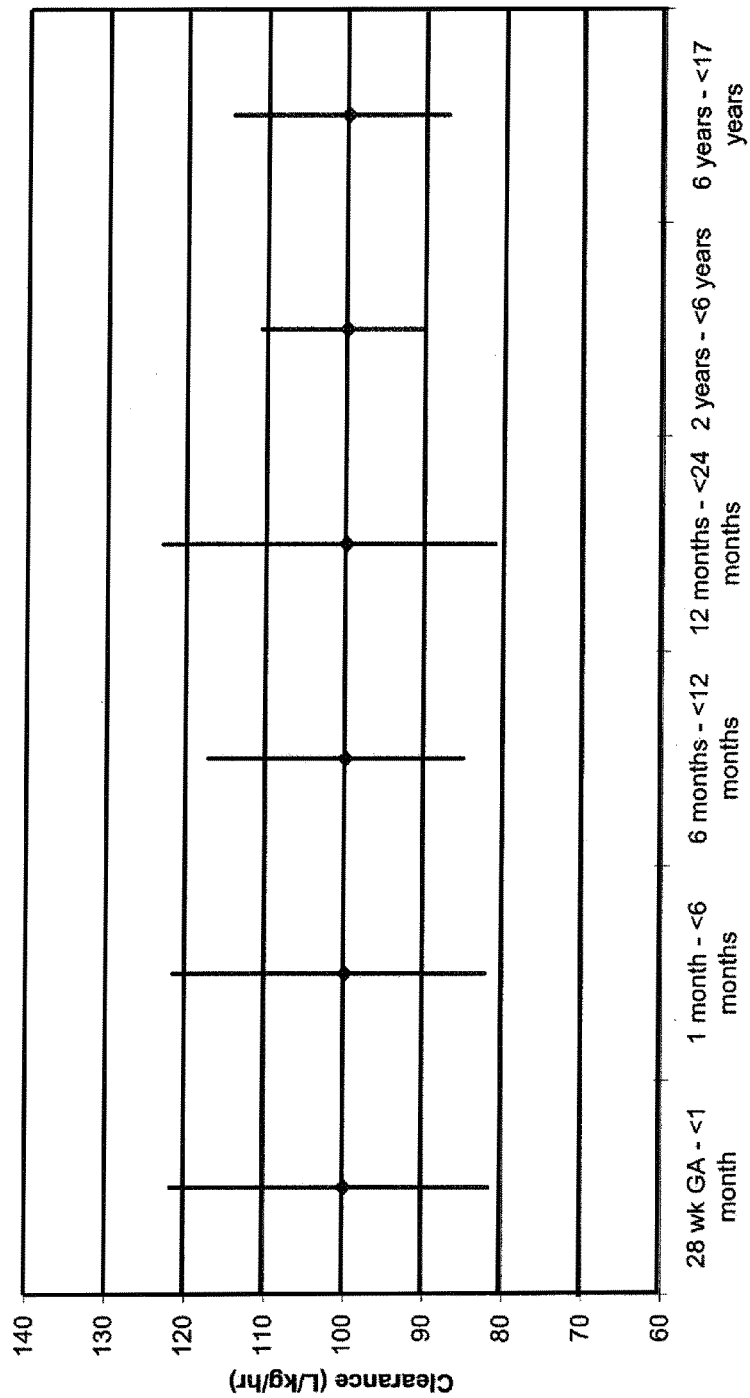

FIG. 26 depicts the 95% confidence intervals for the individual Bayesian estimates expressed as the percent of the geometric mean of dexmedetomidine weight-adjusted CL for each age group as determined from the analysis performed in Example 6.

Figure 27:
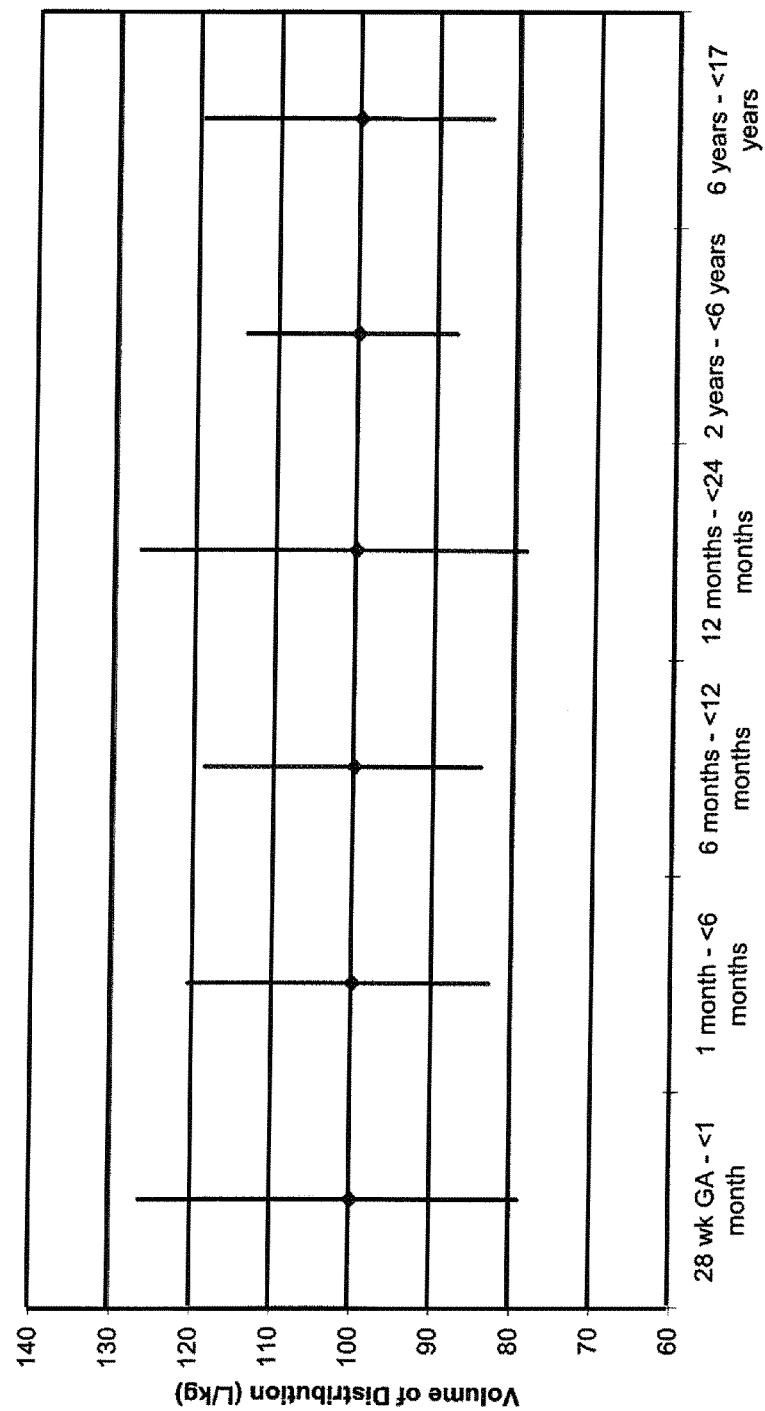

FIG. 27 depicts the 95% confidence intervals for the individual Bayesian estimates expressed as the percent of the geometric mean of dexmedetomidine weight-adjusted volume of distribution for each age group as determined from the analysis performed in Example 6.

Figure 28:
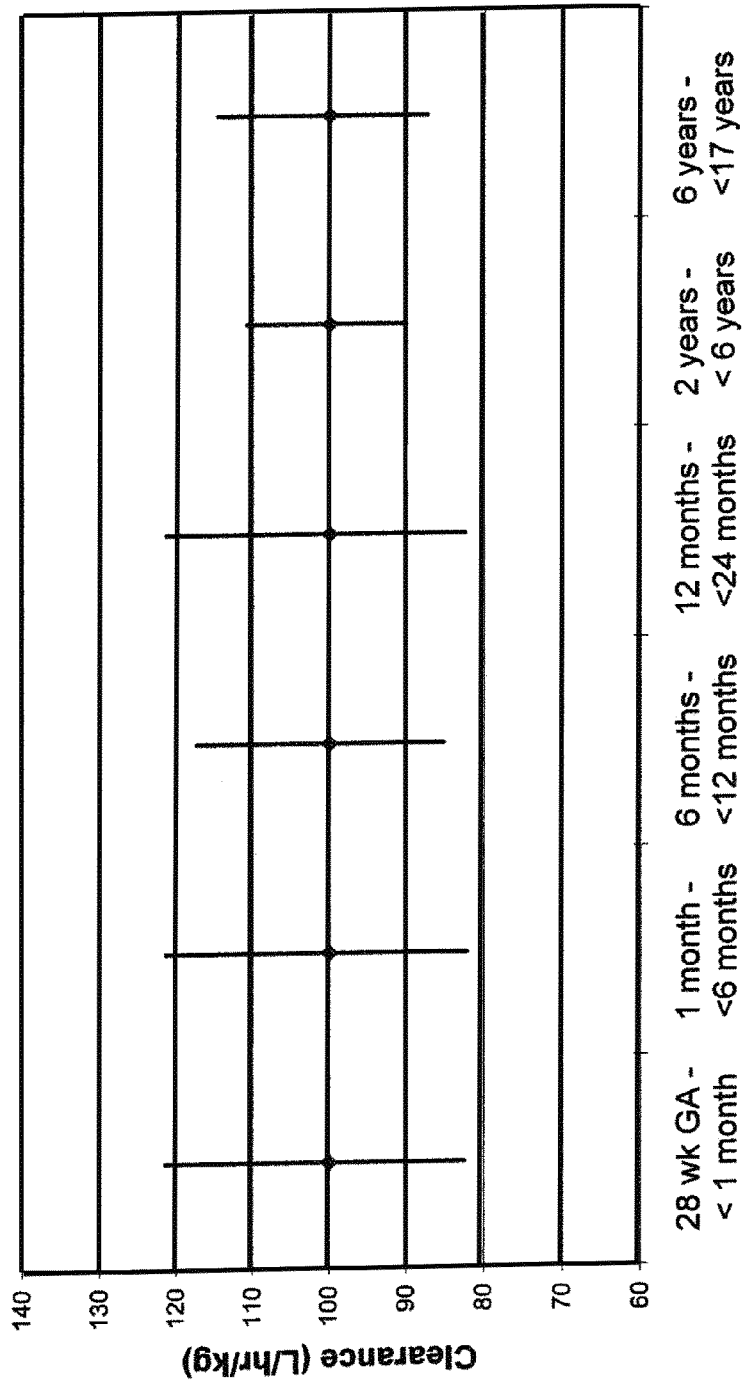

FIG. 28 depicts the 95% confidence intervals for the individual Bayesian estimates expressed as the percent of the geometric mean of dexmedetomidine weight-adjusted CL for each age group as determined from the analysis performed in Example 8.

Figure 29:
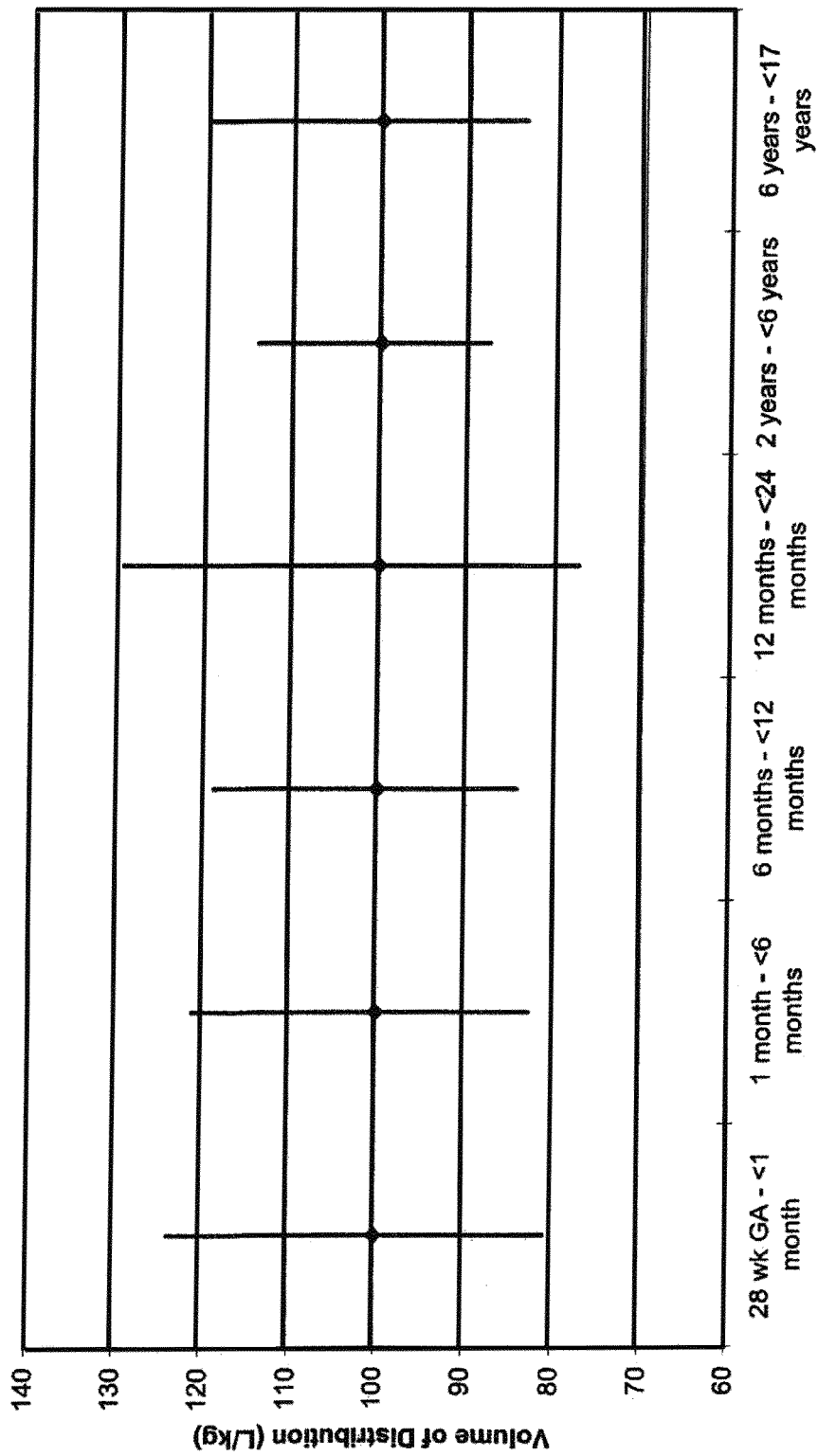
Figure 30A:
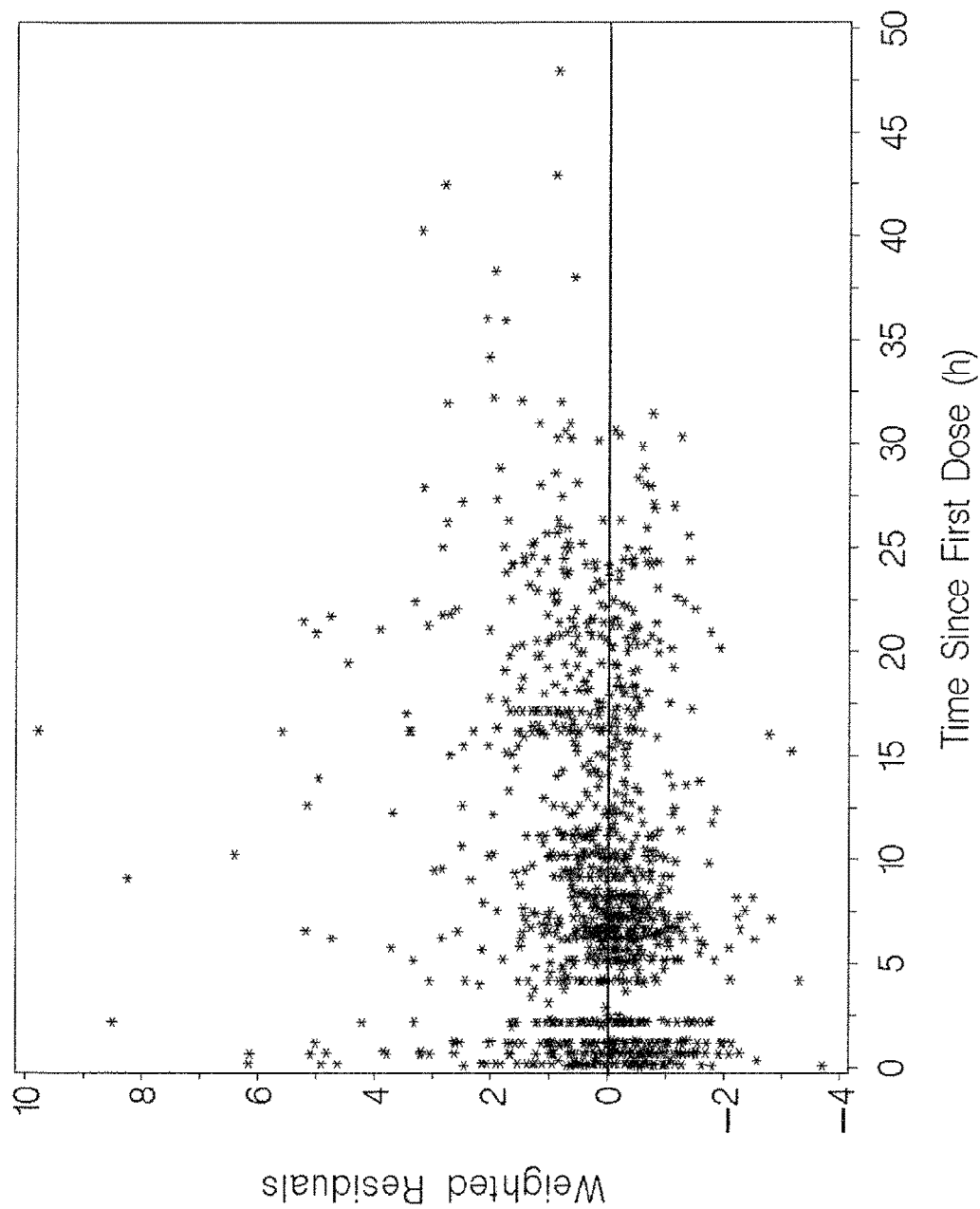
Figure 30B:
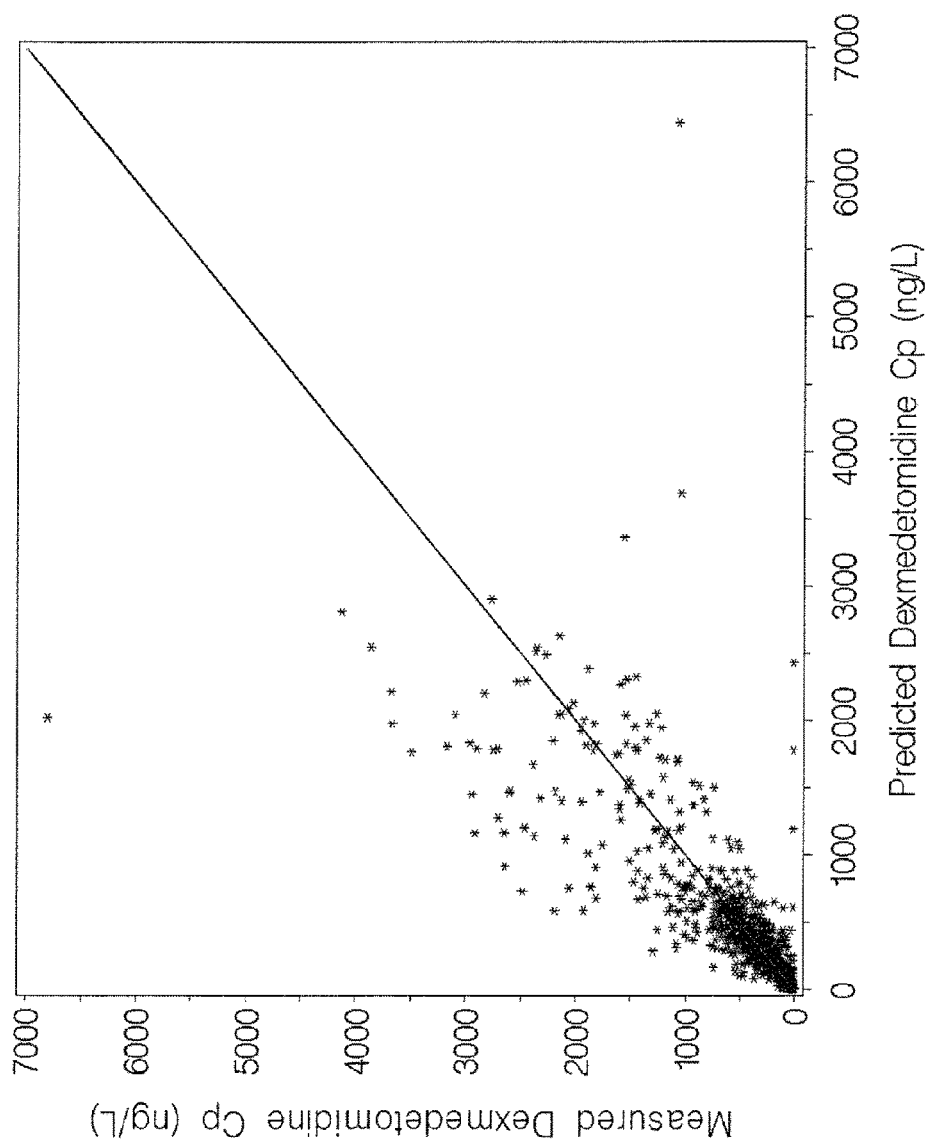
Figure 30C:
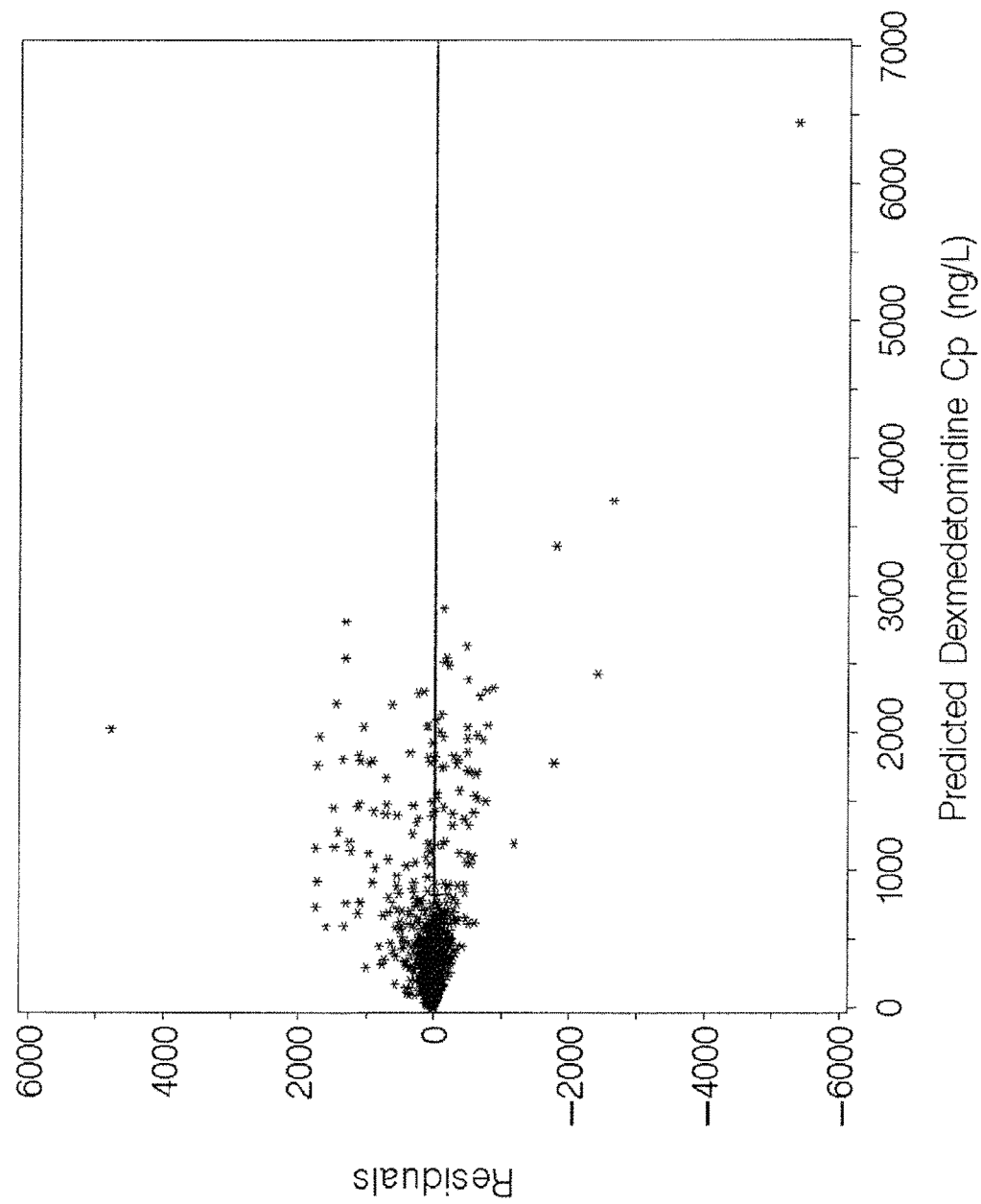
Figure 30D:
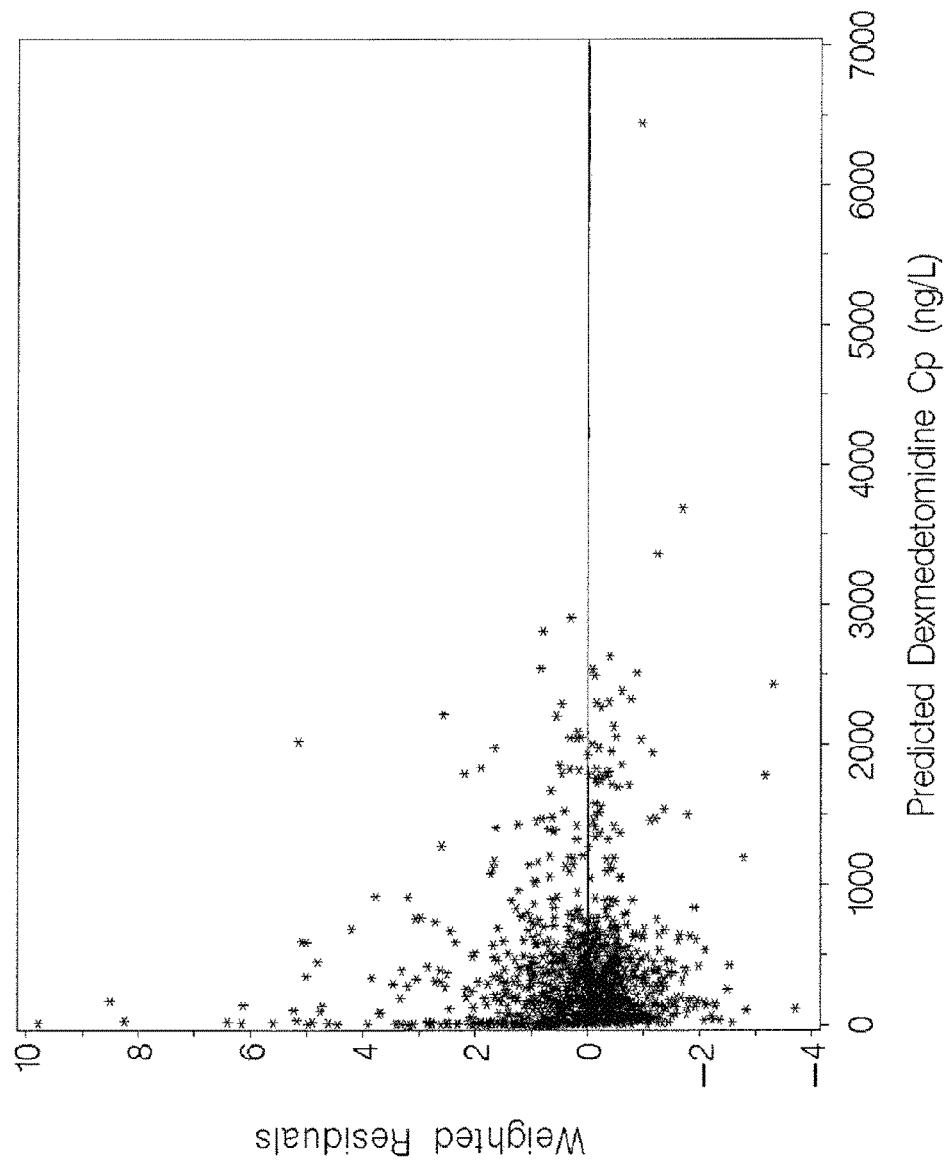
Figure 30E:
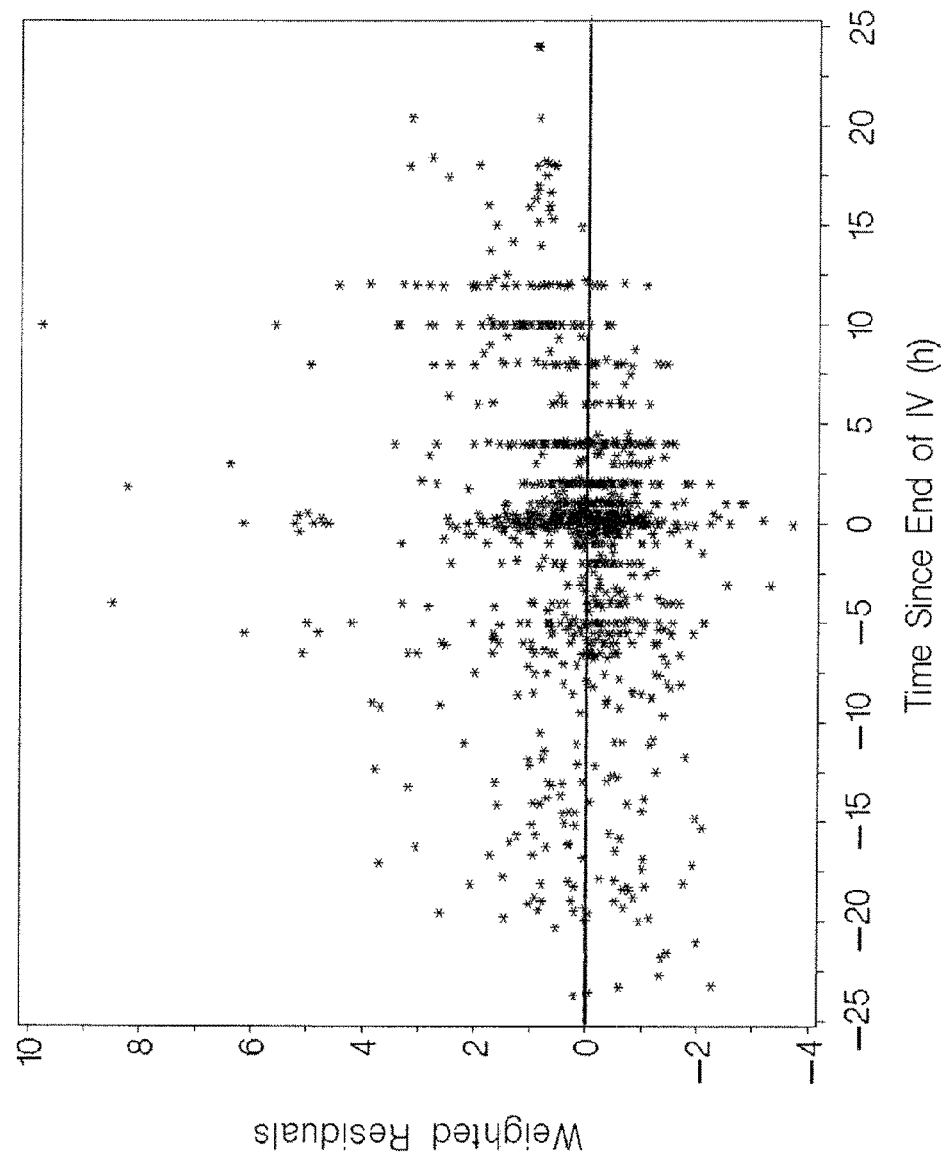
Figure 30F:
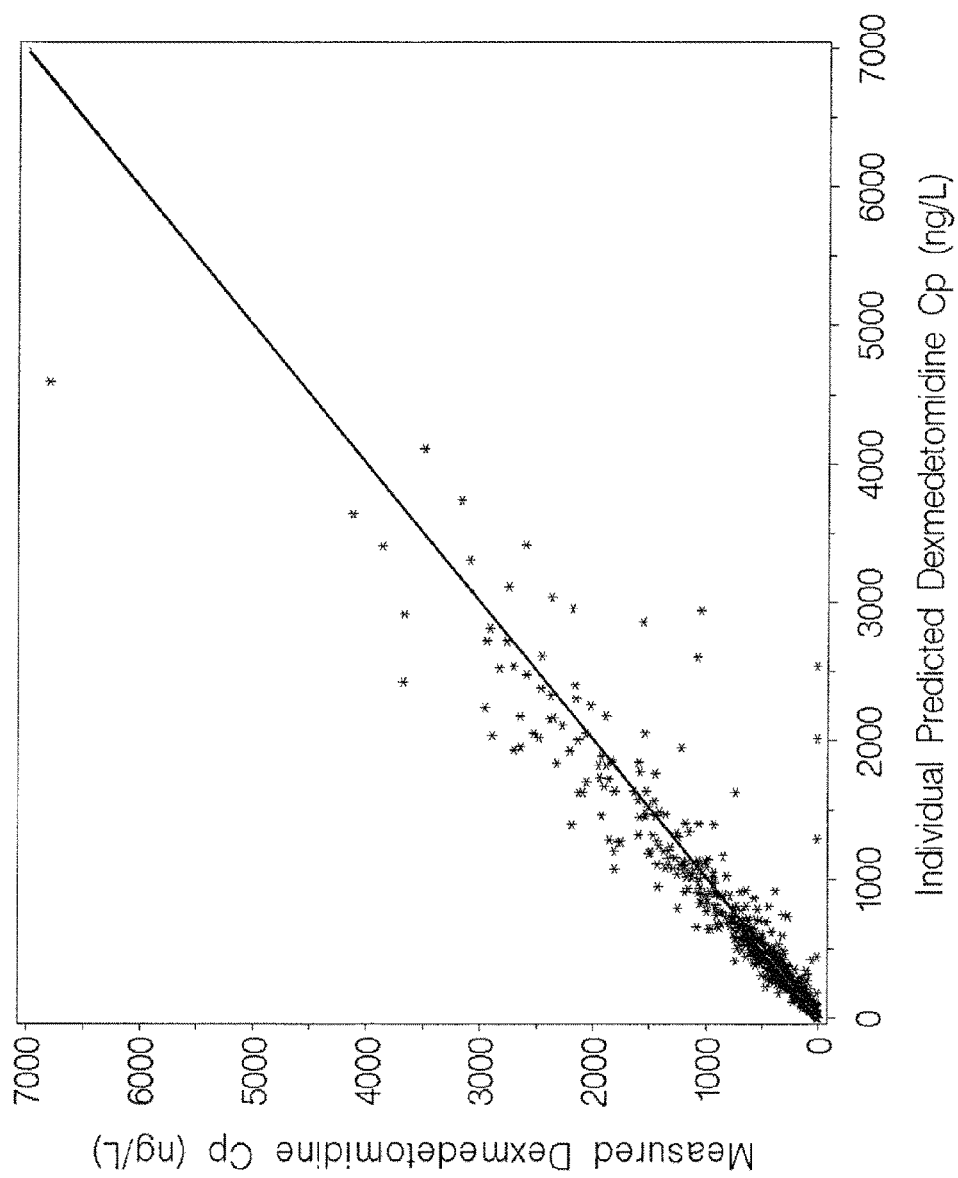
Figure 30G:
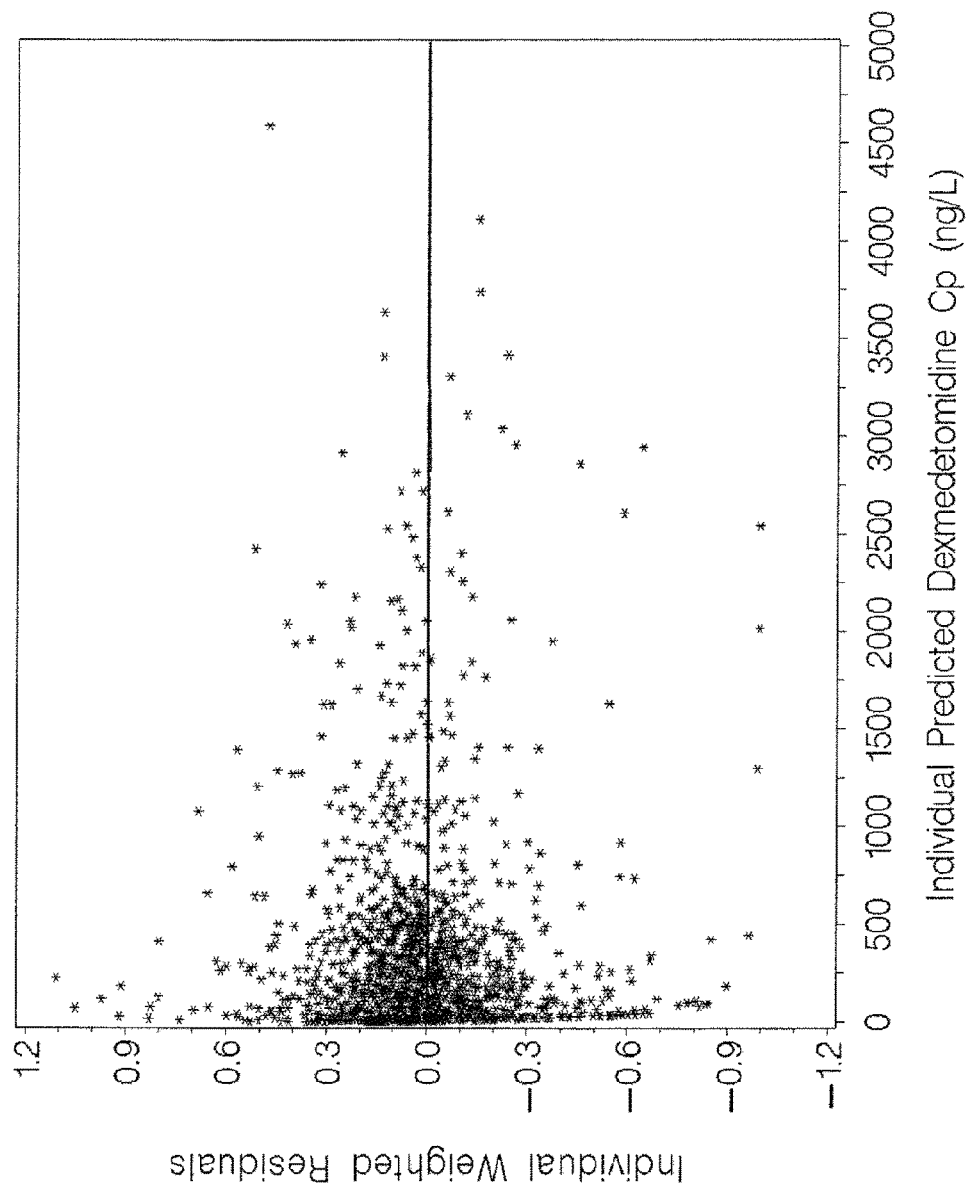
Figure 30H:
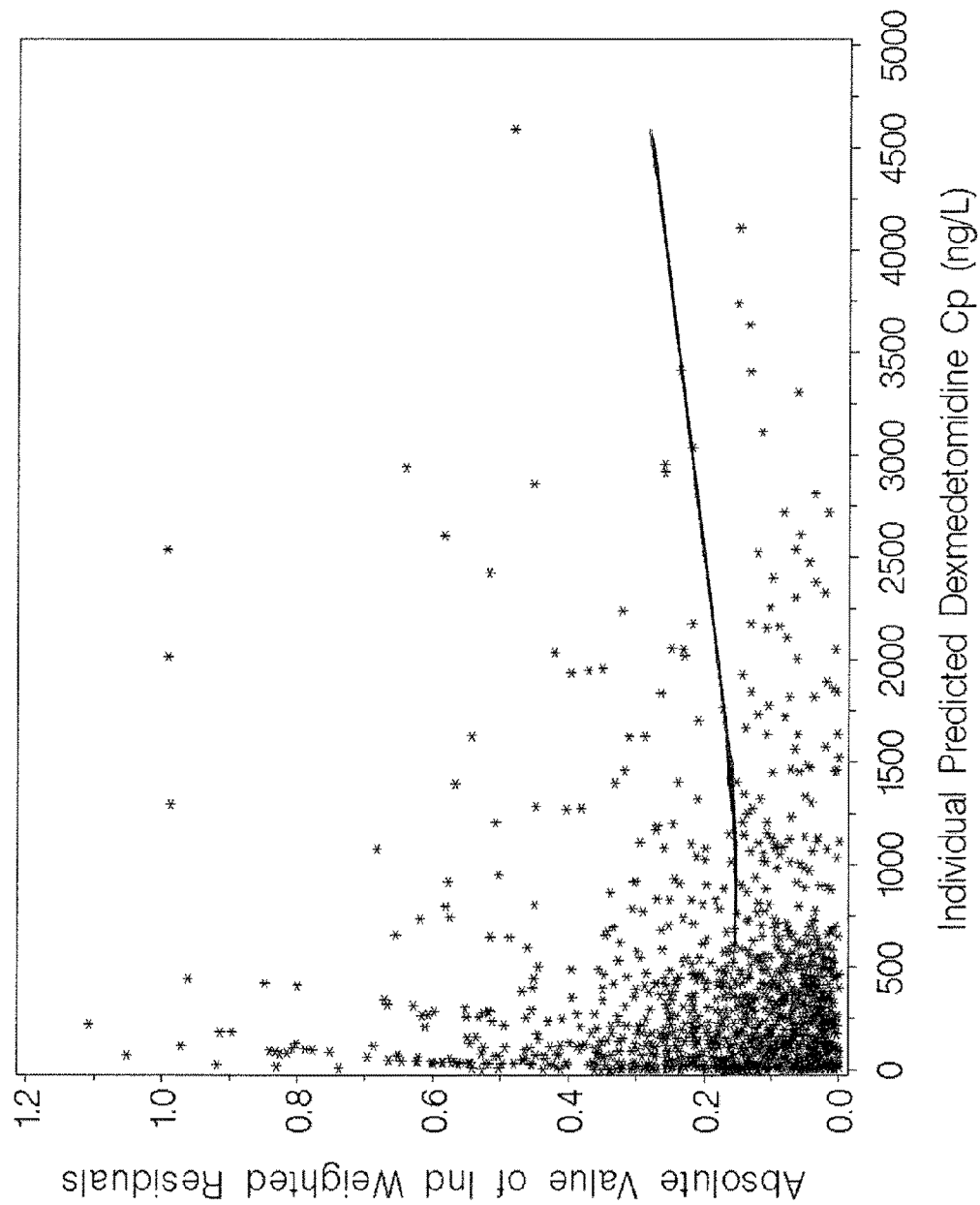

FIG. 29 depicts the 95% confidence intervals for the individual Bayesian estimates expressed as the percent of the geometric mean of dexmedetomidine weight-adjusted volume of distribution for each age group as determined from the analysis performed in Example 8.

FIGS. 30A-H depict the goodness-of-fit plots for the final population pharmacokinetic model for dexmedetomidine of Example 8.

Figure 31A:
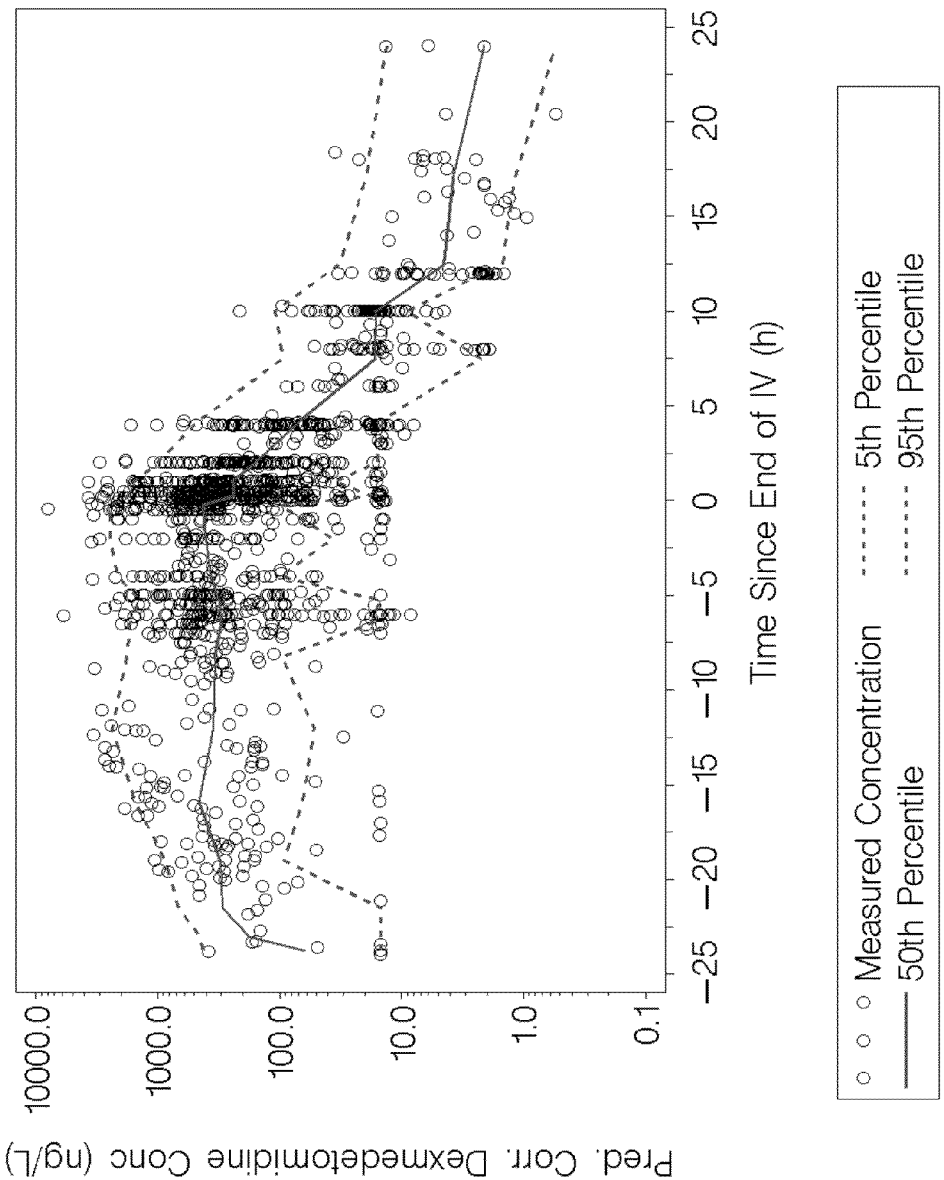
Figure 31B:
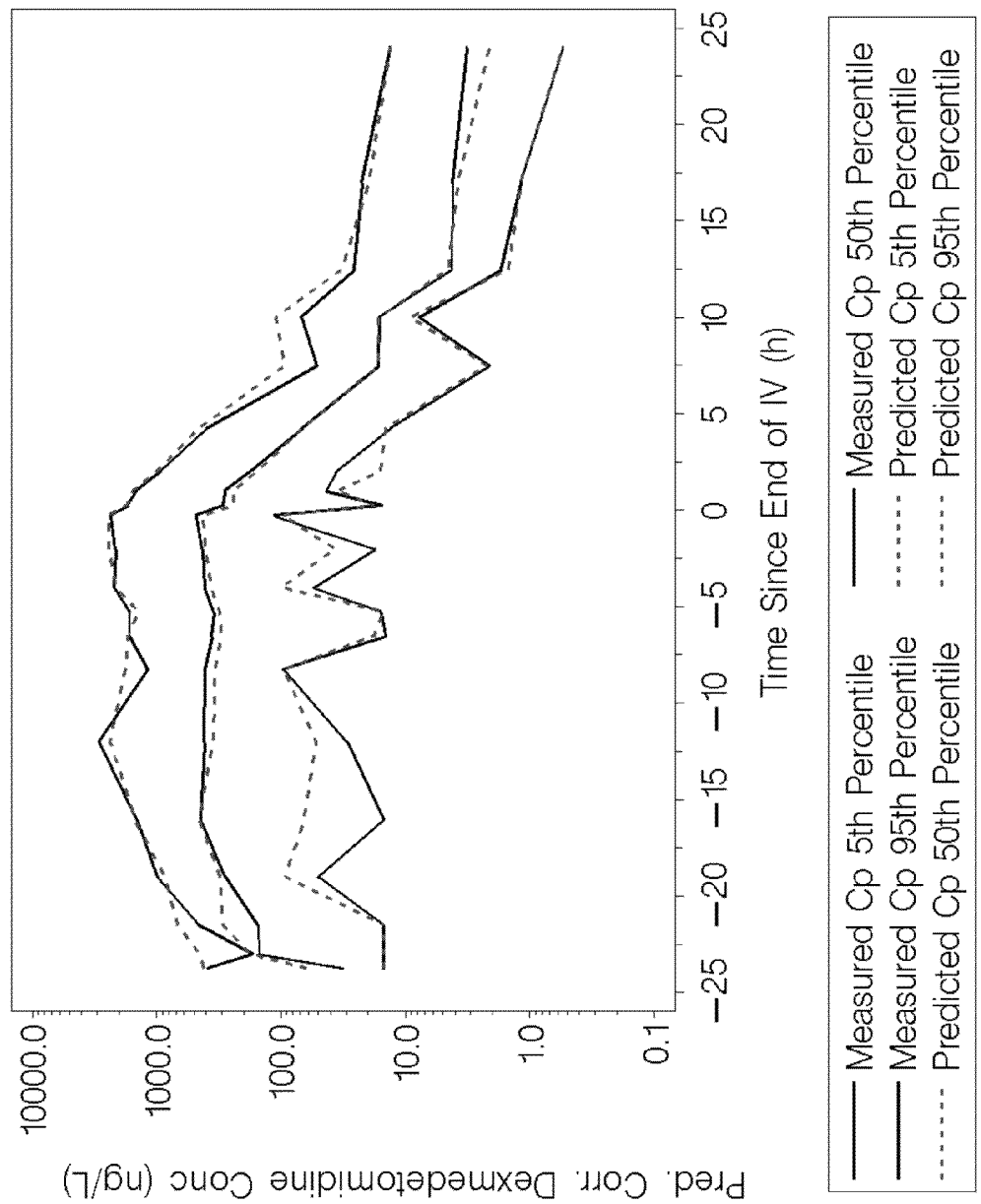

FIGS. 31A-B depict the prediction-corrected visual predictive check results for the dexmedetomidine concentration versus time since end of IV.

Figure 32:
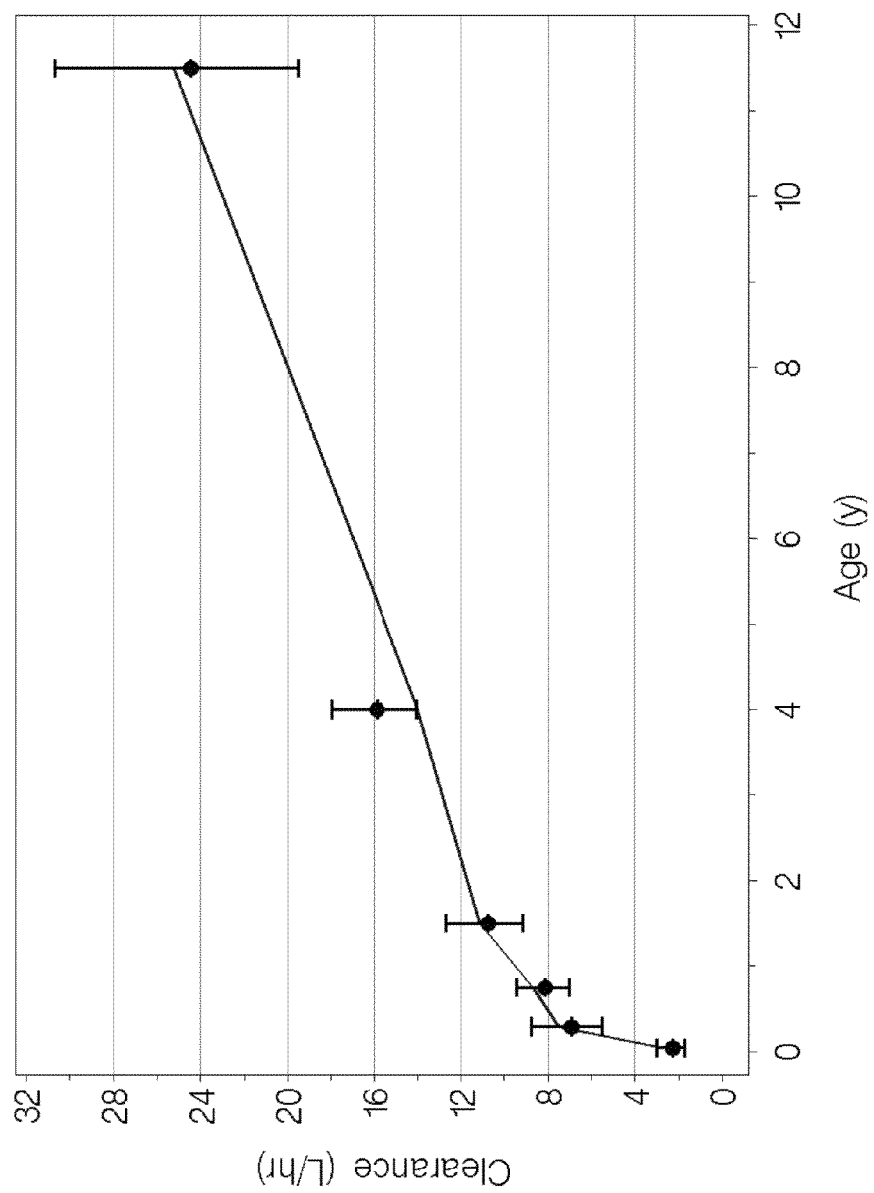
Figure 32:
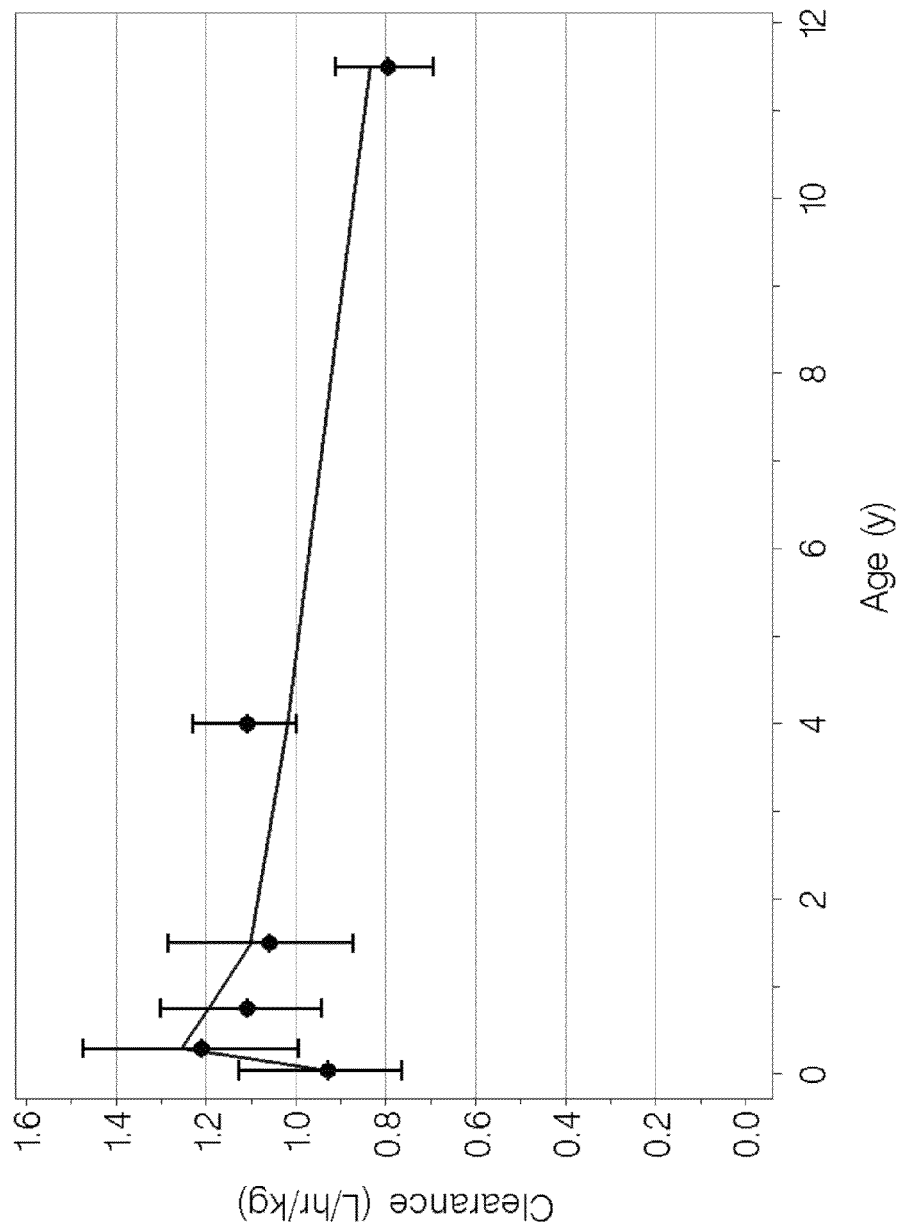

FIG. 32 depicts the geometric means and 95% confidence intervals for the Bayesian estimates of dexmedetomidine clearance and weight-adjusted clearance in specified age groups with the population model-based typical values of clearance and weight-adjusted clearance overlaid.

Figure 33:
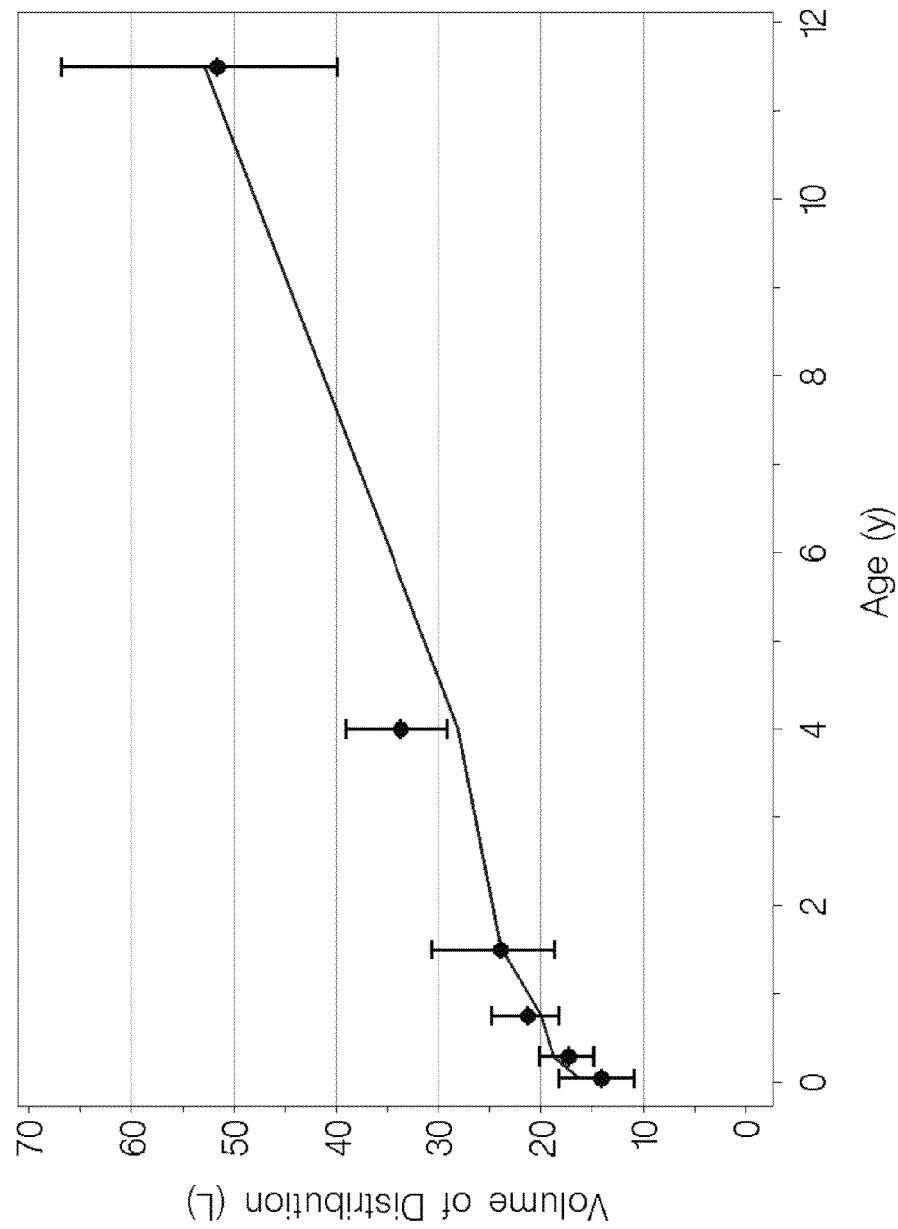
Figure 33:
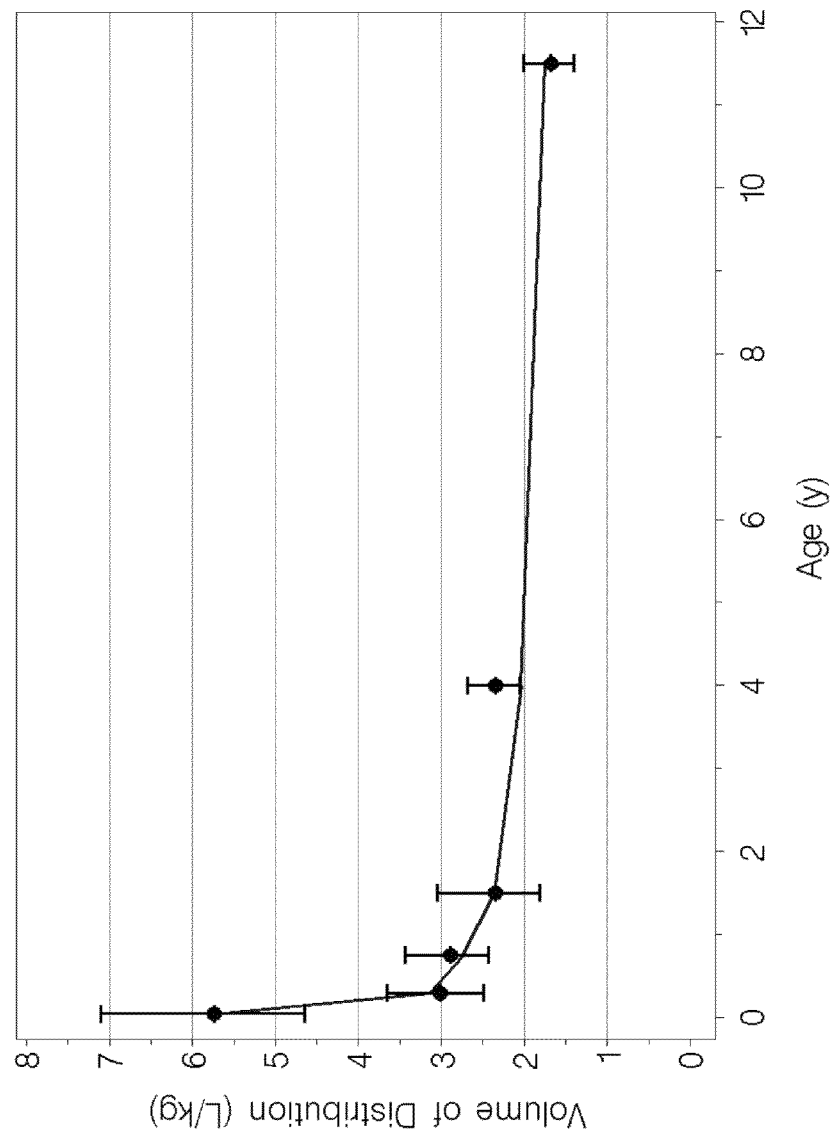

FIG. 33 depicts the geometric means and 95% confidence intervals for the Bayesian estimates of dexmedetomidine volume distribution and weight-adjusted volume of distribution in specified age groups, with the population model-based typical values of volume of distribution and weight-adjusted volume of distribution overlaid.

Figure 34A:
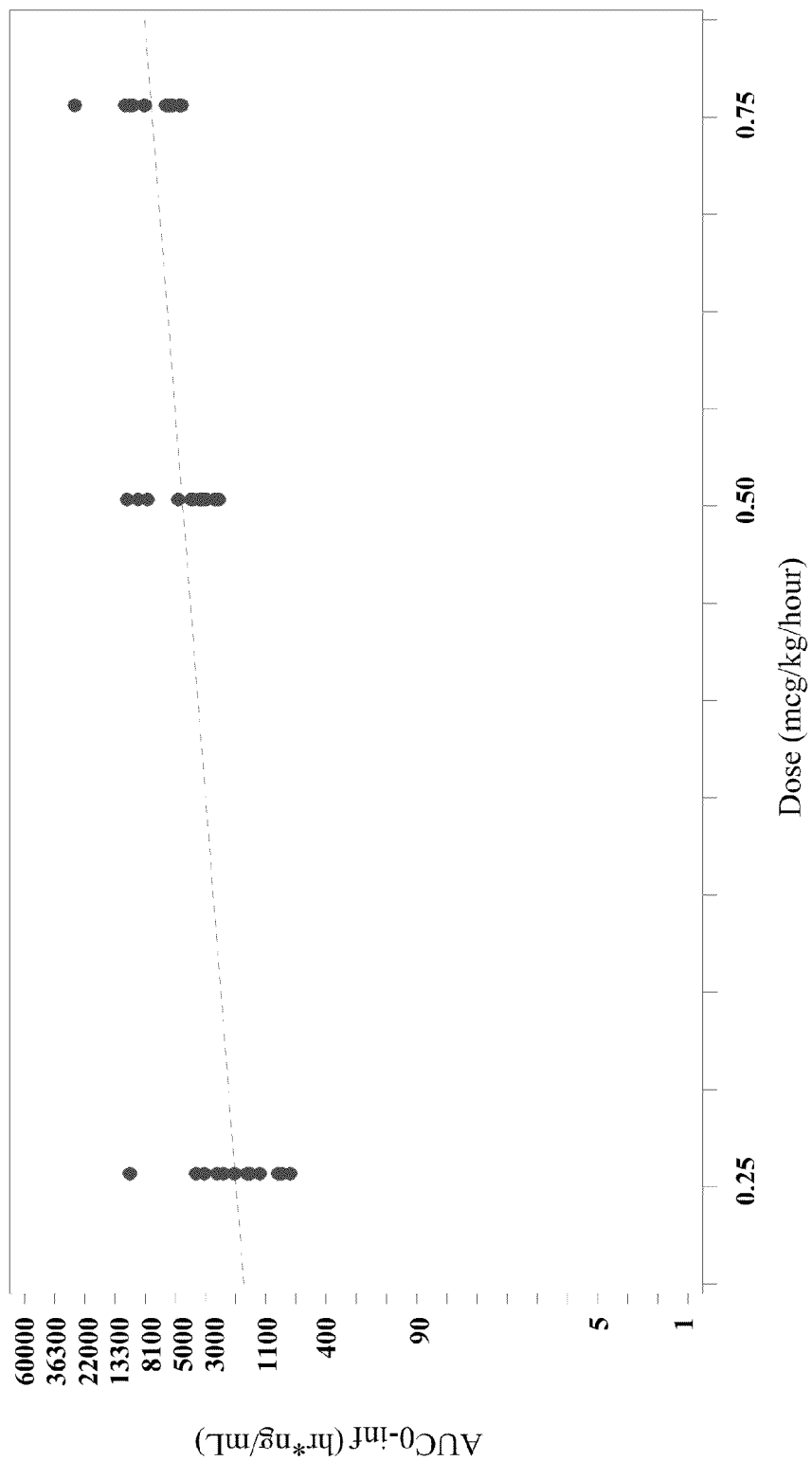
Figure 34B:
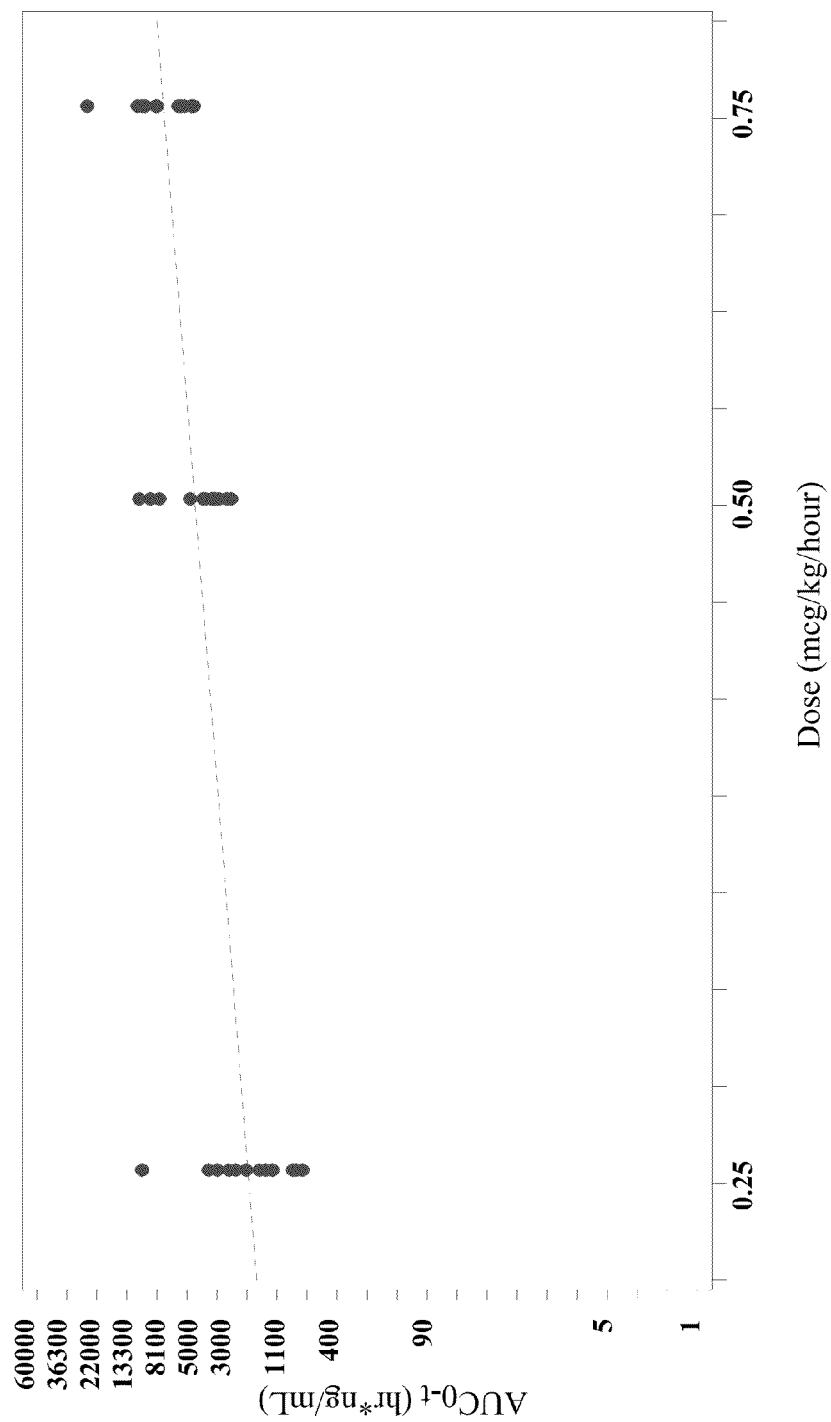
Figure 34C:
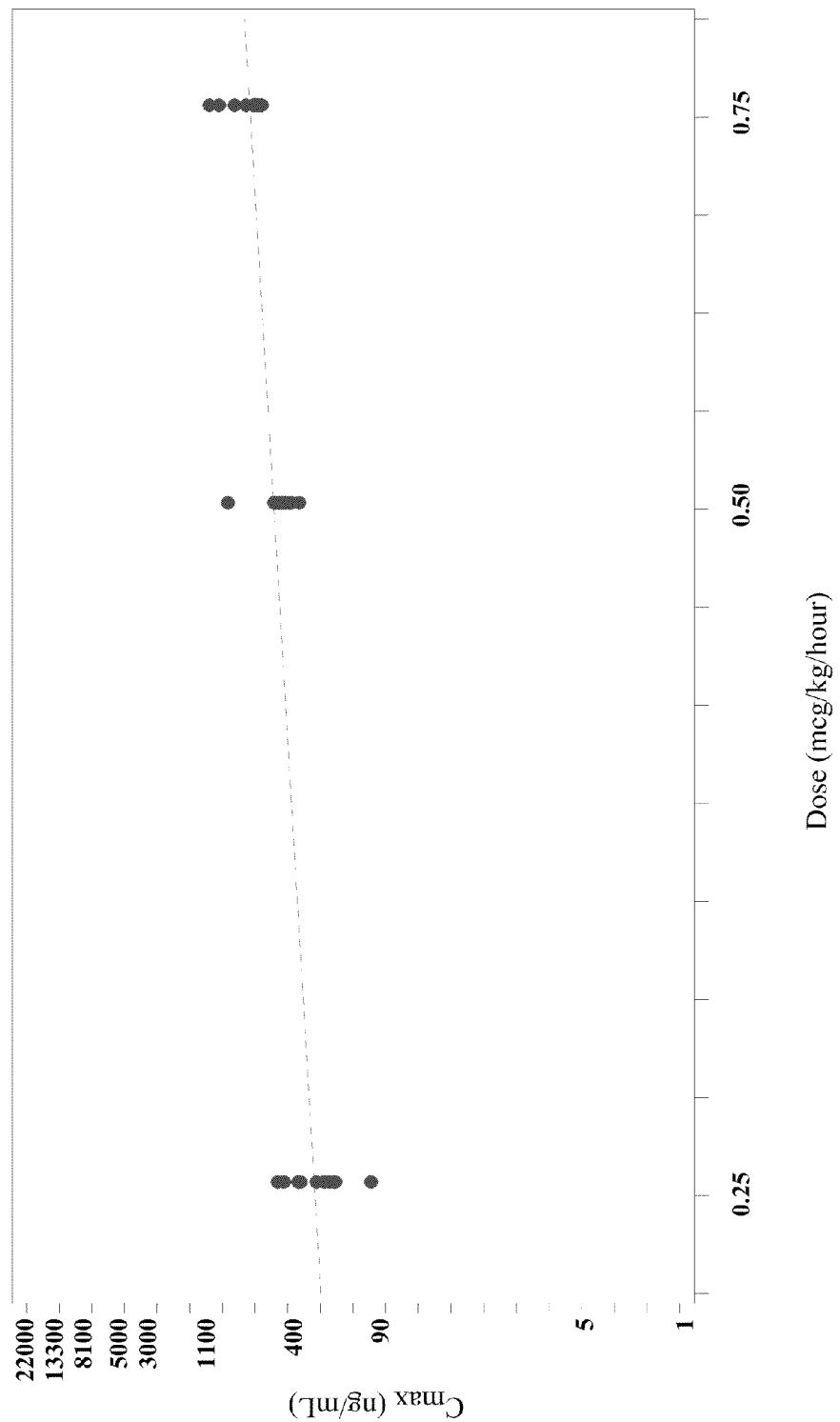

FIGS. 34A-C depict the predicted mean curve for $AUC_{0-inf}$, $AUC_{0-t}$, and $C_{max}$ generated using the power fit model.

Figure 35:
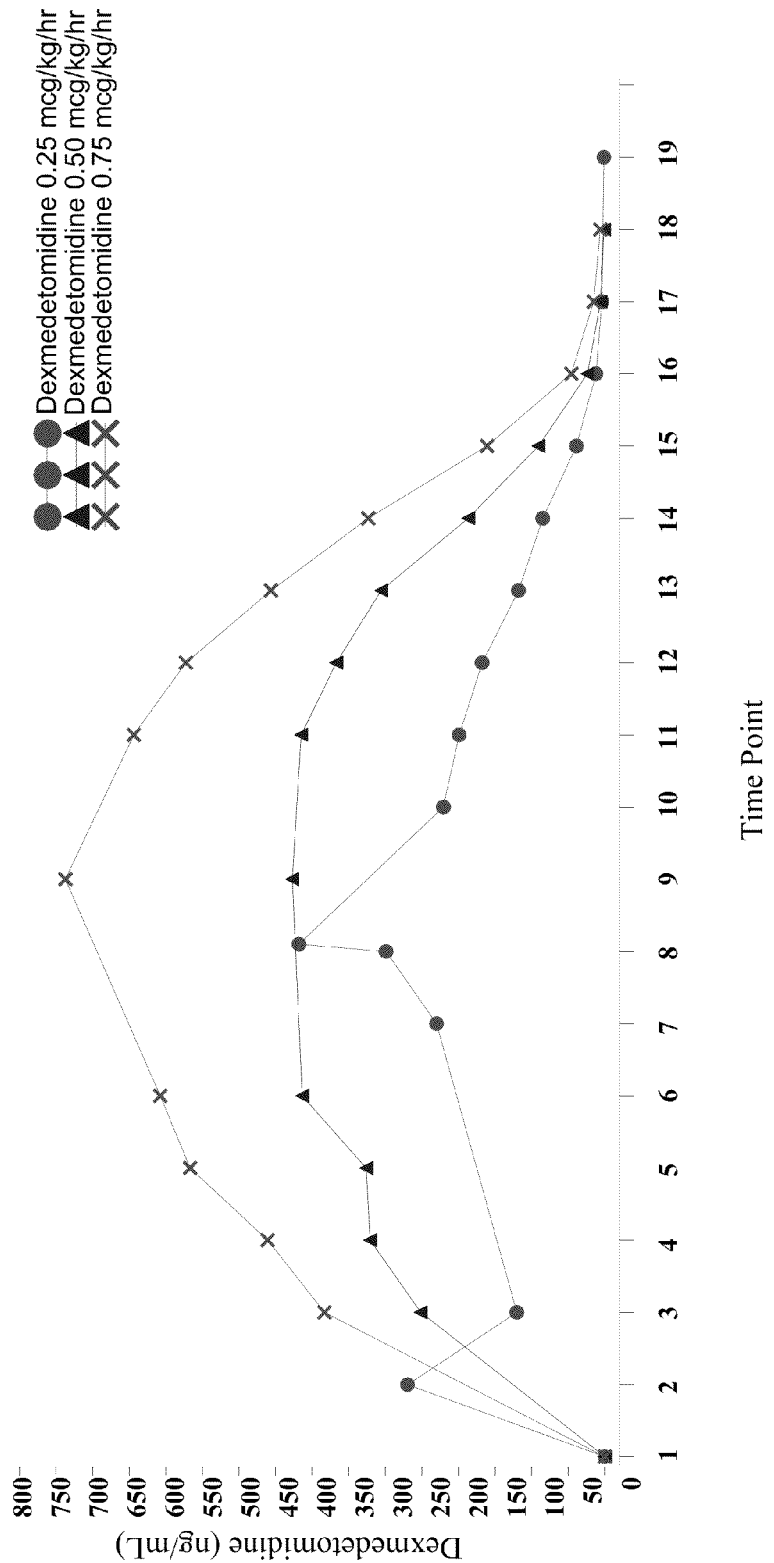

FIG. 35 depicts a linear plot illustrating the mean dexmedetomidine concentrations over time. Time Point: 1=pre-dose, 2=end of bolus, 3=30 minutes after start of infusion, 4=60 minutes after start of infusion, 5=2 hours after start of infusion, 6=4 to 6 hours after start of infusion, 7=6 hours after start of infusion, 8=12 hours after start of infusion, 8.1=23 hours after start of infusion, 9=30 to 15 minutes prior to end of infusion, 10=end of infusion, 11=15 minutes after end of infusion, 12=30 minutes after end of infusion, 13=60 minutes after end of infusion, 14=2 hours after end of infusion, 15-4 hours after end of infusion, 16=8 hours after end of infusion, 17=12 hours after end of infusion, 18=15 to 18 hours after end of infusion, 19=24 hours after end of infusion.

Figure 36A:
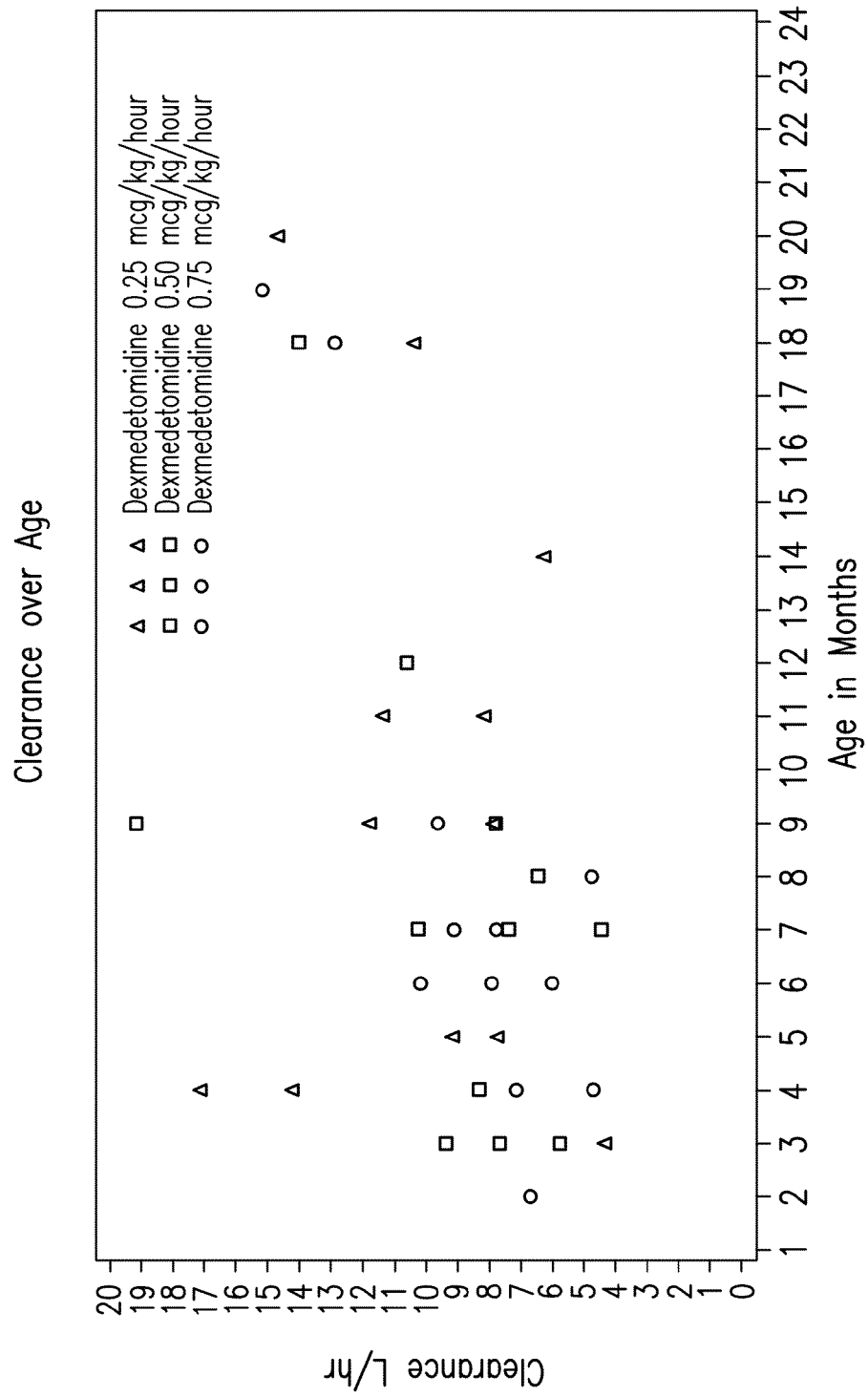
Figure 36B:
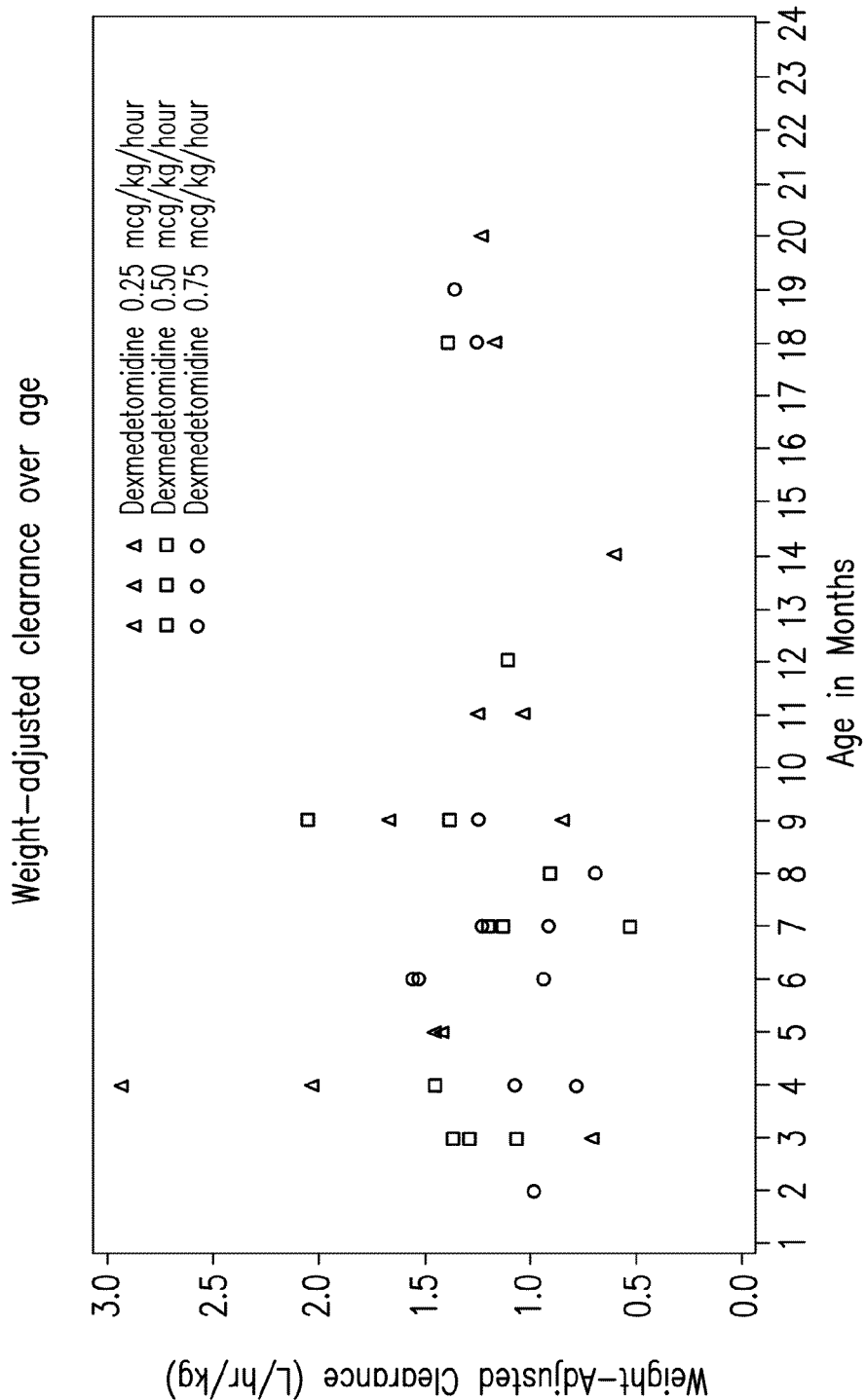

FIGS. 36A-B depict the clearance and weight-adjusted clearance over age.

6. DETAILED DESCRIPTION OF THE INVENTION

The present invention is directed to methods of sedation or analgesia in a pediatric patient in need thereof comprising administration of dexmedetomidine to the patient, wherein the dexmedetomidine is administered in an amount effective to reduce the incidence of neurological damage.

For clarity and not by way of limitation, this detailed description is divided into the following sub-portions:
  6.1 Definitions;
  6.2 Pharmaceutical formulations;
  6.3 Patient populations; and
  6.4 Methods of treatment.

6.1 Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

According to the present invention, the term "dexmedetomidine" as used herein refers to a substantially pure, optically active dextrorotary stereoisomer of medetomidine, as the free base or pharmaceutically acceptable salt. In one, non-limiting embodiment, dexmedetomidine has the formula (S)-4-[1-(2,3-dimethylphenyl)ethyl]-3H-imidazole. A pharmaceutically acceptable salt of dexmedetomidine can include inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, and salicylic acid. Preferably, the dexmedetomidine salt is dexmedetomidine HCl. In other non-limiting embodiments, dexmedetomidine comprises the structure depicted below in Formula I:

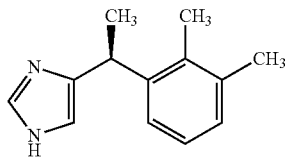

Formula I

The term "pharmaceutical composition" as used in accordance with the present invention relates to compositions that can be formulated in any conventional manner using one or more pharmaceutically acceptable carriers or excipients. A "pharmaceutically acceptable" carrier or excipient, as used herein, means approved by a regulatory agency of the Federal or a state government, or as listed in the U.S. Pharmacopoeia or other generally recognized pharmacopoeia for use in mammals, and more particularly in humans.

The term "dosage" is intended to encompass a formulation expressed in terms of μg/kg/hr, μg/kg/day, mg/kg/day, or mg/kg/hr. The dosage is the amount of an ingredient administered in accordance with a particular dosage regimen. A "dose" is an amount of an agent administered to a mammal in a unit volume or mass, e.g., an absolute unit dose expressed in mg of the agent. The dose depends on the concentration of the agent in the formulation, e.g., in moles per liter (M), mass per volume (m/v), or mass per mass (m/m). The two terms are closely related, as a particular dosage results from the regimen of administration of a dose or doses of the formulation. The particular meaning in any case will be apparent from context.

The terms "therapeutically effective dose," "effective amount," and "therapeutically effective amount" refer to the amount sufficient to produce the desired effect. In some non-limiting embodiments, a "therapeutically effective dose" means an amount sufficient to reduce by at least about 15%, preferably by at least 50%, more preferably by at least 90%, and most preferably prevent, a clinically significant deficit in the activity, function and response of the host. Alternatively, a therapeutically effective amount is sufficient to cause an improvement in a clinically significant condition in the host. These parameters will depend on the severity of the condition being treated, other actions, such as diet modification, that are implemented, the weight, age, and sex of the subject, and other criteria, which can be readily determined according to standard good medical practice by those of skill in the art. In other non-limiting embodiments a therapeutic response may be any response that a user (e.g., a clinician) will recognize as an effective response to the therapy. Thus, a therapeutic response will generally be an induction of a desired effect, such as, for example, sedation or analgesia.

The terms "intensive care unit" or "ICU" as used herein refer to any setting that provides intensive care.

The term "gestational age" as used herein is calculated as the time elapsed since the first day of the last menstrual period. If pregnancy was achieved using assisted reproductive technology, gestational age is calculated by adding two weeks to the gestational age as calculated above.

The term "pediatric patient" as used herein means a human patient that is 17 years old or younger. In certain non-limiting embodiments, the patient is 16 years old or younger, or 15 years old or younger, or 14 years old or younger, or 13 years old or younger, or 12 years old or younger, or 11 years old or younger, or 10 years old or younger, or 9 years old or younger, or 8 years old or younger, or 7 years old or younger, or 6 years old or younger, or 5 years old or younger, or 4 years old or younger, or 3 years old or younger, or 2 years old or younger, or 1 year old or younger, or 6 months old or younger, or 4 months old or younger, or 2 months old or younger, or 1 months old or younger. In particular embodiments, the pediatric patient is between about 12 to about 17 years of age. In one embodiment, the pediatric patient has an age selected from the group consisting of between about 12 to about 17 years of age and about 2 years of age or younger. In one embodiment, the pediatric patient has exited the womb just prior to administration of the dexmedetomidine.

In certain embodiments, the "pediatric patient" is a preterm neonate. As used herein, the term "preterm neonate" refers to a child that is born prior to 37 weeks from the start of the last menstrual period. If pregnancy was achieved using assisted reproductive technology, a child is a preterm neonate if the child is calculated by adding two weeks to the age as calculated above.

In certain embodiments, the pediatric patient has a gestational age of between about 20 weeks and about 44 weeks, or between about 20 weeks and about 40 weeks, or between about 20 weeks and about 38 weeks, or between about 20 weeks and about 36 weeks, or between about 20 weeks and about 34 weeks, or between about 20 weeks and about 30 weeks, or between about 20 weeks and about 28 weeks, or between about 20 weeks and about 24 weeks. In certain embodiments, the pediatric patient has a gestational age of between about 36 weeks and about 44 weeks, or between about 36 weeks and about 42 weeks, or between about 36 weeks and about 40 weeks, or between about 36 weeks and about 38 weeks.

As used herein, the term "neurological damage" refers to various types of neurocognitive, psychocognitive, and/or neuromotor or motor impairment, or combinations thereof, discussed in further detail below.

As used herein, the term "a reduction in the incidence of" refers to a reduction in the severity of, reduction in the number of, prevention of, or delay of the development of one or more incidences thereof, or a combination thereof.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

6.2 Pharmaceutical Compositions

The pharmaceutical compositions of dexmedetomidine suitable for parenteral administration can be in the form of suspensions, solutions, or emulsions, in oily or aqueous vehicles, and can contain formulatory agents such as suspending, stabilizing, solubilizing, and/or dispersing agents. The form can be sterile and can be fluid. It can be stable under the conditions of manufacture and storage and can be preserved against the contaminating action of microorganisms such as bacteria and fungi. Alternatively, the dexmedetomidine can be in sterile powder form for reconstitution with a suitable vehicle before use. The pharmaceutical compositions can be presented in unit dose form, in ampoules, or other unit-dose containers, or in multi-dose containers. Alternatively, the pharmaceutical compositions can be stored in a freeze-dried (lyophilized) condition requiring only the addition of sterile liquid carrier, for example, water for injections immediately prior to use. Extemporaneous injection solutions and suspensions can be prepared from sterile powders, granules or tablets.

In some non-limiting embodiments, the dexmedetomidine composition is formulated as a liquid. In certain non-limiting embodiments, the dexmedetomidine liquid composition comprises dexmedetomidine, or a pharmaceutically acceptable salt thereof, at a concentration of between about 0.005 µg/mL and about 100 µg/mL, or between about 0.005 µg/mL and about 50 µg/mL, or between about 0.005 µg/mL and about 25 µg/mL, or between about 0.005 µg/mL and about 15 µg/mL, or between about 0.005 µg/mL and about 10 µg/mL, or between about 0.005 µg/mL and about 7 µg/mL, or between about 0.005 µg/mL and about 5 µg/mL, or between about 0.005 µg/mL and about 4 µg/mL, or between about 0.005 µg/mL and about 3 µg/mL, or between about 0.005 µg/mL and about 2 µg/mL, or between about 0.005 µg/mL and about 1 µg/mL, or between about 0.005 µg/mL and about 0.5 µg/mL, or between about 0.005 µg/mL and about 0.05 µg/mL.

In certain non-limiting embodiments, the dexmedetomidine liquid composition comprises dexmedetomidine, or a pharmaceutically acceptable salt thereof, at a concentration of about 0.5 µg/mL, or about 1.0 µg/mL, or about 2.0 µg/mL, or about 4.0 µg/mL.

In one embodiment, the dexmedetomidine composition is a premixed formulation that does not require reconstitution or dilution prior to administration to a patient, as disclosed in U.S. application Ser. No. 13/343,672, filed on Jan. 4, 2012, titled "Dexmedetomidine Premix Formulation," is hereby incorporated by reference in its entirety.

Excipients that are suitable for the dexmedetomidine composition include preservatives, suspending agents, stabilizers, dyes, buffers, antibacterial agents, antifungal agents, and isotonic agents, for example, sugars or sodium chloride. As used herein, the term "stabilizer" refers to a compound optionally used in the pharmaceutical compositions of the present invention in order to avoid the need for sulphite salts and increase storage life. Non-limiting examples of stabilizers include antioxidants.

The pharmaceutical composition can comprise one or more pharmaceutically acceptable carriers. The carrier can be a solvent or dispersion medium. Non-limiting examples of pharmaceutically acceptable carriers include water, saline, ethanol, polyol (e.g., glycerol, propylene glycol and liquid polyethylene glycol), oils, and suitable mixtures thereof.

The parenteral formulation can be sterilized. Non-limiting examples of sterilization techniques include filtration through a bacterial-retaining filter, terminal sterilization, incorporation of sterilizing agents, irradiation, heating, vacuum drying, and freeze drying.

6.3 Patient Populations

The presently disclosed subject matter comprises administering dexmedetomidine to a pediatric patient. In certain embodiments, the pediatric patient is intubated. The pediatric patient can be intubated prior to, during, or after administration of the dexmedetomidine. The pediatric patient can be intubated by the nasotracheal, endotracheal, direct oral laryngoscopy or by fibreoptic routes, or via tracheotomy.

In particular embodiments, the patient is critically ill. In one embodiment, the pediatric patient suffers from one or more medical conditions. In certain embodiments, the medical condition is a lung disorder, brain disorder, heart disorder, liver disorder, kidney disorder, eye or ear disorder, gastrointestinal disorder, or skin disorder. Non-limiting examples of lung disorders include respiratory distress syndrome, pneumonia, bronchopulmonary dysplasia, apnea of prematurity, and pneumothorax. Non-limiting examples of brain disorders include intraventricular hemorrhage and cerebral palsy. Non-limiting examples of liver disorders include jaundice. Non-limiting examples of heart disorders include cardiac ischemia and patent ductus arteriosus. Non-limiting examples of eye disorders include retinopathy of prematurity, myopia, and strabismus. Non-limiting examples of other medical conditions includes heroin withdrawal, cocaine withdrawal, alcohol fetal syndrome, HIV-positive status, and Tay Sachs disease.

In one embodiment, the patient has undergone surgery. The patient may undergo surgery prior to, during, and/or after administration of the dexmedetomidine. In certain embodiments, the dexmedetomidine is administered prior to surgery. In one embodiment, the dexmedetomidine is administered prior to surgery for the purpose of reducing an incidence of neurological damage. In some embodiments, the dexmedetomidine is administered prior to and during surgery. In particular embodiments, the dexmedetomidine is administered prior to and after surgery. In certain embodiments, the dexmedetomidine is administered during and after surgery. In particular embodiments, the dexmedetomidine is administered prior to, during, and after surgery.

Surgery refers to any manual or operative methods or manipulations for the treatment or prevention of disease, injury or deformity. Surgery can be performed by a doctor, surgeon or dentist, generally in a hospital or other health care facility. Pediatric patients undergoing surgery can be hospitalized or ambulatory, e.g., out-patient surgery. The surgery can be conservative (e.g. surgery to preserve or remove with minimal risk, diseased or injured organs, tissues, or extremities) or radical (e.g. surgery designed to extirpate all areas of locally extensive disease and adjacent zones of lymphatic drainage).

Non-limiting examples of surgery include surgeries performed on the cardiovascular system, including the heart and blood vessels; surgeries performed on the musculoskeletal system, including the bones and muscles; surgeries performed on the respiratory system, including the trachea and the lungs; surgeries performed on the integumentary system, including the skin and nails; surgeries performed on the mediastinum and diaphragm; surgeries performed on the digestive system, including the esophagus, stomach, gall bladder and intestines; surgeries performed on the urinary system, including the kidneys and bladder; surgeries performed on the male genital system; surgeries performed on the female genital system; surgeries performed on the endocrine system, including the pituitary gland, the adrenal glands, and the endocrine thyroid gland; surgeries performed on the nervous system, including the brain, spinal cord and peripheral nerves; surgeries performed on the eye and ocular adnexa; and surgeries performed on the auditory system.

Non-limiting examples of surgeries performed on the cardiovascular system include the repair of congenital heart defects after birth and heart transplant surgery. Non-limiting examples of surgeries performed on the musculoskeletal system include fracture repair, scoliosis surgery and tendon lengthening. Non-limiting examples of surgeries performed on the respiratory system include lung transplants, thoracotomy and pneumothorax surgery. Non-limiting examples of surgeries performed on the integumentary system include burn treatment and skin grafting. Non-limiting examples of surgeries performed on the mediastinum and diaphragm include treatment of congenital diaphragmatic hernia and removal of mediastinal cysts and tumors. Non-limiting examples of surgeries performed on the digestive system include intestinal resection and treatment of pyloric stenosis. Non-limiting examples of surgeries performed on the urinary system may include kidney transplants, and treatment of bladder divurticula. Non-limiting examples of surgeries performed on the male genital system may include treatment of undescended testes. Non-limiting examples of surgeries performed on the female genital system may include ovarian cystectomy. Non-limiting examples of surgeries performed on the endocrine system may include treatment of hyperparathyroidism. Non-limiting examples of surgeries performed on the nervous system may include laminectomy and corpus callosotomy. Non-limiting examples of surgeries performed on the eye may include strabismus surgery. Non-limiting examples of surgeries performed on the auditory system include cochlear implantation. Additional non-limiting examples of surgery include tonsillectomy, cleft lip and palate repair, treatment of lymphangioma, tracheoesophageal fistula repair, neuroblastoma surgery, and treatment of esophageal atresia. In one embodiment, the patient has undergone cardiopulmonary bypass.

6.4 Methods of Treatment

As noted above, the methods of treatment of the invention are directed to methods of sedation or analgesia in a pediatric patient comprising administration of dexmedetomidine to the patient, wherein the dexmedetomidine is administered in an amount effective to reduce incidence of neurological damage.

The dexmedetomidine for use in the invention can be administered via any suitable route, including parenteral, intravenous, and oral routes. Non-limiting examples of parenteral routes of administration include intravenous, intramuscular, subcutaneous, intraperitoneal or intrathecal. Parenteral administration may be by periodic injections of a bolus of the preparation, or may be administered by intravenous or intraperitoneal administration from a reservoir which is external (e.g., an intravenous bag) or internal (e.g., a bioerodable implant, a bioartificial organ). See, e.g., U.S. Pat. Nos. 4,407,957 and 5,798,113, each incorporated herein by reference in their entireties. Intrapulmonary delivery methods and apparatus are described, for example, in U.S. Pat. Nos. 5,654,007, 5,780,014, and 5,814,607, each incorporated herein by reference in their entireties. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, and transdermal patch. Needleless injector devices are described in U.S. Pat. Nos. 5,879,327; 5,520,639; 5,846,233 and 5,704,911, the specifications of which are herein incorporated herein by reference in their entireties.

In yet another non-limiting embodiment, the therapeutic compound can be delivered in a controlled or sustained release system. For example, a compound or composition may be administered using intravenous infusion, continuous infusion, an implantable osmotic pump, or other modes of administration. In one embodiment, a pump may be used (see Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Langer and Wise eds., 1974, Medical Applications of Controlled Release, CRC Press: Boca Raton, Fla.; Smolen and Ball eds., 1984, Controlled Drug Bioavailability, Drug Product Design and Performance, Wiley, N.Y.; Ranger and Peppas, 1983, J. Macromol. Sci. Rev. Macromol. Chem., 23:61; Levy et al., 1985, Science 228:190; During et al., 1989, Ann. Neurol., 25:351; Howard et al., 9189, J. Neurosurg. 71:105). In yet another embodiment, a controlled release system can be placed in proximity of the therapeutic target, i.e., the brain, thus requiring only a fraction of the systemic dose (see, e.g., Goodson, 1984, in Medical Applications of Controlled Release, Vol. 2, pp. 115-138).

In certain embodiments, the dexmedetomidine is administered as a continuous intravenous dose to a pediatric patient at a concentration of between about 0.005 µg/kg/hr and about 50 µg/kg/hr, or between about 0.005 µg/kg/hr and about 25 µg/kg/hr, or between about 0.005 µg/kg/hr and about 15 µg/kg/hr, or between about 0.005 µg/kg/hr and about 5 µg/kg/hr, or between about 0.005 µg/kg/hr and about 2 µg/kg/hr, or between about 0.005 µg/kg/hr and about 1.5 µg/kg/hr, or between about 0.005 µg/kg/hr and about 1 µg/kg/hr, or between about 0.005 µg/kg/hr and about 0.5 µg/kg/hr, or between about 0.005 µg/kg/hr and about 0.25 µg/kg/hr. In preferred non-limiting embodiments, the concentration is between about 0.025 µg/kg/hr and about 2.0 µg/kg/hr. In particular embodiments, the dexmedetomidine is administered as a continuous intravenous dose to a pediatric patient at a concentration of between about 0.005 µg/kg/hr and about 50 µg/kg/hr, or between about 0.025 µg/kg/hr and about 50 µg/kg/hr, or between about 0.05 µg/kg/hr and about 50 µg/kg/hr, or between about 0.01 µg/kg/hr and about 50 µg/kg/hr, or between about 0.2 µg/kg/hr and about 50 µg/kg/hr, or between about 0.25 µg/kg/hr and about 50 µg/kg/hr, or between about 0.5 µg/kg/hr and about 50 µg/kg/hr, or between about 0.7 µg/kg/hr and about 50 µg/kg/hr, or between about 1.0 µg/kg/hr and about 50 µg/kg/hr, or between about 1.5 µg/kg/hr and about 50 µg/kg/hr, or between about 2.0 µg/kg/hr and about 50 µg/kg/hr, or between about 5.0 µg/kg/hr and about 50 µg/kg/hr, or between about 10 µg/kg/hr and about 50 µg/kg/hr, or between about 20 µg/kg/hr and about 50 µg/kg/hr.

In particular embodiments, the dexmedetomidine is administered as a continuous intravenous dose to a pediatric patient at a concentration of about 0.01 µg/kg/hr, or about 0.025 µg/kg/hr, or about 0.05 µg/kg/hr, or about 0.1 µg/kg/hr, or about 0.2 µg/kg/hr, or about 0.25 µg/kg/hr, or about 0.3 µg/kg/hr, or about 0.4 µg/kg/hr, or about 0.5 µg/kg/hr, or about 0.6 µg/kg/hr, or about 0.7 µg/kg/hr, or about 0.75 µg/kg/hr, or about 0.8 µg/kg/hr, or about 0.9 µg/kg/hr, or about 1.0 µg/kg/hr, or about 1.1 µg/kg/hr, or about 1.2 µg/kg/hr, or about 1.3 µg/kg/hr, or about 1.4 µg/kg/hr, or about 1.5 µg/kg/hr, or about 1.6 µg/kg/hr, or about 1.7 µg/kg/hr, or about 1.8 µg/kg/hr, or about 1.9 µg/kg/hr, or about 2.0 µg/kg/hr, or about 2.1 µg/kg/hr, or about 2.2 µg/kg/hr, or about 2.3 µg/kg/hr, or about 2.4 µg/kg/hr, or about 2.5 µg/kg/hr. In certain embodiments, the dexmedetomidine is administered as a continuous intravenous dose at a concentration of about 3.0 µg/kg/hr, or about 3.5 µg/kg/hr, or about 4.0 µg/kg/hr, or about 4.5 µg/kg/hr, or about 4.0 µg/kg/hr, or about 4.5 µg/kg/hr, or about 5.0 µg/kg/hr, or about 5.5 µg/kg/hr, about 6.0 µg/kg/hr, or about 6.5 µg/kg/hr, or about 7.0 µg/kg/hr, or about 7.5 µg/kg/hr, about 8.0 µg/kg/hr, or about 8.5 µg/kg/hr, or about 9.0 µg/kg/hr, or about 9.5 µg/kg/hr, or about 10 µg/kg/hr, or about 11 µg/kg/hr, or about 12 µg/kg/hr, or about 13 µg/kg/hr, or about 14 µg/kg/hr, or about 15 µg/kg/hr, or about 16 µg/kg/hr, or about 17 µg/kg/hr, or about 18 µg/kg/hr, or about 19 µg/kg/hr, or about 20 µg/kg/hr, or about 21 µg/kg/hr, or about 22 µg/kg/hr, or about 23 µg/kg/hr, or about 24 µg/kg/hr, or about 25 µg/kg/hr, or about 27.5 µg/kg/hr, or about 30 µg/kg/hr, or about 32.5 µg/kg/hr, or about 35 µg/kg/hr, or about 40 µg/kg/hr, or about 45 µg/kg/hr, or about 50 µg/kg/hr.

In particular embodiments, the dexmedetomidine is administered as a continuous intravenous dose for a period of time of between about 1 and about 10 minutes, or between about 1 and about 20 minutes, or between about 1 and about 30 minutes, or between about 1 and about 2 hours, or between about 1 and about 3 hours, or between about 1 and about 4 hours, or between about 1 and about 5 hours, or between about 1 and about 6 hours, or between about 1 and about 7 hours, or between about 1 and about 8 hours, or between about 1 and about 9 hours, or between about 1 and about 10 hours, or between about 1 and about 11 hours, or between about 1 and about 12 hours, or between about 1 and about 13 hours, or between about 1 and about 14 hours, or between about 1 and about 15 hours, or between about 1 and about 16 hours, or between about 1 and about 17 hours, or between about 1 and about 18 hours, or between about 1 and about 19 hours, or between about 1 and about 20 hours, or between about 1 and about 21 hours, or between about 1 and about 22 hours, or between about 1 and about 23 hours, or between about 1 and about 24 hours. In preferred non-limiting embodiments, the dexmedetomidine is administered as a continuous dose for a period of time of between about 6 and about 24 hours. In certain embodiments, the dexmedetomidine is administered as a continuous dose for a period of time of about 6 hours, or about 7 hours, or about 8 hours, or about 9 hours, or about 10 hours, or about 11 hours, or about 12 hours, or about 13 hours, or about 14 hours, or about 15 hours, or about 16 hours, or about 17 hours, or about 18 hours, or about 19 hours, or about 20 hours, or about 21 hours, or about 22 hours, or about 23 hours, or about 24 hours.

In certain non-limiting embodiments, the administration of dexmedetomidine comprises a first loading dose administered prior to a second maintenance dose. When administered as a loading dose followed by a maintenance dose, the loading dose can be a dose of between about 0 µg/kg and about 5 µg/kg, or between about 0.005 µg/kg and about 4.5 µg/kg, or between about 0.005 µg/kg and about 3 µg/kg, or between about 0.005 µs/kg and about 2.5 µg/kg, or between about 0.005 µg/kg and about 2 µg/kg, or between about 0.005 µg/kg and about 1.5 µg/kg, or between about 0.005 µg/kg and about 1 µg/kg, or between about 0.005 µs/kg and about 0.5 µg/kg, or between about 0.005 µg/kg and about 0.25 µg/kg, or between about 0 µg/kg and about 0.4 µg/kg. In preferred non-limiting embodiments, the loading dose is between about 0 µg/kg and about 1.0 µg/kg. In particular embodiments, the loading dose is about 0.01 µg/kg, or about 0.025 µg/kg, or about 0.05 µg/kg, or about 0.1 µg/kg, or about 0.2 µg/kg, or about 0.25 µg/kg, or about 0.3 µg/kg, or about 0.35 µg/kg, or about 0.4 µg/kg, or about 0.5 µg/kg, or about 0.6 µg/kg, or about 0.7 µg/kg, or about 0.8 µg/kg, or about 0.9 µg/kg, or about 1.0 µg/kg, or about 1.1 µg/kg, or about 1.2 µg/kg, or about 1.3 µg/kg, or about 1.4 µg/kg, or about 1.5 µs/kg, or about 1.6 µg/kg, or about 1.7 µg/kg, or about 1.8 µg/kg, or about 1.9 µg/kg, or about 2.0 µg/kg, or about 2.1 µg/kg, or about 2.2 µg/kg, or about 2.3 µg/kg, or about 2.4 µg/kg, or about 2.5 µg/kg.

In certain embodiments, the loading dose is about 3.0 µg/kg, or about 3.5 µg/kg, or about 4.0 µg/kg, or about 4.5 µg/kg, or about 4.0 µg/kg, or about 4.5 µg/kg, or about 5.0 µg/kg, or about 5.5 µg/kg, about 6.0 µg/kg, or about 6.5 µg/kg, or about 7.0 µg/kg, or about 7.5 µg/kg, about 8.0 µg/kg, or about 8.5 µg/kg, or about 9.0 µg/kg, or about 9.5 µg/kg, or about 10 µg/kg, or about 11 kg/kg, or about 12 µg/kg, or about 13 µg/kg, or about 14 µg/kg, or about 15 µg/kg, or about 16 µg/kg, or about 17 µg/kg, or about 18 µg/kg, or about 19 µg/kg, or about 20 µg/kg, or about 21 µg/kg, or about 22 µg/kg, or about 23 µg/kg, or about 24 µg/kg, or about 25 µg/kg, or about 27.5 µg/kg, or about 30 µg/kg, or about 32.5 µg/kg, or about 35 µg/kg, or about 40 µg/kg, or about 45 µs/kg, or about 50 µg/kg.

In certain embodiments, the loading dose is below about 0.5 µg/kg, or below about 0.45 µg/kg, or below about 0.4 µg/kg, or below about 0.35 µg/kg, or below about 0.3 µg/kg, or below about 0.25 µg/kg, or below about 0.2 µg/kg, or below about 0.15 µg/kg, or below about 0.1 µg/kg, or below about 0.05 µg/kg, or below about 0.01 µg/kg. In particular embodiments, no loading dose is administered.

The loading dose can be administered for a period of time of between about 1 and about 5 minutes, or between about 1 and about 10 minutes, or between about 1 and about 15 minutes, or between about 1 and about 20 minutes, or between about 1 and about 25 minutes, or between about 1 and about 30 minutes, or between about 1 and about 45 minutes, or between about 1 and about 60 minutes. Following the loading dose, the maintenance dose can be administered for a period of time as described above for a single continuous dose. In preferred non-limiting embodiments, the loading dose is administered for a period of time of about 10 to about 20 minutes. In particular embodiments, the loading dose is administered for a period of time of about 5 minutes, or about 7.5 minutes, or about 10 minutes, or about 12.5 minutes, or about 15 minutes, or about 20 minutes, or about 25 minutes, or about 30 minutes, or about 35 minutes, or about 40 minutes, about 45 minutes, or about 50 minutes, or about 55 minutes, or about 60 minutes.

In certain non-limiting embodiments, the dexmedetomidine, when administered as a single continuous, loading or maintenance dose, is administered for a period of time of about 1 hour to about 7 days, or about 1 hour to about 4 days, or about 1 hour to about 48 hours, or about 1 hour to about 36 hours, or about 1 hour to about 24 hours, or about 1 hour to about 12 hours. In particular non-limiting embodiments, the dexmedetomidine is administered as a continuous infusion for less than about 72 hours, or less than about 48 hours, or less than about 36 hours, or less than about 24 hours, or less than about 18 hours, or less than about 12 hours, or less than about 6 hours, or less than about 3 hours, or less than about 1 hour, or less than about 30 minutes.

In certain embodiments, the method reduces the amount of rescue medication required. In one embodiment, the rescue medication is a non-dexmedetomidine sedative. In particular embodiments, the presently disclosed method reduces the amount of sedative rescue medication required by between about 5% and about 100%, or between about 5% and about 75%, or between about 5% and about 50%, or between about 5% and about 25%, or between about 5% and about 15%.

In particular embodiments, the sedative rescue medication is a benzodiazepine. Non-limiting examples of benzodiazepines include clonazepam, diazepam, estazolam, flunitrazepam, lorazepam, midazolam, nitrazepam, oxazepam, triazolam, temazepam, chlordiazepoxide, and alprazolam. In particular embodiments, the sedative is a barbiturate. Non-limiting examples of barbiturates include amobarbital, pentobarbital, secobarbital, and phenobarbital. Other examples of sedatives include chloral hydrate, eszopiclone, zaleplon, zolpidem, and zopiclone.

In certain embodiments, the rescue medication is an analgesic. In certain embodiments, the method reduces the amount of analgesic rescue medication required. In particular embodiments, the presently disclosed method reduces the amount of analgesic rescue medication required by between about 5% and about 100%, or between about 5% and about 75%, or between about 5% and about 50%, or between about 5% and about 25%, or between about 5% and about 15%.

In one embodiment, the analgesic is an opioid. Non-limiting examples of opioids include codeine, oxycodone, hydrocodone, fentanyl, morphine, buprenorphine, hydromorphone, methadone, tramadol, meperidine, oxymorphone, and pentazocine. In certain embodiments, the analgesic is an N-methyl-D-aspartate antagonist (NDMA). Non-limiting examples of NDMAs include ketamine, nitrous oxide, and xenon. Other examples of analgesics include clonidine, desflurane, isoflurane, and sevoflurane. The rescue medication may be administered via perioral, parenteral, transnasal (for example, a powder), rectal (for example, as a suppository), or topical administration.

In one embodiment, the presently disclosed method reduces incidence of neurological damage. In particular embodiments, the presently disclosed method reduces the incidence of neurological damage in one or more regions of the brain. Non-limiting examples of brain regions in which the incidence of neurological damage is reduced include cerebral cortex, basal ganglia, olfactory bulb, hypothalamus, thalamus, epithalamus, midbrain, pans, cerebellum, and medulla.

Non-limiting causes of neurological damage include, but are not limited to, the administration of a sedative or analgesic agent, seizure, asphyxia, epilepsy, concussion, cerebral hemorrhage, cord shock, drowning, tumor, immunotherapy, chemotherapy, iatrogenic free-radical toxicity, injury, ataxias, surgery, cardiopulmonary bypass, cerebral palsy, cerebral ischemia, cerebral anoxia injury, autoimmune neurodegeneration, myocardial ischemia, myocardial infarct, stroke, atherosclerosis, acute respiratory failure, coronary artery bypass graft, ulcerative colitis, traumatic brain injury, spinal cord injury, spinal muscular atrophy, vertebral disease, decompression sickness, fetal alcohol syndrome, hepatitis-B, hepatitis-C, hepatitis-G, yellow fever, dengue fever, encephalitis, liver disease, primary cirrhosis, renal disease, pancreatitis, polycystic kidney disease, H. pylori-associated gastric and duodenal ulcer disease, HIV infection, toxoplasmosis, rubella, cytomegalovirus, tuberculosis, meningitis, juvenile diabetes, lichenplanus, uveitis, Behcet's disease, pure red cell aplasia, aplastic anemia, amyotrophic lateral sclerosis, multiple sclerosis, nephrotic syndrome, and combinations thereof.

In particular non-limiting embodiments, the resulting neurological damage includes various types of neurocognitive, psychocognitive, and/or neuromotor or motor impairment, or combinations thereof. Such impairments can be delayed functions or abilities, disrupted functions or abilities, loss of function or ability, inability for develop or learn new abilities, and the like. Non-limiting examples of neurocognitive and/or psychocognitive impairments include learning, memory, executive function, and visuospatial ability impairment. Non-limiting examples of neuromotor impairments include strength, balance, mobility impairment, and combinations thereof. In other non-limiting embodiments, the neurological damage includes developmental delay, cerebral palsy, mental retardation, visual impairment, hearing impairment, autism, paralysis, hemiplegia, a strain condition, a stress condition, a nervous dysfunction such as convulsions, seizure, muscle stiffness, nervous strain and anxiety, and combinations thereof. (See, e.g., Hintz et al. Pediatrics. 2005 June; 115(6): 1645-51.).

The neurological damage impairments may be assessed by well-established criteria including but not limited to an IQ test (See, e.g., (Wechsler, J. Wechsler Preschool and Primary Scale of Intelligence. San Antonio: The Psychological Corp., 1989), the short-story module of the Randt Memory Test (See Randt C, Brown E. Administration manual: Randt Memory Test. New York: Life Sciences, 1983), the Digit Span subtest and Digit Symbol subtest of the Wechsler Adult Intelligence Scale-Revised (See Wechsler D. The Wechsler Adult Intelligence Scale-Revised (WAIS-R). San Antonio, Tex.: Psychological Corporation, 1981.), the Benton Revised Visual Retention Test (See Benton A L, Hansher K. Multilingual aphasia examination. Iowa City University of Iowa Press, 1978), and the Trail Making Test (Part B) (See Reitan R M. Validity of the Trail Making Test as an indicator of organic brain damage. Percept Mot Skills 1958; 8:271-6). Other non-limiting examples of well-established criteria for determining neurological damage include the Bayley Scales of Infant Development (BSID-II) Mental Development Index assessment, the BSID-II Psychomotor Development Index assessment, the Denver Developmental Screening Test, magnetic resonance imaging, vision tests, and hearing tests. Other tests can include standardized interaction and/or observation, such as standardized assessments of socialization, hand-eye coordination, motor control, ability to understand and use sounds and words, and ability to recognize sounds and words.

Non-limiting examples of a reduction in the incidence of neurological damage include a reduction in the severity of, reduction in the number of, prevention of, or delay of the development of one or more incidences of neurological damage, or a combination thereof. In one non-limiting embodiment, a reduction in the incidence of neurological damage includes a better score or assessment as measured by one of the tests or assessments listed above than if an effective amount of dexmedetomidine had not been administered to the pediatric patient.

In particular embodiments, the neurological damage is cellular degeneration or neuronal apoptosis. As used herein, the term "cellular degeneration" refers to cell death as a result of a stimulus, trauma, a pharmaceutical composition, or a pathologic process. As used herein, the term "neuroapoptosis" or "neuronal apoptosis" refers to neuronal cell death associated with programmed cell death. In particular embodiments, the methods reduce the incidence of neuroapoptosis.

Non-limiting examples of cells which can be protected by the presently disclosed methods include neurons and glial cells. Non-limiting examples of neurons which can be protected by the presently disclosed methods include Renshaw cells, Purkinje cells, hippocampal basket cells, cerebellum basket cells, cortex basket cells, cortex interneurons, cerebellum interneurons, pyramidal cells, granule cells, anterior horn cells, and motor neurons. Non-limiting examples of glial cells which can be protected by the presently disclosed methods include neurolemmocytes, satellite cells, microglia, oligodendroglia, and astroglia.

In certain embodiments, the neurological damage includes cell shrinkage, chromatin-clumping with margination, formation of membrane-enclosed apoptotic bodies, and Ash neuronal necrosis.

In one embodiment, the administration of dexmedetomidine reduces the incidence of neurological damage in a cortex lamina layer. In certain embodiments, the reduction occurs in one or more of the cortex lamina layers I-IV. In one embodiment, the reduction in neurological damage occurs in a cortex lamina layer I. In particular embodiments, the reduction in neurological damage occurs in cortex lamina layer II. In certain embodiments, the reduction occurs in both cortex lamina layer I and II.

7. EXAMPLES

The following examples are merely illustrative of the presently disclosed subject matter and they should not be considered as limiting the scope of the invention in any way.

Example 1

Dexmedetomidine Study in Neonates

Initial 30 Patient Study

A 30-subject, open-label, multicenter, safety, efficacy and pharmacokinetic study of dexmedetomidine was conducted on neonates aged≥28 weeks to ≤44 weeks gestational age who required sedation in an intensive care setting for a minimum of 6 hours. The present study investigated the efficacy, pharmacokinetics, and safety of dexmedetomidine safety at three different dose levels in neonates, ages≥28 weeks to ≤44 weeks gestational age, administered as a loading dose followed by continuous infusion for a minimum of 6 hours and up to 24 hours in the neonatal intensive care unit (NICU), cardiac intensive care unit (CICU), or PICU. Gestation age (in weeks) was calculated as the time elapsed between the first day of the last menstrual period and the day of enrollment. If pregnancy was achieved using assisted reproductive technology, gestational age was calculated by adding two weeks to the gestational age as calculated above.

The patients selected for the study were initially intubated and mechanically ventilated preterm neonates≥28 weeks to <36 weeks gestational age and term neonates born at ≥36 weeks to ≤44 weeks gestational age. The former were assigned to Group I and the latter were assigned to Group II. The subjects weighed over 1,000 g at the time of enrollment.

The cardiovascular system in newborns has characteristics that could negatively impact the use of dexmedetomidine in this population. Unlike older infants, children, and adults, the newborn myocardium is not able to increase contractility to increase cardiac output in response to metabolic demands. Instead, neonates are highly dependent on their FIR to increase cardiac output. As a result, bradycardia, a known effect of dexmedetomidine, could decrease cardiac output in neonates. For this reason, the doses selected for study in this population were intentionally lower than those typically used for sedation of older pediatric patients. The lower doses were expected to mitigate an adverse effect of bradycardia, while the immaturity of the blood brain barrier in this population could facilitate the sedating properties of dexmedetomidine because of its high lipid solubility and potentially higher cerebrospinal fluid concentrations; therefore, the lowest dose, 0.05 μg/kg loading dose over 10 or 20 minutes followed by 0.05 μg/kg hr maintenance dose, was expected to effect some sedation in mechanically ventilated subjects in this age group. The highest dose, 0.2 μg/kg loading dose followed by 0.2 μg/kg/hr, was not expected to cause bradycardia.

Each subject received a loading dose of dexmedetomidine over 10 or 20 minutes followed by the appropriate continuous infusion maintenance dose of dexmedetomidine for a minimum of 6 but not more than 24 hours. The dose levels administered to each subject are given in Table 1 below. Subjects were sequentially assigned to the dose levels.

TABLE 1

Dose Levels for Each Age Group

| | Treatment Group | | | |
|---|---|---|---|---|
| Dose Level | Age Group I ≥28 weeks to <36 weeks gestational age (n) | Age Group II ≥36 weeks to ≤44 weeks gestational age (n) | Loading Dose μg/kg | Continuous Infusion Rate μg/kg/hr |
| 1 | 6 | 8 | 0.05 | 0.05 |
| 2 | 0 | 8 | 0.1 | 0.1 |
| 3 | 0 | 8 | 0.2 | 0.2 |

The dexmedetomidine administered was a Precedex® dexmedetomidine HCl injection manufactured by Hospira, Inc. Dexmedetomidine hydrochloride (HCl) injection (100 μg/mL, base) was supplied by Hospira to the investigative sites for infusion. Study medication was prepared (diluted) by the site pharmacy. The loading doses of dexmedetomidine were diluted in 0.9% sodium chloride or dextrose 5% in water to one of the following concentrations: 4 μg/mL solution, 2 μg/mL solution, 1 μg/mL solution, or 0.5 μg/mL solution. Dexmedetomidine was infused using a controlled infusion device. In order to ensure proper infusion, dexmedetomidine was not administered directly into the pulmonary artery.

Dexmedetomidine was administered as a two-stage infusion. A 10- or 20-minute loading dose infusion of dexmedetomidine was administered followed by a continuous fixed maintenance dose infusion of dexmedetomidine for a minimum of 6 and up to 24 hours post-operatively. The dexmedetomidine for maintenance infusion was diluted at the same concentration as for the loading dose of dexmedetomidine. The dexmedetomidine for both the loading and the maintenance infusion was administered at the site of insertion of the IV catheter to avoid flushing the drug. Dexmedetomidine was administered through a designated IV line for dexmedetomidine.

Sedation dosages were calculated using the subject's most recently measured weight prior to commencement of dexmedetomidine. No dosage adjustments were needed for day to day weight fluctuations because the dexmedetomidine duration spanned a maximum of 24 hours.

Exposure to dexmedetomidine is summarized by gestational age in Table 2 (loading dose), Table 3 (maintenance dose), and Table 4 (total dose/time; time of exposure<6 hours, <12 hours, <24 hours, >0-<6 hours, ≥6-<12 hours, ≥12-<24 hours, and ≥24 hours). Median exposure to dexmedetomidine is summarized in Tables 2-4 below. The median data were chosen due to variability in data. Median dexmedetomidine exposure was highest in age Group II, dose level 3. For age Group I, 2 subjects each received infusions lasting between >0-<6 hours, ≥6-<12 hours, and ≥12-<24 hours. For age Group II, the majority of subjects (n=17, 70.8%) received infusions between ≥6-<12 hours, with a median duration of just over 6 hours (370 minutes). Subjects in dose level 3 received the longest maintenance infusion in age Group II at a median of 961.5 minutes (16 hours) compared to the other 2 cohorts in this age group at a median of 360.0-365.0 minutes (approximately 6 hours). All subjects completed the treatment, receiving a minimum of 6 hours of maintenance infusion.

TABLE 2

Median Loading Dose of Dexmedetomidine Exposure

| Median Parameter | Age Group I[a] Dose Level 1 dexmedetomidine 0.05[b] (N = 6) | Age Group II[a] | | | |
|---|---|---|---|---|---|
| | | Dose Level 1 dexmedetomidine 0.05[b] (N = 8) | Dose Level 2 dexmedetomidine 0.1[b] (N = 8) | Dose Level 3 dexmedetomidine 0.2[b] (N = 8) | Total Age Group II[a] (N = 24) |
| | Loading dose | | | | |
| N | 6 | 8 | 8 | 8 | 24 |
| Total loading dose (μg) | 0.07 | 0.18 | 0.31 | 0.70 | 0.31 |
| Duration (min) | 10.0 | 10.0 | 10.0 | 10.0 | 10.0 |

[a]Age Group I = ≥28 to <36 weeks gestational age; Age Group II = ≥36 to ≤44 weeks.
[b]Units are μg/kg for loading dose and μg/kg/hr for maintenance dosing (continuous infusion).

TABLE 3

Median Maintenance Dose of Dexmedetomidine Exposure

| Median Parameter | Age Group I[a] Dose Level 1 dexmedetomidine 0.05[b] (N = 6) | Age Group II[a] | | | |
|---|---|---|---|---|---|
| | | Dose Level 1 dexmedetomidine 0.05[b] (N = 8) | Dose Level 2 dexmedetomidine 0.1[b] (N = 8) | Dose Level 3 dexmedetomidine 0.2[b] (N = 8) | Total Age Group II[a] (N = 24) |
| | Maintenance dose | | | | |
| N | 6 | 8 | 8 | 8 | 24 |
| Total maintenance dose (μg) | 1.30 | 1.08 | 1.87 | 12.20 | 1.87 |
| Duration (min) | 1407.5 | 360.0 | 365.0 | 961.5 | 360.0 |

[a]Age Group I = ≥28 to <36 weeks gestational age; Age Group II = ≥36 to ≤44 weeks.
[b]Units are μg/kg for loading dose and μg/kg/hr for maintenance dosing (continuous infusion).

TABLE 4

Median Total Dose of Dexmedetomidine Exposure

| Median Parameter | Age Group I[a] Dose Level 1 dexmedetomidine 0.05[b] (N = 6) | Age Group II[a] | | | |
|---|---|---|---|---|---|
| | | Dose Level 1 dexmedetomidine 0.05[b] (N = 8) | Dose Level 2 dexmedetomidine 0.1[b] (N = 8) | Dose Level 3 dexmedetomidine 0.2[b] (N = 8) | Total Age Group II[a] (N = 24) |
| | Duration of exposure >0-<6 hours | | | | |
| N | 0 | 0 | 0 | 0 | 0 |
| Total dose (μg) | — | — | — | — | — |
| Duration (min) | — | — | — | — | — |
| | Duration of exposure ≥6-<12 hours | | | | |
| N | 2 | 8 | 7 | 2 | 17 |
| Total dose (μg) | 0.51 | 1.26 | 2.14 | 4.06 | 1.52 |
| Duration (min) | 370.0 | 370.0 | 370.0 | 370.0 | 370.0 |
| | Duration of exposure ≥12-<24 hours | | | | |
| N | 2 | 0 | 1 | 5 | 6 |
| Total dose (μg) | 1.97 | — | 7.76 | 13.32 | 12.96 |
| Duration (min) | 1417.5 | — | 1370.0 | 1040.0 | 1070.0 |
| | Duration of exposure ≥24 hours | | | | |
| N | 2 | 0 | 0 | 1 | 1 |
| Total dose (μg) | 1.35 | — | — | 15.75 | 15.75 |
| Duration (min) | 1450.0 | — | — | 1460.0 | 1460.0 |

[a]Age Group I = ≥28 to <36 weeks gestational age; Age Group II = ≥36 to ≤44 weeks.
[b]Units are μg/kg for loading dose and μg/kg/hr for maintenance dosing (continuous infusion).

Subjects in age Group I received a median total loading dose of 0.07 µg with a median duration of 10 minutes and a median total maintenance dose of 1.30 µg over 1407.5 minutes (23.5 hours). Subjects in age Group II received a median total loading dose of 0.18-0.70 µg over 10 minutes and a median total maintenance dose of 1.08-12.20 µg over 360-961.5 minutes (6-16 hours).

Efficacy evaluations were conducted by assessing the frequency of sedation using the Neonatal Pain, Agitation, and Sedation Scale (N-PASS), developed to assess sedation and pain/agitation in neonates. The N-PASS includes 5 criteria to assess sedation levels, pain, and agitation in neonates. The indicators are as follows: 1) crying/irritability, 2) behavior/state, 3) facial expression, 4) extremities/tone, and 5) vital signs (i.e., HR, RR, SBP, DBP, and $SpO_2$). Whenever possible, the same Investigator or designee obtained N-PASS scores, according to the schedule of activities as shown in Table 5.

The evaluation for the presence of paradoxical reactions (notably rage) was monitored in conjunction with all N-PASS assessments. Rage was protocol-defined and occurred when either the Crying/Irritability or Behavior/State assessment criteria in the N-PASS merited a score of 2. For each of the 5 assessment criteria, the subject would be given one number, −2, −1, 0, +1, or +2. The subject might have some criteria score in the negative sedation side, and other criteria in the positive pain/agitation side, but for a single criterion would score either on the sedation or the pain side, not both. If subject gestational age was <30 weeks, 1 was added into the pain score.

Morphine or fentanyl and/or midazolam could be given for rescue as indicated by a total N-PASS score>3 or by clinical judgment. The dexmedetomidine infusion could be continued during and after the subject was extubated; however, the minimum duration of dexmedetomidine infusion was 6 hours and the maximum duration of infusion was 24 hours. Efficacy measures included the use of rescue medication for sedation or analgesia (incidence and amount used) during dexmedetomidine infusion.

Rescue medication was administered as needed for sedation (midazolam) and pain (fentanyl or morphine), during dexmedetomidine administration based on results of the N-PASS sedation/pain scale. Rescue therapy was indicated when the N PASS total score>3 and the selection of sedative rescue or analgesic rescue was at the discretion of the Investigator. For any bolus administration of rescue therapy, the following sequence of events occurred: The N-PASS score was obtained prior to the administration of rescue medication and within 5 minutes after administration of midazolam. The rescue medicine for sedation was midazolam and the rescue medication for pain was either fentanyl or morphine. Midazolam was administered based on labeling for pediatrics at a recommended dose of 0.05 to 0.15 mg/kg per dose. Rescue fentanyl for pain was administered in a 0.5 to 2 µg/kg bolus or 1 to 2 µg/kg/hr continuous infusion. For continuous infusions of fentanyl, the N-PASS was recorded immediately prior to initiating the continuous infusion. Rescue morphine was administered as a 0.025 to 0.1 mg/kg bolus or 0.01 to 0.02 mg/kg/hr continuous infusion. For continuous infusions of morphine, the N-PASS was recorded immediately prior to initiating the continuous infusion.

Summary statistics for the dexmedetomidine loading doses and maintenance infusion doses are shown in Table 8A below.

TABLE 5

N-PASS—Neonatal Pain, Agitation and Sedation Scale

| Assessment | Sedation | | Sedation/Pain | Pain/Agitation | |
|---|---|---|---|---|---|
| Criteria | −2 | −1 | 0/0 | 1 | 2 |
| Crying Irritability | No cry with painful stimuli | Moans or cries minimally with painful stimuli | No sedation/No pain signs | Irritable or crying at intervals Consolable | High-pitched or silent-continuous cry Inconsolable |
| Behavior State | No arousal to any stimuli No spontaneous movement | Arouses minimally to stimuli Little spontaneous movement | No sedation/No pain signs | Restless, squirming Awakens frequently | Arching, kicking Constantly awake or Arouses minimally/no movement (not sedated) |
| Facial Expression | Mouth is lax No expression | Minimal expression with stimuli | No sedation/No pain signs | Any pain expression intermittent | Any pain expression continual |
| Extremities Tone | No grasp reflex Flaccid tone | Weak grasp reflex ↓ muscle tone | No sedation/No pain signs | Intermittent clenched toes, fists or finger splay Body is not tense | Continual clenched toes, fists, or finger splay Body is tense |
| Vital Signs HR, RR, BP, $SaO_2$ | No variability with stimuli Hypoventilation or apnea | <10% variability from baseline with stimuli | No sedation/No pain signs | ↑ 10-20% from baseline $SaO_2$ 76-85% with stimulation - quick ↑ | ↑ >20% from baseline $SaO_2$ ≤75% with stimulation - slow ↑ Out of sync/fighting vent |

TABLE 5A

Summary Statistics of Dosing-Related Data

| Dose-Related Variable | | 0.05 µg/kg + 0.05 µg/kg/h | 0.10 µg/kg + 0.10 µg/kg/h | 0.20 µg/kg + 0.20 µg/kg/h |
|---|---|---|---|---|
| Loading dose (ng) | Mean (SD) | 125.400 (58.239) | 298.650 (51.136) | 664.250 (114.030) |
| | Median | 120.000 | 312.000 | 676.000 |
| | Min, Max | 56.00, 217.50 | 200.10, 363.00 | 460.00, 830.00 |
| | n | 10 | 8 | 8 |
| Maintenance infusion dose (ng) | Mean (SD) | 1147.563 (546.668) | 2513.618 (2004.047) | 10579.833 (5174.104) |
| | Median | 1080.000 | 1872.000 | 12195.750 |
| | Min, Max | 357.00, 2197.67 | 1317.33, 7425.00 | 2760.00, 16756.00 |
| | n | 10 | 8 | 8 |
| Total dose (ng) | Mean (SD) | 1272.963 (548.969) | 2812.268 (2023.889) | 11244.083 (5249.609) |
| | Median | 1260.000 | 2184.000 | 12960.750 |
| | Min, Max | 416.50, 2292.67 | 1517.43, 7755.00 | 3220.00, 17464.00 |
| | n | 10 | 8 | 8 |
| Loading infusion duration (h) | Mean (SD) | 0.167 (0.000) | 0.229 (0.086) | 0.208 (0.077) |
| | Median | 0.167 | 0.167 | 0.167 |
| | Min, Max | 0.17, 0.17 | 0.17, 0.33 | 0.17, 0.33 |
| | n | 10 | 8 | 8 |
| Maintenance infusion duration (h) | Mean (SD) | 11.292 (8.523) | 8.223 (5.774) | 15.454 (6.887) |
| | Median | 6.000 | 6.083 | 16.025 |
| | Min, Max | 6.00, 24.00 | 6.00, 22.50 | 6.00, 24.00 |
| | n | 10 | 8 | 8 |
| Time between start of doses (min) | Mean (SD) | 18.500 (20.823) | 14.500 (4.629) | 13.125 (4.291) |
| | Median | 10.000 | 12.000 | 11.000 |
| | Min, Max | 10.00, 75.00 | 10.00, 20.00 | 10.00, 20.00 |
| | n | 10 | 8 | 8 |
| Time from end of 1$^{st}$ to beginning of 2$^{nd}$ infusion (min) | Mean (SD) | 8.500 (20.823) | 0.750 (1.035) | 0.625 (0.744) |
| | Median | 0.000 | 0.500 | 0.500 |
| | Min, Max | 0.00, 65.00 | 0.00, 3.00 | 0.00, 2.00 |
| | n | 10 | 8 | 8 |

Safety measures included collection of adverse events (adverse events), heart rate (HR in beats per minute [bpm]), systolic blood pressure (SBP in millimeters of mercury [mmHg]), diastolic blood pressure (DBP in millimeters of mercury [mmHg]), mean arterial pressure (MAP in millimeters of mercury [mmHg]), oxygen saturation by pulse oximetry ($SpO_2$ in percentage), and respiratory rate (RR in breaths/minute [breaths/min]) or ventilator settings, laboratory results, and electrocardiogram (ECG) monitoring.

Arterial, venous, or capillary blood samples (0.15 mL each) for pharmacokinetic analysis were obtained at six or seven protocol-designated times for subjects in age Group I depending upon weight (≥28 weeks to <36 weeks gestational age) and at seven designated times for subjects in age Group II (≥36 weeks through ≤44 weeks gestational age).

Chemistry, hematology and urinalysis samples were obtained for the laboratory tests according to the following schedule of study activities: at screening, after five hours of maintenance but before discontinuation of dexmedetomidine and within 24 hours following the discontinuation of dexmedetomidine infusion. In addition, subjects who were s/p CPB had a sample drawn for ALT level following CPB, but no later than 1 hour from the commencement of dexmedetomidine (this constituted the ALT at baseline). All blood and urine samples were collected in appropriately labeled tubes and sent to the local laboratory for analysis.

Liver function tests (LFTs) were obtained pre- and post-treatment and compared for evidence of hepatic dysfunction. Liver function tests were obtained during the following periods: at screening, after five hours of maintenance but before discontinuation, and in close proximity to 24 hours after discontinuation of the infusion or on the day of discharge, whichever came first. In addition, subjects who were s/p CPB had a sample drawn for ALT level following CPB, but no later than 1 hour from the beginning of the dexmedetomidine infusion. This constituted the ALT at baseline and was not used in reference to exclusion criteria. Liver function tests were defined as: aspartate aminotransferase (AST), ALT, alkaline phosphatase, and total bilirubin. Hepatotoxicity was defined by an ALT>156 U/L or a ≥30% increase from screening value, whichever was greater.

The statistical analyses were performed using SAS™ Statistical Software System (SAS Institute, Inc., Cary, N.C.), version 9.1. All statistical tests were 2 sided and p values≤0.0500, after rounding to 4 decimal places, were considered statistically significant unless otherwise specified. In general, missing data were not imputed. For continuous variables, N, mean, median, SD, minimum, Q1, Q3 and maximum are presented. The mean and median was displayed to 1 decimal place more than the raw value. The standard deviation (SD) is displayed to 2 decimal places more than the raw value. For categorical variables, N and percent is shown. All percentages were reported to I decimal place.

For the final analyses, treatment differences by age groups were assessed for continuous variables using two-way analysis of variance (ANOVA) when assumption of normal distribution is reasonable or by nonparametric tests when this assumption was not met. For ordered categorical variables, the Cochran-Mantel-Haenszel (CMH) test was used. If treatment differences are significant, a pairwise comparison between dose levels was performed. All efficacy variables were analyzed while on dexmedetomidine.

Dexmedetomidine was effective at sedating critically ill, initially intubated and mechanically ventilated premature infants, ≥28 to <36 weeks. No subject in age Group I received rescue midazolam for sedation during dexmedetomidine infusion. At the doses used in this trial, up to 0.2 µg/kg/hr, dexmedetomidine was moderately effective at sedating term neonates. In age Group II, a total of 4 subjects (16.7%) received rescue midazolam (mean dose 0.22 mg/kg) for sedation during dexmedetomidine infusion.

Most premature neonates in age group I did not require additional medication for pain while on dexmedetomidine infusion. One subject (16.7%) in age group I received rescue medication for analgesia during the study infusion. In contrast, more of the term neonates in age group II (58.3%) received rescue medication for analgesia during the study infusion. The increased analgesic requirements in age group II, in particular dose level 3, most likely reflects the higher proportion of post-operative surgical subjects.

All dose levels spent a low period of time with a total N-PASS score>3 indicating most subjects were adequately sedated and not manifesting signs of pain/agitation. Generally, trends in mean change from baseline in vital signs were not clinically meaningful.

Premature neonates, ≤28 to <36 weeks gestational age, appeared to have lower clearance than term neonates which resulted in higher dose-adjusted exposure. These parameters were well estimated at 1 dose level (0.05 µg/kg) for age Group I (≥28 to <36 weeks gestational age) and for all 3 dose levels (0.05 µg/kg, 0.1 µg/kg, and 0.2 µg/kg) for age Group II (≥36 to ≤44 weeks gestational age). The younger subjects appeared to have lower clearance (0.41 L/hr/kg at 0.05 µg/kg dose level in age Group I) than older subjects (0.61 L/hr/kg at 0.05 µg/kg dose level in age Group II) which resulted in higher dose-adjusted exposure. This finding is difficult to interpret because of the lack of pharmacokinetic data available at the 0.1 µg/kg and 0.2 µg/kg dose levels in the younger subjects.

The results of the pharmacokinetic analysis suggest volume of distribution at steady state, weight adjusted ($V_{ssw}$) and the apparent terminal elimination half-life ($t_{1/2}$) were similar across dose levels and age groups. In addition, dexmedetomidine exposure appeared to be dose proportional within the older subjects (age Group II). Dose proportionality within the younger subjects (age Group I) could not be assessed. This finding is difficult to interpret because of the lack of pharmacokinetic data available at the 0.1 µg/kg and 0.2 µg/kg dose levels in the younger subjects. The lower clearance in this age group and higher concentrations are consistent with the greater efficacy observed in the premature neonates (no subjects required rescue midazolam for sedation and 1 subject required rescue medication for analgesia) compared to the term neonates (4 subjects required rescue midazolam for sedation and 14 subjects required rescue medication for analgesia). The $V_{ssw}$ and the $t_{1/2}$ were similar across dose levels and age groups.

Dexmedetomidine was safe and well tolerated in both age groups and at all doses. The adverse effect profile observed is typical of the critically ill, high risk pediatric population and post-operative surgical patients. Treatment-emergent adverse effects were experienced by 2 subjects (33.3%) in age Group I and by 15 subjects (62.5%) in age Group II. In age Group I, dose level 1, no treatment-emergent adverse effects were reported by more than 1 subject. In age Group II, events reported by more than 1 subject were hypokalemia, decreased blood potassium, anger, atelectasis, and pleural effusion. These events were more common and expected in the post-operative open heart surgery subjects.

The time to successful extubation was explored in Precedex-exposed subjects using Kaplan-Meier estimates. Results for this section are not clinically meaningful and therefore are not further discussed due to the high variability in medical history factors.

Most treatment-emergent adverse effects were assessed as not related to treatment, only 2 subjects in the study (in age Group II) experienced treatment-emergent adverse effects assessed as related to treatment. There were no severe treatment-emergent adverse effects reported, 2 subjects in each age group experienced moderate treatment-emergent adverse effects, all other subjects experienced mild treatment-emergent adverse effects. There were no treatment-emergent serious adverse effects leading to death, no other treatment-emergent serious adverse effects, and no treatment-emergent adverse effects that led to dexmedetomidine discontinuation. There were no dose-limiting toxicities that led to dexmedetomidine discontinuation (persistent bradycardia, persistent hypotension, or respiratory depression).

In general, mean changes from baseline were not clinically significant for laboratory parameters, vital signs, physical examination, or ECGs. Dexmedetomidine was effective at sedating critically ill, initially intubated and mechanically ventilated premature infants. No subject in age Group I received rescue midazolam for sedation during the study infusion. At the doses used in this trial, up to 0.2 µg/kg/hr, dexmedetomidine was moderately effective at sedating term neonates. Most premature neonates in age Group I did not require additional medication for pain while on dexmedetomidine infusion. In contrast, more of the term neonates in age Group II (58.3%) received rescue medication for analgesia during the study infusion. The increased analgesic requirements in age Group II, in particular dose level 3, most likely reflects the higher proportion of post-operative surgical subjects. Premature neonates appeared to have lower plasma clearance than term neonates which resulted in higher dose-adjusted exposure and greater efficacy. No subjects discontinued the trial due to treatment-emergent adverse effects. Dexmedetomidine was safe and well tolerated in both age groups and at all doses. The adverse effect profile observed is typical of the critically ill, high risk pediatric population studied.

Additional 6 Patient Cohort

After the study had been initiated with the first original 30 patients, an additional six patients were enrolled in and completed the study (hereinafter the "additional cohort"). The study protocol for the study conducted on the additional cohort is as described above. The additional six patients were neonates aged≥28 weeks to <36 weeks gestational age that required sedation in an intensive care setting for a minimum of 6 hours. These six patients were in dose level 2 and received a loading dose of 0.1 µg/kg and a maintenance dose of 0.1 µg/kg. The dose levels for each age group for the 36 total patients that received dexmedetomidine in this study are given in Table 6 below.

TABLE 6

Dose Levels for Each Age Group

| | Treatment Group | | | |
|---|---|---|---|---|
| Dose Level | Age Group I ≥28 weeks to <36 weeks gestational age (n) | Age Group II ≥36 weeks to ≤44 weeks gestational age (n) | Loading Dose µg/kg | Continuous Infusion Rate µg/kg/hr |
| 1 | 6 | 8 | 0.05 | 0.05 |
| 2 | 6 | 8 | 0.1 | 0.1 |
| 3 | 0 | 8 | 0.2 | 0.2 |

The mean gestational age for the 6 subjects in the additional cohort was 32.5 weeks. There were 3 males and 3 females. The mean weight was 1.71 kg and the mean height was 42.75 cm. The reason for intubation was respiratory disease in 5 of the subjects and sepsis in 1 subject.

All 6 subjects in the additional cohort had received prior therapies before entering this study; the most common of these were anti-infectives, nutrition products, and midazolam or fentanyl. All 6 subjects received concomitant therapies; the most common of these were anti-infectives and nutrition products. All 6 subjects received a wide variety of therapies post-dexmedetomidine infusion.

None of the 6 subjects in the additional cohort required rescue midazolam or morphine during the dexmedetomidine infusion. Only one subject (16.7%) required rescue medication for analgesia during the dexmedetomidine infusion and was administered 2 µg (0.98 µg/kg) fentanyl. The duration of the dexmedetomidine infusion in this subject was 6.5 hours. This subject had a medical history of gastroschisis requiring surgery for placement of a silo as well as respiratory distress syndrome requiring intubation, both ongoing at the time of screening. The subject requiring rescue analgesia was the only subject to have a total N-PASS score below 3, which the subject had for 0.25 hours due to an infiltrated I.V.

The geometric means of plasma pharmacokinetic parameters of dexmedetomidine following a loading dose and a maintenance dose in the cohort for the study addendum (age group I, dose level 2) are shown in Table 7 below.

TABLE 7

Geometric Mean Plasma Pharmacokinetic Parameters for Additional Cohort Patients

| Pharmacokinetic Parameter (units) | Age Group I[a] Dose Level 2 DEX Loading Dose = 0.1 µg/kg Maintenance Dosing = 0.1 µg/kg/hr (N = 6) |
|---|---|
| CL (L/hr) | 0.48 (n = 2) |
| $CL_w$ (L/hr/kg) | 0.29 (n = 2) |
| AUC (0-Last) [(pg/mL)hr] | 708.09 |
| AUC (0-Infinity) [(pg/mL)hr] | 4305.31 (n = 2) |
| AUC (0-Infinity)$_{Dose}$ [(pg/mL)hr/µg] | 2102.55 (n = 2) |
| $C_{max}$ (pg/mL) | 107.22 |
| $V_d$ (L) | 5.71 (n = 2) |
| $V_{dw}$ (L/kg) | 3.47 (n = 2) |
| $V_{ss}$ (L) | 6.25 (n = 2) |
| $V_{ssw}$ (L/kg) | 3.79 (n = 2) |
| $t_{1/2}$ (hr) | 8.32 (n = 2) |

[a]Age group I = ≥ 28 to <36 weeks gestational age

The weight adjusted clearance ($CL_w$) of DEX in the 2 subjects evaluated in the additional cohort was similar to the 1 subject evaluated in age group I, dose level 1 and again lower than observed in age group II subjects. Consistent with the difference in clearance, the dose-adjusted area under the concentration-time curve from zero to infinity, AUC (0-Infinity), evaluated in the additional cohort (n=2), was 4.6 times higher (2102.55 versus 461.04 (pg/mL)hr than that calculated for age group II across all dose levels (n=12). In a similar manner, the concentration at steady-state ($C_{ss}$) was higher in the additional cohort than in the same dose level in age group II (369.67 versus 170.53 pg/mL). However, the maximum concentration ($C_{max}$) was actually lower in the additional cohort versus the same dose level in age group II, 107.22 versus 122.43 pg/mL, respectively. The weight adjusted volume of distribution at steady-state ($V_{ssw}$) was slightly larger in the additional cohort compared to the same dose level in age group II (3.79 versus 2.85 L/kg) and the apparent terminal elimination half-life ($t_{1/2}$) was longer at 8.32 versus 4.77 hours, respectively.

Dexmedetomidine was safe and well tolerated in both age groups and at all doses, including the additional cohort. The adverse events profile observed in the additional cohort is typical of the critically ill, high risk pediatric population.

The limited information from the premature neonates makes interpretation of the effect of age on the pharmacokinetics of dexmedetomidine difficult. However, based on the two dose levels (0.05 and 0.1 µg/kg) tested in age group 1 in the original 30 patient group and the additional cohort, it appeared that clearance was lower, which resulted in total exposure (AUC) that was 4.4 to 4.6 times larger in the premature neonates (n=3) than the term neonates (n=12). This finding is also consistent with higher $C_{ss}$ levels in the premature neonates in age group I, dose levels 1 and 2 compared to the term neonates. The lower clearance in the premature neonates and higher concentrations are consistent with the greater efficacy observed in the premature neonates in both dose levels (no subjects required rescue midazolam for sedation and 2 subjects required rescue medication for analgesia) compared with the term neonates (4 subjects required rescue midazolam for sedation and 14 subjects required rescue medication for analgesia).

The $C_{max}$ and AUC (0-last) appeared lower in the additional cohort compared to the same dose level from the age group II population. These values were: $C_{max}$ 107.22 versus 122.43 pg/mL and AUC (0-Last) 708.09 versus 813.26 (pg/mL)hr, respectively. Lower clearance, higher concentrations, and greater efficacy were observed in the additional cohort of premature neonates and consistent with what was observed in the other premature neonate cohort compared to the term neonates in the original 30 patient population.

Most premature neonates in age group I in the additional cohort and in the original 30 patient population data did not require additional medication for pain while on dexmedetomidine infusion. One subject (16.7%) in each dose level of age group 1 received rescue medication for analgesia during the study infusion. In contrast, in the original 30 patient population, more of the term neonates in age group II (58.3%) received rescue medication for analgesia during the study infusion. The increased analgesic requirements in age group II, in particular dose level 3, most likely reflects the higher proportion of postoperative surgical subjects. Subjects in the additional cohort and in the original 30 patient population data spent a low period of time with a total N-PASS score>3, indicating that most subjects were adequately sedated and not manifesting signs of pain/agitation. Generally, trends in changes from baseline in vital signs in the additional cohort and in the interim analyses data were not clinically meaningful.

Median exposure to dexmedetomidine is summarized in Table 8 below. The median data were chosen due to variability in data. Subjects in age group I, dose level 2 had a lower median total maintenance dose and duration of dexmedetomidine exposure compared to age group I, dose level 1 from the interim analyses: specifically, 1.14 µg versus 1.30 µg with a median duration of 375.0 minutes (6.25 hours) versus 1407.5 minutes (23.5 hours), respectively. Subjects in age group I, dose level 2 had a lower median total maintenance dose but similar duration of dexmedetomidine exposure compared with age group II from the interim analyses at the same dose level: specifically, 1.14 µg versus 1.87 µg with a median duration of 375.0 minutes (6.25 hours) versus 365.0 minutes (6.1 hours), respectively. Five of the 6 subjects received infusions lasting≥6-<12 hours with a median dose of 1.26 µg and duration of 380 minutes (6.3 hours) and 1 subject≥12-<24 hours received a total dose of 4.06 μg and duration of 1285.0 minutes (21.4 hours). All subjects completed the treatment, receiving a minimum of 6 hours of maintenance infusion.

TABLE 8

Median Dose and Duration of Dexmedetomidine Exposure

| Median Parameter | Age Group 1[a] Dose Level 2 DEX 0.1[b] (N = 6) |
|---|---|
| Loading dose | |
| N | 6 |
| Total loading dose (μg) | 0.18 |
| Duration (min) | 20 |
| Maintenance dose | |
| N | 6 |
| Total maintenance dose (μg) | 1.14 |
| Duration (min) | 375.0 |
| Duration of exposure ≥6-<12 hours | |
| N | 5 |
| Total dose (μg) | 1.26 |
| Duration (min) | 380.0 |
| Duration of exposure ≥12-<24 hours | |
| N | 1 |
| Total dose (μg) | 4.06 |
| Duration (min) | 1285.0 |

[a]Age group I = ≥28 to <36 weeks gestational ages.
[b]Units are μg/kg for loading dose and μg/kg/hr for maintenance dosing (continuous infusion).

There was variability between subjects for most hematology tests. In general, no evidence of systematic change for any hematologic variable, chemistry variable, or urinalysis variable were found. Treatment-emergent adverse events pertaining to laboratory results were hypoalbuminemia (n=3) and the following events that occurred in one subject each: hyperbilirubinemia, increased unconjugated blood bilirubin, hypoproteinemia, hypocalcemia, hematuria, and hyperglycemia. All of these laboratory parameters were assessed as not related to dexmedetomidine and are typical of this premature neonate population. Physical examination data was collected. The most common abnormal findings at screening and post-dexmedetomidine administration were in the pulmonary/respiratory system. There were no abnormal, clinically significant electrocardiogram results at screening, during, or post-dexmedetomidine administration. Total fluid input ranged from 49.1 to 162.6 mL and total fluid output ranged from 30 to 224 mL. In general, changes from baseline were not clinically meaningful for laboratory parameters, vital signs, physical examination, or electrocardiogram results in the additional cohort.

Treatment-emergent adverse events were experienced by all 6 subjects in the additional cohort, which are given in Table 9 below. Of the 18 treatment-emergent adverse events reported, only hypoalbuminemia (n=3) was reported in more than one subject. Most treatment-emergent adverse events were assessed as not related to treatment. The only treatment-emergent adverse events that were assessed as related to dexmedetomidine were mild. One subject experienced two treatment-emergent adverse events assessed as related to treatment. One subject experienced three severe treatment-emergent adverse events; two subjects experienced 1 moderate treatment-emergent adverse event each. None of these severe or moderate events were assessed as related to dexmedetomidine. All other events were mild. There were no treatment-emergent serious adverse events leading to death, one subject experienced three treatment emergent serious adverse effects, and no subjects had treatment-emergent adverse events that led to dexmedetomidine discontinuation. There were no treatment emergent dose-limiting toxicities that led to dexmedetomidine discontinuation (persistent bradycardia, persistent hypotension, or respiratory depression).

TABLE 9

Summary of Treatment Emergent Adverse Events by System Organ Class and Preferred Term

| System Organ Class Preferred Term[a] | Dose Level 2 Dex 0.1 (N = 6) |
|---|---|
| Number of Events | 18 |
| Number of Subjects with at least one event | 6 (100.0%) |
| Cardiac disorders | 1 (16.7%) |
| Bradycardia 1 | 1 (16.7%) |
| Cardio-respiratory arrest | 1 (16.7%) |
| General disorders and administration site conditions | 2 (33.3%) |
| Infusion site extravasation | 1 (16.7%) |
| Oedema | 1 (16.7%) |
| Hepatobiliary disorders 1 | 1 (16.7%) |
| Hyperbilirubinaemia | 1 (16.7%) |
| Infections and infestations | 1 (16.7%) |
| Sepsis | 1 (16.7%) |
| Investigations | 2 (33.3%) |
| Blood bilirubin unconjugated increased | 1 (16.7%) |
| Oxygen saturation decreased | 1 (16.7%) |
| Metabolism and nutrition disorders | 3 (50.0%) |
| Hyperglycaemia | 1 (16.7%) |
| Hypoalbuminaemia | 3 (50.0%) |
| Hypocalcaemia | 1 (16.7%) |
| Hypoproteinaemia | 1 (16.7%) |
| Psychiatric disorders | 1 (16.7%) |
| Anger | 1 (16.7%) |
| Renal and urinary disorders | 1 (16.7%) |
| Haematuria | 1 (16.7%) |

Note:
Percentages are based on the number of subjects in each dose level and age group.
Subjects are counted once within each system organ class or for each preferred term and may have had more than one adverse event.
[a]All investigator adverse event terms were coded using MedDRA dictionary version 13.0.

The mean gestational age for group I-level 1 and 2 was 30.3 and 32.5 wks and for group II-levels 1-3, 38.7 wks. Adequate level of sedation was seen in most patients and rescue sedation with midazolam (0.22±0.26 mg/kg) was given only in 4 patients (17%) in group II. Rescue analgesia with fentanyl was given in 2 (17%) patients in group I, and 11 (46%) patients in group II. Additionally 4 (21%) patients in group II received rescue morphine. In group I, level 1 and 2, dexmedetomidine clearance ($CL_w$) was 0.41 and 0.29 L/hr/kg, maximum plasma concentration ($C_{max}$) was 102 and 107 pg/mL, volume of distribution ($V_{ssw}$) was 2.7 and 3.8 L/kg, and elimination $t_{1/2}$ 3 and 8 hrs respectively. In group 2, level 1, 2 and 3 $CL_w$ was 0.61, 0.64 and 0.73 L/hr/kg, $C_{max}$ was 78, 122, 325 pg/mL, $V_{ssw}$ 1.4, 2.8 and 2 L/kg, and $t_{1/2}$ 3, 5 and 3 hrs respectively. A lower $CL_w$ was observed in group I along with a total exposure (AUC) that was 4.5 times larger than group II. The safety profile observed was typical of the critically ill, high risk pediatric population and post-operative surgical patients. Adverse events were reported in 8 (67%) patients in group I and 15 (62%) patients in group II but in only 2 (8%) patients these adverse events were assessed as related to dexmedetomidine. None had serious adverse events related to dexmedetomidine or adverse events needing dexmedetomidine discontinuation.

The overall efficacy conclusions of the study were not affected by the update with the additional cohort. Dexmedetomidine was effective at sedating critically ill, initially intubated and mechanically ventilated premature infants, ≥28 to <36 weeks, in the additional cohort and in original 30 patient population. No subject in the original 30 patient population or the additional cohort in age group I, dose levels 1 or 2, received rescue midazolam for sedation during dexmedetomidine infusion. In the original 30 patient population, at the doses used in this trial, up to 0.2 μg/kg/hr, dexmedetomidine was effective at sedating term neonates. In age group II, a total of 4 subjects (16.7%) received rescue midazolam (mean dose 0.22 mg/kg) for sedation during dexmedetomidine infusion.

Most premature neonates in age group I in the additional cohort and in the interim analyses data did not require additional medication for pain while on dexmedetomidine infusion. One subject (16.7%) in each dose level of age group 1 received rescue medication for analgesia during the study infusion. In contrast, in the interim analyses, more of the term neonates in age group II (58.3%) received rescue medication for analgesia during the study infusion. The increased analgesic requirements in age group II, in particular dose level 3, most likely reflects the higher proportion of postoperative surgical subjects.

Subjects in the additional cohort and in the interim analyses data spent a low period of time with a total N-PASS score>3 indicating most subjects were adequately sedated and not manifesting signs of pain/agitation.

Lower clearance, higher concentrations, and greater efficacy were observed in the additional cohort of premature neonates and consistent with what was observed in the other premature neonate cohort in the interim analyses compared to the term neonates in the interim analyses.

Subjects in the additional cohort of age group I, dose level 2, had a lower median total maintenance dose and duration of dexmedetomidine exposure compared to age group I, dose level 1 in the interim analyses. The additional cohort of subjects also had a lower median total maintenance dose but similar duration of dexmedetomidine exposure compared to age group II at the same dose level.

Example 2

Dexmedetomidine Study in Pediatric Intensive Care Unit Subjects

A 175-subject, randomized, double-blind, dose-controlled, multicenter study of dexmedetomidine was conducted on initially intubated and mechanically ventilated pediatric subjects in the pediatric intensive care setting. The present study investigated the efficacy, pharmacokinetics, and safety of dexmedetomidine at four different dose levels. The subjects were between the ages of 1 month and less than 17 years. For neonates who were born prematurely, the age was corrected based on gestational age until 3 months of actual birth age. The subjects were mechanically ventilated prior to and during the commencement of dexmedetomidine, and were anticipated to require a minimum of 6 hours of continuous intravenous (IV) sedation. The subjects could be intubated by nasotracheal, endotracheal or via tracheotomy.

Subjects also had to have an American Association of Anesthesiologists (ASA) classification of 1, 2, 3, or 4, and a University of Michigan Sedation Scale (UMSS) score of 1, 2, 3, or 4 at the start of infusion of dexmedetomidine.

Subjects were randomized into one of two treatment groups. Within each treatment group, the loading and maintenance doses were stratified according to the presence or absence of cardiopulmonary bypass (CPB). The treatment groups are given in Table 10 below. A total of 89 subjects were randomized to Group 1 (low dose) and 86 were randomized to Group 2 (high dose). Of these, 83 subjects in the low dose group and 81 subjects in the high dose received randomized dexmedetomidine for at least 6 hours.

TABLE 10

Doses of Dexmedetomidine

| Diagnosis | Group 1 Low dose | Group 2 High dose |
|---|---|---|
| s/p CPB | Loading dose: 0.2 μg/kg<br>Maintenance dose titration range (0.025-0.5 μg/kg/hr) | Loading dose 0.5 μg/kg<br>Maintenance dose titration range (0.1-0.7 μg/kg/hr) |
| All other diagnoses | Loading dose 0.3 μg/kg<br>Maintenance dose titration range (0.05-0.5 μg/kg/hr) | Loading dose 0.6 μg/kg<br>Maintenance dose titration range (0.2-1.4 μg/kg/hr) |

The median age of age groups combined was 10.7 months (range: 0.9 months to 16.3 years) in the low dose group and 14.7 months (range: 1.3 months to 16.2 years) in the high dose group. Height and weight were similar across dose groups and by underlying condition (median height of age groups combined: low dose 68.0 cm, high dose 76.5 cm; median weight of age groups combined: low dose 8.1 kg; high dose 8.5 kg). Slightly more subjects overall were male than female (low dose, 59.6% male; high dose, 55.8% male). Demographics were similar between treatment groups with most subjects critically ill from severe congenital cardiopulmonary disease (ASA P3).

Patients were further assigned to age group I or II. The number of subjects in each subgroup is given in Table 11 below.

TABLE 11

Number of Subjects in Each Subgroup (Enrolled Subjects)

| | Group 1 Low Dose | | | Group 2 High Dose | | |
|---|---|---|---|---|---|---|
| | s/p CPB[a]<br>N = 36 | Other Dx[b]<br>N = 53 | Total<br>N = 89 | s/p CPB[c]<br>N = 37 | Other Dx[d]<br>N = 49 | Total<br>N = 86 |
| Age Group I[e] | 25 | 38 | 63 | 26 | 34 | 60 |
| Age Group II[f] | 11 | 15 | 26 | 11 | 15 | 26 |
| Total | 36 | 53 | 89 | 37 | 49 | 86 |

Dx = diagnosis
[a]Dex dose is loading dose (LD) = 0.2/Maintenance dose (MD) = 0.025-0.5 μg/kg/hour
[b]Dex dose is LD = 0.3/MD = 0.05-0.5 μg/kg/hour
[c]Dex dose is LD = 0.5/MD = 0.1-0.7 μg/kg/hour
[d]Dex dose is LD = 0.6/MD = 0.2-1.4 μg/kg/hour
[e]Age group I = ≥1 month to <24 months;
[f]Age group II = ≥24 months to <17 years old In age group I, median age was 8.51 months (low dose) and 9.75 months (high dose); in age group II, median age was 6.32 years (low dose) and 7.57 years (high dose). Subjects had similar screening ASA classification in both age groups and both dexmedetomidine dose groups with the majority of subjects having high risk with severe systemic disease, P3. Subjects who underwent open-heart surgery were mostly high risk P3 and there were similar numbers of subjects in the low dose (72.2%) and high dose (73.0%) dexmedetomidine.

All subjects (100.0%) in the high dose group and all except one subject in the low dose group received at least one concomitant medication during the study; concomitant medication use was similar across dose groups. Concomitant medications taken by at least 50.0% of subjects in a dose group, excluding midazolam, fentanyl, and morphine, the use of which was permitted as rescue medication per protocol, were furosemide, acetaminophen, potassium chloride, and heparin. As expected in the s/p CPB groups following open heart surgery, >90% of subjects were on inotropic support postoperatively. Inotropic support with milrinone and dobutamine was similar in both the low and high dose dexmedetomidine groups s/p CPB.

Subjects received an optional loading dose of dexmedetomidine over 10 or 20 minutes followed by the appropriate maintenance dose. Each subject received a continuous infusion maintenance dose of dexmedetomidine for a minimum of 6 but not more than 24 hours.

The dexmedetomidine administered was a Precedex® dexmedetomidine HCl injection manufactured by Hospira, Inc. For subjects s/p CPB, the low dose dexmedetomidine group was titrated between 0.025-0.5 µg/kg/hr and the high dose dexmedetomidine group was titrated between 0.1-0.7 µg/kg/hr; for all other diagnoses, the low dose dexmedetomidine group was titrated between 0.05-0.5 µg/kg/hr and the high dose dexmedetomidine groups was titrated between 0.2-1.4 µg/kg/hr. The continuous infusion of dexmedetomidine was administered for a minimum of 6 and a maximum duration of 24 hours.

The dexmedetomidine administered was a Precedex® dexmedetomidine HCl injection manufactured by Hospira, Inc. Dexmedetomidine hydrochloride (HCl) injection (100 µg/mL, base) was supplied by Hospira to the investigative sites for infusion. Study medication was prepared (diluted) by the site pharmacy. The optional loading doses of dexmedetomidine were diluted in 0.9% sodium chloride or dextrose 5% in water to one of the following concentrations: 4 µg/mL solution for the high dose group and 2 µg/mL solution for the low dose group. Dexmedetomidine was infused using a controlled infusion device. The dexmedetomidine could be administered by a designated IV line for dexmedetomidine and could also be administered via a designated IV line of dexmedetomidine attached to a Y-site adapter, or through a specified side port if given through a central line. No other medications were to be bolused through the dexmedetomidine infusion line. The same syringe or bag used for the loading dose could be used for maintenance—only the rate of infusion changed.

If rescue midazolam was necessary, the dexmedetomidine dose was titrated upwards and the need to administer additional midazolam was reassessed following dexmedetomidine administration. If rescue pain medication was necessary, then fentanyl or morphine was administered after the subject was first treated with an increase in the dexmedetomidine infusion rate, at age-specific doses, or as a continuous infusion. Subjects receiving continuous infusions of fentanyl or morphine prior to randomization could continue these infusions throughout study drug administration if required.

Prior to the start of drug infusion, a baseline score on the UMSS was obtained. The UMSS scale is given in Table 12 below. If a loading dose was administered, the UMSS score was obtained immediately before loading and at 5 and 10 minutes during the loading dose. If the loading dose occurred over 20 minutes, then the UMSS score was obtained at 15 minutes. If no loading dose was administered, the UMSS score was obtained at the start of the maintenance infusion and at 5, 10, 15, 30, and 60 minutes for the first hour. The UMSS score was obtained every 4 hours during the remainder of the maintenance infusion. IF rescue medication was administered, the UMSS score was measured immediately before and 5 minutes after the rescue medication was administered. The UMSS score was also obtained immediately before and 5 minutes after a non-pharmacological intervention, such as swaddling, cuddling, or rocking.

TABLE 12

University of Michigan Sedation Scale

| Clinical Score | Level of Sedation |
| --- | --- |
| 0 | Awake/Alert |
| 1 | Minimally Sedated: Tired/sleepy, appropriate response to verbal conversation and/or sounds. |
| 2 | Moderately Sedated: Somnolent/sleeping, easily aroused with light tactile stimulation. |
| 3 | Deeply sedated: Deep sleep, arousable only with significant physical stimulation. |
| 4 | Unarousable |

Chemistry, hematology and urinalysis samples were obtained for the laboratory tests. A baseline cortisol level test was conducted prior to the start of dexmedetomidine administration. For CPB subjects, this blood draw was obtained postoperatively within 90 minutes following the start of dexmedetomidine. An ACTH-stimulation test were performed at the conclusion of dexmedetomidine infusion.

Safety measures included collection of adverse events (adverse events), heart rate (HR in beats per minute [bpm]), systolic blood pressure (SBP in millimeters of mercury [mmHg]), diastolic blood pressure (DBP in millimeters of mercury [mmHg]), mean arterial pressure (MAP in millimeters of mercury [mmHg]), oxygen saturation by pulse oximetry ($SpO_2$ in percentage), and respiratory rate (RR in breaths/minute [breaths/min]) or ventilator settings, laboratory results, and electrocardiogram (ECG) monitoring.

The statistical analyses were performed using SAS™ Statistical Software System (SAS Institute, Inc., Cary, N.C.), version 9.1. All statistical tests were 2 sided and p values≤0.0500, after rounding to 4 decimal places, were considered statistically significant unless otherwise specified. In general, missing data were not imputed. For continuous variables, N, mean, median, SD, minimum, Q1, Q3 and maximum are presented. The mean and median was displayed to 1 decimal place more than the raw value. The standard deviation (SD) is displayed to 2 decimal places more than the raw value. For categorical variables, N and percent is shown. All percentages were reported to 1 decimal place.

Exposure to dexmedetomidine was highest in the high dose and generally greater in the other diagnoses group. The average maintenance dose of dexmedetomidine in µg/kg/hr in the low dose was 0.33 µg/hr/hr with s/p CPB subjects requiring slightly less maintenance infusion to maintain target sedation. Similarly, in the high dose dexmedetomidine group the maintenance infusion averaged 0.59 µg/kg/hr, with s/p CPB subjects requiring less maintenance infusion. The median duration of maintenance infusion was 1215.0 minutes (20.3 hours) for the low dose group and 1127.5 minutes (18.8 hours) for the high dose group. Median total loading dose was higher for subjects ASA class P3 and P4 than P1 and P2. The median total maintenance dose was similar for ASA Class P1 and P2, and P3 and P4 subjects. The median exposure to dexmedetomidine is given in Table 13 below. The time of exposure is given in Table 14 below.

TABLE 13

Median Exposure to Study Drug by Time Points

| Median Parameter - Age Groups Combined | Group 1 Low Dose | | | Group 2 High Dose | | |
|---|---|---|---|---|---|---|
| | s/p CPB dexmedetomidine dose N = 36 | Other Dx dexmedetomidine dose N = 53 | Total N = 89 | s/p CPB dexmedetomidine dose N = 37 | Other Dx dexmedetomidine dose N = 49 | Total N = 86 |
| *Loading dose* | | | | | | |
| N | 11 | 19 | 30 | 12 | 20 | 32 |
| Total loading dose (μg) | 2.40 | 2.55 | 2.48 | 3.59 | 4.50 | 4.14 |
| Duration (min) | 10.0 | 10.0 | 10.0 | 15.0 | 17.5 | 17.5 |
| *Loading dose; ASA Class: P1 and P2* | | | | | | |
| N | 3 | 7 | 10 | 2 | 7 | 9 |
| Total loading dose (μg) | 1.70 | 2.55 | 2.20 | 5.75 | 3.60 | 3.60 |
| Duration (min) | 10.0 | 10.0 | 10.0 | 15.0 | 10.0 | 10.0 |
| *Loading dose; ASA Class: P3 and P4* | | | | | | |
| N | 8 | 12 | 20 | 10 | 13 | 23 |
| Total loading dose (μg) | 2.78 | 2.78 | 2.78 | 3.38 | 4.80 | 4.50 |
| Duration (min) | 10.0 | 10.0 | 10.0 | 15.0 | 20.0 | 20.0 |
| *Maintenance dose* | | | | | | |
| N | 36 | 53 | 89 | 37 | 49 | 86 |
| Average maintenance dose (μg/kg/hr) | 0.30 | 0.35 | 0.33 | 0.52 | 0.67 | 0.59 |
| Total maintenance dose (μg) | 48.67 | 44.85 | 45.93 | 68.60 | 143.81 | 76.56 |
| Duration (min) | 1114.5 | 1380.0 | 1215.0 | 840.0 | 1252.0 | 1127.5 |
| *Maintenance dose: ASA Class P1 and P2* | | | | | | |
| N | 9 | 22 | 31 | 5 | 16 | 21 |
| Average maintenance dose (μg/kg/hr) | 0.33 | 0.35 | 0.34 | 0.55 | 0.64 | 0.59 |
| Total maintenance dose (μg) | 49.20 | 52.63 | 52.14 | 81.74 | 162.79 | 115.21 |
| Duration (min) | 1110.0 | 1287.5 | 1215.0 | 790.0 | 1374.5 | 1225.0 |
| *Maintenance dose: ASA Class P3 and P4* | | | | | | |
| N | 27 | 31 | 58 | 32 | 33 | 65 |
| Average maintenance dose (μg/kg/hr) | 0.30 | 0.35 | 0.32 | 0.51 | 0.67 | 0.57 |
| Total maintenance dose (μg) | 48.15 | 42.39 | 42.91 | 59.27 | 112.75 | 74.67 |
| Duration (min) | 1119.0 | 1430.0 | 1264.0 | 975.0 | 1159.0 | 1120.0 |

TABLE 14

Time of Exposure

| Median Parameter - Age Groups Combined | Group 1 Low Dose | | | Group 2 High Dose | | |
|---|---|---|---|---|---|---|
| | s/p CPB dexmedetomidine dose N = 36 | Other Dx dexmedetomidine dose N = 53 | Total N = 89 | s/p CPB dexmedetomidine dose N = 37 | Other Dx dexmedetomidine dose N = 49 | Total N = 86 |
| *Time of exposure <1 hour* | | | | | | |
| N | — | — | — | — | 1 | 1 |
| Total dose (μg) | | | | | 7.25 | 7.25 |
| | | | | | 47.0 | 47.0 |

TABLE 14-continued

| | Time of Exposure | | | | | |
|---|---|---|---|---|---|---|
| | Group 1 Low Dose | | | Group 2 High Dose | | |
| Median Parameter - Age Groups Combined | s/p CPB dexmedetomidine dose N = 36 | Other Dx dexmedetomidine dose N = 53 | Total N = 89 | s/p CPB dexmedetomidine dose N = 37 | Other Dx dexmedetomidine dose N = 49 | Total N = 86 |
| *Time of exposure >1 hour* | | | | | | |
| N | 36 | 53 | 89 | 37 | 48 | 85 |
| Average maintenance dose (µg/kg/hr) | 0.30 | 0.35 | 0.33 | 0.52 | 0.67 | 0.59 |
| Total dose (µg) | 48.67 | 46.31 | 46.85 | 68.60 | 146.90 | 79.44 |
| Duration (min) | 1121.0 | 1390.0 | 1215.0 | 848.0 | 1288.5 | 1133.0 |
| *Time of exposure >6 hours* | | | | | | |
| N | 31 | 49 | 80 | 30 | 45 | 75 |
| Average maintenance dose (µg/kg/hr) | 0.31 | 0.35 | 0.33 | 0.52 | 0.67 | 0.59 |
| Total maintenance dose (µg) | 50.69 | 51.49 | 50.97 | 78.49 | 172.80 | 88.26 |
| Duration (min) | 1160.0 | 1415.0 | 1343.5 | 1050.5 | 1320.0 | 1170.0 |
| *Time of exposure >12 hours* | | | | | | |
| N | 26 | 39 | 65 | 23 | 41 | 64 |
| Average maintenance dose (µg/kg/hr) | 0.31 | 0.35 | 0.33 | 0.54 | 0.66 | 0.60 |
| Total maintenance dose (µg) | 53.67 | 59.71 | 56.09 | 86.24 | 172.80 | 112.82 |
| Duration (min) | 1307.5 | 1439.0 | 1411.0 | 1142.0 | 1395.0 | 1266.0 |
| *Time of exposure 0-6 hours* | | | | | | |
| N | 5 | 4 | 9 | 7 | 4 | 11 |
| Average maintenance dose (µg/kg/hr) | 0.23 | 0.39 | 0.30 | 0.49 | 0.63 | 0.56 |
| Total dose (µg) | 11.99 | 9.31 | 11.16 | 25.67 | 30.16 | 28.57 |
| Duration (min) | 357.0 | 147.5 | 353.0 | 360.0 | 305.0 | 360.0 |
| *Time of exposure >6-12 hours* | | | | | | |
| N | 5 | 10 | 15 | 7 | 4 | 11 |
| Average maintenance dose (µg/kg/hr) | 0.33 | 0.34 | 0.33 | 0.50 | 0.96 | 0.56 |
| Total dose (µg) | 25.90 | 41.49 | 36.55 | 31.59 | 106.61 | 34.19 |
| Duration (min) | 470.0 | 438.0 | 466.0 | 533.0 | 542.5 | 533.0 |

Overall the high dose dexmedetomidine group was clinically better sedated than the low dose dexmedetomidine groups with 54.3% of high dose subjects not requiring rescue midazolam compared to 44.6% in the low dose dexmedetomidine groups, although this was not statistically significant (p=0.2751). By age, a smaller percentage of subjects in age group II did not require rescue midazolam for sedation in comparison with age group I in both dexmedetomidine dose groups; this difference was not statistically significant (p=0.6723). In both dose groups subjects undergoing open heart surgery with CPB received more rescue midazolam than those in the other diagnoses groups. The greatest difference between treatment groups was in the heart surgery subjects with more subjects in both age groups receiving high dose dexmedetomidine than low dose dexmedetomidine and not requiring midazolam sedation rescue. The difference was 22.73%, although it was not statistically significant (p=0.0974). Table 15 contains number and percent of subjects who did not require midazolam for sedation during treatment. Table 16 contains the differences between treatment groups in percentage of subjects who did not require midazolam for sedation during treatment.

TABLE 15

Number and Percent of Subjects Who Did Not Require Rescue Midazolam for Sedation During the Treatment Period While Intubated

| Number and Percent of Subjects[a] | s/p CPB dexmedetomidine dose | Other Dx dexmedetomidine dose | Total | s/p CPB dexmedetomidine dose | Other Dx dexmedetomidine dose | Total |
|---|---|---|---|---|---|---|
| Total ASA Class | N = 33 | N = 50 | N = 83 | N = 34 | N = 47 | N = 81 |
| Age Group I[b] | 5 (15.2) | 20 (40.0) | 25 (30.1) | 10 (29.4) | 20 (42.6) | 30 (37.0) |
| Age Group II[c] | 4 (12.1) | 8 (16.0) | 12 (14.5) | 7 (20.6) | 7 (14.9) | 14 (17.3) |
| Total | 9 (27.3) | 28 (56.0) | 37 (44.6) | 17 (50.0) | 27 (57.4) | 44 (54.3) |

TABLE 15-continued

Number and Percent of Subjects Who Did Not Require Rescue Midazolam for Sedation During the Treatment Period While Intubated

| Number and Percent of Subjects[a] | s/p CPB dexmede-tomidine dose | Other Dx dexmede-tomidine dose | Total | s/p CPB dexmede-tomidine dose | Other Dx dexmede-tomidine dose | Total |
|---|---|---|---|---|---|---|
| ASA Class: P1, P2 | N = 8 | N = 21 | N = 29 | N = 5 | N = 16 | N = 21 |
| Age Group I[b] | 1 (12.5) | 8 (38.1) | 9 (31.0) | 1 (20.0) | 7 (43.8) | 8 (38.1) |
| Age Group II[c] | 0 | 4 (19.0) | 4 (13.8) | 0 | 2 (12.5) | 2 (9.5) |
| Total | 1 (12.5) | 12 (57.1) | 13 (44.8) | 1 (20.0) | 9 (56.3) | 10 (47.6) |
| ASA Class: P3, P4 | N = 25 | N = 29 | N = 54 | N = 29 | N = 31 | N = 60 |
| Age Group I[b] | 4 (16.0) | 12 (41.4) | 16 (29.6) | 9 (31.0) | 13 (41.9) | 22 (36.7) |
| Age Group II[c] | 4 (16.0) | 4 (13.8) | 8 (14.8) | 7 (24.1) | 5 (16.1) | 12 (20.0) |
| Total | 8 (32.0) | 16 (55.2) | 24 (44.4) | 16 (55.2) | 18 (58.1) | 34 (56.7) |

[a]Number and percent of subjects who did not require rescue midazolam for sedation based on achieving and maintaining a target UMSS range of 1 to 3 while intubated.
[b]Age group I = ≥1 month to <24 months
[c]Age group II = ≥24 months to <17 years old

TABLE 16

Differences Between Treatment Groups in Percentage of Subjects who did not Require midazolam for Sedation During the Treatment Period While Intubated

| Underlying Condition/ Age Group | Group 1 Low Dose | Group 2 High Dose | Difference (Group 1-2)[b] | p-value[c] |
|---|---|---|---|---|
| Total ASA Class | | | | |
| All Diagnoses [n (%)][a] | 37/83 (44.6) | 44/81 (54.3) | −9.74 | 0.2751 |
| Age Group I[d] | 25/57 (43.9) | 30/56 (53.6) | −9.71 | 0.3984 |
| Age Group II[e] | 12/26 (46.2) | 14/25 (56.0) | −9.85 | 0.6723 |
| s/p CPB [n (%)] | 9/33 (27.3) | 17/34 (50.0) | −22.73 | 0.0974 |
| Age Group I[d] | 5/22 (22.7) | 10/23 (43.5) | −20.75 | 0.2461 |
| Age Group II[e] | 4/11 (36.4) | 7/11 (63.6) | −27.27 | 0.3938 |
| Other Diagnoses [n (%)] | 28/50 (56.0%) | 27/47 (57.4%) | −1.45 | 1.0000 |
| Age Group I[d] | 20/35 (57.1) | 20/33 (60.6) | −3.46 | 0.9653 |
| Age Group II[e] | 8/15 (53.3) | 7/14 (50.0) | 3.33 | 1.0000 |
| ASA Class: P1, P2 | | | | |
| All Diagnoses [n (%)][a] | 13/29 (44.8) | 10/21 (47.6) | −2.79 | 1.0000 |
| Age Group I[d] | 9/19 (47.4) | 8/15 (53.3) | −5.96 | 1.0000 |
| Age Group II[e] | 4/10 (40.0) | 2/6 (33.3) | 6.67 | 1.0000 |
| s/p CPB [n (%)] | 1/8 (12.5) | 1/5 (20.0) | −7.50 | 1.0000 |
| Age Group I[d] | 1/6 (16.7) | 1/3 (33.3) | −16.67 | 1.0000 |
| Age Group II[e] | 0/2 | 0/2 | 0.00 | — |
| Other Diagnoses [n (%)] | 12/21 (57.1) | 9/16 (56.3) | 0.89 | 1.0000 |
| Age Group I[d] | 8/13 (61.5) | 7/12 (58.3) | 3.21 | 1.0000 |
| Age Group II[e] | 4/8 (50.0) | 2/4 (50.0) | 0.00 | 1.0000 |
| ASA Class: P3, P4 | | | | |
| All Diagnoses [n (%)][a] | 24/54 (44.4) | 34/60 (56.7) | −12.22 | 0.2645 |
| Age Group I[d] | 16/38 (42.1) | 22/41 (53.7) | −11.55 | 0.4228 |
| Age Group II[e] | 8/16 (50.0) | 12/19 (63.2) | −13.16 | 0.6594 |
| s/p CPB [n (%)] | 8/25 (32.0) | 16/29 (55.2) | −23.17 | 0.1515 |
| Age Group I[d] | 4/16 (25.0) | 9/20 (45.0) | −20.00 | 0.3722 |
| Age Group II[e] | 4/9 (44.4) | 7/9 (77.8) | −33.33 | 0.3336 |
| Other Diagnoses [n (%)] | 16/29 (55.2) | 18/31 (58.1) | −2.89 | 1.0000 |
| Age Group I[d] | 12/22 (54.5) | 13/21 (61.9) | −7.36 | 0.8573 |
| Age Group II[e] | 4/7 (57.1) | 5/10 (50.0) | 7.14 | 1.0000 |

[a]Subjects who did not require rescue midazolam for sedation based on achieving and maintaining a target UMSS range 1-3 while intubated.
[b]Mean difference between treatment groups in percentage of subjects who did not require rescue midazolam for sedation based on achieving and maintaining a target UMSS of 1-3 while intubated.
[c]P-value for risk difference for 2 x 2 table from Chi-Square test with continuity correction.
[d]Age group I = ≥1 month to <24 months
[e]Age group II = ≥24 months to <17 years old All age groups and diagnoses receiving the high dose of dexmedetomidine were in the targeted UMSS range 87.8 to 99.2% of the time compared to 85.5 to 99.0% of the time in the low dose dexmedetomidine groups. There were no statistical differences between dexmedetomidine dose groups in the absolute time or percentage of time subjects were in the target sedation range (UMSS 1-3). All age groups and diagnoses receiving the low dose of dexmedetomidine were out of the target UMSS range 1.0 to 14.5% of the time compared to 0.8 to 12.2% of the time in the high dose dexmedetomidine groups. There were no statistical differences between dexmedetomidine dose groups in the absolute time or percentage of time subjects were out of the target sedation range (UMSS<1 or >3).

Overall, more rescue midazolam for sedation (total dose and dose/kg) was required in the low dose dexmedetomidine groups than the high dose dexmedetomidine groups, although the differences were not statistically significant. With the age groups combined, 46/83 subjects (55.4%) in the low dose dexmedetomidine group required rescue midazolam for sedation compared with 37/81 subjects (45.7%) in the high dose dexmedetomidine group. Median total amount of rescue midazolam required for sedation while intubated during the treatment period for the subjects that required rescue midazolam for sedation was 1.965 mg (range: 0.19-30.80 mg) in the low dose group and 2.00 mg [range: 0.10-13.20 mg]) the high dose group; and median amount of rescue midazolam per kg was 0.266 mg/kg (range: 0.02-1.49 mg/kg) in the low dose group and 0.179 mg/kg (range: 0.02-1.11 mg/kg) in the high dose group. Results were similar by age group.

With the age groups combined, 53/83 subjects (63.9%) in the low dose dexmedetomidine group and 44/81 subjects (54.3%) in the dexmedetomidine high dose dexmedetomidine group received rescue fentanyl for analgesia while intubated during the treatment period. Median total amount of rescue fentanyl required for analgesia for the subjects who required rescue fentanyl was 46.00 μg (range: 1.50-593.00 μg) in the low dose group and 35.13 μg (range: 1.50-750.00 μg) in the high dose; and median amount per kg of rescue fentanyl required for analgesia was 4.13 μg/kg (range: 0.10-83.52 μg/kg) in the low dose group and 3.25 μg/kg (range: 0.08-35.98 μg/kg) in the high dose group.

With the age groups combined, 35/83 subjects (42.2%) in the low dose group and 32/81 subjects (39.5%) in the dexmedetomidine high dose group received rescue morphine for analgesia while intubated during the treatment period. Median total amount of rescue morphine required for analgesia for the subjects who required rescue morphine was 1.80 mg (range: 0.25-20.50 mg) in the low dose dexmedetomidine group and 1.63 mg (range: 0.32-15.00 mg) in the high dose dexmedetomidine group; and median amount of rescue morphine per kg was 0.20 mg/kg (range: 0.03-4.10 mg/kg) in the low dose dexmedetomidine group and 0.17 mg/kg (range: 0.05-0.57 mg/kg) in the high dose dexmedetomidine group. Difference in time to first rescue medication was not statistically significant; median time from start of dexmedetomidine infusion to first dose of rescue medication was 1.6 hours (95% CI: 0.93, 3.38) in the low dose dexmedetomidine group and 2.0 hours (95% CI: 1.07, 3.75) in the high dose group.

The time to extubation was estimated from the first termination of mechanical ventilation within the dexmedetomidine infusion period until the 24-hour follow-up. If the subject's ventilator setting was not available, and dexmedetomidine was discontinued because it was no longer required for sedation, extubation time was estimated as the end of dexmedetomidine date/time. Subjects with no measurable time to extubation as described above were excluded from analysis. If extubation was successful, the subject was considered to have the event. Subjects who were not extubated were censored; time of censoring was set to the time of the subject's last observation during the corresponding evaluable period and might represent time of subject's withdrawal from the study, time of death, or the time of the last recorded observation during the evaluable period, whichever happened first. Median time to successful extubation was 23.8 hours (95% CI: 18.55, N/A) in the low dose dexmedetomidine group and 20.5 hours (95% CI: 17.13, 23.33) in the high dose dexmedetomidine group; the difference was not statistically significant.

In general, moderate or severe adverse events were more common in the low dose than high dose dexmedetomidine groups and there were more actual events reported in age group I than age group II: in age group I, moderate and severe treatment-related adverse events were experienced by 17 (27.0%; 30 events) and 10 subjects (16.7%; 17 events) in the low and high dose groups, respectively; and in age group II, moderate and severe treatment-related adverse events were experienced by 8 (30.8%; 13 events) and 6 subjects (23.1%; 9 events) in the low and high dose groups, respectively. Overall, 5/175 subjects (2.9%) reported a total of seven severe treatment-related adverse events; all severe treatment-related adverse events were reported in the low dose dexmedetomidine groups. The severe treatment-related adverse events reported were myocarditis, pyrexia, status epilepticus, dyspnea, ventricular fibrillation, chest pain, and wheezing. The severe myocarditis event was also considered a serious treatment-related adverse event.

Treatment-related adverse events experienced by 2 or more subjects in a dose group in age group I were hypotension (3 subjects [4.8%] and 5 subjects [8.3%], in the low and high dose dexmedetomidine groups, respectively), agitation (2 [3.2%] and 4 [6.7%]), and bradycardia (2 [3.2%] and 2 [3.3%]), and hypertension (2 [3.2%] in the low dose dexmedetomidine group); and in age group II, hypotension (2 subjects [7.7%] in the high dose group).

Serious treatment-related adverse events and treatment-related adverse events that led to dexmedetomidine or study discontinuation were only reported in age group I. Two serious treatment-related adverse events were reported in this study, myocarditis (1 subject, low dose) and apnea (1 subject, high dose); both events were considered possibly or probably related to dexmedetomidine. Seven subjects (4.0%) experienced a total of 8 treatment-related adverse events that led to discontinuation of dexmedetomidine (respiratory rate decreased and respiratory acidosis [each 1 subject, low dose] and bradycardia, device electrical finding, endotracheal intubation complication, agitation, apnea, hypotension [each 1 subject, high dose]). Two subjects experienced treatment-related adverse events that led to study discontinuation (oxygen saturation decreased and agitation [1 subject, high dose] and hypotension [1 subject, low dose]). There were 4 deaths, all unrelated to dexmedetomidine. No subjects stopped dexmedetomidine due to death.

Whereas the median amount (total and per kg) of rescue midazolam for sedation and rescue fentanyl and morphine was not statistically significantly different between the low and high dose dexmedetomidine groups, total and per/kg doses of rescue midazolam for sedation, rescue fentanyl for analgesia, and rescue morphine for analgesia trended higher in the low dose dexmedetomidine group.

The study demonstrates that dexmedetomidine was clinically effective at sedating critically ill, initially intubated infants and children following major cardiac surgery with CPB and non-cardiac surgery. There was a non-significant (p=0.2751) dose-response effect observed with more subjects (54.3%) in the high dose dexmedetomidine groups not requiring rescue midazolam to maintain the target sedation than in the low dose dexmedetomidine groups (44.6%), irrespective of age. High dose dexmedetomidine was most effective in the heart surgery subjects (s/p CPB) with more subjects of both age groups who received high dose dexmedetomidine than low dose dexmedetomidine not requiring midazolam sedation rescue (p=0.0974, difference 22.73%). All age groups and diagnoses receiving the high dose of dexmedetomidine were in the target UMSS range (1-3) 87.8 to 99.2% of the time compared to 85.5 to 99.0% of the time in the low dose dexmedetomidine groups; the difference was not statistically significant.

Example 3

Pharmacokinetics of Dexmedetomidine in Pediatric Patients

The present study characterizes the pharmacokinetic and pharmacodynamic profile of dexmedetomidine administered as an intravenous (IV) loading dose followed by a continuous IV infusion in pediatric subjects.

A 56-subject, open-label, multicenter, escalating dose study of dexmedetomidine was conducted on initially intubated and mechanically ventilated pediatric subjects who required sedation in an intensive care setting and was anticipated to require a minimum of 6 hours but not to exceed 24 hours of continuous IV sedation. The present study investigated the pharmacokinetics and pharmacodynamics of dexmedetomidine. The subjects were at least 2 years old and less than 17 years old.

The subjects were separated into two age groups. Group I consisted of children who were at least 2 years old and younger than 6 years old and Group II consisted of children who were at least 6 years old and younger than 17 years old. Within each group there were four escalating dosing levels (Table 17). The subject disposition and demographics of the study are described in Table 18.

A total of 69 subjects were enrolled into the study. Of those, 59 received dexmedetomidine (any amount) and were included in the safety population (26 in Group I, 33 in Group II).

A total of 56 subjects completed the study, 26 in Group I and 30 in Group II. Three patients from Group II were prematurely discontinued from the study due to protocol deviations (1 subject each from Dose Levels 1, 2 and 3).

The full evaluable population consisted of 57 subjects who received the study drug infusion for at least 5 hours (26 in Group I, 31 in Group II). Two subjects from Group II were excluded from the full evaluable population.

Subjects in Group I were primarily male (57.7%) and White (88.5%) with a mean (SD) age of 3.7 (1.12) years. Subjects in Group II were primarily female (63.6%) and White (72.7%) with a mean (SD) age of 10.3 (3.24) years, as shown in Table 18.

The dexmedetomidine administered to the subjects was a Precedex® dexmedetomidine HCl injection (manufactured and supplied by Hospira, Inc.). Dexmedetomidine hydrochloride (HCl) injection (100 μg/mL, base) was supplied to the investigative sites for infusion. Study medication was prepared (diluted) by the site pharmacy to 4 μg/mL in 0.9% sodium chloride and was not refrigerated. The dexmedetomidine was administered as a two-stage IV infusion using a controlled infusion device through a designated IV line, but never directly into the pulmonary artery.

Dexmedetomidine was administered as a two-stage IV infusion with a loading dose infusion for 10 minutes and was immediately followed by a continuous fixed maintenance dose for a minimum of 6 to a maximum of 24 hours, at four increasing dose levels. Each dose increase was dependent on the tolerability of the previous dose. After the subjects completed the dexmedetomidine maintenance infusion, the post-infusion procedures were initiated and continued for 24 hours.

The primary evaluation was the estimation of dexmedetomidine pharmacokinetic parameters for each age group by dose level including AUC (area under the plasma concentration-time curve), $C_{max}$ (observed peak plasma concentration), $C_{s}$ (steady state concentration), CL (plasma clearance), $V_{ss}$ (volume of steady state distribution) and $t_{1/2}$ (terminal half-life).

Safety monitoring included treatment emergent adverse events (TEAEs) (severity, relationship to study drug), vital signs, clinical laboratory results and electrocardiogram (ECG) and physical exam finding.

The dexmedetomidine infusion began after discontinuation of all other sedative and analgesic agents and the subject attained a Ramsay Sedation Scale (RSS) of 2, 3, or 4. The RSS is a clinically derived scale used to quantify depth of anesthesia and has been used in children ranging in age from 1 month to 18 years old. The RSS scale is given in Table 19 below. Rescue medication (midazolam or fentanyl) was administered as needed for sedation and pain, respectively, during study drug administration based on results of the sedation (RSS) and pain (Face, Legs, Activity, Cry, and Consolability [FLACC]) scales. After the discontinuation of dexmedetomidine infusion, further sedation and analgesia was provided per standard of care.

TABLE 17

Study Design

| Group I (Ages ≥2 through <6 years old) Group II (Ages ≥6 through <17 years old) | Loading Dose (10 minutes) | Maintenance Infusion (at least 6 hours and up to 24 hours) | Post-Treatment Period |
|---|---|---|---|
| Level 1 | 0.25 μg/kg | 0.2 μg/kg/hr | 24 hours |
| Level 2 | 0.50 μg/kg | 0.4 μg/kg/hr | 24 hours |
| Level 3 | 1.00 μg/kg | 0.7 μg/kg/hr | 24 hours |
| Level 4 | 1.00 μg/kg | 2.0 μg/kg/hr | 24 hours |

Abbreviations:
DEX = dexmedetomidine

TABLE 18

Subject Demographics-Safety Population

| | Group I | | | | Group II | | | |
|---|---|---|---|---|---|---|---|---|
| Characteristic Mean (SD) | Dose Level 1 (N = 8) | Dose Level 2 (N = 6) | Dose Level 3 (N = 6) | Dose Level 4 (N = 6) | Dose Level 1 (N = 8) | Dose Level 2 (N = 8) | Dose Level 3 (N = 9) | Dose Level 4 (N = 8) |
| Age (years) | 3.4 (1.03) | 3.6 (0.98) | 4.3 (1.50) | 3.6 (0.96) | 9.3 (2.23) | 10.4 (3.99) | 11.1 (3.64) | 10.4 (3.15) |
| % Male | 50.0 | 50.0 | 66.7 | 66.7 | 25.0 | 37.5 | 22.2 | 62.5 |
| % White | 87.5 | 100.0 | 83.3 | 83.3 | 62.5 | 75.0 | 88.9 | 62.5 |
| Weight (kg) | 14.6 (3.02) | 13.8 (3.55) | 16.5 (4.55) | 13.7 (1.75) | 40.5 (28.65) | 32.6 (17.42) | 37.1 (24.42) | 38.5 (19.36) |
| Height (cm) | 96.6 (6.35) | 94.8 (10.42) | 101.5 (10.31) | 101.2 (12.64) | 131.8 (17.71) | 133.6 (23.57) | 132.4 (18.99) | 138.1 (25.52) |

Abbreviations:
DEX = dexmedetomidine

TABLE 19

Ramsay Sedation Scale

| Clinical Score | Level of Sedation |
|---|---|
| 1 | Patient is anxious and agitated or restless, or both. |
| 2 | Patient is cooperative, orientated and tranquil. |
| 3 | Patient responds to command only. |
| 4 | Patient exhibits brisk response to light glabellar (between the eyebrows) tap or loud auditory stimulus. |
| 5 | Patient exhibits a sluggish response to light glabellar tap or loud auditory stimulus. |
| 6 | Patient exhibits no response to stimulus. |

The level of sedation was assessed first using the RSS and then the Richmond Agitation Sedation Scale (RASS) immediately after completion of the RSS. The RASS has been used and validated to quantify depth of anesthesia in adults in the ICU setting; however it has not been validated in infants and children. The purpose of using the RASS in this study was to evaluate the suitability of the RASS in children who were 2 years old to younger than 17 years old. The RASS scale is given in Table 20 below.

TABLE 20

Richmond Agitation Sedation Scale (RASS)

| Score | Term | Description |
|---|---|---|
| +4 | Combative | Overtly combative, violent, immediate danger to staff |
| +3 | Very agitated | Pulls or removes tube(s) or catheter(s); aggressive |
| +2 | Agitated | Frequent non-purposeful movement, fights ventilator |
| +1 | Restless | Anxious but movements not aggressive, vigorous |
| 0 | Alert and calm | |
| −1 | Drowsy | Not fully alert, but has sustained awakening (eye-opening/eye contact) to voice (>10 seconds) |
| −2 | Light Sedation | Briefly awakens with eye contact to voice (<10 seconds) |
| −3 | Moderate Sedation | Movement or eye opening to voice (but no eye contact) |
| −4 | Deep Sedation | No response to voice, but movement or eye opening to physical stimulation. |
| −5 | Unarousable | No response to voice or physical stimulation |

Based on the RSS and RASS scores and clinical judgment, additional rescue sedation with IV midazolam was administered if subjects were not completely sedated. For subjects 6 months to 5 years old, the midazolam dose was 0.05 to 0.1 mg/kg. For subjects 6 to 12 years old, the midazolam dose was 0.025 to 0.05 mg/kg. Subjects who were older than 12 years were administered 1 mg/kg of midazolam.

Pain was assessed using the Faces, Legs, Activity, Cry, and Consolability (FLACC) scale. The FLACC scale is a valid and reliable observational tool used as a measure of pain in children ranging in age from 2 months to 18 years old. The FLACC scale is given in Table 21 below.

TABLE 21

Faces, Legs, Activity, Cry, and Consolability Scale

| | Scoring | | |
|---|---|---|---|
| Category | 0 | 1 | 2 |
| Face | No particular expression or smile | Occasional grimace or frown, withdrawn, disinterested | Frequent to constant quivering chin, clenched jaw |
| Legs | Normal position or relaxed | Uneasy, restless, tense | Kicking, or legs drawn up |
| Activity | Lying quietly, normal position, moves easily | Squirming, shifting back and forth, tense | Arched, rigid, or jerking |
| Cry | No cry (awake or asleep) | Moans or whimpers; occasional complaint | Crying steadily, screams or sobs, frequent complaints |
| Consolability | Content, relaxed | Reassured by occasional touching, hugging or being talked to, distractible | Difficult to console or comfort |

Rescue fentanyl IV was administered at the recommended dose of 0.25 to 1 μg/kg as needed to treat pain based on clinical judgment or FLACC scores greater than 4 while receiving dexmedetomidine infusion. FLACC scores were documented before and within five minutes after the administration of any rescue fentanyl. Each of the five FLACC scale categories was scored from 0 to 2, which resulted in a total score between zero and ten.

Prior medications, defined as medications taken within 48 hours prior to the start of study drug infusion, were taken by 96.6% of the study subjects. The most frequently used prior medications reported for use by subjects were from the nervous system (94.9%), alimentary tract and metabolism (83.1%), and musculoskeletal system (79.7%) drug classes and included the following: fentanyl citrate (81.4%), midazolam (66.1%), magnesium sulfate (28.8%), ranitidine (28.8%), and vecuronium (27.1%).

Concomitant medications were defined as infusion and noninfusion medications received during the study drug infusion period through the post-study drug administration period. Concomitant noninfusion medications were taken by all subjects (100%) and infusion medications were taken by 39.0% of subjects in the enrolled population. The most frequently used concomitant noninfusion medications reported were from the nervous system (100%), alimentary tract and metabolism (98.3%), and antiinfectives for systemic use (96.6%) drug class and included the following: fentanyl citrate (88.1%), midazolam (67.8%), magnesium sulfate (35.6%), and cephalothin (32.2%). The most frequently used concomitant infusion medications reported were from the cardiovascular system (30.5%), blood and blood forming organs (28.8%), nervous system (23.7%), and alimentary tract and metabolism (22.0%) drug class and included the following: milrinone (23.7%), papaverine (20.3%), heparin (18.6%), fentanyl citrate (6.8%), and midazolam (5.1%).

Subjects receiving continuous IV infusions of fentanyl were able to have these infusions re-started after starting the dexmedetomidine infusion. Subjects who were receiving continuous infusions of fentanyl had FLACC scores recorded immediately before and within five minutes after any change in the dose of the fentanyl infusion.

The subjects had to be initially intubated when starting the dexmedetomidine treatment. Once subjects had met site-specified respiratory criteria, they could undergo tracheal extubation, at any time following the start of the loading dose. The dexmedetomidine infusion could be continued during and after the extubation process. Sedation levels and vital signs were monitored and recorded in the peri-extubation period.

The pharmacodynamic and safety measures monitored included: sedation levels (by RSS and RASS scores), heart rate (HR), blood pressure (BP), respiratory rate (RR), and oxygen saturation by pulse oximetry ($SpO_2$). The BP, HR, SpO2, and RR were recorded prior to the loading dose, at 5 and 10 minutes during the load, and hourly during the maintenance infusion, as close as possible (up to 5 minutes prior) to the scheduled pharmacokinetic sampling times, and concurrent with the RSS, RASS, and the FLACC scale. Cardiac monitoring was continuous. A 12-lead ECG was obtained after five hours of maintenance infusion but before discontinuing the infusion. After discontinuing the infusion, HR, BP, RR, and $SpO_2$ were recorded every 15 minutes for the first hour, every 30 minutes for 2 hours, every hour for 3 hours and then every 4 hours until last pharmacokinetic sample was obtained. Vital signs were obtained in conjunction with the pharmacokinetic samples, up to five minutes prior.

The dexmedetomidine infusion rate was not titrated during this trial. After the discontinuation of the dexmedetomidine infusion, further sedation and analgesia may have been provided per standard of care; however, dexmedetomidine was not restarted until after the last pharmacokinetic sample was obtained.

Venous or arterial blood samples were collected for determination of plasma dexmedetomidine concentrations. Blood samples were collected via a peripheral venous, central venous, peripherally inserted central venous catheter (PICC) or arterial line into heparinized vacutainer tubes for pharmacokinetic analysis. An arterial line must have already been in place as part of the standard of care in order to have been used for sample collection. In no case was an arterial line placed for the sole reason of collection of pharmacokinetic samples. Additionally, all pharmacokinetic samples were drawn consistently from either a venous or an arterial access for the duration of the study; interchangeability between venous and arterial draws was not allowed. Blood samples were collected at each of the following time points: no more than 30 minutes prior to the start of the loading dose; within five minutes before the loading dose was finished and simultaneous with the start of the maintenance infusion; 0.5, 1, 2 and 4 to 6 hours after the start of maintenance infusion; within 30 minutes prior to the end of maintenance infusion, which must have been within 24 hours of start of maintenance infusion; ten minutes after the maintenance infusion had ended; and 0.5, 1, 2, 4 and 10 hours after the maintenance infusion had ended.

For pharmacokinetic analyses, venous blood samples (1 mL) were collected in heparinized tubes at a site opposite from the site of infusion (e.g., left arm vs. right arm). Samples were not drawn from the second lumen of a multi-lumen catheter through which drug was being administered. If arterial blood samples (1 mL) were collected, heparinized tubes were also used.

The pharmacokinetic analysis was performed using model independent methods. The primary evaluation was the assessment of dexmedetomidine pharmacokinetics on the full evaluable population. As used herein, the term "full evaluable population" refers to the pediatric subjects who received at least 5 hours of dexmedetomidine infusion. As used herein, the term "safety population" refers to the pediatric subjects who received any amount of dexmedetomidine.

Pharmacokinetic parameters were estimated by non-compartmental methods. Parameters estimated included: AUC (area under the plasma concentration-time curve), $C_{max}$ (observed peak plasma concentration), CL (plasma clearance), $C_{ss}$ (steady state concentration), $V_{ss}$ (volume of steady state distribution), and $t_{1/2}$ (terminal half-life).

Additional parameters were determined as deemed appropriate. Plasma concentrations and resultant pharmacokinetic parameters were summarized by descriptive statistics, number of subjects, arithmetic mean, SD, coefficient of variation (CV), median, and range (minimum and maximum).

An assessment of dose proportionality was made for AUC and $C_{max}$ among the dose levels administered. The Power Analysis approach and data visualization techniques were used for this assessment.

The primary evaluation was the assessment of dexmedetomidine pharmacokinetics. The pharmacokinetic analyses were summarized for each age group by dose level for the full evaluable population, as a primary analysis. Data from all full evaluable subjects were included in the analysis. The pharmacokinetic parameters were estimated by non-compartmental methods. Summary statistics for the pharmacokinetic parameters were tabulated. Only subjects with sufficient pharmacokinetic and pharmacodynamic data to calculate the pharmacokinetic and pharmacodynamic parameters were included in the analysis population.

In order to identify pharmacokinetic variation among different dosing levels and different age groups, plots of mean plasma dexmedetomidine concentrations vs. time curve during the study drug infusion period and post-study drug infusion by dose level were produced for each age group. An overlay plot of individual plasma dexmedetomidine concentrations vs. time by dose level was generated. Descriptive statistics of $C_{ss}$, $C_{max}$, $V_{ss}$, CL, AUC, $t_{1/2}$, time of maximum concentration ($t_{max}$), terminal elimination rate constant ($\lambda z$), volume of distribution ($V_d$), and weight-adjusted CL and $V_d$ were summarized by dose level for each age group. Within each dose level, a 2-sample t-test was used to assess the difference of these pharmacokinetic parameters between age groups. The overall dose level by age group was assessed with a 2-way analysis of variance. In addition, $V_{ss}$ and CL were also summarized by pooling data from all dose levels within each age group, and a 2-sample t-test was used to assess the difference between age groups.

Scatter plots of $V_{ss}$ and CL vs. age (yrs) and $V_{ss}$ and CL vs. weight (kg) were visually produced with data pooled from all dose levels and age groups. The association between these pharmacokinetic parameters, adjusted for weight or dose, was assessed by linear or non-linear regression analysis based on the results from the dose proportionality analysis.

The pharmacodynamic analyses were summarized for each age group by dose level for the full evaluable population, as a primary analysis, and for the safety population, as a secondary analysis. The following descriptive statistics were summarized by dose level for each age group: $RSS_5$, $RSS_{avg}$, N (%) of subjects who received rescue midazolam, time to first use of rescue midazolam, total amount of rescue midazolam, N (%) of subjects who received rescue fentanyl, total amount of rescue fentanyl, N (%) of subjects who were converted to alternative sedative or analgesic therapy, time to successful extubation, and change from baseline in mean, maximum, and minimum values of HR, SBP, DBP, MAP, RR, $SpO_2$ during infusion and post-infusion. As used herein, the term "baseline" refers to just prior to loading of dexmedetomidine.

The following descriptive statistics were also summarized, respectively, for subjects who received dexmedetomidine alone and for subjects who received dexmedetomidine with co-administration of midazolam or fentanyl: $RSS_5$, $RSS_{avg}$, N (%) of subjects who were converted to alternative sedative or analgesic therapy, time to extubation, change from baseline in mean, max, and min values of HR, SBP, DBP, MAP, RR, SpO$_2$ during infusion and post-infusion. These analyses were performed for each age group by pooling data from all dose levels within the age group.

In addition, the time to the first rescue medication for sedation and the time to successful extubation were assessed with the Kaplan-Meier method. Treatment group comparison and/or subjects who received dexmedetomidine alone and subjects who received dexmedetomidine with co-administration of midazolam or fentanyl for successful extubation were then assessed with log-rank and Wilcoxon tests.

The relationship between the level of sedation and plasma concentration, supplemental sedation requirements, and impact of dexmedetomidine alone, and with co-administration of midazolam or fentanyl, on sedation, HR, and BP was analyzed. Subsequent pharmacokinetic and pharmacodynamic relationships and modeling were done to identify covariates that may further explain inter-individual variability in the pharmacokinetic and pharmacodynamic parameters.

The statistical analyses, summary tables, and data listings were performed or prepared using SAS® software, Version 9.1. Pharmacokinetic parameters were calculated using the computer program WinNonlin (Version 5.1 or higher—PharSight, Mountainview, Calif.).

Summaries of the percentages of subjects stratified by dose level and age group who were intubated and simultaneously received rescue midazolam for sedation during the treatment period are presented in Table 22 for the full evaluable population. A summary of the weight-adjusted total amount of rescue medication (midazolam, fentanyl) required for sedation and analgesia while intubated during the treatment period for the full evaluable population is shown in Table 23. A summary of the total amount of rescue medication (midazolam, fentanyl) required for sedation and analgesia while intubated during the treatment period for the full evaluable population is shown in Table 24. A smaller percentage of subjects in Group II received rescue midazolam for sedation in comparison with Group I across all treatment groups in the full evaluable population, except for in the Dose Level 4 treatment group, (37.5% vs. 50.0%, 42.9% vs. 66.7%, 25.0% vs. 50.0%, and 25.0% vs. 16.7% in the Dose Level 1, 2, 3, and 4 treatment groups, respectively, in Group II vs. Group I, respectively). The differences between age groups in the number of subjects that received rescue midazolam were not statistically significant in any of the treatment groups for both the full evaluable and safety populations. For the safety population overall, there were no statistically significant differences between dose level groups in the total amount of rescue medications required for sedation or analgesia in subjects while intubated.

TABLE 22

Summary of Percentage of Subjects Who Received Rescue Midazolam for Sedation During Treatment Period While Intubated, Stratified by Dose Level and Age Group - Full Evaluable Population

| Parameter/ Statistics | Dose Level 1 N = 16 | Dose Level 2 N = 13 | Dose Level 3 N = 14 | Dose Level 4 N = 14 | P-value |
|---|---|---|---|---|---|
| Group I n (%) | 4 (50.0) | 4 (66.7) | 3 (50.0) | 1 (16.7) | 0.2446[b] |
| Group II n (%) | 3 (37.5) | 3 (42.9) | 2 (25.0) | 2 (25.0) | 0.5110[b] |
| Total Age Group n (%) | 7 (43.8) | 7 (53.8) | 5 (35.7) | 3 (21.4) | — |
| P-values for Differences[a] | 1.0000 | 0.5921 | 0.5804 | 1.0000 | — |
| Overall CMH Test[c] | — | — | — | — | 0.9997 |
| Raw Mean Scores Differ DF | — | — | — | — | 1 |
| Probability | — | — | — | — | 0.3174 |

Abbreviations:
CMH = Cochran-Mantel-Haenszel;
midazolam = midazolam

[a]Differences between age Groups I and II within each dose level using Fisher's exact test.
[b]P-value of Cochran-Armitage trend test within age group.
[c]Overall Cochran-Mantel-Haenszel test with a strata age group.

Note:
Group I: Ages ≥2 through 6 years old; Group II: Ages ≥6 through 17 years old.

Note:
Dose Level 1- Dex LD = 0.25/CD = 0.2 µg/kg/hr
Dose Level 2- Dex LD = 0.50/CD = 0.4 µg/kg/hr
Dose Level 3- Dex LD = 1.00/CD = 0.7 µg/kg/hr
Dose Level 4- Dex LD = 1.00/CD = 2.00 µg/kg/hr

TABLE 23

Summary of Weight-Adjusted Total Amount of Rescue Medication (Midazolam, Fentanyl) Required for Sedation and Analgesia While Intubated During the Treatment Period - Full Evaluable Population.

| Total Amount of Rescue Medication | Dose Level 1 DEX N = 16 | Dose Level 2 DEX N = 13 | Dose Level 3 DEX N = 14 | Dose Level 4 DEX N = 14 | P-value |
|---|---|---|---|---|---|
| Midazolam (mg/kg)[a] | | | | | |
| Mean (SD) | 0.067 (0.1024) | 0.087 (0.1646) | 0.109 (0.2229) | 0.045 (0.1053) | |
| Median (Min, Max) | 0 (0, 0.31) | 0.028 (0, 0.60) | 0 (0, 0.82) | 0 (0, 0.30) | |
| Wilcoxon | | | | | 0.5766[b] |
| Median | | | | | 0.3751[b] |
| Fentanyl (µg/kg)[a] | | | | | |
| Mean (SD) | 2.24 (2.114) | 191.13 (668.890) | 2.84 (5.572) | 2.26 (2.601) | |
| Median (Min, Max) | 1.91 (0, 8.0) | 2.68 (0, 2417.0) | 1.54 (0, 22.0) | 1.75 (0, 8.0) | |

TABLE 23-continued

Summary of Weight-Adjusted Total Amount of Rescue Medication (Midazolam, Fentanyl) Required for Sedation and Analgesia While Intubated During the Treatment Period - Full Evaluable Population.

| Total Amount of Rescue Medication | Dose Level 1 DEX N = 16 | Dose Level 2 DEX N = 13 | Dose Level 3 DEX N = 14 | Dose Level 4 DEX N = 14 | P-value |
|---|---|---|---|---|---|
| Wilcoxon |  |  |  |  | 0.6896[b] |
| Median |  |  |  |  | 0.3471[b] |

Abbreviations:
CD = continuous dose;
DEX = dexmedetomidine;
LD = loading dose;
MAX = maximum;
midazolam = midazolam;
Min = minimum
Note:
Dose Level 1- Dex LD = 0.25/CD = 0.2 μg/kg/hr
Dose Level 2- Dex LD = 0.50/CD = 0.4 μg/kg/hr
Dose Level 3- Dex LD = 1.00/CD = 0.7 μg/kg/hr
Dose Level 4- Dex LD = 1.00/CD = 2.00 μg/kg/hr
[a]Descriptive statistics are computed based on total number of subjects whether or not they used any amount of rescue medication for sedation during the treatment period while intubated, within each dose level.
[b]P-values from Proc NPAR1WAY for specified tests.

TABLE 24

Summary of Total Amount of Rescue Medication (Midazolam, Fentanyl) Required for Sedation and Analgesia While Intubated During the Treatment Period - Full Evaluable Population.

| Total Amount of Rescue Medication | Dose Level 1 DEX N = 16 | Dose Level 2 DEX N = 13 | Dose Level 3 DEX N = 14 | Dose Level 4 DEX N = 14 | P-value |
|---|---|---|---|---|---|
| Midazolam (mg/kg)[a] | | | | | |
| Mean (SD) | 1.292 (1.8682) | 1.369 (2.3948) | 2.141 (3.9875) | 0.769 (1.8408) | |
| Median (Min, Max) | 0 (0, 6.00) | 1.000 (0, 8.82) | 0 (0, 12.72) | 0 (0, 6.00) | |
| Wilcoxon | | | | | 0.5148[b] |
| Median | | | | | 0.3751[b] |
| Fentanyl (μg)[a] | | | | | |
| Mean (SD) | 49.72 (72.396) | 3575.97 (12507.111) | 51.61 (67.885) | 35.46 (39.323) | |
| Median (Min, Max) | 36.00 (0, 300.0) | 55.00 (0, 45198.8) | 30.00 (0, 270.0) | 33.00 (0, 120.0) | |
| Wilcoxon | | | | | 0.5676[b] |
| Median | | | | | 0.6249[b] |

Abbreviations:
CD = continuous dose;
DEX = dexmedetomidine;
LD = loading dose;
MAX = maximum;
midazolam = midazolam;
Min = minimum
Note:
Dose Level 1- Dex LD = 0.25/CD = 0.2 μg/kg/hr
Dose Level 2- Dex LD = 0.50/CD = 0.4 μg/kg/hr
Dose Level 3- Dex LD = 1.00/CD = 0.7 μg/kg/hr
Dose Level 4- Dex LD = 1.00/CD = 2.00 μg/kg/hr
[a]Descriptive statistics are computed based on total number of subjects whether or not they used any amount of rescue medication for sedation during the treatment period while intubated, within each dose level.
[b]P-values from Proc NPAR1WAY for specified tests.

The time to first rescue medication for sedation and analgesia in the full evaluable population, as presented in Table 25, demonstrated a trend reflecting longer median times to first rescue with increasing dose levels with similar time intervals for Dose Levels 2 and 3 treatment groups (2.2 and 2.5 hours), while the time to first rescue medication was shorter for the Dose Level 1 treatment group (1.0 hours) and longer for the Dose Level 4 treatment group (7.8 hours). This trend was not statistically significant (P=0.2391 Log-Rank), as shown in Table 26. A comparable trend was observed in the safety population, except the effect was not monotonic. The time to rescue for the Dose Level 2 treatment group (2.5 hours) was slightly greater than the Dose Level 3 treatment group (2.4 hours).

TABLE 25

Summary of Time (Hours) to First Dose of Rescue Medication for Sedation and Analgesia - Full Evaluable Population

| Parameter | Dose Level 1 Dex | Dose Level 2 Dex | Dose Level 3 Dex | Dose Level 4 Dex | Overall P-value[c] |
|---|---|---|---|---|---|
| Median[a] | 1.0 | 2.2 | 2.5 | 7.8 | |
| 95% CI[b] | (0.417, 3.500) | (0.600, 3.333) | (1.367, 3.867) | (1.250)[d] | |
| N (%) Censored | 4 (25.0) | 2 (15.4) | 1 (7.1) | 6 (42.9) | |
| Log-Rank | | | | | 0.2391 |
| Wilcoxon | | | | | 0.2021 |

Abbreviations:
CD = continuous dose;
DEX = dexmedetomidine;
LD = loading dose;
MAX = maximum;
midazolam = midazolam;
Min = minimum Note:
Dose Level 1- Dex LD = 0.25/CD = 0.2 µg/kg/hr
Dose Level 2- Dex LD = 0.50/CD = 0.4 µg/kg/hr
Dose Level 3- Dex LD = 1.00/CD = 0.7 µg/kg/hr
Dose Level 4- Dex LD = 1.00/CD = 2.00 µg/kg/hr

[a]Descriptive statistics are computed based on total number of subjects whether or not they used any amount of rescue medication for sedation during the treatment period while intubated, within each dose level.
[b]P-values from Proc NPAR1WAY for specified tests.
[c]P-value from Log-Rank and Wilcoxon tests for difference between treatment groups (using PROC LIFETEST with strata dose level).
[d]CI lower bound only. No upper bound.

TABLE 26

Summary of Time (Hours) to First Dose of Rescue Medication for Sedation and Analgesia - Full Evaluable Population

| Parameter | Dose Level 1 Dex | Dose Level 2 Dex | Dose Level 3 Dex | Dose Level 4 Dex | Overall P-value[c] |
|---|---|---|---|---|---|
| Median[a] | 1.0 | 2.5 | 2.4 | 7.8 | |
| 95% CI[b] | (0.417, 3.500) | (0.600, 9.667) | (1.367, 3.417) | (1.250)[d] | |
| N (%) Censored | 4 (25.0) | 3 (21.4) | 1 (6.7) | 6 (42.9) | |
| Log-Rank | | | | | 0.2617 |
| Wilcoxon | | | | | 0.2254 |

Abbreviations:
CD = continuous dose;
CI = confidence interval;
DEX = dexmedetomidine;
LD = loading dose Note:
Summary of time to first dose of rescue medication for sedation and analgesia done using Kaplan-Meier Estimates, Log-Rank and Wilcoxon tests.

Note:
Dose Level 1- Dex LD = 0.25/CD = 0.2 µg/kg/hr
Dose Level 2- Dex LD = 0.50/CD = 0.4 µg/kg/hr
Dose Level 3- Dex LD = 1.00/CD = 0.7 µg/kg/hr
Dose Level 4- Dex LD = 1.00/CD = 2.00 µg/kg/hr Note:
If the subject received rescue medication, the subject is considered to have the event. If the subject did not complete the treatment/discontinued, the subject is censored.
[a]Median time to successful extubation from start of DEX infusion in hours.
[b]95% CI for median.
[c]P-value from Log-Rank and Wilcoxon tests for difference between treatment groups (using PROC LIFETEST with strata dose level).
[d]CI lower bound only. No upper bound.

In Group I, the mean total doses were 30.9200, 100.1147, 94.0000, and 663.5800 µg for the Dose Level 1, 2, 3, and 4 treatment groups, respectively, with the exception of the Dose Level 3 treatment group that showed a small decrease, exposure generally increased as the dose level increased. In Group II, the mean total doses were 73.1150, 236.9350, 269.2444, and 586.2825 µg for the Dose Level 1, 2, 3, and 4 treatment groups. For all treatment groups in Group II, exposure increased as the dose level increased. The total exposure to dexmedetomidine for the safety population is given in Table 27 below.

TABLE 27

Total Exposure for Dexmedetomidine - Safety Population

| | Group I - Dose Level | | | | Group II - Dose Level | | | |
|---|---|---|---|---|---|---|---|---|
| | 1 | 2 | 3 | 4 | 1 | 2 | 3 | 4 |
| Mean Total Dose (µg) | 30.9 | 100.1 | 94.0 | 663.6 | 73.1 | 236.9 | 269.2 | 586.3 |

Summary statistics for the dexmedetomidine loading doses and maintenance infusion doses are shown in Table 27A below.

TABLE 27A

Summary Statistics of Dosing-Related Data

| Dose-Related Variable | | 0.25 µg/kg + 0.20 µg/kg/h | 0.50 µg/kg + 0.40 µg/kg/h | 1.00 µg/kg + 0.70 µg/kg/h | 1.00 µg/kg + 2.00 µg/kg/h |
|---|---|---|---|---|---|
| Loading dose (ng) | Mean (SD) | 7021.333 (6098.953) | 12237.143 (7955.193) | 28765.333 (21368.168) | 36904.286 (35112.824) |
| | Median | 4400.000 | 9800.000 | 23400.000 | 20900.000 |
| | Min, Max | 2800.00, 24800.00 | 5200.00, 35480.00 | 12000.00, 98000.00 | 12000.00, 140000.00 |
| | n | 15 | 14 | 15 | 14 |
| Maintenance infusion dose (ng) | Mean (SD) | 42797.333 (33346.443) | 108335.571 (86027.962) | 170381.333 (151015.142) | 473520.000 (196870.668) |
| | Median | 26520.000 | 104400.000 | 117600.000 | 462200.000 |

TABLE 27A-continued

Summary Statistics of Dosing-Related Data

| Dose-Related Variable | | 0.25 µg/kg + 0.20 µg/kg/h | 0.50 µg/kg + 0.40 µg/kg/h | 1.00 µg/kg + 0.70 µg/kg/h | 1.00 µg/kg + 2.00 µg/kg/h |
|---|---|---|---|---|---|
| | Min, Max | 12000.00, 125200.00 | 22760.00, 360920.00 | 58800.00, 595600.00 | 153080.00, 828800.00 |
| | n | 15 | 14 | 15 | 14 |
| Total dose (ng) | Mean (SD) | 49818.667 (38564.475) | 120572.714 (92121.808) | 199146.667 (158726.350) | 510424.286 (202156.184) |
| | Median | 32000.000 | 117000.000 | 141600.000 | 474800.000 |
| | Min, Max | 14800.00, 150000.00 | 33200.00, 396400.00 | 70800.00, 635200.00 | 165880.00, 892360.00 |
| | n | 15 | 14 | 15 | 14 |
| Loading infusion duration (h) | Mean (SD) | 0.167 (0.000) | 0.167 (0.000) | 0.167 (0.000) | 0.167 (0.000) |
| | Median | 0.167 | 0.167 | 0.167 | 0.167 |
| | Min, Max | 0.17, 0.17 | 0.17, 0.17 | 0.17, 0.17 | 0.17, 0.17 |
| | n | 15 | 14 | 15 | 14 |
| Maintenance infusion duration (h) | Mean (SD) | 7.919 (3.855) | 11.514 (6.771) | 8.792 (5.371) | 10.196 (4.837) |
| | Median | 6.000 | 7.000 | 7.000 | 7.075 |
| | Min, Max | 487, 15.83 | 2.25, 20.82 | 2.50, 20.25 | 6.00, 17.67 |
| | n | 15 | 14 | 15 | 14 |
| Time between start of doses (min) | Mean (SD) | 10.533 (1.302) | 10.214 (0.579) | 10.400 (1.298) | 10.357 (1.336) |
| | Median | 10.000 | 10.000 | 10.000 | 10.000 |
| | Min, Max | 10.00, 15.00 | 10.00, 12.00 | 10.000, 15.00 | 10.00, 15.00 |
| | n | 15 | 14 | 15 | 14 |
| Time from end of 1$^{st}$ to beginning of 2$^{nd}$ infusion (min) | Mean (SD) | 0.533 (1.302) | 0.214 (0.579) | 0.400 (1.298) | 0.357 (1.336) |
| | Median | 0.000 | 0.000 | 0.000 | 0.000 |
| | Min, Max | 0.00, 5.00 | 0.00, 2.00 | 0.00, 5.00 | 0.00, 5.00 |
| | n | 15 | 14 | 15 | 14 |

Figure 1:
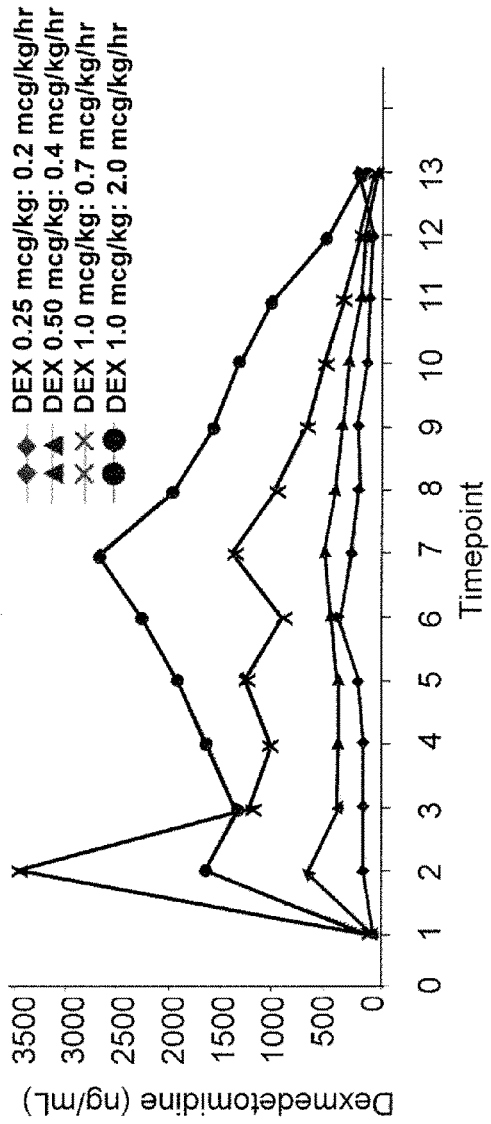
FIG. 1 depicts the mean plasma concentration of dexmedetomidine over time for the full evaluable population in Example 3.

The mean dexmedetomidine concentration profiles (over time) for the Dose Levels 1 and 2 were similar and remained generally the same over time as illustrated in FIG. 1. For the Dose Level 3 treatment group, the mean plasma dexmedetomidine concentration showed a sharp increase at the end of the loading dose compared to other dose levels. The sharp increase was the result an excessively high plasma dexmedetomidine concentration at the end of the loading dose in a subject (Subject 123009) in the Dose Level 3 treatment group. Subject 123009 had a mean area under the concentration-time curve from time zero to the time of the last measurable concentration ($AUC_{0-t}$)=116910.2 µg/mL/hr and area under the concentration-time curve from time zero to the time infinity ($AUC_{0-\infty}$)=117264.1 µg/mL/hr, and $C_{max}$=28804.30 µg/mL). Mean plasma concentrations of dexmedetomidine tended to increase with increasing dose levels. The highest mean plasma concentrations were observed in the Dose Level 4 treatment group. The mean concentration at the end of the maintenance infusion, AUC, $C_{ss}$, and $C_{max}$ values increased with increasing dose.

The mean half-life values for the Dose Level 1, 2, 3, and 4 treatment groups (combined across age groups) were 1.546, 1.743, 2.045, and 2.145 hours, respectively. The apparent increase in half-life with increasing dose levels is due to many of the concentrations used to calculate the half-life for the lower dose levels being below the limit of quantitation.

Statistically significant differences were observed between Groups I and II within each dose level for the pharmacokinetic parameters of $V_d$ (p=0.0046), weight adjusted $V_d$ (p=0.0040), and CL (p=0.0078), and weight adjusted CL (p=0.0094), as shown in Table 28.

TABLE 28

Summary of Statistically Significant Differences Between Group I and Group II Subjects Within Each Dose Level for Pharmacokinetic Parameters - Full Evaluable Population

| | Geometric Means[a,b] | | | | |
|---|---|---|---|---|---|
| Parameter/ Statistics | Dose Level 1 DEX N = 16 | Dose Level 2 DEX N = 14 | Dose Level 3 DEX N = 15 | Dose Level 4 DEX N = 14 | P-Value |
| Group I | | | | | |
| $V_d$ | 36.91 | 31.77 | 46.64 | 36.29 | |
| CL | 16.24 | 12.73 | 16.59 | 11.93 | |
| Group II | | | | | |
| $V_d$ | 51.70 | 61.17 | 46.58 | 72.82 | |
| CL | 24.69 | 24.76 | 16.44 | 25.36 | |
| Differences[c] | | | | | |
| $V_d$ | −0.337 (−1.399, 0.725) | −0.655 (−1.096, −0.215) | 0.001 (−0.626, 0.628) | −0.696 (−1.212, −0.181) | 0.0046 |
| CL | −0.419 (−1.669, 0.831) | −0.665 (−1.068, −0.262) | 0.009 (−0.663, 0.680) | −0.754 (−1.389, −0.119) | 0.0078 |

Abbreviations:
CD = continuous dose;
CL = plasma clearance;
DEX = dexmedetomidine;
LD = loading dose;
PK = pharmacokinetics;
$V_d$ = volume of distribution
Note:
Dose Level 1- Dex LD = 0.25/CD = 0.2 µg/kg/hr
Dose Level 2- Dex LD = 0.50/CD = 0.4 µg/kg/hr
Dose Level 3- Dex LD = 1.00/CD = 0.7 µg/kg/hr
Dose Level 4- Dex LD = 1.00/CD = 2.00 µg/kg/hr Statistically significant differences ($p<0.05$) were observed in PK parameters by dose level for $AUC_{0-t}$, $C_{max}$, $t_{1/2}$, $AUC_{0-\infty}$, $C_{ss}$ and $\lambda z$ and by age for Css ($p=0.0167$), $C_{max}$ ($p=0.0053$), $V_d$ ($p=0.0089$) and CL ($p=0.0125$), and weight adjusted $V_d$ ($p=0.0055$) and CL ($p=0.0190$).

Pharmacokinetic parameters of dexmedetomidine in the full evaluable population were summarized using descriptive statistics and are presented in Table 29. Similar results were obtained in subjects that underwent cardiopulmonary bypass surgery.

TABLE 29

Summary of Pharmacokinetic Parameters - Full Evaluable Population

| Parameter/ Statistics | Dose Level 1 DEX | Dose Level 2 DEX | Dose Level 3 DEX | Dose Level 4 DEX |
|---|---|---|---|---|
| *Primary Pharmacokinetic Parameters* | | | | |
| $AUC_{0-t}$ [(μg/mL)hr] (N) | 14 | 13 | 14 | 14 |
| Mean (SD) | 2681.332 (2353.3418) | 6460.576 (3766.4657) | 16992.540 (29927.3911) | 28531.864 (17496.3985) |
| Median (Min, Max) | 1540.417 (779.88, 9266.09) | 5247.638 (1900.23, 12194.00) | 5606.310 (4257.50, 116910.2) | 25411.857 (10027.42, 68850.45) |
| % CV | 87.77 | 58.30 | 176.12 | 61.32 |
| $AUC_{0-\infty}$ [(μg/mL)hr] (N) | 12 | 13 | 14 | 14 |
| Mean (SD) | 3153.518 (3343.3451) | 6673.163 (3781.2183) | 17300.539 (29935.7647) | 28970.541 (17936.8970) |
| Median (Min, Max) | 1583.539 (923.23, 12681.98) | 5521.515 (2023.22, 12413.04) | 6078.304 (4568.71, 117264.1) | 25675.767 (10093.96, 70764.26) |
| % CV | 106.02 | 56.66 | 173.03 | 61.91 |
| $C_{max}$ (μg/mL)(N) | 14 | 13 | 14 | 14 |
| Mean (SD) | 480.437 (625.9946) | 847.691 (633.7352) | 3385.569 (7384.0699) | 3090.939 (1625.5241) |
| Median (Min, Max) | 266.465 (169.58, 2558.19) | 581.040 (399.60, 2456.03) | 966.235 (534.11, 28804.30) | 2686.210 (1540.85, 6810.13) |
| % CV | 130.30 | 74.76 | 218.10 | 52.59 |
| $T_{max}$ (hours)(N) | 14 | 13 | 14 | 14 |
| Mean (SD) | 7.307 (5.7937) | 8.805 (9.5105) | 2.174 (2.7535) | 6.815 (5.9039) |
| Median (Min, Max) | 6.042 (0.08, 16.17) | 5.683 (0.12, 20.93) | 0.167 (0.08, 6.33) | 5.417 (0.13, 17.60) |
| % CV | 79.29 | 108.01 | 126.66 | 86.63 |
| $t_{1/2}$ (hours)(N) | 12 | 13 | 14 | 14 |
| Mean (SD) | 1.546 (0.3401) | 1.743 (0.3018) | 2.045 (0.6582) | 2.145 (0.6763) |
| Median (Min, Max) | 1.556 (1.03, 2.28) | 1.687 (1.27, 2.45) | 1.795 (1.24, 3.33) | 2.125 (0.98, 3.33) |
| % CV | 22.00 | 17.31 | 32.18 | 31.53 |
| $\lambda_z$ (1/hour)(N) | 12 | 13 | 14 | 14 |
| Mean (SD) | 0.469 (0.1062) | 0.408 (0.0672) | 0.369 (0.1037) | 0.360 (0.1350) |
| Median (Min, Max) | 0.446 (0.30, 0.67) | 0.411 (0.28, 0.54) | 0.386 (0.21, 0.56) | 0.326 (0.21, 0.71) |
| % CV | 22.64 | 16.46 | 28.13 | 37.56 |
| $C_{ss}$ (μg/mL)(N) | 12 | 13 | 14 | 14 |
| Mean (SD) | 402.026 (535.1718) | 539.848 (166.7423) | 1347.284 (1308.0988) | 2827.144 (1169.4226) |
| Median (Min, Max) | 197.991 (149.71, 2056.54) | 513.902 (282.31, 868.84) | 947.907 (637.50, 5743.55) | 2665.409 (1602.66, 5429.48) |
| % CV | 133.12 | 30.89 | 97.09 | 41.36 |
| $V_d$ (L)(N) | 12 | 13 | 14 | 14 |
| Mean (SD) | 61.982 (66.0605) | 50.632 (26.2671) | 52.328 (25.5848) | 62.186 (34.7628) |
| Median (Min, Max) | 42.960 (13.76, 238.30) | 40.657 (23.67, 95.26) | 51.303 (17.22, 100.71) | 57.802 (23.17, 138.40) |
| % CV | 106.58 | 51.88 | 48.89 | 55.90 |
| $V_{ss}$ (L)(N) | 12 | 13 | 14 | 14 |
| Mean (SD) | 56.808 (44.5127) | −8.363 (156.5060) | 32.789 (22.5478) | 43.652 (30.6577) |
| Median (Min, Max) | 40.264 (4.25, 144.02) | 30.633 (−522.63, 83.53) | 30.400 (3.38, 88.22) | 33.114 (12.09, 122.08) |
| % CV | 78.36 | −1871.30 | 68.77 | 70.23 |
| Weight-adjusted $V_d$ (L/kg)(N) | 12 | 13 | 14 | 14 |
| Mean (SD) | 2.167 (0.8564) | 2.315 (0.8392) | 2.441 (1.3576) | 2.484 (0.9016) |
| Median (Min, Max) | 2.429 (0.28, 3.38) | 2.486 (1.31, 4.04) | 2.187 (0.57, 5.83) | 2.152 (1.19, 4.41) |

TABLE 29-continued

Summary of Pharmacokinetic Parameters - Full Evaluable Population

| Parameter/ Statistics | Dose Level 1 DEX | Dose Level 2 DEX | Dose Level 3 DEX | Dose Level 4 DEX |
|---|---|---|---|---|
| % CV | 39.53 | 36.24 | 55.62 | 36.30 |
| CL (L/hr)(N) | 12 | 13 | 14 | 14 |
| Mean (SD) | 32.208 (40.3982) | 20.268 (10.3508) | 18.565 (8.6995) | 22.199 (14.1623) |
| Median (Min, Max) | 19.531 (5.37, 147.15) | 16.040 (10.43, 39.50) | 16.170 (3.76, 39.47) | 16.890 (7.42, 49.96) |
| % CV | 125.43 | 51.07 | 46.86 | 63.80 |
| Weight-adjusted CL (L/hr/kg)(N) | 12 | 13 | 14 | 14 |
| Mean (SD) | 1.039 (0.4826) | 0.919 (0.3021) | 0.842 (0.3339) | 0.849 (0.3010) |
| Median (Min, Max) | 1.196 (0.11, 1.65) | 0.884 (0.55, 1.66) | 0.881 (0.13, 1.27) | 0.803 (0.35, 1.28) |
| % CV | 46.46 | 32.88 | 39.65 | 35.44 |

Figure 2:
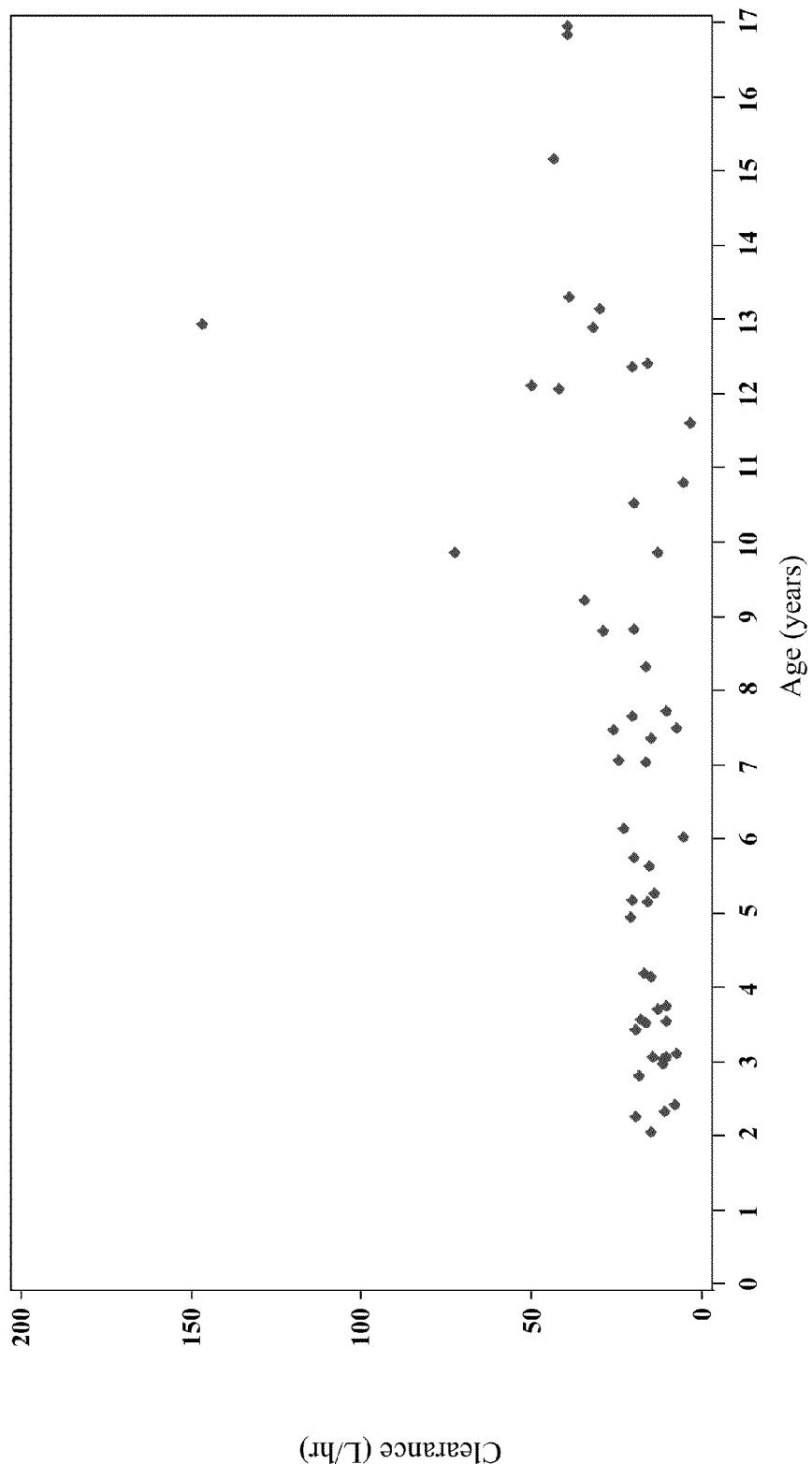
FIG. 2 depicts the plasma clearance over age for the full evaluable population in Example 3.
Figure 3:
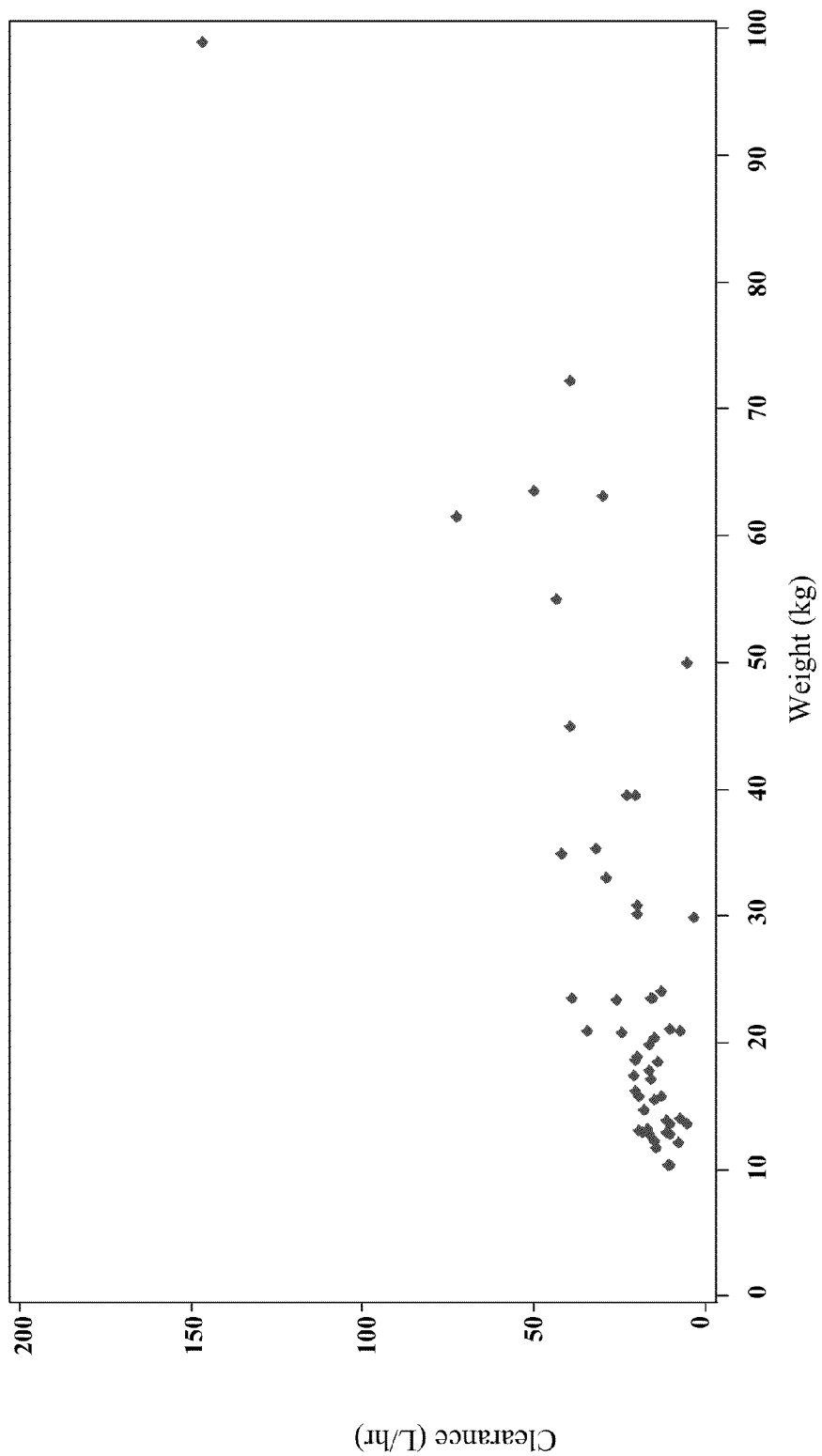
FIG. 3 depicts the plasma clearance over weight for the full evaluable population in Example 3.
Figure 4:
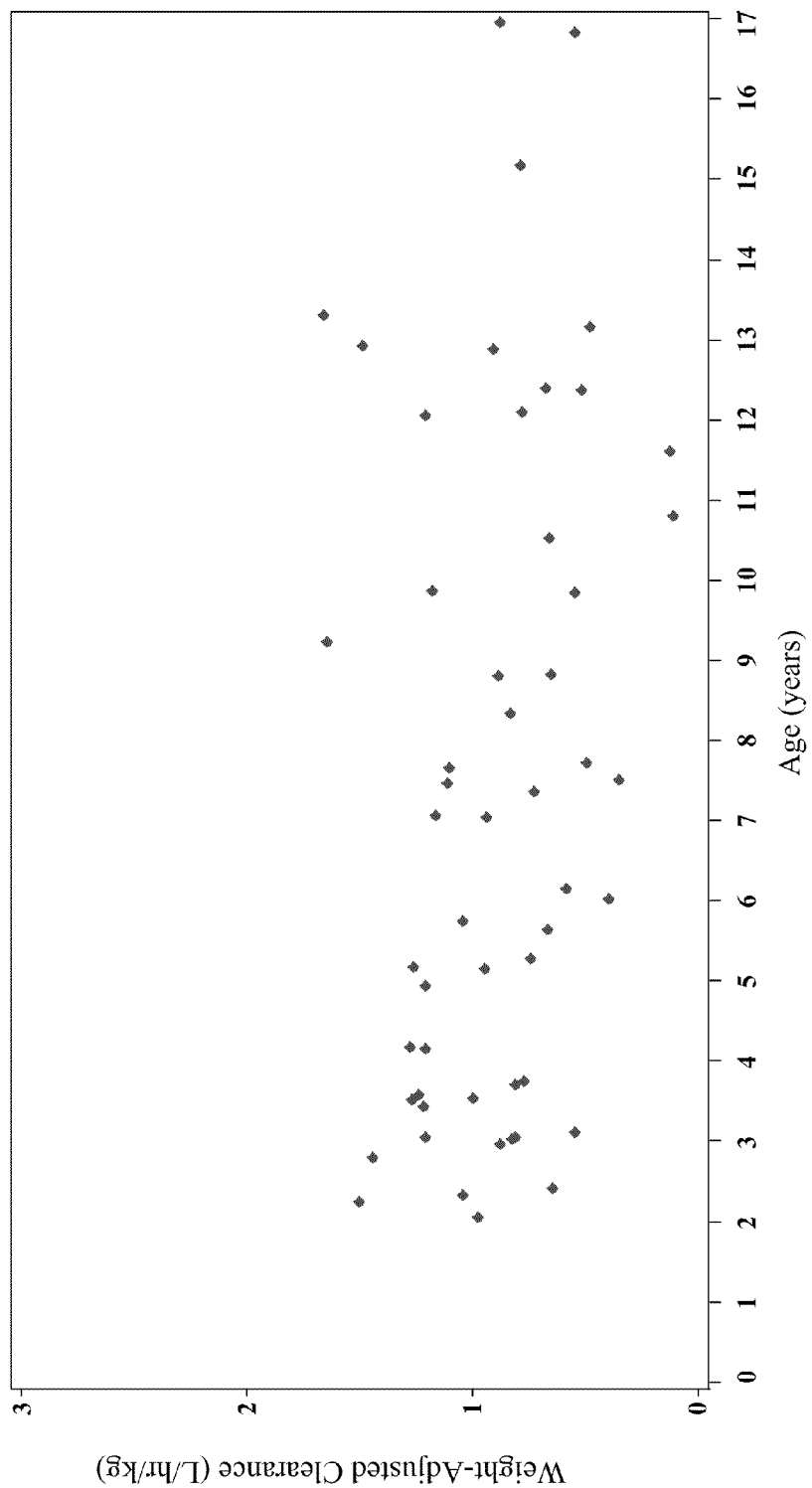
FIG. 4 depicts the weight-adjusted plasma clearance versus age for the full evaluable population in Example 3.
Figure 5:
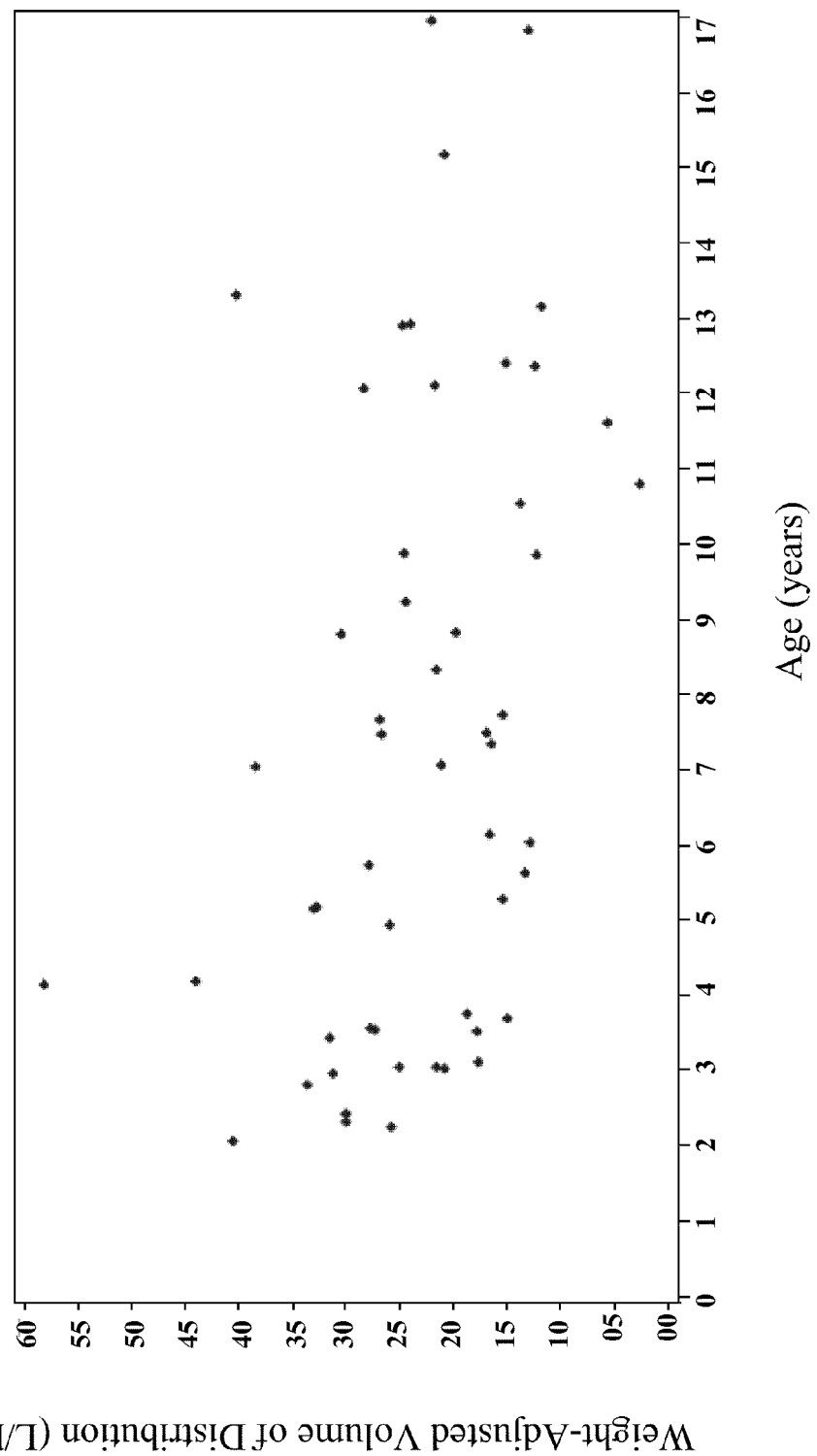
FIG. 5 depicts the weight-adjusted volume of distribution versus age for the full evaluable population in Example 3.
Figure 6:
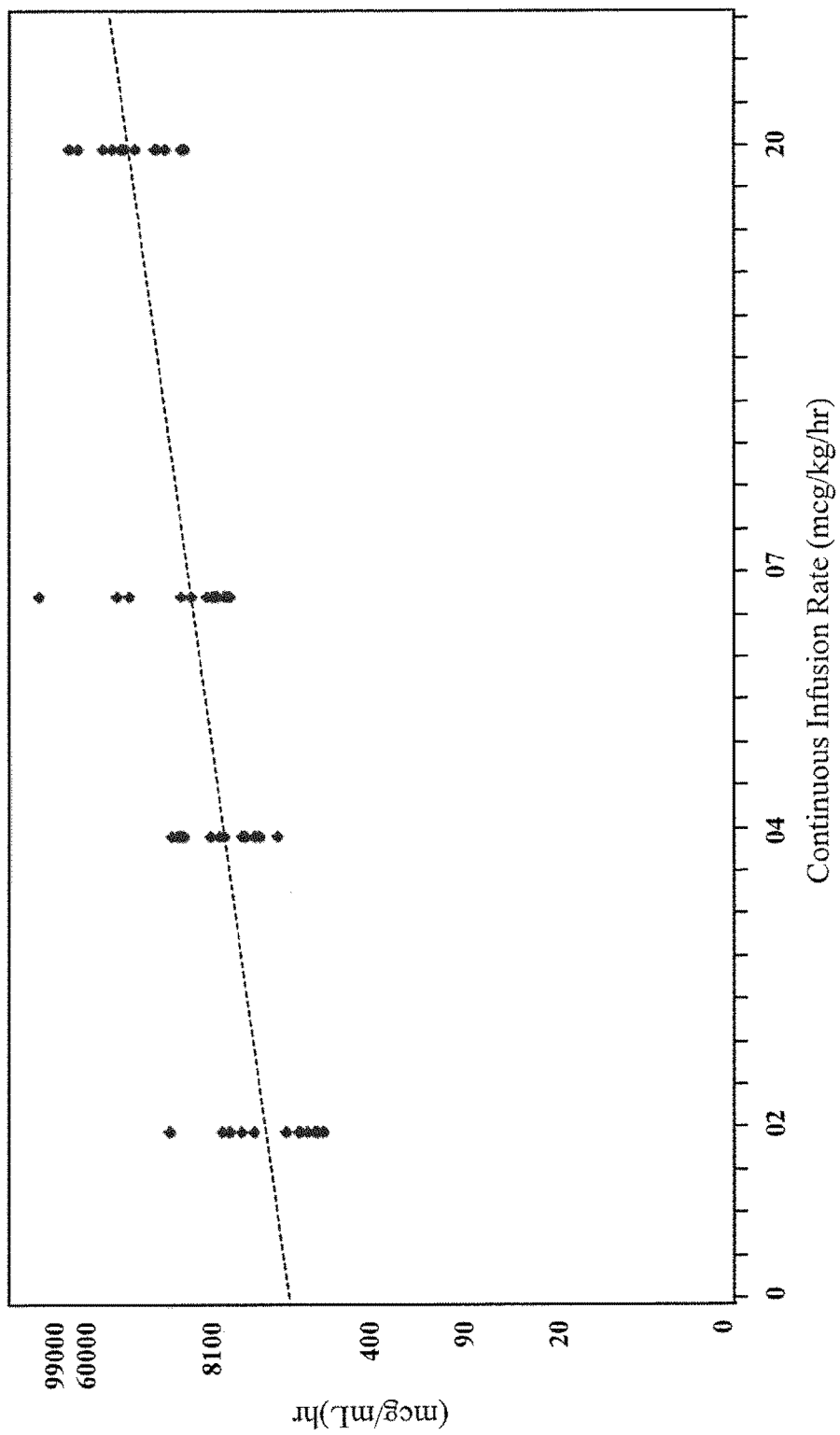
FIG. 6 depicts the predicted mean curves for $AUC_{0-\infty}$ generated using the power fit model for Example 3.
Figure 7:
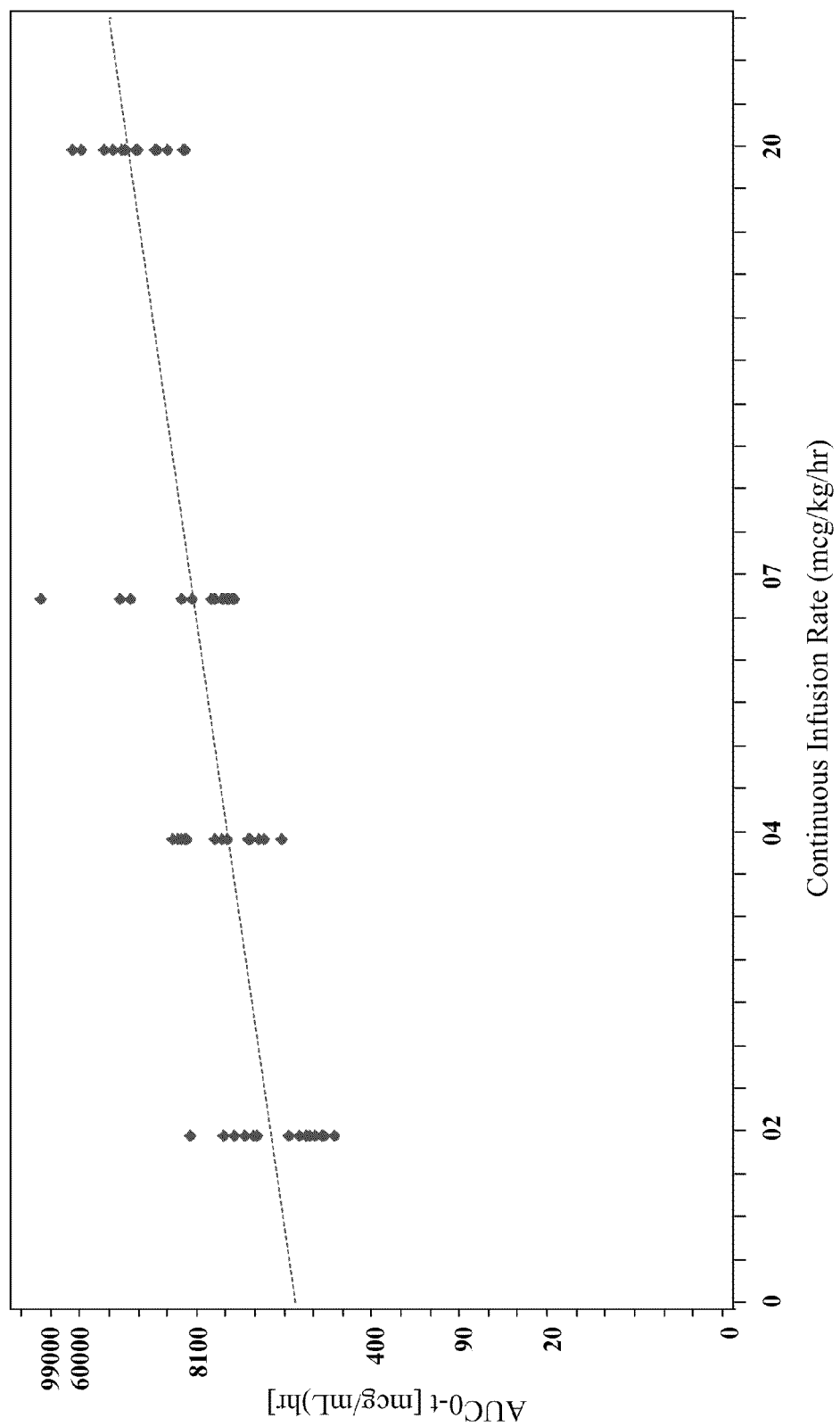
FIG. 7 depicts the predicted mean curves for $AUC_{0-t}$ generated using the power fit model for Example 3.
Figure 8:
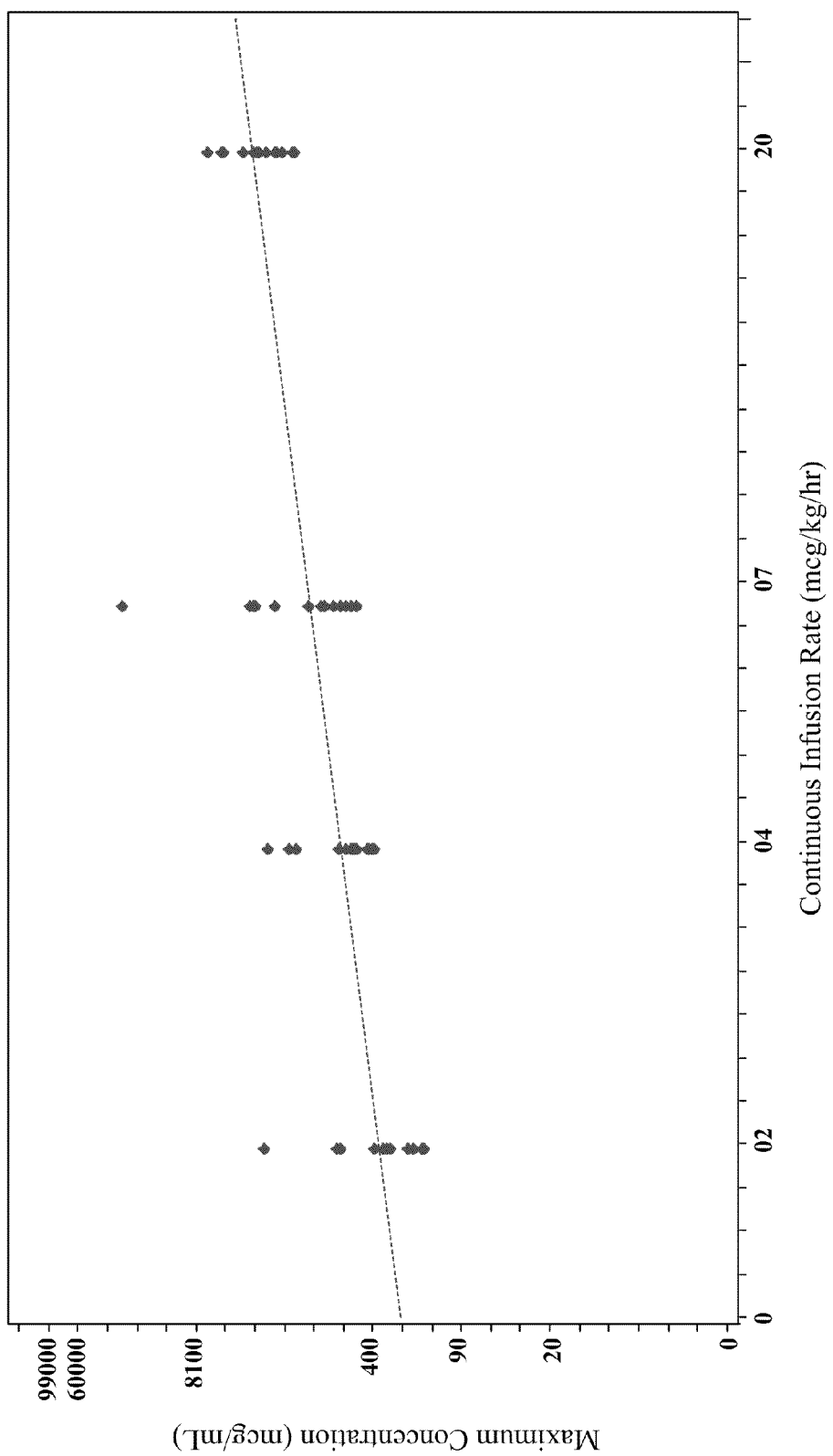
FIG. 8 depicts the predicted mean curves for $C_{max}$ generated using the power fit model for Example 3.
Figure 9:
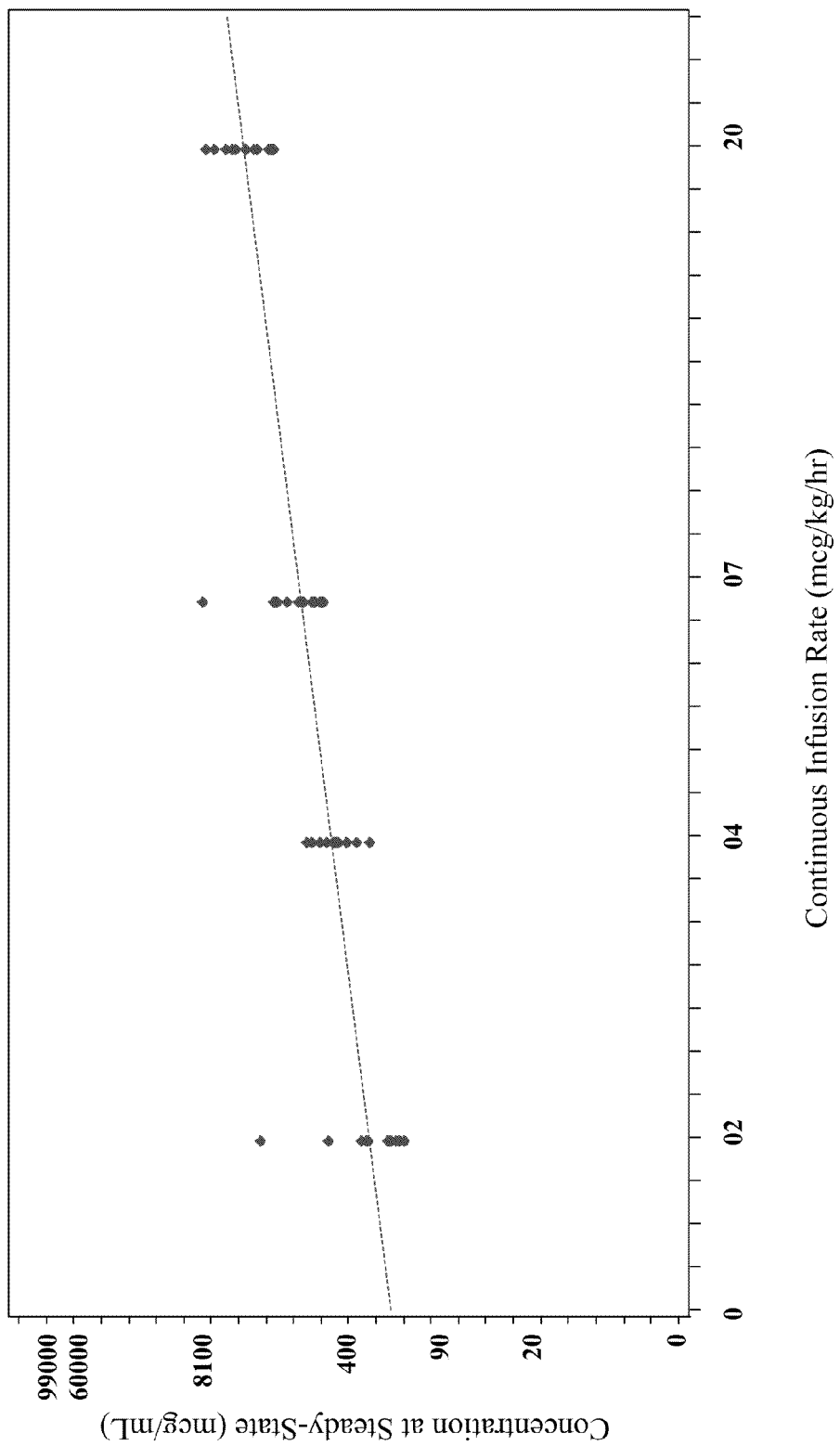
FIG. 9 depicts the predicted mean curves for $C_{ss}$ generated using the power fit model for Example 3.

Abbreviations:
$\lambda z$ = terminal elimination rate constant;
$AUC_{0-\infty}$ = area under the concentration-time curve from time zero to the time infinity;
$AUC_{0-t}$ = area under the concentration-time curve from time zero to the time of the last measurable concentration;
CD = continuous dose;
CL = plasma clearance;
$C_{max}$ = observed peak plasma concentration;
$C_{ss}$ = steady state concentration;
CV = coefficient of variation;
DEX = dexmedetomidine;
LD = loading dose;
Max = maximum;
Min = minimum;
$T_{max}$ = time of maximum concentration;
$t_{1/2}$ = terminal elimination half-life;
$V_d$ = volume of distribution;
$V_{ss}$ = volume of steady state distribution.
Note:
Dose Level 1- Dex LD = 0.25/CD = 0.2 μg/kg/hr
Dose Level 2- Dex LD = 0.50/CD = 0.4 μg/kg/hr
Dose Level 3- Dex LD = 1.00/CD = 0.7 μg/kg/hr
Dose Level 4- Dex LD = 1.00/CD = 2.00 μg/kg/hr Plasma clearance over age, weight and weight-adjusted clearance over age are presented in FIGS. 2-4, respectively. Weight-adjusted clearance for 2-year-old patients was approximately 1 L/hr/kg and decreased with age until values were approximately that observed in adults (0.6 L/kg/hr).

The pharmacokinetic analysis demonstrated dose proportionality and a linear relationship among the Dose Level 1, 2, 3, and 4 treatment groups and AUC and $C_{max}$. The predicted mean curves for $AUC_{0-\infty}$, $AUC_{0-t}$, $C_{max}$, and $C_{ss}$ generated using the power fit model are presented in FIGS. 6-9, respectively. As dose increased, AUC and $C_{max}$ increased in proportion (FIG. 1 and Table 29).

$AUC_{0-\infty}$ and $AUC_{0-t}$ of dexmedetomidine displayed positive linearity among the Dose Level 1, 2, 3, and 4 treatment groups. The $C_{max}$ of dexmedetomidine displayed positive linearity for the Dose Level 1, 2, and 3 treatment groups and showed a slight decrease in the Dose Level 4 treatment group. The apparent $t_{1/2}$ of dexmedetomidine was 1.546, 1.743, 2.045, and 2.145 hours for the Dose Level 1, 2, 3, and 4 treatment groups, respectively. Statistically significant differences were observed between Groups I and II only for the pharmacokinetic parameters of $V_d$ (p=0.0046), weight-adjusted $V_d$ (p=0.0040), CL (p=0.0078), and weight-adjusted CL (p=0.0094). Weight-adjusted clearance decreased with age until values were approximately that observed in adults. No noticeable increases or decreases in $V_d$ or weight-adjusted $V_d$ for increasing age or weight were observed.

Statistically significant differences were observed for the pharmacokinetic parameters for the main effect of dose level for $AUC_{0-t}$, $AUC_{0-\infty}$, $C_{ss}$, $C_{max}$, $\lambda z$, and $t_{1/2}$ and the main effect age for $C_{ss}$, $C_{max}$, $V_d$, weight-adjusted $V_d$, CL, and weight-adjusted CL using a two-way analysis of variance (ANOVA). However, there were no statistically significant dose level by age group interactions observed for any of the pharmacokinetic parameters. A summary of key pharmacokinetic parameters for the full evaluable population is given in Table 30 below.

TABLE 30

Summary of Key Pharmacokinetic Parameters for the Full Evaluable Population

| Parameter | Dose Level 1 DEX (N = 14) | Dose Level 2 DEX (N = 13) | Dose Level 3 DEX (N = 14) | Dose Level 4 DEX (N = 14) | P-value[a] |
|---|---|---|---|---|---|
| $AUC_{0-t}$ [(pg/mL) hr] | 2681.3 (2353.34) | 6460.6 (3766.47) | 16992.5 (29927.39) | 28531.9 (17496.40) | <0.0001 |
| $C_{max}$ (pg/mL) | 480.4 (625.99) | 847.7 (633.74) | 3385.6 (7384.07) | 3090.9 (1625.52) | <0.0001 |
| $t_{1/2}$ (hr) | 1.5 (0.34) | 1.7 (0.30) | 2.0 (0.66) | 2.1 (0.68) | 0.0381 |

TABLE 30-continued

Summary of Key Pharmacokinetic Parameters for the Full Evaluable Population

| Parameter | Dose Level 1 DEX (N = 14) | Dose Level 2 DEX (N = 13) | Dose Level 3 DEX (N = 14) | Dose Level 4 DEX (N = 14) | P-value[a] |
|---|---|---|---|---|---|
| $AUC_{0-\infty}$ [(pg/mL) hr] | 3153.5 (3343.35) | 6673.2 (3781.22) | 17300.5 (29935.76) | 28970.5 (17936.90) | <0.0001 |
| $C_{ss}$ (pg/mL) | 402.0 (535.17) | 539.8 (166.74) | 1347.3 (1308.10) | 2827.1 (1169.42) | <0.0001 |
| $\lambda_z$ (1/hr) | 0.5 (0.11) | 0.4 (0.07) | 0.4 (0.10) | 0.4 (0.14) | 0.0381 |
| $V_d$ (L) | 62.0 (66.06) | 50.6 (26.27) | 52.3 (25.58) | 62.2 (34.76) | 0.8210 |
| Weight-adjusted $V_d$ (L/kg) | 2.2 (0.86) | 2.3 (0.84) | 2.4 (1.36) | 2.5 (0.90) | 0.6394 |
| CL (L/hr) | 32.2 (40.40) | 20.3 (10.35) | 18.6 (8.70) | 22.2 (14.16) | 0.8439 |
| Weight-adjusted CL (L/hr/kg) | 1.0 (0.48) | 0.9 (0.30) | 0.8 (0.33) | 0.8 (0.30) | 0.8769 |

Abbreviations:
$\lambda z$ = terminal elimination rate constant;
$AUC_{0-\infty}$ = area under the concentration-time curve from time zero to the time infinity;
$AUC_{0-t}$ = area under the concentration-time curve from time zero to the time of the last measurable concentration;
CL = plasma clearance;
$C_{max}$ = observed peak plasma concentration;
$C_{ss}$ = steady state concentration;
DEX = dexmedetomidine;
LD = loading dose;
$t_{1/2}$ = terminal elimination half-life;
Vd = volume of distribution.
[a]Results of two-way analysis of variance (ANOVA) to evaluate the effect of dose level on age group for PK parameters.
Note:
Dose Level 1- Dex LD = 0.25/CD = 0.2 µg/kg/hr
Dose Level 2- Dex LD = 0.50/CD = 0.4 µg/kg/hr
Dose Level 3- Dex LD = 1.00/CD = 0.7 µg/kg/hr
Dose Level 4- Dex LD = 1.00/CD = 2.00 µg/kg/hr The pharmacodynamic parameters measured in Groups I and II were level of sedation, number of subjects who received rescue medication (midazolam and fentanyl), amount of rescue medication required for sedation and analgesia, vital signs (HR, SBP, DBP, MAP, RR, and SpO$_2$), time to successful extubation, and comparison of $RSS_{avg}$ with $AUC_{0-\infty}$ and $C_{ss}$. The RSS scores (e.g., $RSS_5$ and $RSS_{avg}$) were generally similar across dose levels and between Groups I and II, although the $RSS_5$ and $RSS_{avg}$ scores in the Dose Level 4 treatment group of Group II were slightly higher compared to other treatment groups in Groups I and II. For subjects that received dexmedetomidine alone, the $RSS_5$ and $RSS_{avg}$ scores were higher across treatment groups in Group II compared to Group I. For subjects that received dexmedetomidine with the co-administration of midazolam or fentanyl, the $RSS_5$ and $RSS_{avg}$ scores were generally similar between subjects in all treatment groups and across age groups with the exception of subjects in the Dose Level 4 treatment group in Group II. The RSS5 and RSSavg scores in the Dose Level 4 treatment group of Group II (RSS5=4.5 and RSSavg=4.5) were slightly higher compared to other treatment groups (RSS5 scores range=2.5 to 3.7) in Groups I and II in the full evaluable population. Similar results were observed in the safety population.

Figure 10:
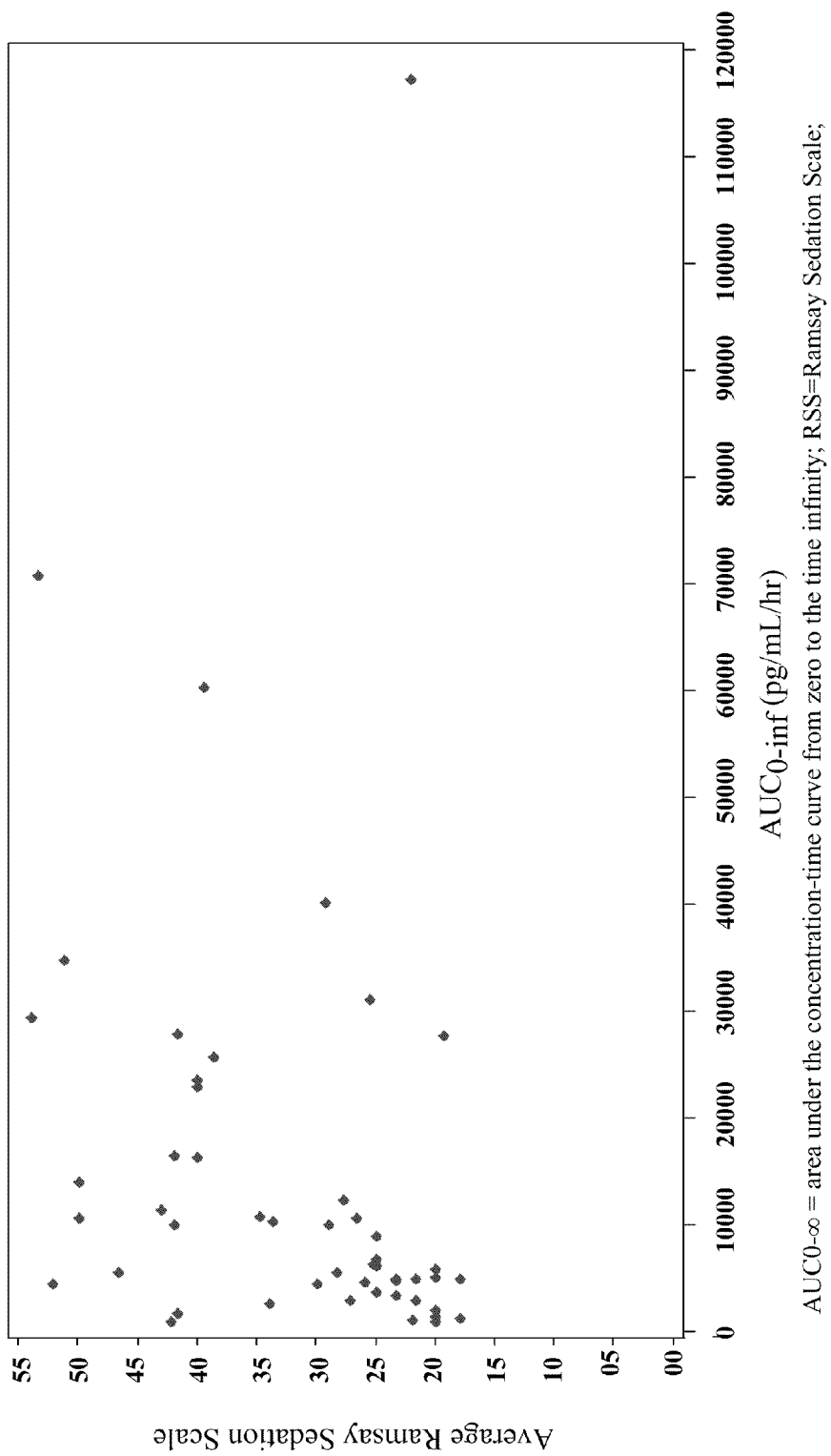
FIG. 10 depicts the average Ramsay Sedation Score (RSS) versus $AUC_{0-\infty}$ for the full evaluable population.
Figure 11:
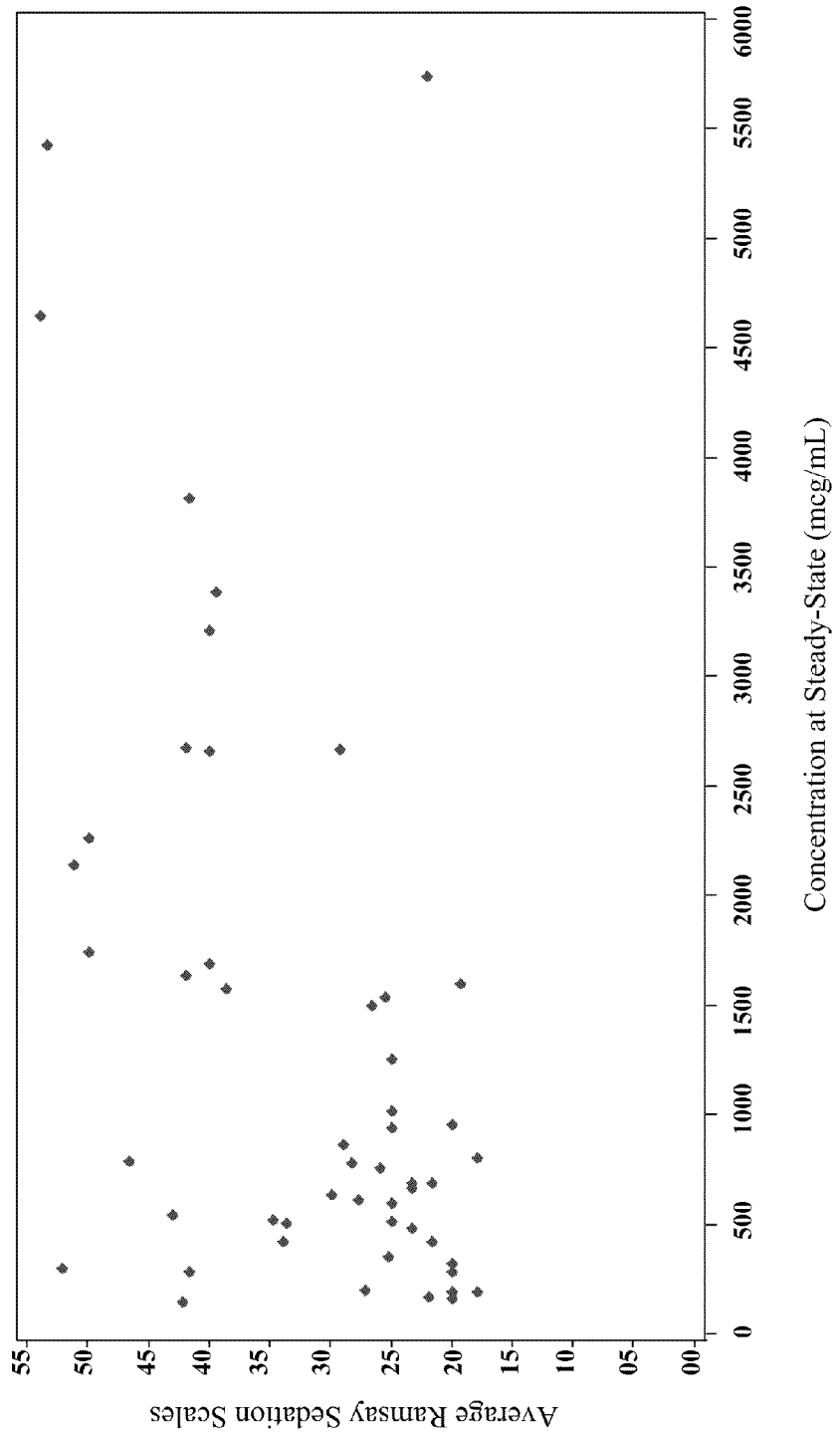
FIG. 11 depicts the average Ramsay Sedation Score (RSS) versus $C_{ss}$ for the full evaluable population.

As described above, one subject in the Dose Level 3 treatment group had extremely high plasma dexmedetomidine concentration at the end of the loading infusion. The plasma concentration data from this subject skewed the calculated AUC and $C_{ss}$ results. FIGS. 10 and 11 show the relationship between $RSS_{avg}$ and AUC and $C_{ss}$, respectively. With this subject, who had a mean AUC value of 117264.1 µg hr/mL and $C_{ss}$ of 5743.55 µg/mL, excluded from the analyses, there was an increase in $RSS_{avg}$ with increasing AUC and $C_{ss}$.

A smaller percentage of subjects in Group II received rescue midazolam for sedation compared to Group I across all treatment groups. In comparison to the other three dose level treatment groups, fewer subjects in the Dose Level 4 treatment group required rescue medication. There was also an increase in the time to the administration of the first dose of rescue medication in this treatment group in the Dose Level 4 treatment group, because of the increased level of sedation in this treatment group. The differences between these age groups in the number of subjects that received rescue midazolam were not statistically significant in any age group at any dose level. The amount of rescue medication required for sedation and analgesia during the treatment period was similar across all dose levels. No statistically significant differences were observed in the amount of midazolam or fentanyl used as rescue medication for sedation or analgesia between treatment groups in the safety population. In general, the majority of subjects treated across age groups and dose levels required co-administration of midazolam or fentanyl with dexmedetomidine with the exception of Group II Dose Level 4 treatment group, in which 3 of 8 subjects received co-administration of midazolam or fentanyl.

In the full evaluable population, the median times to extubation increased with dose. The time intervals for the Dose Levels 1, 2, and 3 treatment groups were similar (0.6-1.7 hours), while the time to extubation Dose Level 4 treatment group was longer (6.8 hours). The effect was not statistically significant (p=0.3041). Similar results were seen for the safety population. The summary of time to successful extubation for the full evaluable population is given in Table 31 below.

TABLE 31

Summary of Time to Successful Extubation - Full Evaluable Population

| Parameter | Dose Level 1 | Dose Level 2 | Dose Level 3 | Dose Level 4 | Overall P-value[c] |
|---|---|---|---|---|---|
| Median[a] | 0.6 | 0.8 | 1.7 | 6.8 | — |
| 95% CI[b] | (0.433, 3.000) | (0.533, 2.417) | (0.633, 4.417) | (0.667, 7.333) | — |
| N (%) Censored | 3 (18.8) | 0 | 2 (14.3) | 2 (14.3) | — |
| Log-Rank | — | — | — | — | 0.3041 |
| Wilcoxon | — | — | — | — | 0.1555 |

Abbreviations:
CD = continuous dose;
CI = confidence interval;
DEX = dexmedetomidine;
LD = loading dose;
Note:
Summary of time to successful extubation was done using Kaplan-Meier Estimates, Log-Rank and Wilcoxon tests.
Note:
Dose Level 1- Dex LD = 0.25/CD = 0.2 μg/kg/hr
Dose Level 2- Dex LD = 0.50/CD = 0.4 μg/kg/hr
Dose Level 3- Dex LD = 1.00/CD = 0.7 μg/kg/hr
Dose Level 4- Dex LD = 1.00/CD = 2.00 μg/kg/hr
Note:
If extubation was successful, the subject is considered to have the event. If the subject did not complete the treatment/discontinued, the subject is censored.
[a]Median time to successful extubation from start of DEX infusion in hours.
[b]95% CI for median.
[c]P-value from Log-Rank and Wilcoxon tests for difference between treatment groups (using PROC LIFETEST with strata dose level).

No clinically meaningful trends in the mean change from baseline in HR, SBP, DBP, MAP, RR, or $SpO_2$ were observed in Group I and Group II subjects during infusion and post-infusion. Similarly, no clinically meaningful trends were seen in the mean change from baseline in HR, SBP, DBP, or MAP in subjects stratified by whether or not they underwent cardiopulmonary bypass surgery.

Treatment-related adverse events occurred primarily during the loading dose and only in Dose Levels 3 and 4. The most frequently reported non drug-related treatment emergent adverse effects in both age groups were pyrexia, vomiting, hypokalaemia, and hypertension. In Group I (26 subjects), the treatment-related TEAEs were bradycardia (2 subjects), hypotension (1 subject), sedation (2 subjects), hypertension (1 subject). In Group II (33 subjects), the treatment-related TEAEs were bradycardia (1 subject), sedation (1 subject), hypertension (5 subjects), and chills (1 subject).

The majority of these adverse effects were considered not related to the study drug and mild or moderate in intensity. Numerical differences were observed in several hematology, chemistry, and urinalysis parameters with increasing or decreasing trends among treatment groups in lymphocytes, neutrophils, platelets, ALP, AST, and bilirubin. Although numerical changes occurred, no clinically meaningful trends in the mean change from baseline in HR, SBP, DBP, MAP, RR, and SpO2 between treatment groups were observed among treatment groups. Respiratory rate was not affected. Similar results were obtained in subjects stratified by whether or not they underwent cardiopulmonary bypass surgery.

The change from Baseline in SBP tended to increase from Dose Level 1 to 4 for subjects who underwent CPB surgery. These differences were not clinically significant. No similar observation was noted in subjects who did not undergo CPB surgery.

Except for the slightly higher SBP observed in subjects who underwent CPB surgery in the Dose Level 4 treatment group, the 4 dose levels of dexmedetomidine studied were generally well tolerated in this study and there were no clinically meaningful differences observed between dose levels in the safety profile of dexmedetomidine.

There were no clinically meaningful changes from baseline in the clinical laboratory test results observed across treatment groups during infusion and post-infusion. Hematology results that showed large numerical changes from Baseline included lymphocytes, neutrophils, and platelets. Chemistry results that showed large numerical changes from Baseline included ALP, AST, and bilirubin.

The majority of ECG findings reported were normal or abnormal but not clinically significant. The majority of subjects had unremarkable physical examination findings in all body system categories except the cardiopulmonary body system. No clinically meaningful changes in vital signs, laboratory test results or ECGs were observed across treatment groups during infusion and post-infusion. In general, dexmedetomidine was well tolerated in intubated and mechanically ventilated pediatric patients in this study.

No deaths were reported. One subjected experienced convulsion that was considered mild and not related to study drug. Drug-related treatment-emergent adverse effects (TEAEs) were reported at Dose Levels 3 and 4, as shown in Table 32.

TABLE 32

Drug-Related Treatment-Emergent Events by Preferred Term - Safety Population

| Group I | | | | |
|---|---|---|---|---|
| | DEX Dose Level 1 (N = 8) | DEX Dose Level 2 (N = 6) | DEX Dose Level 3 (N = 6) | DEX Dose Level 4 (N = 6) |
| Subjects with at least 1 Drug-Related TEAE, n (%) | 0 | 0 | 1 (16.7) | 4 (66.7) |
| Number of Drug-related TEAE | 0 | 0 | 2 | 4 |
| Bradycardia | 0 | 0 | 1 (16.7) | 1 (16.7) |
| Sedation | 0 | 0 | 0 | 2 (33.3) |
| Hypertension | 0 | 0 | 1 (16.7) | 0 |
| Hypotension | 0 | 0 | 0 | 1 (16.7) |

| Group II | | | | |
|---|---|---|---|---|
| | DEX Dose Level 1 (N = 8) | DEX Dose Level 2 (N = 8) | DEX Dose Level 3 (N = 9) | DEX Dose Level 4 (N = 8) |
| Subjects with at least 1 Drug-Related TEAE, n (%) | 0 | 0 | 2 (22.2) | 4 (50.0) |
| Number of Drug-related TEAE | 0 | 0 | 3 | 4 |
| Bradycardia | 0 | 0 | 1 (11.1) | 0 |
| Chills | 0 | 0 | 1 (11.1) | 0 |
| Sedation | 0 | 0 | 0 | 1 (12.5) |
| Hypertension | 0 | 0 | 1 (11.1) | 3 (37.5) |

Abbreviations:
DEX = dexmedetomidine;
TEAE = Treatment Emergent Adverse Events.
Investigator adverse event (AE) terms were coded to preferred terms using Medical Dictionary for Regulatory Activities (MedDRA) dictionary version 11.0).
Percentages are based on the number of subjects in each treatment group by age group.
Subjects are counted once within each system organ class or for each preferred term and may have had more than 1 TEAE.
Related is any event that was assessed as either unknown relation, unlikely, possibly, probably/likely or certainly related to study medication.
If a subject had more than one occurrence of the same TEAE, the highest relationship to study drug was summarized.
Note:
Dose Level 1- Dex LD = 0.25/CD = 0.2 μg/kg/hr
Dose Level 2- Dex LD = 0.50/CD = 0.4 μg/kg/hr
Dose Level 3- Dex LD = 1.00/CD = 0.7 μg/kg/hr
Dose Level 4- Dex LD = 1.00/CD = 2.00 μg/kg/hr

Example 4

Effects of Dexmedetomidine in the Prenatal Cynomolgus Monkey Brain

The study was conducted to determine the potential neuroapoptotic effect of dexmedetomidine in prenatal Cynomolgus monkey brains by administering dexmedetomidine to pregnant monkeys. The overall objective of this study was to demonstrate that dexmedetomidine, an anesthetic with a different mechanism of action than that of isoflurane or ketamine, does not cause neuroapoptosis in prenatal cynomolgus monkey brains. The purpose of the immunohistochemistry analysis of this study was to assess and characterize the regions of interest histopathologically, and to characterize and compare test article-induced apoptosis between groups.

The monkey model used is that described in Slikker et al. Tax. Sci. 2007; 98(1), 145-58, which is hereby incorporated by reference in its entirety. The fetus was removed from the pregnant female at 120±7 days gestation after a 12 hour intravenous fusion of dexmedetomidine followed by a 6 hour post-infusion observation period. The fetal brain was collected by cesarean section. The treatment groups are shown in Table 33 below.

TABLE 33

Experimental design

| Groups (n = 5) | Treatment | Route of administration | Dose |
|---|---|---|---|
| 1 | Cage control | Not applicable | Not applicable |
| 2 | Ketamine | Intramuscular + Intravenous infusion | 20 mg/kg im + 20-50 mg/kg/hr |
| 3 | Dexmedetomidine | Intravenous injection + Intravenous infusion | 3 ug/kg × 10 min + 3 ug/kg/hr |
| 4 | Dexmedetomidine | Intravenous injection + Intravenous infusion | 30 µg/kg × 10 min + 30 µg/kg/hr |

Following treatment, animals were sacrificed, and brain tissues were fixed in 10% neutral buffered formalin via perfusion. A vibratome microtome was used to generate serial unstained brain sections at 50- to 70-µm thicknesses, yielding approximately 800 sections per brain. Fixed brain tissue was processed from 20 animals. For each animal, approximately 25 intervaled sections per brain were stained with the following stains: hematoxylin and eosin (H&E), silver stain, terminal deoxynucleotidyl transferase dUTP nick end labeling (TUNEL), and activated Caspase 3 (AC3). The sections were evaluated by an American College of Veterinary Pathologists (ACVP) board-certified pathologist, including the use of image analysis to assess and compare the incidence and distribution of apoptotic cells in the TUNEL- and AC3-stained sections.

Fixed tissues were gross trimmed, processed, oriented and embedded in paraffin, and sectioned at approximately 35- to 40-µm thicknesses. Each brain was carefully oriented and gross trimmed into each block to assure correlative symmetry between animals. Six consecutive blocks were prepared for each brain and spanned the entire frontal cortex. Approximately 100 unstained sections were microtomed for each block for a total of about 600 sections per animal. For each block, section level 1, 25, 50 and 100 were selected for staining. Assessments were conducted to assure that the section levels selected and examine correlated well between animals. Assessments were also conducted to confirm that the ketamine-induced lesions were confined to the 1 and 2 layers of the frontal cortex and that the lesion was distributed consistently in this region in all animals as reported by Slikker. Approximately 25 serial sections from each brain were stained by one of the following techniques. H&E stain was used to define general histology and morphology. Silver staining was used to visualize neurodegeneration. TUNEL is a method for detecting DNA fragmentation by labeling the terminal end of nucleic acids. AC3, detected by IHC antibody staining, is a marker for apoptotic cells. Following staining, tissues were evaluated by light microscopy by a board-certified veterinary pathologist. All procedures were consistent with CBI SOPs; details are maintained in the study records.

The modified silver method was employed on brain sections. See Xuemin Ye et al. 2001, Brain Research Protocols 8, 104-112, which is hereby incorporated by reference in its entirety. Briefly, the sections were de-waxed in xylene and rehydrated in alcohol. The following steps were employed: dehydrate with 50, 75, and 97% 1-propanol for at least 5 minutes each; esterified in sulfuric acid/1-propanol at 56° C. for 16 hours; rehydrate with 50 and 25% 1-propanol followed by two changes of distilled water, 5 minutes each; wash with 1% acetic acid for exactly 10 minutes; place in the developing solution until the sections turn brown in color (ca. 6-8 minutes); terminate development by washing with 1% acetic acid (30 minutes); and dehydrate, clear and cover slip.

For activated caspase 3 staining, tissues were deparaffinized, hydrated, and subjected to heated citrate buffer antigen retrieval. Tissues were stained on a DAKO Autostainer. Tissues were reacted with peroxidase and two protein blocks. Following rinsing in buffer, tissues were then incubated at room temperature for 60 minutes with 1:275 dilution of AC-3 (Abeam) followed by incubation for 30 minutes with Envision goat anti-rabbit secondary antibody (Envision). The immunoreaction was visualized with DAB and counterstaining with hematoxylin. Both positive (human tonsil) and negative tissues (human uterus), plus tissues stained with irrelevant antibody and with saline were included.

For TUNEL staining, tissues were deparaffinized, hydrated, and subjected to heated citrate buffer antigen retrieval. Tissues were stained either on a DAKO Autostainer or were hand stained using the Trevigen TACS 2TdT-DAB In Situ Apoptosis Detection Kit. Both positive (human tonsil) and negative tissues (human uterus), plus tissues stained with irrelevant antibody and with saline were included.

Extensive areas of the frontal cortex and multiple levels through the frontal cortex were examined with special emphasis on the lamina. The remainder of the brain tissue on the slides was also examined for any other lesions. Representative photomicrographs were taken. H&E-silver-stained, TUNEL and AC3 sections were qualitatively examined by the Study Pathologist, a veterinary pathologist certified by the American College of Veterinary Pathologists (ACVP). The incidence and severity of the lesions (presence of apoptosis and cell injury) were scored using the accepted industry scoring system: 0=normal, 1=minimal, 2=mild, 3=moderate; and 4=severe.

Severity scoring of the treatment-related findings is presented in Table 34. There were abundant neuroapoptotic lesions of the cortex present in the ketamine-treated group, while there were minimal changes seen in the dexmedetomidine-treated groups, particularly in the low (therapeutic)-dose group.

TABLE 34

Summary of severity scoring of neuroapoptotic lesions

| Group | Treatment | Dose | Fetal Brains Examined | HE | Silver | Activated caspase 3 | TUNEL |
|---|---|---|---|---|---|---|---|
| 1 | Cage control | Untreated | 5 | 0.0 ± 0.0 | 0.6 ± 0.6 | 0.8 ± 0.6 | 0.0 ± 0.0 |
| 2 | Ketamine | 20 mg/kg im + 20-50 mg/kg/hr | 5 | 1.9 ± 1.2 | 2.0 ± 0.8 | 3.5 ± 0.7 | 2.9 ± 1.1 |
| 3 | Dexmedetomidine | 3 ug/kg × 10 min + 3 ug/kg/hr | 5 | 0.1 ± 0.3 | 1.0 ± 1.1 | 1.4 ± 0.6 | 0.1 ± 0.2 |
| 4 | Dexmedetomidine | 30 μg/kg + 30 μg/kg/hr | 5 | 0.0 ± 0.1 | 0.4 ± 0.6 | 1.8 ± 0.9 | 0.8 ± 0.9 |

Figure 12:
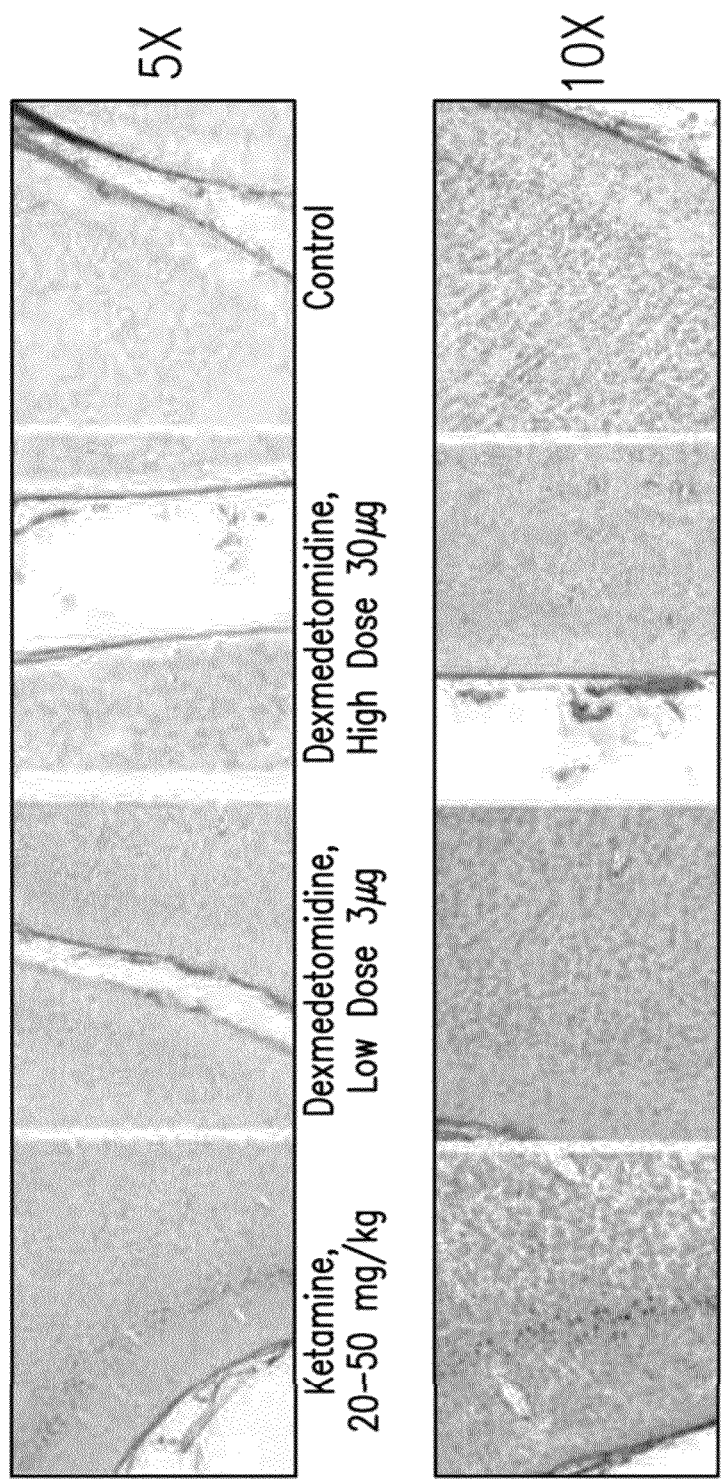
FIG. 12 depicts representative photomicrographs of TUNEL staining of the frontal cortex of neonatal monkeys at 5× and 10× magnification.
Figure 13:
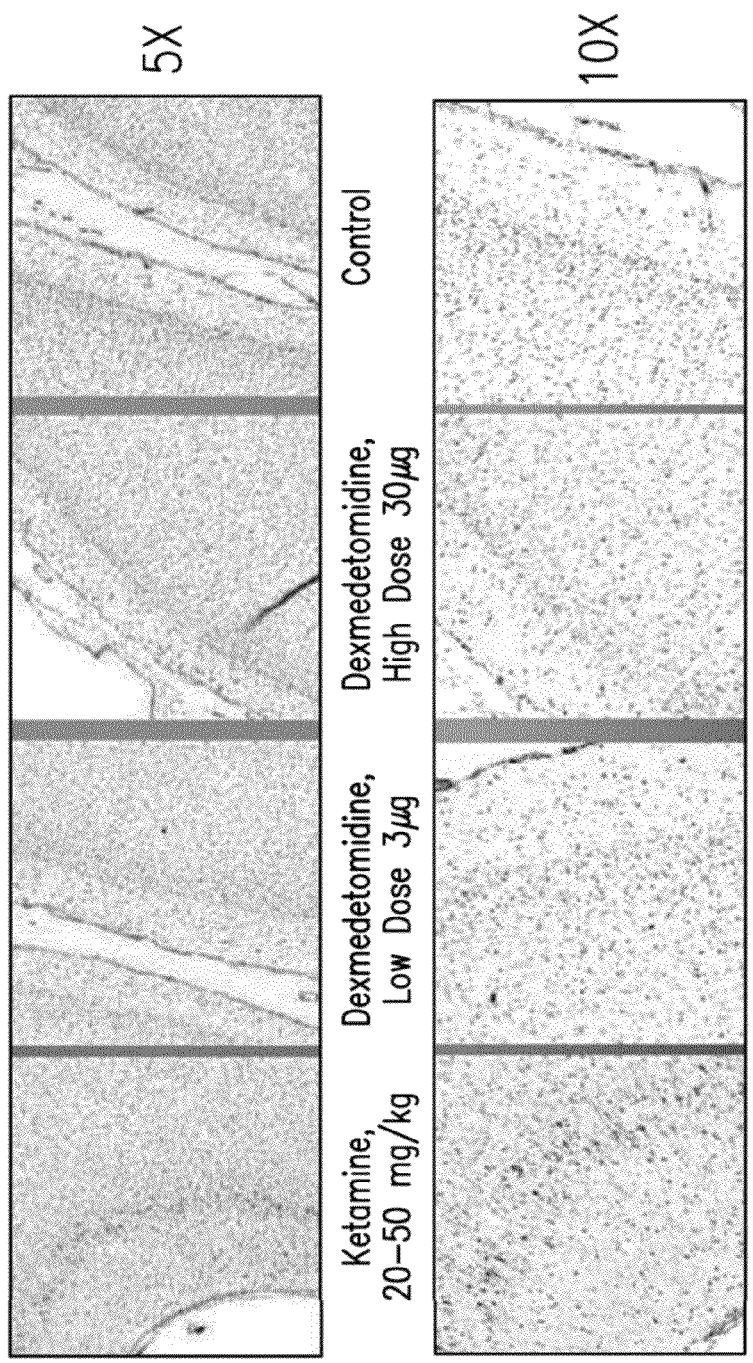
FIG. 13 depicts representative photomicrographs of activated caspase 3 staining of the frontal cortex of neonatal monkeys at 5× and 10× magnification.
Figure 14:
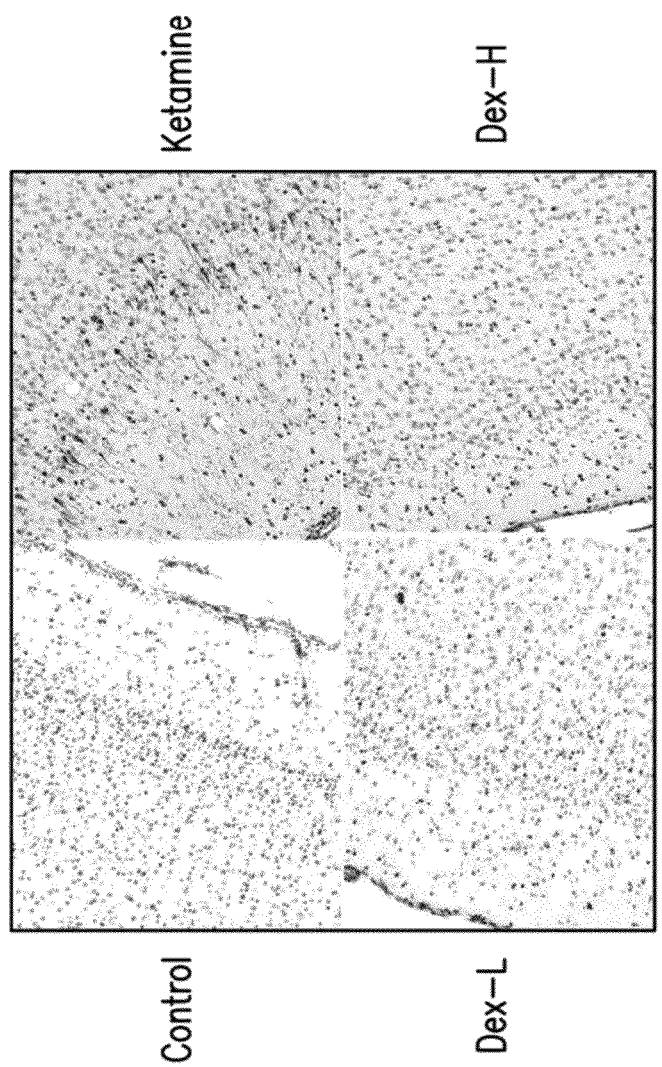
FIG. 14 depicts representative photomicrographs of activated caspase 3 staining of the frontal cortex of neonatal monkeys at 20× magnification.
Figure 15:
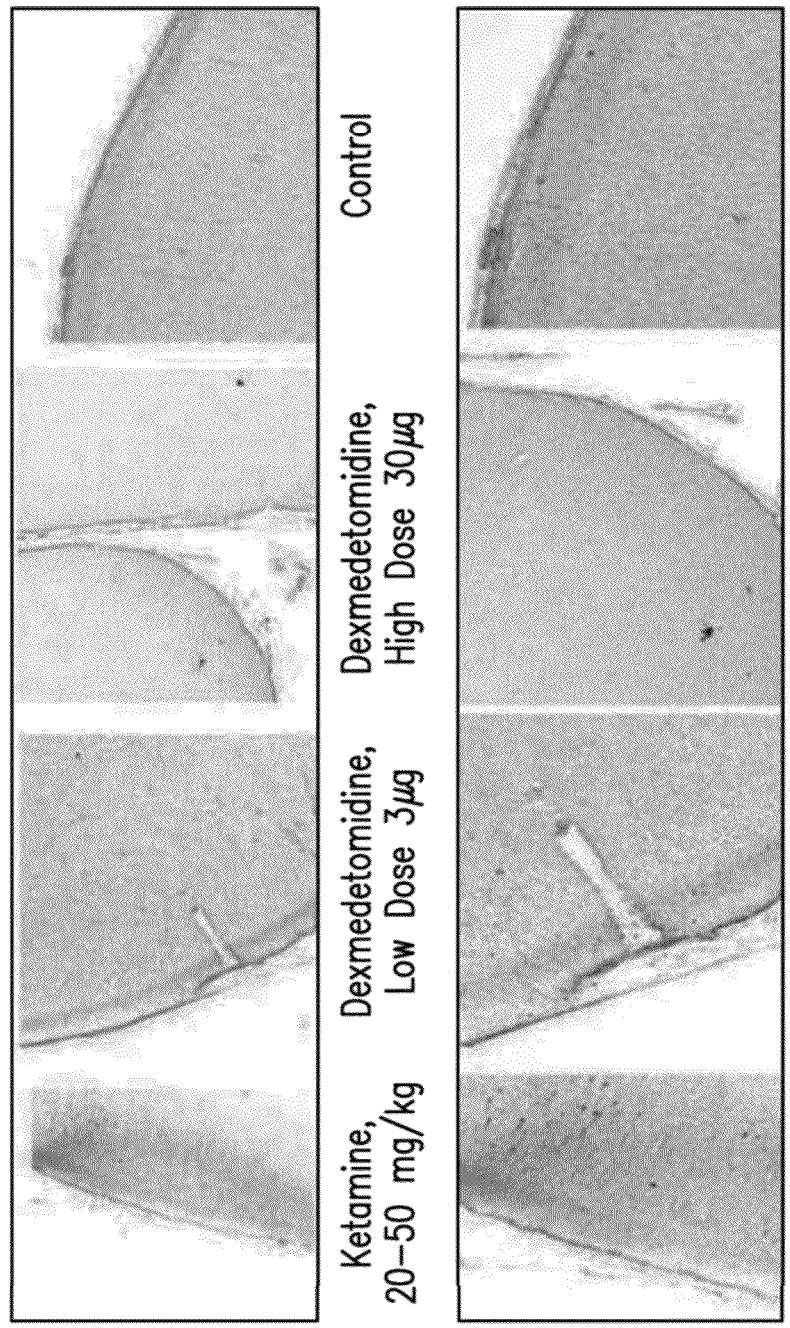
FIG. 15 depicts representative photomicrographs of the silver staining of the frontal cortex of neonatal monkeys at 20× magnification.

Severity scoring of the treatment-related findings is presented in Table 34. Representative photomicrographs of TUNEL staining of frontal cortexes are shown in FIG. 12. Representative photomicrographs of AC3 staining of frontal cortexes are shown in FIGS. 13 and 14. Representative photomicrographs of silver staining of frontal cortexes are shown in FIG. 15.

In Group 1, untreated brains, examination of HE, Silver, TUNEL and AC3 stained sections from the frontal cortex demonstrated no or rare, sporadically damaged and apoptotic cells in the layers of frontal cortex. There was some low intensity positive nuclear AC3 staining particularly in the white matter, which is indicative of normal fetal development. There were also a few TUNEL positive cells in other areas of the brain, but there were no differences between control and treated brains.

In Group 2, the ketamine-treated group, examination of HE, Silver, TUNEL and AC3 sections from the frontal cortex demonstrated a moderate to large number of damaged and apoptotic cells that was dramatically increased in comparison to untreated and dexmedetomidine-treated brains. AC3 marks neurons that are undergoing apoptotic degeneration after exposure to apoptogenic drugs including isoflurane. AC3 stained cells are also the same cells that are stained by silver stains that mark cells that are dead or dying. AC3 also reveals if cells are in an early or advanced state of degeneration and what type of cell is undergoing degeneration (Bambrink, 2010). In early states, there is abundant AC3 protein in the cell body and processes, therefore the degenerate cell can be visualized microscopically. Following cell death, the cell body becomes condensed and rounded up.

Both of these morphologies were abundantly visible in ketamine-treated brains but were minimally visible in the dexmedetomidine-treated brains. The lesions seen in this study were characterized by a moderate multifocal amount of necrolytic debris, degenerate axons and cell bodies and apoptotic nuclei in the layers of the I-VI lamina of the cortex with the most intense staining in layer I and II. The cell types affected included cells with the morphology and arborization patterns of γ-aminobutyric acid-ergic inhibitory interneurons (layer II) and small pyramidal neurons (likely glutamateric, thought to project to the visual neurons in the contralateral hemisphere) (Bambrink, 2010). Affected large multipolar neurons (commonly in layers V and VI), large and small pyramidal neurons (layers IV and V) and interneurons in layer II were also evident.

These observations are very similar to those described by Bambrink, 2010 with isoflurane-treated rhesus monkeys. There were also sporadic AC-3 positive cells scattered in the deeper white matter in all groups, including control.

In Group 3, the low dose dexmedetomidine group, examination of HE, Silver, TUNEL and AC3 stained sections from the frontal cortex demonstrated a low number of damaged and apoptotic cells in comparison to ketamine-treated brains. The lesions were characterized by a mild multifocal amount of necrolytic debris, degenerate axons and cell bodies and apoptotic nuclei of the 1st and 2nd layers of cortex. The same cell types were involved as was seen with ketamine, only the numbers were markedly reduced in comparison to ketamine. Their incidence and severity was also less then that seen with the higher dose of dexmedetomidine.

In Group 4, the high dose dexmedetomidine group, examination of HE, Silver, TUNEL and AC3 stained sections from the frontal cortex demonstrated a low number of damaged and apoptotic cells that was increased in comparison to ketamine-treated brains. The lesions were characterized by a mild multifocal amount of neerolytic debris, degenerate axons and cell bodies and apoptotic nuclei of the 1st and 2nd layers of cortex. The same cell types were involved as was seen with ketamine, only the numbers were markedly reduced in comparison to ketamine.

The results from this study indicate that treatment with 20 mg/kg IM+20-50 mg/kg/hr ketamine was associated with marked neuroapoptosis and cellular damage with necrosis primarily in layers I and II of the cortex. This was a diffuse and uniform multifocal to diffuse lesion extending through the frontal cortex including layers I-VI, but primarily in layers 1 and 2. There were no significant neuroapoptotic lesions present in the untreated group. In animals receiving dexmedetomidine there was no to minimal neuroapoptosis present following either 3 ug/kg×10 min+3 ug/kg/hr or 30 ug/kg×30 min+3 ug/kg/hr. Lesions were less severe in the low-dose animals, indicative of a dose response and the lesions were clearly much less severe than the ketamine treated animals. These findings suggest that dexmedetomidine is not associated with significant neuroapoptosis. In particular, these findings suggest that dexmedetomidine is not associated with significant neuroapoptosis at the low dose.

Example 5

Pharmacokinetics of Dexmedetomidine in Pediatric Patients Aged 1 Month to 24 Months The present study characterizes the pharmacokinetic and pharmacodynamic profile of dexmedetomidine administered as an intravenous (IV) loading dose followed by a continuous IV infusion in pediatric subjects.

A 36-patient, open-label, single center, escalating dose study of dexmedetomidine was conducted on pediatric subjects who were postoperative from cardiac surgery. The study investigated the pharmacokinetics and pharmacodynamics of dexmedetomidine. The subjects were 1 month to 24 months old with tracheal intubation or mechanical ventilation in the immediate postoperative period, and planned tracheal extubation within 24 hours after surgery. The subjects received one of the doses given in Table 35 below.

The primary objectives of this study were as follows:

To define the pharmacokinetics of increasing doses of dexmedetomidine administered as an intravenous bolus followed by a continuous IV infusion (CIVI) in infants who were postoperative from cardiac surgery.

To describe the pharmacodynamic effects of dexmedetomidine in infants (age: 1 month to 2 years) who were post-operative surgical patients during the 24-hour period prior to, and during, extubation.

The secondary objectives were as follows:

To obtain correlation data on the relationship between level of sedation and dexmedetomidine plasma drug concentration in infants post-operative from cardiac surgery and To evaluate safety in the 1 month to 2 year old patient population.

This was a single center, phase I dose escalation pharmacokinetic study of a single bolus dose of dexmedetomidine followed by a continuous infusion for up to 24 hours, in infants who were immediately post-operative from cardiac surgery and required tracheal intubation with mechanical ventilation in the post-operative period. This dose-response study of dexmedetomidine in infants consisted of two phases: a screening/enrollment phase, and a dose escalation phase.

Patients whose parents or legal guardians provided informed consent were screened within 7 days prior to enrollment. The screening/enrollment phase was performed first. Infants (1 month to 2 years of age) who were pre-operative from surgery were screened. Infants were eligible for the study if they were post-operative from cardiac surgery and required mechanical ventilation in the post-operative period with tracheal extubation expected within the first 24 post-operative hours. Enrollment criteria had to have been met within 7 days prior to enrollment. The dose escalation phase followed the screening/enrollment phase. All patients received 4 mg/kg orally of pentobarbital, an intra-operative IV dose of 20 µg/kg of fentanyl, an IV dose of 0.2 mg/kg of pancuronium on induction and another 0.2 mg/kg on institution of bypass. Three bolus and infusion dose combinations of dexmedetomidine were administered as follows: cohorts of 12 patients each received either low-dose dexmedetomidine (0.35 µg/kg IV bolus administered over 10 minutes, 0.25 µg/kg/hour continuous IV infusion), moderate-dose dexmedetomidine (0.7 µg/kg IV bolus administered over 10 minutes, 0.5 µg/kg/hour continuous IV infusion) or high-dose dexmedetomidine (1 µg/kg IV bolus over 10 minutes, 0.75 µg/kg/hour continuous IV infusion). Dexmedetomidine infusion was continued during the extubation process and tracheal extubation occurred when patients had met the respiratory criteria. Inter-patient dose escalation is shown in Table 35.

TABLE 35

Inter-Patient Escalation

| Dose Level | Loading Dose (µg/kg) | Continuous IV Infusion Rate (µg/kg/hour) |
|---|---|---|
| 1 | 0.35 | 0.25 |
| 2 | 0.7 | 0.5 |
| 3 | 1 | 0.75 |

Twelve patients were studied at each dose level. If more than 2 patients at a dose level experienced a dose-limiting toxicity (DLT) that was possibly, probably, or definitely related to study drug, the maximum tolerated dose (MTD) for the drug would have been exceeded and no additional patients would be studied at that dose level. If the MTD was exceeded at the first dose level, then the subsequent cohort of patients would be treated at a loading dose of 0.25 µg/kg and an infusion of 0.14 µg/kg/hour. If the MTD had been exceeded at the second or third dose levels, enrollment to the protocol would have been stopped.

The decision to escalate the dose was based on the review of safety and pharmacokinetic data for all patients in the previous cohort. If the median clearance was less than 70% of that reported in the adult population (35 L/hour), then accrual to the study was stopped.

This dose escalation study included dose cohorts of 1) 0.35 µg/kg bolus, 0.25 µg/kg/hour infusion; 2) 0.7 µg/kg bolus, 0.5 µg/kg/hour infusion; 3) or 1 µg/kg bolus, 0.75 µg/kg/hour infusion. This study provided pharmacokinetic data that would allow for improved dosing recommendations in a critically ill population of patients (infants who were post-operative from cardiac surgery and required mechanical ventilation in the post-operative period). This population of patients included, but was not limited to, infants diagnosed with Teratology of Fallot, atrio-ventricular canal defects, ventricular septal defects, coarctation of the aorta, bi-directional glen, hemi-fontan, and fontan completions. The Bispectral Index Scale (BIS) was used to measure sedation, and explore the utility of a non-invasive measurement of sedation in infants who were postoperative from cardiac surgery. Also, this study was designed to obtain preliminary data on the relationship between the level of sedation and dexmedetomidine plasma drug concentration in infants postoperative from cardiac surgery. Safety was also evaluated in this study.

A patient was eligible for study participation if he or she met the following criteria: was ≥1 month and ≤24 months of age; was post-operative from cardiac surgery with tracheal intubation/mechanical ventilation in the immediate post-operative period; had planned tracheal extubation within 24 hours post-operatively; adequate renal function (defined as serum creatinine≤0.6 mg/dL at age 1 month to 12 months or serum creatinine≤1.0 mg/dL at age>12 months to 24 months); adequate liver function (defined as total bilirubin≤1.5 mg/dL and serum glutamic pyruvic transaminase (SGPT)≤165 U/L for 1 month to 12 months and ≤90 U/L for >12 months to 24 months); had isolated heart surgery; and all parents or legal guardians of the patient signed a written informed consent.

A patient was not eligible for study participation if he or she met any of the following criteria: received another investigational drug within the past 30 days or received continuous infusions of muscle relaxants in the post-operative setting; had a positive blood culture without a subsequent negative culture or other evidence of ongoing serious infection; in the opinion of the investigator, would not be able to comply with the safety monitoring requirements of the study; showed signs or symptoms of elevated intracranial pressure (including, but not limited to, Cushing's triad (hypertension, bradycardia, and bradypnea), lethargy, bulging fontanelle, and seizures; had post-operative hypotension based on age (1 month to 2 months: systolic≤45 mm Hg, diastolic≤25 mm Hg, or mean arterial blood pressure≤35 mm Hg; >2 months to 6 months: systolic≤55 mm Hg, diastolic≤35 mm Hg, or mean arterial blood pressure≤45 mm Hg; and >6 months to 24 months: systolic≤65 mm Hg, diastolic≤45 mm Hg, or mean arterial blood pressure≤55 mm Hg); or had pre-existing bradycardia based on age (1 month to 2 months: heart rate≤90 bpm; 2 months to 12 months: heart rate≤80 bpm; >12 months to 24 months: heart rate≤70 bpm); had a heart block;

weighed <5 kg; or who, in the opinion of the investigator, was not an appropriate candidate for an investigational drug study.

Patients were discontinued from the study if any of the following occurred: there was a DLT, including bradycardia, hypotension, oversedation, or serious adverse effect; the patient's parent/guardian refused further protocol therapy; non-compliance that, in the opinion of the investigator, did not allow for ongoing participation in the study; and the investigator judged that withdrawal was in the best interest of the patient.

Patients who were off protocol therapy were followed until they met the off-study criteria which was defined as 30 days after the last dose of the investigational agent, death, lost to follow up, or withdrawal of consent for any further data submission. Follow-up data were required unless consent was withdrawn.

Eligible patients, who met all the inclusion criteria and none of the exclusion criteria, received 4 mg/kg orally of pentobarbital premedication, an intra-operative dose of 20 μg/kg of fentanyl, 0.2 mg/kg of pancuronium on induction and another 0.2 mg/kg on institution of bypass as intra-operative anesthetic. This was followed by administration of study drug where dexmedetomidine (0.35 μg/kg, 0.7 μg/kg, or 1 μg/kg) was administered as an IV loading dose over 10 minutes followed by a continuous maintenance IV infusion of 0.25 μg/kg/hour, 0.5 μg/kg/hour, or 0.75 μg/kg/hour. Patients received one of three loading/maintenance regimens of dexmedetomidine as follows: cohorts of 12 patients received low-dose dexmedetomidine (0.35 μg/kg bolus, 0.25 μg/kg/hour infusion), moderate-dose (0.7 μg/kg bolus, 0.5 μg/kg/hour infusion) or high-dose dexmedetomidine (1 μg/kg bolus, 0.75 μg/kg/hour infusion). Dexmedetomidine infusion was continued during the extubation process and tracheal extubation occurred when patients had met the respiratory criteria.

Study drug consisted of the test drug (investigational product), Precedex® (dexmedetomidine HCl injection), 118 μg of dexmedetomidine and 9 μg of sodium chloride in water, IV. The study drug was supplied as a clear, colorless, isotonic solution with a pH of 4.5. The solution was preservative free and contained no additives or chemical stabilizers. It was freely soluble in water with a pKa of 7. Dexmedetomidine was obtained by commercial supply for this study and was stored in the Pharmacy at a controlled room temperature of 15° C. to 30° C. (59° F. to 86° F.). Freezing was avoided.

Patients who met the selection criteria were enrolled in the study. Thirty-eight patients were enrolled in this study. Thirty-six patients completed the study drug infusion: 12 patients in each of the low, moderate and high dose cohorts. Randomization was not conducted in this study; this was a dose escalation study of a single bolus of dexmedetomidine followed by a continuous IV infusion for up to 24 hours in infants immediately post-operatively.

The study drug, dexmedetomidine, was administered as a bolus dose over 10 minutes followed by a continuous IV infusion to patients who returned from the operating room tracheally intubated, with planned tracheal extubation within 24 hours. Twelve patients were studied at each dose level. If more than 2 patients at a dose level experienced a DLT that was possibly, probably, or definitely attributable to the study drug, the MTD for the drug was considered to be exceeded and no additional patients were studied at that dose level. If the MTD was exceeded at the first dose level, then the subsequent cohort of patients were to be treated at a loading dose of 0.25 μg/kg and an infusion of 0.14 μg/kg/hr. If the MTD had been exceeded at the second or third dose levels, enrollment to the protocol would have been stopped. The dose levels were studied consecutively with pharmacokinetic analysis following the completion of each dose level. If the median clearance was less than 70% of that reported in the adult population (35 L/hr), accrual to the study was stopped. This was an unblinded study.

Patients were not allowed to receive continuous infusions of muscle relaxants in the postoperative setting. Additional sedation or analgesia in the form of fentanyl (0.25 to 1 μg/kg/dose), morphine (10 to 100 μg/kg/dose), or midazolam (10 to 100 μg/kg/dose) was allowed for those patients who were identified by the clinical team as being "under sedated". Any additional sedation medications, the dose, route of administration, and date and time of administration were recorded. Any medications taken during the study, other than the study drug, were recorded.

It is statistically reliable and clinically relevant to use power assessment and confidence intervals to detect dose proportionality, in which dose increases with an expected proportional increase in both AUC and $C_{max}$. The University of Michigan Sedation Score (UMSS) is a validated pediatric sedation scale and is used as a pharmacodynamic measurement for the Example 5 study. Other pharmacokinetic, PD, and safety measurements in this study are widely used and are generally recognized as reliable, accurate, and relevant for the study. The pharmacokinetic variables for assessment included: observed peak plasma concentration ($C_{max}$), time of observed peak plasma concentration ($T_{max}$), area under the plasma concentration-time curve from time zero to the last quantifiable time point ($AUC_{0-t}$), area under the plasma concentration-time curve from time zero to infinity ($AUC_{0-inf}$), terminal elimination rate constant ($\lambda z$), terminal half-life ($t_{1/2}$), end of infusion concentration (steady state, $C_{ss}$), plasma clearance (Cl), weight adjusted clearance ($Cl_w$), volume of distribution ($V_d$), and weight adjusted volume of distribution ($V_{dw}$). The primary PD variables assessed the level of sedation using BIS and the University of Michigan Sedation Scale Safety variables included exposure to study drug, adverse events (adverse effects), hepatotoxicity, DLT, laboratory results, vital signs, use of concomitant medication, and 12-lead electrocardiogram.

For the drug concentration measurements, approximately 14 mL of blood (14 samples per patient) were collected from each patient. Blood samples (1 mL) were collected in heparinized tubes for pharmacokinetic evaluation of plasma dexmedetomidine. For the low dose treatment group, blood samples were collected at time zero for the bolus dose, at the end of the bolus dose, at 0.5 hours after start of infusion, at the end of the maintenance infusion, and at 0.25, 0.5, 1, 2, 4, 8, 12, and 24 hours after the end of the maintenance infusion. For the remaining cohorts, blood samples were collected prior to the bolus dose, in close proximity to 0.5, 1, 2, and 4 to 6 hours after the start of the infusion, at 15-30 minutes prior to end of infusion (EOI), and at 0.25, 0.5, 1, 2, 4, 8, 12, and 15 to 18 hours after the EOI. Samples were collected from a different site than that of the infusion site. Samples were not collected from the 2nd lumen of the multi-lumen catheter through which the drug was administered. The exact time that the sample was collected along with the exact time that the drug was administered were recorded. Plasma was separated and stored at −80° C. until assayed. The lower limit of quantification in plasma is ≤4.24 pg/mL for dexmedetomidine. Each heparinized tube was labeled with the patient's study number, the study identification number, and the date and time that the sample was collected. Data were recorded on the Pharmacokinetic Study Form, which accompanied the sample.

The primary pharmacokinetic evaluation was to define the pharmacokinetics of increasing doses of dexmedetomidine administered as an IV bolus followed by a continuous IV infusion in infants who were postoperative from cardiac surgery. Data from all fully evaluable patients (those receiving at least 2 hours of dexmedetomidine infusion) were included in the analysis.

The pharmacodynamic assessments monitored continuously every hour until 24 hours after the discontinuation of the infusion included heart rate, blood pressure, mean arterial blood pressure, cardiac rhythm, oxygen saturation, and respiratory rate. The Bispectral Index Scale (BIS, Aspect Medical Systems, Natick, Mass.) and the University of Michigan Sedation Scale (UMSS) were used to assess the level of sedation.

The Bispectral Index Scale (BIS) integrates various electroencephalogram (EEG) descriptors into a single variable. The BIS readout is a dimensionless number scaled from 100 to 0, with 100 representing an awake EEG and zero representing complete electrical silence (cortical suppression). BIS and hypnotic drug dose have been shown to correspond to a statistically significant, linear, monotonic fashion during clinical trials, with BIS decreasing as the hypnotic dose is increased. The BIS monitor was applied to the patient's forehead prior to the bolus dose, and remained until the EOI. A member of the clinical team periodically did a sensor check to be sure signal quality and proper sensor application/adhesion were maintained. BIS values, with the exception of the Signal Quality Index (SQI) were blinded. Pre-stimulation BIS values were recorded for sedation assessments (or during non-stimulated times). The maximal BIS reading during stimulation was also recorded. The "resting" BIS values or those at non-stimulated times, along with the change in BIS with stimulation, were valuable in assessing not only the sedation drug effect, but also the analgesic properties of the drug, and thus provided better data to assess the PD of the drug. The investigators were blinded to the BIS readout until after the study was completed. The maximum BIS readout and the corresponding SQI were recorded for each hour that the patient was on study. The BIS sensor was removed from the patient's head after the infusion had been discontinued, and the patient had been declared awake by the clinical care team.

The UMSS is a simple, valid and reliable tool that facilitates rapid and frequent assessment and documentation of depth of sedation in children. The UMSS is a simple observational tool that assesses the level of alertness on a 5-point scale ranging from 1 (wide awake) to 5 (unarousable with deep stimulation). The UMSS score was assessed by the clinical nurse caring for the patient, and recorded every hour until the BIS sensor was removed.

Adverse events were reported in a routine manner at scheduled times during the trial. Certain adverse effects were reported in an expedited manner to allow for optimal monitoring of patient safety and care. Adverse events were reviewed at bi-weekly meetings by the principal investigator (PI), co-PI, and study coordinator. Events were classified as either adverse effects or serious adverse effects.

An adverse effect was defined as any untoward medical occurrence that presented itself during treatment or administration with a pharmaceutical product and which may or may not have a causal relationship with the treatment. A treatment-emergent adverse event (treatment-emergent adverse effect) was defined as any adverse effect with onset or worsening reported by a patient from the time that the first dose of study drug was administered until 24 hours had elapsed following discontinuation of study drug administration. An adverse effect that occurred during the treatment period was defined as any adverse effect with onset or worsening reported by a patient from the date/time of the start of study drug administration until the data/time of study drug discontinuation. An adverse effect that occurred post study drug was defined as any adverse effect with onset or worsening reported by the patient at a date/time which was later than the date/time of study drug discontinuation within the specific period. Adverse events were also classified by severity (mild, moderate, or severe). A serious adverse effect was defined as any untoward medical occurrence that at any dose resulted in death, was life threatening, required inpatient hospitalization or prolongation of existing hospitalization, created persistent or significant disability/incapacity, or a congenital anomaly/birth defect. MedWatch reports were completed for each event. Events were classified by the treating clinician and study coordinator. Events were classified as unlikely, possibly, or probably related to the study drug and either previously described (expected), or undescribed (unexpected). The PI was notified by pager or telephone of any serious adverse effects. All drug-related and previously undescribed toxicities were reviewed within 24 hours by the PI. Serious adverse effects that were expected because of the surgical procedure did not require expedited review and were reviewed bi-weekly. Previously undescribed toxicities and all serious adverse effects were reported to the IRB in writing by the investigator within 72 hours of the event. A letter summarized any adverse reactions or events that occurred, and the event outcome was described. If more than one unexpected or previously described serious adverse effect attributable to study drug was observed, accrual to the protocol was suspended. An ad hoc committee comprising the PI, subspecialty lead investigator, and at least 2 subspecialists not participating in the trial were convened by the PI within 24 hours of the second event. An assessment of the risks to patients were made, and a recommendation to continue with the study or close the trial were made to the IRB for review. If a decision was made to continue with the trial, the modifications to the protocol, the updated assessment of risks and benefits, and a modified informed consent were to be submitted to the IRB.

A dose limiting toxicity (DLT) was defined as any of the events that are possibly, probably, or definitely attributable to dexmedetomidine and fall under the following:

bradycardia defined by age: heart rate≤80 bpm (1 month to 2 months); heart rate≤70 bpm (>2 months to 12 months); heart rate≤60 bpm (>12 months to 24 months)

hypotension defined by age:

systolic≤40 mm Hg, diastolic≤20 mm Hg, or mean arterial blood pressure (MAP)≤30 mm Hg (1 month to 2 months)

systolic≤50 mm Hg, diastolic≤30 mm Hg, or MAP≤40 mm Hg (>2 months to 6 months)

systolic≤60 mm Hg, diastolic≤40 mm Hg, or MAP≤50 mm Hg (>12 months to 24 months)

bradypnea: respiratory rate≤14 bpm in extubated patients oversedation deemed clinically relevant by the clinical care providers or requiring intervention. Clinical signs included difficulty arousing with moderate stimulation, bradypnea (respiratory rate≤14), bradycardia, and hypotension and serious adverse event.

Laboratory data for the clinical laboratory tests was collected as standard of care were also reviewed during the study and included arterial blood gas, lactate, basic metabolic panel, magnesium, phosphorus, coagulation panel, liver function panel, and complete blood count. Approximately 14 mL of blood was collected from each patient for the clinical laboratory tests during the study.

Additional safety assessments were carried out including physical examination, 12-lead electrocardiogram, hepatotoxicity, and sedation/analgesia supplemental medication titration.

The statistical analyses were performed using SAS, version 9.1. Pharmacokinetic parameters were determined by non-compartmental analysis using WinNonlin Pro Version 5.1. All statistical tests were two-sided, and p-values≤0.05 were considered statistically significant (after rounding to 4 decimal places), unless specified otherwise. Descriptive statistics (number of patients [N], mean, median, standard deviation (SD), minimum, and maximum) were used to summarize continuous variables. Coefficient of variation (CV) was calculated for continuous pharmacokinetic variables. For $T_{max}$ (a discrete variable), N, median, minimum and maximum were displayed. The mean and median were displayed to one decimal place more than the raw value. For categorical variables, N and percent were shown. All percentages were reported to one decimal place. Patient listings of all collected and recorded data as well as derived variables were presented. Changes noted between analyses defined in the protocol and those defined in the SAP included:

There were two discrepancies between the study and the protocol. One regarded the definition of a DLT. The study defines DLT to include bradycardia and hypotension defined by age, and clinically relevant oversedation, and serious adverse effects as DLTs. The protocol included only bradycardia defined by age, hypotension defined by age, and bradypnea defined by respiratory rate.

Another discrepancy was in regards to the collection of ECG data. The protocol stated that ECGs were obtained pre- and post-treatment and compared for evidence of new ischemia. ECG charts and QT intervals were not available and there was no plan to analyze the ECG data.

The protocol referenced collection of plasma samples for pharmacogenomic testing; however, no samples were collected for pharmacogenomic testing or analysis.

Four patient populations were defined in this study.

Enrolled Population: All patients who signed inform consent were in the Enrolled Population.

Intent-to-Treat (ITT) Population: Patients who were treated and were protocol compliant were included in the ITT Population.

Safety Population: All patients who received study drug were included in the Safety Population. This population was used in all safety analyses.

Pharmacokinetic Analysis Population: All patients who received at least 2 hours of dexmedetomidine infusion were included in the Pharmacokinetic Analysis Population.

Plasma samples were assayed for dexmedetomidine concentrations. The following parameters were calculated for each patient: $AUC_{0-t}$, $AUC_{0-inf}$, $C_{max}$, $T_{max}$, Cl, $Cl_w$, $V_d$, weight adjusted volume of distribution ($V_{dw}$), $\lambda z$, $t_{1/2}$, and $C_{ss}$. Area under the plasma concentration-time curve (AUC) and $C_{max}$ were the primary pharmacokinetic parameters.

Model-independent methods were used by Hospira to determine the pharmacokinetic parameters described above using Non-Compartmental Analysis of WinNonlin version 5.1 (Pharsight, Mountain View Calif., USA). Summary statistics for these parameters were tabulated. Geometric means and coefficients of variation were presented for AUC and $C_{max}$.

An assessment of dose proportionality was made for AUC and $C_{max}$ among the dose levels administered within an age group and overall. The Power Analysis approach and data visualization techniques were used for this assessment.

Dose proportionality was evaluated statistically using the Power Model. The Power Model has the form: parameter=a (dose)b×random error, where a and b are the coefficient and exponent, respectively of the equation. The power model was analyzed using linear regression after log transformation using the following equation: ln(parameter)=ln(a)+b×ln (dose)+random error. Dose proportionality was concluded if the 95% confidence interval (CI) for b included 1 or, b=0 (H0) was not rejected when applied to dose-normalized parameters.

Data visualization techniques included the plotting of weight adjusted clearance over age, AUC, and $C_{max}$ against administered dose to determine if trends were present in the data that would indicate the need for further assessment.

An exploratory assessment of a potential pharmacokinetic/PD relationship was undertaken. The relationship of PD parameters such as sedation level or need for rescue sedation medication and pharmacokinetic parameters AUC or $C_{max}$ were explored.

The pharmacodynamic analysis was summarized by dose level for ITT and Pharmacokinetic Populations. The PD assessments contained sedation levels and vital signs that were monitored continuously every hour until 24 hours after the discontinuation of the infusion. Parameters included heart rate, blood pressure, MAP, cardiac rhythm, oxygen saturation and respiratory rate. Descriptive statistics (arithmetic mean, SD, median, minimum and maximum) were calculated for quantitative PD data as well as for the changes from Baseline by dose level. The BIS and the UMSS were used to assess the level of sedation.

The UMSS score was summarized by count and percentage of patients for each sedation level by dose level. The number and percentage of patients using fentanyl, morphine, or midazolam during study drug administration was summarized by dose level and treatment differences were assessed by Fisher's Exact Test. The total amount of fentanyl, morphine, and midazolam was summarized descriptively for each dose level, and by time period after the start of infusion in each dose level. The time frame was to be analyzed for total amount of sedation medication after start of infusion at 4 hours, 4 to 8 hours, 8 to 12 hours, and 0 to 24 hours. Exploratory analysis was performed for the relationship between exposure of pharmacokinetic parameters (such as AUC, $C_{max}$, or $C_{ss}$) and usage of sedation medication (such as total dose).

Descriptive statistics were used to summarize vital signs measurements for heart rate, blood pressure, temperature, mean arterial blood pressure (MAP), respiratory rate, and saturation of peripheral oxygen ($SpO_2$) in a dose-dependent manner with time compared with Baseline. Treatment differences in the mean change from Baseline on each timepoint were assessed by one-way analysis of variance (ANOVA) with treatment factor in the model.

All safety data were listed by patients. Safety data included exposure of study drug, adverse effects, cardiac ischemia, liver function tests, DLT assessments, clinical laboratory evaluations, physical exams, and the use of concomitant medications. Descriptive statistics (arithmetic mean, SD, median, minimum and maximum) were calculated for quantitative safety data as well as for the difference from Baseline, when appropriate.

The exposure to study medication was quantified according to the bolus dose and maintenance dose of study drug administered. Loading dose (or bolus dose) was summarized using the parameters of total dose and duration of dose. Maintenance dose was summarized using the total dose, and total duration of dose (in hours). Total dose equaled loading dose+ CIVI rate×duration of dose. Duration of dose and total hours of dose were both calculated using time of last administration minus time of first administration, excluding interruptions. The patient's weight was carried forward to use in dose calculation.

Adverse events were coded using the most updated version of the Medical Dictionary for Regulatory Activities (MedDRA Version 11.0) available and summarized by dose level for the number of patients reporting the adverse effect and the number of adverse effects reported. A by-patient adverse effect data listing included verbatim term, coded term, treatment group, severity, and relationship to treatment provided. Serious adverse events associated with death and adverse effects leading to discontinuation of study drug were also summarized and listed. A treatment-emergent adverse effect was defined as any adverse effect with onset or worsening reported by a patient from the time that the first dose of study drug was administered until 24 hours had elapsed following discontinuation of the study drug. For summaries by severity, if a patient had multiple events occurring in the same system organ class (SOC) or same preferred term, then the event with the highest severity was summarized. Any adverse effect with a missing severity was summarized as severe. Similar methodology was applied to relationship to study drug.

Laboratory test results for change from Baseline were tabulated descriptively by treatment. All laboratory values outside the normal range were flagged in the data listings. Patients were evaluated by body system and were categorized as normal or abnormal. Since ECG charts and QT intervals were not available, ECG data were not analyzed. A summary of hepatotoxicity was presented by number and percentage of patients by dose level in each scheduled visit.

The sample size was based on the determination of the pharmacokinetic profile of dexmedetomidine. Based on an estimated inter-patient variability of 50% for steady state concentration, a sample size of 36 evaluable patients was to be sufficient to detect a difference (alpha 0.05, power 80%) for AUC and $C_{ss}$ between the three dosing groups. Twelve evaluable patients were to be enrolled into each dose group. Based on clinical intensive care unit (CICU) patient census, it was estimated that 15 months would be required to complete enrollment.

Patient disposition is summarized in Table 36.

TABLE 36

| Disposition of Patients - Enrolled Patients | | | | |
|---|---|---|---|---|
| Patients (%) | Low Dose[a] N = 12 | Moderate Dose[b] N = 12 | High Dose[c] N = 14 | Total N = 38 |
| Patients who completed treatment | 12 (100.0) | 12 (100.0) | 12 (85.7) | 36 (94.7) |

TABLE 36-continued

| Disposition of Patients - Enrolled Patients | | | | |
|---|---|---|---|---|
| Patients (%) | Low Dose[a] N = 12 | Moderate Dose[b] N = 12 | High Dose[c] N = 14 | Total N = 38 |
| Patients who prematurely discontinued study | 1 (8.3) | 0 | 2 (14.3)[d] | 3 (7.9) |
| Patients in Safety Population | 12 (100.0) | 12 (100.0) | 14 (100.0) | 38 (100.0) |
| Patients in Intent-to-Treat Population | 12 (100.0) | 12 (100.0) | 12 (85.7) | 36 (94.7) |
| Patients in Pharmacokinetic Population | 12 (100.0) | 12 (100.0) | 12 (85.7) | 36 (94.7) |

[a]Low-dose dexmedetomidine (0.35 µg/kg bolus, 0.25 µg/kg/hour infusion).
[b]Moderate-dose dexmedetomidine (0.7 µg/kg bolus, 0.5 µg/kg/hour infusion).
[c]High-dose dexmedetomidine (1.0 µg/kg bolus, 0.75 µg/kg/hour infusion).
[d]Two patients in the high dexmedetomidine dose group discontinued the study and were not included in the ITT Population.

Thirty-eight patients were enrolled into the study and assigned into one of 3 treatment groups: low-dose dexmedetomidine (0.35 µg/kg bolus, 0.25 µg/kg/hour infusion), moderate-dose dexmedetomidine (0.7 µg/kg bolus, 0.5 µg/kg/hour infusion), or high-dose dexmedetomidine (1.0 µg/kg bolus, 0.75 µg/kg/hour infusion). Of the 38 enrolled patients, 3 (7.9%) discontinued the study prematurely. One patient in the low-dose dexmedetomidine treatment group completed study drug infusion and subsequently discontinued the study. Two patients in the high-dose dexmedetomidine treatment group discontinued the study prematurely; these patients were not included in the Pharmacokinetic Population. 36 of the 38 enrolled patients (94.7%) completed treatment.

All 38 patients enrolled into the study received at least 1 dose of study medication and were included in the Safety Population. Thirty-six patients received at least 2 hours of dexmedetomidine infusion and had sufficient concentration data to calculate the primary pharmacokinetic parameters; these patients were included in the Pharmacokinetic Population. Thirty-six patients in the ITT Population completed treatment.

Patients who prematurely discontinued treatment were recorded. Protocol deviations were also recorded. Demographics of the patient population were collected as well as medical and birth history. Prior and concomitant medications were also recorded.

Summary statistics for the dexmedetomidine loading doses and maintenance infusion doses are shown in Table 37.

TABLE 37

| Summary Statistics of Dosing-Related Data | | | | |
|---|---|---|---|---|
| Dose-Related Variable | | 0.35 µg/kg + 0.25 µg/kg/h | 0.70 µg/kg + 0.50 µg/kg/h | 1.00 µg/kg + 0.75 µg/kg/h |
| Loading dose (ng) | Mean (SD) | 2782.000 (701.169) | 5144.417 (1169.842) | 7468.333 (1759.374) |
| | Median | 2620.000 | 4907.000 | 6850.000 |
| | Min, Max | 1876.00, 4165.00 | 3787.00, 7070.0 | 5100.00, 11200.00 |
| | n | 12 | 12 | 12 |

TABLE 37-continued

| Summary Statistics of Dosing-Related Data | | | | |
|---|---|---|---|---|
| Dose-Related Variable | | 0.35 µg/kg + 0.25 µg/kg/h | 0.70 µg/kg + 0.50 µg/kg/h | 1.00 µg/kg + 0.75 µg/kg/h |
| Maintenance infusion dose (ng) | Mean (SD) | 17699.500 (14649.792) | 34790.417 (18282.909) | 57580.000 (29129.275) |
| | Median | 13638.000 | 31060.500 | 45864.000 |
| | Min, Max | 7375.00, 61707.00 | 10443.00, 68425.00 | 2669.00, 117300.00 |
| | n | 12 | 12 | 12 |
| Total dose (ng) | Mean (SD) | 20481.500 (14922.818) | 39934.833 (18364.830) | 65048.333 (28941.225) |
| | Median | 16589.500 | 35950.000 | 53799.000 |
| | Min, Max | 9853.00, 65347.00 | 15427.00, 73255.00 | 35196.00, 124200.00 |
| | n | 12 | 12 | 12 |
| Loading infusion duration (h) | Mean (SD) | 0.182 (0.021) | 0.168 (0.021) | 0.183 (0.038) |
| | Median | 0.167 | 0.167 | 0.183 |
| | Min, Max | 0.17, 0.22 | 0.12, 0.20 | 0.12, 0.27 |
| | n | 12 | 12 | 12 |
| Maintenance infusion duration (h) | Mean (SD) | 8.901 (6.055) | 9.853 (6.055) | 10.961 (6.635) |
| | Median | 6.610 | 8.619 | 8.708 |
| | Min, Max | 4.17, 23.75 | 2.94, 23.82 | 4.18, 22.65 |
| | n | 12 | 12 | 12 |
| Time between start of doses (min) | Mean (SD) | 14.500 (2.646) | 11.917 (2.610) | 12.833 (1.899) |
| | Median | 14.500 | 11.500 | 13.000 |
| | Min, Max | 11.00, 20.00 | 7.00, 17.00 | 10.00, 16.00 |
| | n | 12 | 12 | 12 |
| Time from end of 1$^{st}$ to beginning of 2$^{nd}$ infusion (min) | Mean (SD) | 3.583 (2.429) | 1.833 (2.167) | 1.833 (1.403) |
| | Median | 3.00 | 1.500 | 2.000 |
| | Min, Max | 1.00, 8.00 | 0.00, 7.00 | 0.00, 4.00 |
| | n | 12 | 12 | 12 |

Two patients were excluded from the pharmacokinetic analysis. Both patients were in the high dexmedetomidine dose group. Thirty-six patients had sufficient concentration data to calculate the pharmacokinetic parameters and were included in the pharmacokinetic analysis set. Patients who were treated and protocol compliant were included in the ITT Population. The pharmacokinetic population and ITT included the same patients; therefore, analysis for baseline characteristics was identical for the ITT and the pharmacokinetic profiles. Safety profile was analyzed for the Safety Population; thirty-eight patients received at least 1 dose of study medication and were included in the Safety Population.

The pharmacokinetic profile demonstrated linearity and dose proportionality among 0.25, 0.50 and 0.75 µg/kg/hour dose levels; as dose increased, AUC and $C_{max}$ increased in proportion. The mean doses were given as 20.5, 40.4, and 65.1 µg to 0.25, 0.50 and 0.75 µg/kg/hour dose levels, respectively), and as shown, exposure increased accordingly. $AUC_{0-inf}$, $AUC_{0-t}$ and $C_{max}$ of dexmedetomidine displayed positive linearity among 0.25, 0.50 and 0.75 µg/kg/hour dose levels. The apparent $t_{1/2}$ of dexmedetomidine was 2.33 hrs, 2.12 hrs, and 3.05 hrs for low, moderate, and high dose levels, respectively. The geometric mean slope among the three dose levels and the 95% confidence intervals were 1.263 (0.820, 1.706) for $AUC_{0-inf}$ and 0.898 (0.652, 1.143) for $C_{max}$. A similar positive linear trend was shown among the three age groups 1 to <6 months, 6 to <12 months and 12 to 24 months.

The statistical analysis for assessing dose proportionality for the three doses of dexmedetomidine is presented in Table 38. Dose proportionality can be concluded for $AUC_{0-t}$, $AUC_{0-inf}$ and $C_{max}$ given that the 95% CI for slope included one for these parameters.

TABLE 38

| Dose proportionality analysis of dexmedetomidine pharmacokinetic parameters - PK population | | | | |
|---|---|---|---|---|
| | Geometric Means | | | |
| Parameter (units) | Dexmedetomidine Low Dose$^a$ N = 12 | Dexmedetomidine Moderate Dose$^b$ N = 12 | Dexmedetomidine High Dose$^c$ N = 12 | Slope$^d$ (95% CIs) |
| All PK Population | | | | |
| n | 12 | 12 | 12 | |
| $AUC_{0-t}$ [hr * (ng/mL)] | 1804.57 | 4163.01 | 7453.03 | 1.282 (0.835, 1.729) |
| $AUC_{0-inf}$ [hr * (ng/mL)] | 1851.13 | 4195.77 | 7492.29 | 1.263 (0.820, 1.706) |
| $C_{max}$ (ng/mL) | 277.59 | 460.66 | 760.76 | 0.898 (0.652, 1.143) |
| Age 1 to <6 months | | | | |
| n | 5 | 4 | 3 | |
| $AUC_{0-t}$ [hr * (ng/mL)] | 1630.18 | 4171.58 | 7477.55 | 1.380 (0.631, 2.129) |
| $AUC_{0-inf}$ [hr * (ng/mL)] | 1668.59 | 4209.96 | 7511.57 | 1.362 (0.621, 2.103) |
| $C_{max}$ (ng/mL) | 260.44 | 444.34 | 847.52 | 1.010 (0.455, 1.566) |

TABLE 38-continued

Dose proportionality analysis of dexmedetomidine pharmacokinetic parameters - PK population

| Parameter (units) | Dexmedetomidine Low Dose[a] N = 12 | Geometric Means Dexmedetomidine Moderate Dose[b] N = 12 | Dexmedetomidine High Dose[c] N = 12 | Slope[d] (95% CIs) |
|---|---|---|---|---|
| Age 6 to <12 months | | | | |
| n | 4 | 6 | 7 | |
| $AUC_{0-t}$ [hr * (ng/mL)] | 1542.76 | 4647.87 | 8392.11 | 1.541 (0.828, 2.255) |
| $AUC_{0-inf}$ [hr * (ng/mL)] | 1601.44 | 4675.95 | 8435.14 | 1.512 (0.804, 2.221) |
| $C_{max}$ (ng/mL) | 286.81 | 500.04 | 762.71 | 0.891 (0.489, 1.292) |
| Age 12 to 24 months | | | | |
| n | 3 | 2 | 2 | |
| $AUC_{0-t}$ [hr * (ng/mL)] | 2634.53 | 2979.07 | 4895.66 | 0.501 (−1.098, 2.100) |
| $AUC_{0-inf}$ [hr * (ng/mL)] | 2669.84 | 3010.96 | 4929.13 | 0.495 (−1.092, 2.083) |
| $C_{max}$ (ng/mL) | 295.55 | 387.09 | 641.22 | 0.654 (0.130, 1.177) |

[a]Low dose dexmedetomidine: 0.35 μg/kg bolus, 0.25 μg/kg/hour infusion.
[b]Moderate dose dexmedetomidine: 0.7 μg/kg bolus, 0.5 μg/kg/hour infusion.
[c]High dose dexmedetomidine: 1.0 μg/kg bolus, 0.75 μg/kg/hour infusion.
[d]Estimate slopes were computed from linear regression of log (PK parameters) versus log (dose) over dose range.
CI = confidence interval The predicted mean curve for $AUC_{0-inf}$, $AUC_{0-t}$, and $C_{max}$ generated using the power fit model are presented in FIGS. 34A-C.

A linear plot illustrating the mean dexmedetomidine concentrations over time is shown in FIG. 35. The mean dexmedetomidine concentration profiles (over time) for the three treatment groups were similar, as illustrated in FIG. 35. Mean plasma concentrations of dexmedetomidine tended to increase with increased doses of dexmedetomidine. The highest mean plasma concentrations were observed in the high-dose dexmedetomidine treatment group. AUC and $C_{max}$ values increased with increasing dose. Half-life values were independent of dose of level. The mean half-life values for the low, moderate and high dose combinations were 2.33, 2.12 and 3.05 hours, respectively. Pharmacokinetic parameters of dexmedetomidine were summarized using descriptive statistics and are presented in Table 39.

TABLE 39

Summary of Pharmacokinetic Parameters - ITT Population

| Parameter/ Statistics | Low Dose[a] N = 12 | Moderate Dose[b] N = 12 | High Dose[c] N = 12 |
|---|---|---|---|
| Primary Pharmacokinetic Parameters | | | |
| $AUC_{0-t}$ (hr * ng/mL) | | | |
| Mean (SD) | 2472.6 (2651.38) | 4761.3 (2855.34) | 8644.5 (5998.26) |
| Median (Min, Max) | 1656.3 (721.9, 10420.7) | 3443.5 (2364.2, 10891.8) | 6910 (4400.6, 25990.7) |
| % CV | 107.2 | 60.0 | 69.4 |
| $AUC_{0-inf}$ (hr * ng/mL) | | | |
| Mean (SD) | 2511.9 (2651.99) | 4793.9 (2864.88) | 8686.5 (6016.70) |
| Median (Min, Max) | 1671.9 (735.0, 10458.3) | 3469.1 (2389.8, 10961.0) | 6948.0 (4441.0, 26078.4) |
| % CV | 105.6 | 59.8 | 69.3 |
| $C_{max}$ (hr/mL) | | | |
| Mean (SD) | 300.1 (116.75) | 479.6 (172.99) | 786.4 (233.96) |
| Median (Min, Max) | 296.5 (113, 473) | 440.0 (339, 1010) | 681.5 (602, 1340) |
| % CV | 39 | 36 | 30 |
| Secondary Pharmacokinetic Parameters | | | |
| $T_{max}$ (hour)[d] | | | |
| Median (Min, Max) | 2.39 (0.17, 18.98) | 6.98 (1.20, 23.83) | 6.13 (0.68, 22.55) |
| % CV | 130.48 | 73.90 | 93.98 |
| $t_{1/2}$ (hour) | | | |
| Mean (SD) | 2.33 (1.305) | 2.12 (0.788) | 3.05 (1.947) |
| Median (Min, Max) | 1.87 (1.14, 5.79) | 2.02 (1.00, 3.89) | 2.40 (1.65, 8.35) |
| % CV | 55.93 | 37.18 | 63.77 |
| λz (1/hour) | | | |
| Mean (SD) | 0.37 (0.151) | 0.37 (0.141) | 0.28 (0.108) |
| Median (Min, Max) | 0.37 (0.12, 0.61) | 0.34 (0.18, 0.69) | 0.29 (0.08, 0.42) |
| % CV | 41.34 | 38.17 | 38.19 |

TABLE 39-continued

Summary of Pharmacokinetic Parameters - ITT Population

| Parameter/<br>Statistics | Low Dose[a]<br>N = 12 | Moderate Dose[b]<br>N = 12 | High Dose[c]<br>N = 12 |
|---|---|---|---|
| Cl (L/hour) | | | |
| Mean (SD) | 10.24 (3.753) | 9.27 (4.001) | 8.49 (3.145) |
| Median (Min, Max) | 9.74 (4.30, 17.12) | 8.05 (4.44, 19.17) | 7.84 (4.70, 15.17) |
| % CV | 36.66 | 43.17 | 37.02 |
| $Cl_w$ (L/hour/kg) | | | |
| Mean (SD) | 1.36 (0.637) | 1.24 (0.362) | 1.13 (0.278) |
| Median (Min, Max) | 1.24 (0.60, 2.93) | 1.24 (0.53, 2.05) | 1.15 (0.69, 1.55) |
| % CV | 46.90 | 29.27 | 24.62 |
| $V_d$ (L) | | | |
| Mean (SD) | 30.54 (11.015) | 27.20 (11.798) | 36.02 (24.467) |
| Median (Min, Max) | 29.09 (16.83, 54.09) | 27.34 (11.97, 48.33) | 27.53 (16.21, 95.34) |
| % CV | 36.06 | 43.38 | 67.93 |
| $V_{dw}$ (L/kg) | | | |
| Mean (SD) | 3.97 (1.432) | 3.71 (1.693) | 5.32 (4.865) |
| Median (Min, Max) | 3.53 (2.01, 5.93) | 3.36 (1.74, 7.75) | 3.34 (2.70, 18.69) |
| % CV | 36.05 | 45.60 | 91.53 |

[a]Low-dose dexmedetomidine: (0.35 µg/kg bolus, 0.25 µg/kg/hour infusion).
[b]Moderate-dose dexmedetomidine: (0.7 µg/kg bolus, 0.5 µg/kg/hour infusion).
[c]High-dose dexmedetomidine: (1.0 µg/kg bolus, 0.75 µg/kg/hour infusion).
[d]$T_{max}$ is presented as median only (minimum, maximum).
CV = coefficient of variation,
ITT = Intent-to-Treat,
max = maximum,
min = minimum,
N, n = number of patients,
SD = standard deviation Clearance and weight-adjusted clearance over age are presented in FIG. 36. No noticeable increase or decrease in clearance or weight-adjusted clearance for increasing age was observed. No additional regression analysis was performed between age and pharmacokinetic parameters.

A summary of the level of sedation, measured with the UMSS, at each time point during the treatment period for the enrolled population is presented in Table 40. Patients had deep sedation (UMSS 3-4) from pre-dose to 2 hours after infusion, and maintained a moderate level of sedation (UMSS 1-3) after 4 hours infusion through the end of infusion for all dose levels. There was a correlated relationship between plasma concentration and UMSS for low dose 30 minutes after start of infusion, moderate dose 8 hours after end of infusion, and high dose 30-15 minutes prior to end of infusion and 60 minutes after end of infusion. With the UMSS, fewer patients were categorized as "unarousable" at 1 hour post-infusion as compared with Pre-bolus/Baseline, for all three dexmedetomidine dose groups. After 1 hour of post-infusion of dexmedetomidine, the level of sedation had decreased for all dose groups. Patients became less sedated from the time of infusion to 6 hours post-infusion. This was apparent with all 3 doses of dexmedetomidine; the incidence of patients who were "unarousable" at Pre-bolus/Baseline was 91.7%, 91.7%, and 83.3% for the low, moderate, and high-dose dexmedetomidine groups, respectively. At six hours post-infusion, the incidence of patients who were "moderately sedated/somnolent" was 58.3%, 41.7%, and 50.0% for each of the dexmedetomidine dose groups.

TABLE 40

Summary of Level of Sedation (UMSS) at Selected Time Points During Treatment Period - ITT Population

| | Number (%) of Patients | | | |
|---|---|---|---|---|
| Time Point<br>Characteristic | Low Dose[a]<br>N = 12 | Moderate Dose[b]<br>N = 12 | High Dose[c]<br>N = 12 | p-values[d] |
| Pre-bolus/Baseline | | | | 0.5788 |
| Awake and alert | 0 | 0 | 0 | |
| Minimally sedated/Sleepy | 1 (8.3) | 0 | 0 | |
| Moderately sedated/Somnolent | 0 | 0 | 0 | |
| Deeply sedated/Deep sleep | 0 | 1 (8.3) | 1 (8.3) | |
| Unarousable | 11 (91.7) | 11 (91.7) | 10 (83.3) | |
| Post-bolus/Pre-infusion | | | | 0.4288 |
| Awake and alert | 0 | 0 | 0 | |
| Minimally sedated/Sleepy | 1 (8.3) | 0 | 0 | |
| Moderately sedated/Somnolent | 0 | 1 (8.3) | 0 | |
| Deeply sedated/Deep sleep | 1 (8.3) | 2 (16.7) | 0 | |
| Unarousable | 10 (83.3) | 9 (75.0) | 11 (91.7) | |

TABLE 40-continued

Summary of Level of Sedation (UMSS) at Selected Time Points During Treatment Period - ITT Population

| Time Point Characteristic | Low Dose[a] N = 12 | Moderate Dose[b] N = 12 | High Dose[c] N = 12 | p-values[d] |
|---|---|---|---|---|
| Post Infusion Hour 1 | | | | 0.4880 |
| Awake and alert | 0 | 0 | 0 | |
| Minimally sedated/Sleepy | 1 (8.3) | 0 | 0 | |
| Moderately sedated/Somnolent | 1 (8.3) | 0 | 2 (16.7) | |
| Deeply sedated/Deep sleep | 1 (8.3) | 3 (25.0) | 1 (8.3) | |
| Unarousable | 9 (75.0) | 9 (75.0) | 8 (66.7) | |
| Post Infusion Hour 3 | | | | 0.1834 |
| Awake and alert | 0 | 0 | 0 | |
| Minimally sedated/Sleepy | 2 (16.7) | 2 (16.7) | 1 (8.3) | |
| Moderately sedated/Somnolent | 3 (25.0) | 2 (16.7) | 4 (33.3) | |
| Deeply sedated/Deep sleep | 7 (58.3) | 3 (25.0) | 2 (16.7) | |
| Unarousable | 0 | 5 (41.7) | 4 (33.3) | |
| Post Infusion Hour 6 | | | | 0.8306 |
| Awake and alert | 0 | 1 (8.3) | 1 (8.3) | |
| Minimally sedated/Sleepy | 2 (16.7) | 3 (25.0) | 0 | |
| Moderately sedated/Somnolent | 7 (58.3) | 5 (41.7) | 6 (50.0) | |
| Deeply sedated/Deep sleep | 1 (8.3) | 2 (16.7) | 2 (16.7) | |
| Unarousable | 1 (8.3) | 1 (8.3) | 1 (8.3) | |
| Post Infusion Hour 10 | | | | 0.5512 |
| Awake and alert | 3 (25.0) | 1 (8.3) | 3 (25.0) | |
| Minimally sedated/Sleepy | 2 (16.7) | 4 (33.3) | 2 (16.7) | |
| Moderately sedated/Somnolent | 1 (8.3) | 4 (33.3) | 1 (8.3) | |
| Deeply sedated/Deep sleep | 2 (16.7) | 1 (8.3) | 3 (25.0) | |
| Unarousable | 0 | 1 (8.3) | 0 | |
| Post Infusion Hour 14 | | | | 0.5683 |
| Awake and alert | 2 (16.7) | 2 (16.7) | 4 (33.3) | |
| Minimally sedated/Sleepy | 0 | 3 (25.0) | 2 (16.7) | |
| Moderately sedated/Somnolent | 4 (33.3) | 3 (25.0) | 2 (16.7) | |
| Deeply sedated/Deep sleep | 2 (16.7) | 1 (8.3) | 1 (8.3) | |
| Unarousable | 0 | 0 | 0 | |
| Post Infusion Hour 18 | | | | 0.3840 |
| Awake and alert | 0 | 1 (8.3) | 2 (16.7) | |
| Minimally sedated/Sleepy | 2 (16.7) | 3 (25.0) | 0 | |
| Moderately sedated/Somnolent | 2 (16.7) | 1 (8.3) | 2 (16.7) | |
| Deeply sedated/Deep sleep | 1 (8.3) | 0 | 0 | |
| Unarousable | 0 | 1 (8.3) | 0 | |
| Post Infusion Hour 22 | | | | 0.4821 |
| Awake and alert | 1 (8.3) | 1 (8.3) | 0 | |
| Minimally sedated/Sleepy | 0 | 0 | 0 | |
| Moderately sedated/Somnolent | 2 (16.7) | 0 | 1 (8.3) | |
| Deeply sedated/Deep sleep | 0 | 0 | 0 | |
| Unarousable | 0 | 1 (8.3) | 0 | |
| Post Infusion Hour 26 | | | | — |
| Awake and alert | 0 | 0 | 0 | |
| Minimally sedated/Sleepy | 1 (8.3) | 0 | 0 | |
| Moderately sedated/Somnolent | 0 | 0 | 0 | |
| Deeply sedated/Deep sleep | 0 | 0 | 0 | |
| Unarousable | 0 | 0 | 0 | |

[a]Low-dose dexmedetomidine: (0.35 µg/kg bolus, 0.25 µg/kg/hour infusion).
[b]Moderate-dose dexmedetomidine: (0.7 µg/kg bolus, 0.5 µg/kg/hour infusion).
[c]High-dose dexmedetomidine: (1.0 µg/kg bolus, 0.75 µg/kg/hour infusion).
[d]P-values are from Cochran-Mantel-Haenszel test.
Note:
Patient 33 UMSS scores were not applicable due to continuous infusion of neuromuscular blockade.
ITT = Intent-to-Treat,
— = not applicable,
N = number of patients,
UMSS = University of Michigan Sedation Scale A summary of the level of sedation (BIS scores) at each time point during the treatment period for the ITT Population was reviewed. Patients became less sedated from the time of infusion to 6 hours post-infusion. This was more apparent with the low and moderate doses of dexmedetomidine; the pre-infusion mean changes from Baseline maximum BIS values were −1.0±9.72 and −5.8±113.22 for patients in the low and moderate dose groups, respectively. Six hours post-infusion, the mean changes from Baseline maximum BIS values were 12.7±28.52 and 14.2±12.21 for patients in the low and moderate dose groups, respectively. Patients who received the highest dose of dexmedetomidine also became increasingly awake with time; however, the mean changes from Baseline to up to 6 hours post-infusion were less than observed with the lower doses; the preinfusion mean change from the Baseline maximum BIS score was −8.2±13.43, and at 6 hours post-infusion it was 2.3±14.86. The SQI at each time point during the treatment period for the ITT Population was summarized. The SQI values were similar among the three dexmedetomidine dose groups at post-bolus dose/pre-infusion and remained consistently stable through 16 hours post infusion; there was more variability after 16 hours post-infusion of dexmedetomidine.

An analysis of the correlation between the UMSS score and dexmedetomidine plasma concentration is presented in Table 41. The Pearson correlation was used to test zero correction of dexmedetomidine of plasma and UMSS scores, significant correlation was observed at the following timepoints: 30 minutes after start of infusion of low dose-dexmedetomidine (p=0.0266), 8 hours after the EOI of moderate dose dexmedetomidine (p=0.0423), and 30 to 15 minutes prior to the EOI (p=0.0255) and 60 minutes after the EOI (0.0502) of high-dose dexmedetomidine. With the exception of these time points, dexmedetomidine plasma concentrations did not correlate with UMSS sedation scores.

TABLE 41

Analysis of Correlation between the University of Michigan Sedation Scale and Dexmedetomidine Plasma Concentration - ITT Population

| | Statistics | | | | | | | | |
|---|---|---|---|---|---|---|---|---|---|
| | Low Dose[a] N-12 | | | Moderate Dose[b] N = 12 | | | High Dose[c] N = 12 | | |
| Timepoint | Dex Plasma | UMSS | p-value | Dex Plasma | UMSS | p-value | Dex Plasma | UMSS | p-value |
| Pre-dose | | | | | | | | | |
| n | 12 | 12 | | 12 | 12 | | 11 | 11 | |
| Mean (SD) | 0 | 3.8 (0.87) | | 0 | 3.9 (0.29) | | 0 | 3.9 (0.30) | |
| Median (Min, Max) | 0 | 4.0 (1, 4) | | 0 | 4.0 (3, 4) | | 0 | 4.0 (3, 4) | |
| End of bolus | | | | | | | | | |
| n | 12 | 12 | | 0 | 0 | | 0 | 0 | |
| Mean (SD) | 269.7 (127.08) | 3.7 (0.89) | 0.1517 | N/A | N/A | — | N/A | N/A | — |
| Median (Min, Max) | 208.0 (106, 473) | 4.0 (1, 4) | | N/A | N/A | | N/A | N/A | |
| 30 min after start of infusion | | | | | | | | | |
| n | 12 | 12 | | 11 | 11 | | 11 | 11 | |
| Mean (SD) | 120.4 (31.76) | 3.5 (1.00) | 0.0266 | 250.5 (76.56) | 3.5 (0.69) | 0.1935 | 390.9 (185.66) | 3.8 (0.60) | 0.4164 |
| Median (Min, Max) | 125.5 (39, 155) | 4.0 (1, 4) | | 238.0 (161, 413) | 4.0 (2, 4) | | 339.0 (146, 765) | 4.0 (2, 4) | |
| 60 min after start of infusion | | | | | | | | | |
| n | 0 | 0 | | 8 | 8 | | 8 | 8 | |
| Mean (SD) | N/A | N/A | — | 336.3 (186.45) | 3.8 (0.46) | 0.8044 | 424.4 (147.62) | 3.4 (0.92) | 0.9112 |
| Median (Min, Max) | N/A | N/A | | 317.0 (115, 711) | 4.0 (3, 4) | | 463.0 (138, 578) | 4.0 (2, 4) | |
| 2 hours after start of infusion | | | | | | | | | |
| n | 0 | 0 | | 11 | 11 | | 11 | 11 | |
| Mean (SD) | N/A | N/A | — | 326.1 (127.04) | 3.4 (0.81) | 0.4939 | 560.6 (119.26) | 3.2 (0.87) | 0.5981 |
| Median (Min, Max) | N/A | N/A | | 300 (159, 620) | 4.0 (2, 4) | | 586.0 (281, 702) | 3.0 (2, 4) | |
| 4 to 6 hours after start of infusion | | | | | | | | | |
| n | 0 | 0 | | 11 | 11 | | 10 | 10 | |
| Mean (SD) | N/A | N/A | — | 413.4 (222.55) | 1.6 (1.03) | 0.2884 | 592.9 (82.56) | 2.4 (0.84) | 0.9560 |
| Median (Min, Max) | N/A | N/A | | 367.0 (112, 1010) | 2.0 (0, 3) | | 613 (393, 689) | 2.0 (1, 4) | |
| 6 hours after start of infusion | | | | | | | | | |
| n | 7 | 7 | | 0 | 0 | | 0 | 0 | |
| Mean (SD) | 230.0 (111.54) | 2.3 (1.25) | 0.1466 | N/A | N/A | — | N/A | N/A | — |
| Median (Min, Max) | 187.0 (113, 428) | 2.0 (0, 4) | | N/A | N/A | | N/A | N/A | |

TABLE 41-continued

Analysis of Correlation between the University of Michigan Sedation Scale and Dexmedetomidine Plasma Concentration - ITT Population

| | Statistics | | | | | | | | |
|---|---|---|---|---|---|---|---|---|---|
| | Low Dose[a] N-12 | | | Moderate Dose[b] N = 12 | | | High Dose[c] N = 12 | | |
| Timepoint | Dex Plasma | UMSS | p-value | Dex Plasma | UMSS | p-value | Dex Plasma | UMSS | p-value |
| 12 hours after start of infusion | | | | | | | | | |
| n | 2 | 2 | | 0 | 0 | | 0 | 0 | |
| Mean (SD) | 299.0 (165.46) | 2.0 (0.00) | — | N/A | N/A | — | N/A | N/A | — |
| Median (Min, Max) | 299.0 (182, 416) | 2.0 (2, 2) | | N/A | N/A | | N/A | N/A | |
| 30-15 min prior to end of infusion | | | | | | | | | |
| n | 0 | 0 | | 11 | 11 | | 9 | 9 | |
| Mean (SD) | N/A | N/A | — | 423.6 (164.14) | 1.6 (1.03) | 0.5137 | 801.3 (281.08) | 2.3 (0.50) | 0.0255 |
| Median (Min, Max) | N/A | N/A | | 394.0 (307, 890) | 2.0 (0, 4) | | 686.0 (504, 1340) | 2.0 (2, 3) | |
| End of infusion | | | | | | | | | |
| n | 12 | 12 | | 0 | 0 | | 0 | 0 | |
| Mean (SD) | 220.5 (98.04) | 1.5 (1.09) | 0.3485 | N/A | N/A | — | N/A | N/A | — |
| Median (Min, Max) | 205.5 (77, 420) | 2.0 (0, 3) | | N/A | N/A | | N/A | N/A | |
| 15 min after end of infusion | | | | | | | | | |
| n | 1 | 1 | | 9 | 9 | | 7 | 7 | |
| Mean (SD) | 272.0 (N/A) | 3.0 (N/A) | — | 423.3 (194.88) | 1.7 (1.12) | 0.3181 | 758.0 (282.80) | 2.6 (0.98) | 0.3601 |
| Median (Min, Max) | 272.0 (272, 272) | 3.0 (3, 3) | | 383.0 (254, 925) | 1.0 (0, 3) | | 680.0 (493, 1280) | 3.0 (1, 4) | |
| 30 minutes after end of infusion | | | | | | | | | |
| n | 6 | 6 | | 2 | 2 | | 1 | 1 | |
| Mean (SD) | 192.7 (93.68) | 2.3 (1.03) | 0.8999 | 318.5 (30.41) | 2.5 (0.71) | — | 447.0 (N/A) | 2.0 (N/A) | — |
| Median (Min, Max) | 171.0 (84, 347) | 2.0 (1, 4) | | 318.5 (297, 340) | 2.5 (2, 3) | | 447.0 (447, 447) | 2.0 (2, 2) | |
| 60 min after end of infusion | | | | | | | | | |
| n | 6 | 6 | | 10 | 10 | | 9 | 9 | |
| Mean (SD) | 99.2 (68.05) | 0.8 (0.75) | 0.1082 | 310.9 (107.54) | 1.7 (1.16) | 0.2190 | 504.4 (271.32) | 1.6 (1.24) | 0.0502 |
| Median (Min, Max) | 85.5 (37, 216) | 1.0 (0, 2) | | 285.0 (189, 582) | 1.5 (0,4) | | 431.0 (115, 1080) | 2.0 (0, 3) | |
| 2 hours after end of infusion | | | | | | | | | |
| n | 11 | 11 | | 10 | 10 | | 10 | 10 | |
| Mean (SD) | 84.3 (59.49) | 1.8 (0.75) | 0.8720 | 188.4 (67.88) | 1.1 (0.88) | 0.8269 | 351.6 (179.77) | 1.3 (1.6) | 0.3666 |
| Median (Min, Max) | 60.0 (31, 207) | 2.0 (1, 3) | | 174.5 (88, 332) | 1.0 (0, 2) | | 268.5 (213, 772) | 1.0 (0, 3) | |
| 4 hours after end of infusion | | | | | | | | | |
| n | 7 | 7 | | 9 | 9 | | 7 | 7 | |
| Mean (SD) | 50.7 (36.09) | 1.1 (0.90) | 0.5451 | 93.8 (61.29) | 0.8 (1.30) | 0.6763 | 185.3 (131.80) | 1.3 (1.11) | 0.1680 |
| Median (Min, Max) | 45.0 (8, 96) | 1.0 (0, 2) | | 72.0 (28, 232) | 0.0 (0, 4) | | 116.0 (45, 411) | 1.0 (0, 3) | |
| 8 hours after end of infusion | | | | | | | | | |
| n | 6 | 6 | | 4 | 4 | | 7 | 7 | |
| Mean (SD) | 13.2 (15.04) | 1.2 (0.98) | 0.5885 | 12.4 (12.45) | 1.0 (0.82) | 0.0423 | 51.2 (51.88) | 0.4 (0.79) | 0.4667 |

TABLE 41-continued

Analysis of Correlation between the University of Michigan Sedation Scale and
Dexmedetomidine Plasma Concentration - ITT Population

| | Statistics | | | | | | | | |
|---|---|---|---|---|---|---|---|---|---|
| | Low Dose[a] N-12 | | | Moderate Dose[b] N = 12 | | | High Dose[c] N = 12 | | |
| Timepoint | Dex Plasma | UMSS | p-value | Dex Plasma | UMSS | p-value | Dex Plasma | UMSS | p-value |
| Median (Min, Max) 12 Hours after end of infusion | 10.0 (0, 39) | 1.5 (0, 2) | | 10.3 (0, 29) | 1.0 (0, 2) | | 19.5 (10, 143) | 0.0 (0, 2) | |
| n | 2 | 2 | | 2 | 2 | | 2 | 2 | |
| Mean (SD) | 10.0 (14.14) | 1.0 (1.41) | — | 4.2(5.99) | 1.0 (0.00) | — | 36.0 (26.87) | 1.5 (0.71) | — |
| Median (Min, Max) 15 to 18 hours after end of infusion | 10.0 (0, 20) | 1.0 (0, 2) | | 4.2 (0, 8) | 1.0 (1, 1) | | 36.0 (17, 55) | 1.5 (1, 2) | |
| n | 0 | 0 | | 1 | 1 | | 0 | 0 | |
| Mean (SD) | N/A | N/A | — | 0 (N/A) | 0 (N/A) | — | N/A | N/A | — |
| Median (Min, Max) | N/A | N/A | | 0.0 (0, 0) | 0.0 (0, 0) | | N/A | N/A | |

Note:
Correlation p-values (Pearson product moment) assessed within treatment groups.
[a]Low-dose dexmedetomidine (0.35 µg/kg bolus, 0.25 µg/kg/hour infusion).
[b]Moderate-dose dexmedetomidine (0.7 µg/kg bolus, 0.5 µg/kg/hour infusion).
[c]High-dose dexmedetomidine (1.0 µg/kg bolus, 0.75 µg/kg/hour infusion).
DEX = dexmedetomidine,
ITT = Intent-to-Treat,
max = maximum,
min = minimum,
N, n = number of patients,
SD = standard deviation,
UMSS = University of Michigan sedation scale An analysis of the correlation between UMSS scores and dexmedetomidine plasma $AUC_{0-t}$ was conducted. The data presentation was not clinically meaningful.

An analysis of the correlation between the UMSS scores and $Cl_w$ of dexmedetomidine from plasma was conducted. The strongest correlation was observed for the low dose; significant correlations were observed at pre-infusion (p=0.0015), 1 hour post-infusion (p=0.0191), and 12 hours post-infusion (p=0.0385). A significant correlation was also observed for the high dose of dexmedetomidine at the time infusion was discontinued (p=0.0295). An analysis of the correlation between the UMSS scores and Cl of dexmedetomidine was conducted. Significant correlation between UMSS scores and clearance of dexmedetomidine was observed for low-dose dexmedetomidine at pre-infusion and 12 hours post-infusion (p=0.0371 and p=0.0470, respectively).

Only patients with sufficient pharmacokinetic data to calculate the primary pharmacokinetic parameters were included in the pharmacokinetic analysis population. In general, missing data were not imputed.

Pharmacokinetic sample collection times and the respective observed values for dexmedetomidine were reviewed by patient for patients that received the low dose-dexmedetomidine (0.25 µg/kg/hour), for patients that received the moderate-dose dexmedetomidine (0.5 µg/kg/hour), and for patients that received the high-dose dexmedetomidine (0.75 µg/kg/hour). Pharmacokinetic parameters reviewed as natural log transformed values for dexmedetomidine. Pharmacokinetic parameters displayed as observed values for dexmedetomidine were also reviewed.

An analysis of the correlation between the UMSS score and dexmedetomidine plasma concentration is presented in Table 41. There was no data presenting relationship to response. A significant correlation for UMSS score and dexmedetomidine plasma concentration was observed at the following timepoints: 30 minutes after start of infusion of low-dose dexmedetomidine (p=0.0266), 30 to 15 minutes prior to the end of infusion of high-dose dexmedetomidine (p=0.0255), and 8 hours after the end of infusion of moderate-dose dexmedetomidine (p=0.0423).

The pharmacokinetic profile demonstrated linearity and dose proportionality among 0.25, 0.50 and 0.75 µg/kg/hour dose levels; as dose increased, AUC and $C_{max}$ increased in proportion. The mean doses were given as 20.5, 40.4, and 65.1 µg to 0.25, 0.50 and 0.75 µg/kg/hour dose levels, respectively; as shown dose increased accordingly. $AUC_{0-inf}$ and $C_{max}$ of dexmedetomidine were dose-proportional at the 0.25 to 0.75 µg/kg/hour dose level. The apparent $t_{1/2}$ of dexmedetomidine was 2.33 hrs, 2.12 hrs, and 3.05 hrs for the low, moderate, and high dose levels, respectively. The geometric mean slope among the three dose levels and 95% confidence intervals were 1.263 (0.820, 1.706) for $AUC_{0-inf}$, and 0.898 (0.652, 1.143) for $C_{max}$. A dose-dependent increase in mean plasma concentration, $AUC_{0-t}$, and $AUC_{0-inf}$ was observed between the three dexmedetomidine dose groups. Dose proportionality was concluded for $AUC_{0-t}$, $AUC_{0-inf}$, and $C_{max}$ for dexmedetomidine in this study. No notable differences in weight-adjusted clearance versus age were observed for any dose groups.

Patients had deep sedation (UMSS 3-4) from pre-dose to 2 hours after infusion, and maintained a moderate level of sedation (UMSS 1-3) after 4 hours infusion through the end of infusion for all dose levels. There was a correlated relationship between plasma concentration and UMSS for low dose 30 minutes after start of infusion, moderate dose 8 hours after end of infusion, and high dose 30-15 minutes prior to end of infusion and 60 minutes after end of infusion.

Thirty-eight patients received at least one dose of dexmedetomidine and were included in the safety analysis set, Two patients (assigned to the high-dose dexmedetomidine treatment group) did not complete the study treatment; these patients were not included in the ITT or pharmacokinetic analysis. Twelve patients within each treatment group (36 patients total) completed study drug infusion. Exposure to study drug is summarized in Table 42. The mean doses given to the 36 ITT patients were 20.5, 40.4, and 65.1 µg for the 0.25, 0.50 and 0.75 µg/kg/hour dose levels, respectively as shown dose increased accordingly. The mean duration of dose infused was approximately 9.1, 10.0, and 11.2 hours for low, moderate, and high dose levels, respectively.

TABLE 42

Summary of Exposure to Dexmedetomidine (Total Dose) - ITT Population

| | Low Dose[a]<br>N = 12 | Moderate Dose[b]<br>N = 12 | High Dose[c]<br>N = 12 |
|---|---|---|---|
| Total dose (µg)[d] | | | |
| Mean (SD) | 20.5 (14.92) | 40.4 (18.32) | 65.1 (28.91) |
| Median (Min, Max) | 16.6 (10, 65) | 39.0 (15, 73) | 53.9 (35, 124) |
| Duration of Dose (min)[e] | | | |
| Mean (SD) | 544.8 (362.89) | 601.3 (363.96) | 669.0 (396.82) |
| Median (Min, Max) | 407.5 (260, 1434) | 526.5 (187, 1441) | 533.0 (264, 1369) |

[a]Low-dose dexmedetomidine: (0.35 µg/kg bolus, 0.25 µg/kg/hour infusion).
[b]Moderate-dose dexmedetomidine: (0.7 µg/kg bolus, 0.5 µg/kg/hour infusion).
[c]High-dose dexmedetomidine: (1.0 µg/kg bolus, 0.75 µg/kg/hour infusion).
[d]Total dose equals the sum of loading and maintenance doses.
[e]Duration of total dose is the sum of loading and maintenance dose duration.
ITT = Intent-to-Treat,
max = maximum,
min = minimum,
N = number of patients,
SD = standard deviation All 38 patients in the safety population and 36 ITT patients experienced at least 1 treatment-emergent adverse effect during the time that the first dose of dexmedetomidine was administered until 24 hours had elapsed following discontinuation of study drug administration. Thirty-three patients experienced treatment-emergent adverse effects considered to be treatment-related. The SOCs with the highest incidence of treatment-emergent adverse effects included the vascular disorders SOC (10 patients [83.3%] while receiving the low dose of dexmedetomidine, 10 patients [83.3%] while receiving the moderate dose of dexmedetomidine, and 14 patients [100.0%] during treatment with the high dose of dexmedetomidine) and the metabolism and nutrition disorders SOC (10 patients [83.3%] while receiving the low dose of dexmedetomidine, 12 patients [100.0%] while receiving the moderate dose of dexmedetomidine, and 7 patients [50.0%] while receiving the high dose of dexmedetomidine); and cardiac disorders SOC (3 patients [25.0%] during treatment with the low dose of dexmedetomidine, 4 patients [33.3%] during treatment with the moderate dose of dexmedetomidine, and 4 patients [28.6%] during treatment with the high dose of dexmedetomidine).

The majority of Treatment-emergent adverse effects were considered mild in intensity (9 patients [75.0%] for the low dose of dexmedetomidine, 9 patients [75.0%] for the moderate dose of dexmedetomidine, and 7 patients [50.0%] for the high dose of dexmedetomidine). A small percentage of Treatment-emergent adverse effects was considered moderate in intensity (2 patients [16.7%] for the low dose of dexmedetomidine, 3 patients [25.0%] for the moderate dose of dexmedetomidine, and 7 patients [50.0%] for the high dose of dexmedetomidine). One patient in the low-dose dexmedetomidine treatment group experienced a Treatment-emergent adverse effect that was considered severe. The majority of Treatment-emergent adverse effects were considered drug-related: low-dose dexmedetomidine (11 patients, 91.7%); moderate-dose dexmedetomidine (11 patients, 91.7%); and high-dose dexmedetomidine (11 patients, 78.6%).

One hundred and seventy-one (171) treatment-emergent adverse effects were reported by 38 patients in the Safety Population. Four patients, 3 in the high dose group and 1 in the moderate dose group experienced a treatment-emergent adverse effect leading to discontinuation of study drug. No patients discontinued study drug as a result of death. The most commonly reported treatment-emergent adverse effects were hyperglycemia and hypertension. The incidence of hyperglycemia was higher with the moderate dose of dexmedetomidine compared with the low dose and high dose of dexmedetomidine (low-dose dexmedetomidine, 83.3%; moderate-dose dexmedetomidine, 100.0%; high-dose dexmedetomidine, 50.0%). The incidence of hypertension was similar across all three dose groups of dexmedetomidine (low-dose dexmedetomidine, 66.7%; moderate-dose dexmedetomidine, 58.3%; high-dose dexmedetomidine, 71.4%).

Study drug-related treatment-emergent adverse effect of hypertension occurred with the highest incidence (low-dose dexmedetomidine, 66.7%; moderate-dose dexmedetomidine, 58.3%; high-dose dexmedetomidine, 50.0%). The incidence of drug-related treatment-emergent adverse effects was similar across all three dose groups of dexmedetomidine. The majority of treatment-emergent adverse effects experienced by patients in the low and moderate dexmedetomidine dose groups were mild in intensity (low dose, 9 patients, 75.0%; moderate dose, 9 patients, 75.0%).

A smaller percentage of patients experienced treatment-emergent adverse effects that were moderate in intensity in the low and moderate dexmedetomidine dose groups (low dose, 2 patients, 16.7%; moderate dose, 3 patients, 25.0%). A similar percentage of patients experienced both mild and moderate treatment-emergent adverse effects in the high dexmedetomidine treatment group; 7 patients, 50.0% experienced mild treatment-emergent adverse effects and 7 patients, 50.0% experienced moderate treatment-emergent adverse effects. Only one severe treatment-emergent adverse effect was reported and that was in the low dexmedetomidine dose group.

Twenty-five patients experienced at least one treatment-emergent adverse effect considered by the investigator to be mild during the study. Twelve patients experienced at least one treatment-emergent adverse effect considered to be moderate, and 1 patient experienced at least one treatment-emergent adverse effect considered to be severe in intensity. One death was reported during the study. Four patients experienced treatment-emergent adverse effects that led to discontinuation of study drug.

There were no meaningful differences in clinical laboratory test results, select vital signs (systolic blood pressure, diastolic blood pressure, mean arterial blood pressure, body temperature, respiratory rate), or physical examination findings between the three dexmedetomidine dose levels. Clinically significant hematology abnormalities were observed for 1 patient (8.3%) each in the low and moderate-dose dexmedetomidine groups (anemia) and two patients (16.7%) in the low-dose dexmedetomidine group (thrombocytopenia). With the exception of one patient in the low-dose dexmedetomidine group that had thrombocytopenia, none of these reported adverse effects were treatment-emergent. Greater mean change in heart rate was observed for patients in the high-dose dexmedetomidine treatment group compared to the other treatment groups at all time points.

The following clinically significant abnormalities in chemistry laboratory data considered as adverse events were observed: hyperkalemia (one patient in each dose group), hypernatremia (one patient in the low dose group), hypocalcemia (one patient in each low and moderate dose group), hypoglycemia (one patient each in the low and moderate dose groups), and hypokalemia (one patient each in the low and moderate dose groups).

Treatment-emergent adverse effects associated with vascular disorders included hypertension (8 patients, low dose; 7 patients, moderate dose; and 10 patients, high dose) and hypotension (5 patients, low dose; 5 patients, moderate dose; and 10 patients, high dose). A statistically significant treatment difference for change from Baseline for heart rate, up to and including Post Infusion Hour 5, was observed. Treatment-emergent adverse effects associated with heart rate included tachycardia in 3 patients administered low-dose dexmedetomidine, 1 patient administered moderate-dose dexmedetomidine, and 3 patients administered high-dose dexmedetomidine. A statistically significant treatment difference for change from Baseline in temperature was observed Post Infusion Hour 28; temperature change from Baseline was −1.43±1.559° C., 0.30±0.265° C., and 1.46±1.041° C. for the low, moderate, and high dose of dexmedetomidine, respectively (p=0.008); no significant differences were observed at any other time point. Treatment-emergent adverse effects associated with body temperature included hypothermia (1 patient, low dose and 2 patients, moderate dose), and hyperthermia (1 patient, low dose and 1 patient, high dose). No clinically meaningful changes in respiratory rate were observed and no related adverse effects were reported. No physical examination findings were considered clinically significant or were reported as adverse effects. ECG results were reported as adverse effects for 7 patients. ECG-related adverse effects included ischemia (2 patients both in the low dose group), ECG inverted T-wave (1 patient in the low dose group), elevated ST segment (1 patient in the low dose group), bradycardia (1 patient in the moderate dose group), ECG change (1 patient in the high dose group), and sinus bradycardia complete heart block (1 patient in the high dose group).

Hepatotoxicity, as defined in the SAP, was reported in 1 patient (8.3%) in the low dose group (within 24 hours of discontinuation of infusion), 1 patient (8.3%) in the moderate dose group (2 to 4 weeks post-infusion or at the next follow-up visit), and 2 patients (14.3%) in the high dose group (within 24 hours of discontinuation of infusion); no adverse effects related to hepatotoxicity were reported. No patients reported DLT in this study.

Fentanyl was administered as an additional intra-operative sedation agent to patients in each dexmedetomidine dose level. The amount of fentanyl administered was lower in patients receiving moderate (69.32 µg), and high (80.20 µg) doses of dexmedetomidine compared to those receiving low (99.32 µg) levels. Post-operatively, patients were administered fentanyl, midazolam, and morphine sulfate. There was no treatment difference observed related to the quantity of additional sedation received for any of the additional sedation agents. At most time points observed post-infusion, there was an increase in the percentage of patients who were administered additional sedation or analgesia for patients that received moderate levels of dexmedetomidine compared to those who received low levels. For most time points post-infusion, there was a decrease in the percentage of patients that received additional sedation or analgesia in the dexmedetomidine high dose level compared to those in the low dose level. There was no clear relationship between dexmedetomidine dose level and the quantity of fentanyl, midazolam, and morphine sulfate administered to patients at any post-infusion time point observed.

This was a single center, phase I dose escalation pharmacokinetic, pharmacodynamic study of a single bolus dose of dexmedetomidine followed by a continuous infusion for up to 24 hours in infants who were immediately post-operative from cardiac surgery and required tracheal intubation with mechanical ventilation in the post-operative period. Dexmedetomidine is a highly selective alpha2 agonist with hypnotic and anxiolytic properties attributed to the alpha2A-adrenoreceptors in the locus ceruleus. Dexmedetomidine was initially approved in 1999 for the sedation of intubated and mechanically ventilated patients in the intensive care setting for up to 24 hours, and dexmedetomidine was recently approved as a short term (<24 hours) sedative medication for use in adult non-intubated patients requiring sedation prior to and during surgical and other procedures. Thirty-eight infants, status post-cardiac surgery, were assigned to three treatment groups: low-dose dexmedetomidine (12 patients), moderate-dose dexmedetomidine (12 patients), and high-dose dexmedetomidine (14 patients). Thirty-six patients, 12 in each dose group, completed the dexmedetomidine infusion. Patients were predominantly Caucasian (61.1%) with a mean age of 8.3 months. Patients in the low-dose dexmedetomidine group received 0.35 µg/kg bolus, 0.25 µg/kg/hour infusion, patients in the moderate-dose dexmedetomidine group received 0.7 µg/kg bolus, 0.5 µg/kg/hour infusion, and patients in the high-dose dexmedetomidine group received 1 µg/kg bolus, 0.75 µg/kg/hour infusion. Pharmacokinetic samples were collected prior to the bolus dose through up to 18 hours after the EOI time points for measurement of dexmedetomidine pharmacokinetic parameters. There were 36 patients in the Pharmacokinetic Population; 36 patients completed treatment. Sedation and analgesic properties of the drug were to be assessed by a periodic check of the BIS monitor until after infusion was discontinued and the patient was deemed awake by the clinical care team. The UMSS score was also assessed on an hourly basis until the BIS sensor was removed.

The primary variables for pharmacokinetic assessment of dexmedetomidine were observed peak plasma concentration ($C_{max}$), area under the plasma concentration-time curve from time zero to the last quantifiable timepoint ($AUC_{0-t}$), area under the plasma concentration-time curve from time zero to infinity ($AUC_{0-inf}$), time of observed peak plasma concentration ($T_{max}$), terminal elimination rate constant ($\lambda z$), terminal half-life ($t_{1/2}$), end of infusion concentration (steady state $C_{ss}$), plasma clearance (Cl), and volume of distribution ($V_d$). Dose-proportionality was demonstrated with the analysis of mean values of $C_{max}$, $AUC_{0-t}$, and $AUC_{0-inf}$. There was no apparent change in clearance and weight-adjusted clearance across the age range in this study. Pharmacodynamic assessments were monitored continuously every hour until 24 hours after the discontinuation of the infusion and included heart rate, blood pressure, mean arterial blood pressure, cardiac rhythm, oxygen saturation, and respiratory rate. The BIS and the UMSS were used to assess the level of sedation. There were no meaningful differences in systolic blood pressure, diastolic blood pressure, mean arterial blood pressure, body temperature, respiratory rate), or physical examination findings between the 3 dexmedetomidine dose levels. Administration of a higher bolus dose resulted in a deeper level of sedation (BIS); the change from Baseline was less for patients that received the high dose of dexmedetomidine than the lower doses up to 6 hours post-infusion. Of the 38 patients in the Safety Population, all patients experienced at least 1 adverse effect that was considered treatment-emergent. Thirty-three patients experienced at least one adverse effect that was considered to be treatment-related. The SOCs with the highest incidence of treatment-emergent adverse effects included the vascular disorders SOC (10 patients [83.3%] while receiving the low dose of dexmedetomidine, 10 patients [83.3%] while receiving the moderated dose of dexmedetomidine, and 14 patients [100.0%] during treatment with the high dose of dexmedetomidine) and the metabolism and nutrition disorders SOC (10 patients [83.3%] while receiving the low dose of dexmedetomidine, 12 patients [100.0%] while receiving the moderate dose of dexmedetomidine, and 7 patients [50.0%] while receiving the high dose of dexmedetomidine). In this study, no patients experienced a DLT.

In alignment with the primary objectives of this study, dose-dependent increases in pharmacokinetic (mean plasma concentration, $AUC_{0-t}$, and $AUC_{0-inf}$) and level of sedation were demonstrated in this study. At most time points investigated, no significant correlation between the level of sedation and serum plasma concentration, $AUC_{0-t}$, or $AUC_{0-inf}$ was observed for any doses tested. In addition, no correlation between UMSS scores and clearance of dexmedetomidine (weight adjusted and non-weight-adjusted) was observed at the majority of time points tested. Dexmedetomidine was generally well tolerated in infant postoperative cardiac patients.

The following conclusions were derived regarding the administration of dexmedetomidine for infants post-operative from cardiac surgery:

The pharmacokinetic profile demonstrated linearity and dose proportionality among 0.25, 0.50 and 0.75 µg/kg/hour dose levels; as dose increased, AUC and $C_{max}$ increased in proportion.

Patients had deep sedation (UMSS 3-4) from pre-dose to 2 hours after infusion, and maintained a moderate level of sedation (UMSS 1-3) after 4 hours infusion through the end of infusion for all dose levels.

There was a correlated relationship between plasma concentration and UMSS for low dose 30 minutes after start of infusion, moderate dose 8 hours after end of infusion, and high dose 30-15 minutes prior to end of infusion and 60 minutes after end of infusion.

There was no apparent change in clearance or weight-adjusted clearance across the age range studied in this study.

At the majority of time points, there was no correlation observed between serum plasma concentration of dexmedetomidine and the level of sedation or clearance of dexmedetomidine.

Greater mean change in heart rate was observed for patients in the high-dose dexmedetomidine treatment group compared to the other treatment groups.

The doses of dexmedetomidine administered in this study were generally well tolerated.

No clinically meaningful differences in the safety profile were observed between the three dose groups.

Example 6

Pooled Pharmacokinetic Data of Dexmedetomidine in Pediatric Patients

The pharmacokinetic data from the Example 1 study, the Example 3 study, and the Example 5 study were pooled. Data was included for patients who received treatment with dexmedetomidine and had at least 1 measurable plasma concentration with the associated dosing and sample timing information. For Example 1, the only subjects included were in the original 30 patient population study. For Example 5, data was only included from patients who had received at least 2 hours of a maintenance infusion of dexmedetomidine and who had at least one measurable plasma concentration with the associated dosing and sample timing information. A population pharmacokinetics analysis of dexmedetomidine, including covariate assessment, was performed on the data.

Full-profile pharmacokinetics sampling was performed in all subjects in the Example 5 and Example 3 studies. In the Example 1 study, blood was collected at 6 or 7 protocol-designated times for subjects based on subject age and weight. In the Example 1 study, blood samples (0.15 mL) for pharmacokinetics analysis were collected via a central or peripheral venous or arterial line unless access was unavailable, in which case samples were collected from a capillary draw (heel stick). Where appropriate, blood samples were drawn at a site opposite from the site of infusion. Subjects in Group I who weighed less than 2 kg had blood drawn at the end of the loading dose, 10 to 14 h after the start of the maintenance infusion, at the end of the maintenance infusion, 10 to 30 minutes post-maintenance, and 3 to 4 h and 6 to 10 h post-maintenance. Subjects in Group I who weighed at least 2 kg had blood drawn at the end of the loading dose, 4 to 8 h and 10 to 14 h after the start of the maintenance infusion, at the end of the maintenance infusion, and 10 to 30 minutes post-maintenance, and 1 to 2 h and 6 to 10 h post-maintenance. Subjects in Group II had blood drawn at the end of the loading dose, 4 to 8 h after the start of the maintenance infusion, at the end of the maintenance infusion, 10 to 30 minutes post-maintenance, and 1 to 2 h, 3 to 4 h, and 6 to 10 hrs post-maintenance.

In the Example 5 study, blood samples (1 mL) for pharmacokinetics measurements were drawn at a site distant from the infusion. Blood was drawn according to the following schedule: prior to the loading dose, 0.5, 1, 2, 4 to 6 hrs after the start of the maintenance infusion, 30 to 15 minutes prior to end of the maintenance infusion, and 0.25, 0.5, 1, 2, 4, 8, 12, and 15 to 18 hrs after the end of the maintenance infusion.

In Study Example 3, venous blood samples (1 mL) for pharmacokinetics measurements were collected at a site opposite from the site of infusion. Blood was drawn according to the following schedule: ≤30 minutes prior to the loading dose, within 5 minutes before the end of the loading dose, 0.5, 1, 2, 4 to 6 h after the start of the maintenance infusion, within 30 minutes prior to the end of the maintenance infusion, and 10 minutes, 0.5, 1, 2, 4, and 10 hrs after the end of the maintenance infusion.

Blood samples were collected into labeled tubes containing heparin as anticoagulant. A validated high-performance liquid chromatography-tandem mass spectrometry method for quantitation of dexmedetomidine in human plasma was used. The lower limit of quantitation (LLOQ) was 4.24 pg/mL for the Example 5 study, 30.24 pg/mL for Study Example 3, and 29.97 pg/mL for the Example 1 study. For Study Example 3 and the Example 1 study, dosing information, pharmacokinetics sampling information, dexmedetomidine concentrations, and covariate data were merged, as necessary, to construct a time-ordered sequence of relevant events for each subject from the start time of the first dose until the time of last blood sample in analysis-ready datasets. Analysis-ready datasets for Study Example 3 and the Example 1 study were set together with the supplemented analysis-ready dataset for the Example 5 study.

The potential of selected covariates to explain variability in the pharmacokinetics parameters for dexmedetomidine was explored. The following time-invariant (stationary) demographic and clinical covariates were determined at the screening visit and were assumed to remain constant for the duration of the trial:

Body weight, kg
Age, years
Alanine aminotransferase, U/L
Total bilirubin, mg/dL
Ethnicity: 1=Caucasian, 2=Black, 3=Asian, 4=Native American, 5=Hispanic, 6=other
Sex: 0=male, 1=female
Heart physiology: 0=double-ventricle, 1=single-ventricle
Use of concomitant glucuronidation pathway inhibitors 24 h prior to or during surgery or during the treatment period: 0=no, 1=yes
Intravenous albumin infusion: 0=no, 1=yes
Cardio-pulmonary bypass use: 0=no, 1=yes
Gestational age: 1=preterm (≥28 through <36 weeks), 0=term (≥36 through ≤44 weeks) and
Site of sampling, 0=venous, 1=arterial, 2=capillary (heel stick).

Site of sampling was recorded only in the Example 1 study and was assumed to be venous for the studies where no information was recorded. The effect of concomitant metabolic inducers could not be explored due to the limited timeframe for the past medication history collection as specified in the Example 5 study (that is, 24 h prior to surgery). Aspartate aminotransferase and serum albumin data were not available from the Example 5 study and were, therefore, not considered as possible covariates.

Although dexmedetomidine is a substrate of CYP2A6, comprehensive literature review regarding inhibition of CYP2A6 identified a very limited number of commercially available drugs shown to inhibit this CYP enzyme. When the likelihood of use of these agents in a pediatric population was considered, further covariate evaluation of this factor was determined to be unnecessary.

SAS Version 9.1 or later was used for data preparation, summary statistics, and graphical displays. Summary statistics were computed to describe dependent and independent variables, including mean, median, standard deviation, and other measures, as appropriate. Population pharmacokinetic modeling was performed using the computer program NONMEM®, Version VI, Level 2.0. NONMEM analyses were performed on Intel x86 computers running the OpenSUSE 10.2 distribution of Linux. The Fortran compiler used was the GNU Fortran compiler, part of the GCC Version 3.3.5 compiler.

For each analysis, NONMEM computes the minimum value of the objective function (MVOF), a statistic that is proportional to minus twice the log likelihood of the data. In the case of hierarchical models, the change in the MVOF produced by the inclusion of a parameter is asymptotically $\chi^2$-distributed with the number of degrees of freedom equal to the number of parameters added to or deleted from the model. The first-order conditional estimation (FOCE) with interaction method was used at all stages of the model development process.

A variety of graphs and tables were generated from the analysis dataset to understand the informational content of the data with respect to the anticipated model, to search for extreme values and/or potential outliers, to assess possible trends in the data, and to determine if any errors were made in the manipulation of the data and creation of the analysis dataset. This exploratory analysis was also used to confirm the appropriateness of the models to be tested and to verify model assumptions. Data visualization techniques were used to search for patterns and extreme values that may have caused significant bias during the analysis. An outlier was defined as an aberrant observation that significantly deviated from the rest of the observations measured in a particular subject. The general procedure that was followed for the development of the pharmacokinetics model of dexmedetomidine is outlined below.

1. Exploratory data analysis.
2. Refinement of the dexmedetomidine population pharmacokinetics model originally developed by Example 5 using the pooled Example 5 study data and Study Example 3 data, including covariate analysis.
3. Further refinement of the dexmedetomidine population pharmacokinetics model after data from the Example 1 study became available and was pooled with the previous dataset. The influence of covariates on the pharmacokinetics parameters was re-evaluated.
4. Final model evaluation using prediction-corrected visual predictive check (VPC) procedure. To avoid potential multicollinearity or confounding of effects in covariate submodels, the correlations between covariates were examined. Pairwise scatterplots of all continuous covariates and boxplots of continuous covariates versus categorical covariates were generated. With the exception of body weight and age, which were expected to be correlated in this population, in no case were 2 highly correlated covariates included in the same parameter-covariate model.

A linear, open, 2-compartment model for dexmedetomidine was tested initially as a potential base structural model. This model was refined based on the dexmedetomidine concentration data from the Example 5 and Example 3 studies in order to determine appropriate characterization of the random effects. While this model included effects of body weight, age, time on CPB, and cardiac physiology (single or double ventricle) on disposition parameters, the base structural model initially evaluated for this analysis did not include covariate effects unless such effects were required to achieve model stability. It was assumed that the effects of weight and age would be considered part of the base structural model given the characteristics of this patient population and their likely impact on pharmacokinetics. When the data from the Example 1 study became available, the population pharmacokinetics model was applied to the pooled dataset and again refined. The influence of covariates on the pharmacokinetics parameters was re-evaluated.

Covariate analyses were performed to explore measurable sources of dexmedetomidine variability in pharmacokinetics model parameters with estimated interindividual variability (IIV), Table 43 lists the parameters for which the covariate effects were considered.

TABLE 43

Covariates Evaluated for Relationships With Dexmedetomidine Clearance and/or Volume of the Central Compartment

| Covariate | Parameter | |
|---|---|---|
| | CL | Vc |
| Body weight | + | + |
| Age | + | + |
| Alanine aminotransferase | + | |
| Bilirubin | + | |
| Ethnicity | + | + |
| Sex | + | + |
| Heart physiology | + | |
| Glucuronidation enzyme inhibitors | + | |
| Albumin infusion | + | + |
| Site of sampling | + | + |
| Cardiopulmonary bypass | + | + |

Abbreviations:
CL, elimination clearance;
Vc, volume of the central compartment.

Graphical and statistical approaches were used to develop the covariate models and to assess the mathematical forms of their relationships and their statistical significance. Following the development of the base structural pharmacokinetics model, the influence of covariates on selected pharmacokinetics parameters for dexmedetomidine was evaluated univariately. Diagnostic plots illustrating the relationships between the unexplained IIV in CL and Vc and covariates were examined to identify possible trends, as well as the appropriate functional form (for example, linear, power, or exponential) to be tested for the parameter-covariate relationship. Covariates contributing at least a 3.84 change in the MVOF ($\alpha=0.05$, 1 degree of freedom for $\chi2$-distribution) and a 5% reduction in IIV in the parameter of interest were included in the model and the process was repeated. The error models for IIV in the full multivariable model were re-evaluated following completion of forward selection.

Univariate backward elimination proceeded after all adjustments had been made to the error models. A covariate was considered significant and kept in the model if it contributed at least a 10.83 change in the MVOF ($\alpha=0.001$, 1 degree of freedom for $\chi2$-distribution) when removed from the model. The reduced multivariable model, with all significant covariates, was evaluated for any remaining biases in the IIV and residual variability (RV) error models. Diagnostic plots of the unexplained IIV in the parameters versus all covariates were evaluated to detect any inadequacies or biases in the covariate models and to assure no trends remain that may indicate a potential relationship had not been sufficiently described by the model. The model was checked for possible simplifications of covariate equations, such as power functions that can be reduced to linear functions (power term approximately 1.0) or significant discrete group covariates that could be redefined using fewer groups or parameters. Goodness-of-fit diagnostic plots were examined for model misfit.

The adequacy of the final model was evaluated using a simulation-based prediction corrected VPC method. The final model was used to simulate 1000 replicates of the analysis dataset with NONMEM. Statistics of interest were calculated from the simulated and observed data for comparison; for example, the 5th, 50th (median), and 95th percentiles of the distributions of the dexmedetomidine concentrations within discrete bins (ranges) of time, treatment group, and age were calculated. These percentiles of the simulated concentrations were then plotted versus time since the end of the maintenance infusion, with the original observed dataset and/or percentiles based on the observed data overlaid to visually assess concordance between the model-based simulated data and the observed data.

Due to the wide range of doses used in these studies and the spectrum of subjects with regard to age (and weight), the prediction-corrected VPC, as suggested by Bergstrand, et al, with bins defined by time, treatment group, and age, was utilized. (See AAPS J. 2011; 13(2):143-151). This technique provides an enhanced ability to diagnose possible model misspecification by removing the variability introduced in an ordinary VPC when binning across a potentially large variability in dose or other influential covariates. A total of 1448 dexmedetomidine concentration records from 131 subjects and 3 studies were received. After exclusions, 1279 dexmedetomidine concentrations collected from 120 subjects in these studies were available for analysis (Table 44).

TABLE 44

Data Disposition for Each Study Included in the Population Pharmacokinetic Analysis

| | Samples Excluded | Subjects Affected | Subjects Excluded | Number Remaining Following the Excluded | |
|---|---|---|---|---|---|
| | | | | Samples | Subjects |
| Example 1 Study | | | | | |
| Dexmedetomidine randomized subjects | NA | NA | NA | NA | 37 |
| Randomized subjects with no concentration records | 0 | 2 | 2 | NA | 34 |
| Dexmedetomidine concentration records received from Hospira, Inc. | NA | NA | NA | 228 | 34 |

TABLE 44-continued

Data Disposition for Each Study Included in the Population Pharmacokinetic Analysis

| | Samples Excluded | Subjects Affected | Subjects Excluded | Number Remaining Following the Excluded | |
|---|---|---|---|---|---|
| | | | | Samples | Subjects |
| Missing concentration values | 28 | 8 | 4 | 200 | 30 |
| All concentrations below lower limit of quantitation | 27 | 4 | 4 | 173 | 26 |
| Sub-total prior to outlier exclusions | NA | NA | NA | NA | NA |
| Improbable concentrations based on EDA plots[a] | 17 | 5 | 2 | 156 | 24 |
| Observations associated with extremely high weighted residual values during model development[a] | 3 | 2 | 0 | 153 | 24 |
| Total remaining | NA | NA | NA | 153 | 24 |
| | Example 5 Study | | | | |
| Dexmedetomidine randomized subjects | NA | NA | NA | NA | 36 |
| Dexmedetomidine concentration records received from Hospira, Inc. | NA | NA | NA | 479 | NA |
| Concentrations below lower limit of quantitation | 36 | 36 | 0 | 443 | 36 |
| Sub-total prior to outlier exclusions | NA | NA | NA | 443 | 36 |
| Observations associated with weighted residual values >7 during base model development[a] | 5 | 4 | 0 | 438 | 36 |
| Subjects with extremely long bypass time[a,b] | 11 | 1 | 1 | 427 | 35 |
| Total remaining | NA | NA | NA | 427 | 35 |
| | Example 3 Study | | | | |
| Dexmedetomidine randomized subjects | NA | NA | NA | NA | 59 |
| Dexmedetomidine concentration records received from Hospira, Inc. | Na | NA | NA | 741 | NA |
| Missing concentration value | 9 | 6 | 0 | 732 | 59 |
| Pre-dose concentrations below lower limit of quantitation | 57 | 57 | 0 | 675 | 59 |
| All concentrations below lower limit of quantitation | 12 | 1 | 1 | 663 | 58 |
| Sub-total prior to outlier exclusions | NA | NA | NA | 663 | 58 |
| Extremely high concentrations noted during EDA[a] | 4 | 2 | 0 | 659 | 58 |
| Observations associated with weighted residual values >7 during base model development[a] | 23 | 16 | 0 | 636 | 58 |
| Subjects excluded from analysis due to infusion length shorter than allowed per protocol or lack of samples collected[a] | 9 | 3 | 3 | 627 | 55 |
| Implausible concentration value[a] | 1 | 1 | 0 | 626 | 55 |
| Subject to extremely high CL value[a] | 11 | 1 | 1 | 615 | 54 |
| Total remaining | NA | NA | NA | 615 | 54 |
| Total prior to outlier exclusions[a] | NA | NA | NA | 1279 | 120 |
| Total for pooled data | NA | NA | NA | 1195 | 113 |

Abbreviations:

EDA, exploratory data analysis;

NA, not applicable.

[a] Note: Rows representing observations designated as outliers.

[b] Su F, Nicolson SC, Gastonguay MR, et al. Population pharmacokinetics of dexmedetomidine in infants after open heart surgery. *Anesth Analog.* 2010; 110(5): 1383-1392.

Table 45 summarizes the numbers of subjects and dexmedetomidine concentration values included in the analysis, by study and randomized treatment group.

TABLE 45

Summary of the Numbers of Subjects and Dexmedetomidine Concentrations, by Study and Dexmedetomidine Treatment Group

| Study | Dexmedetomidine Treatment Group (Loading Dose + Maintenance Infusion Rate) | Number of Subjects | Number of Concentrations |
|---|---|---|---|
| Example 1 | 0.05 µg/kg + 0.05 µg/kg/h | 10 | 63 |
| | 0.10 µg/kg + 0.10 µg/kg/h | 8 | 55 |
| | 0.20 µg/kg + 0.20 µg/kg/h | 8 | 55 |
| Subtotals for Example 1 | | 26 | 173 |
| Example 5 | 0.35 µg/kg + 0.25 µg/kg/h | 12 | 139 |
| | 0.70 µg/kg + 0.50 µg/kg/h | 12 | 152 |
| | 1.00 µg/kg + 0.75 µg/kg/h | 12 | 152 |
| Subtotals for Example 5 | | 36 | 443 |
| Example 3 | 0.25 µg/kg + 0.20 µg/kg/h | 15 | 169 |
| | 0.50 µg/kg + 0.40 µg/kg/h | 14 | 159 |
| | 1.00 µg/kg + 0.70 µg/kg/h | 15 | 167 |
| | 1.00 µg/kg + 2.00 µg/kg/h | 14 | 168 |
| Subtotals for Example 3 | | 58 | 663 |
| Overall | | 120 | 1279 |

Subject demographic characteristics, overall and by study, are shown in Table 46.

TABLE 46

Summary of Demographic Characteristics, by Study

| Subject Characteristic | | Example 1 Study | Example 5 Study | Example 3 Study | Overall |
|---|---|---|---|---|---|
| Age (y) | Mean (SD) | 0.041 (0.029) | 0.716 (0.404) | 7.397 (4.193) | 3.799 (4.555) |
| | Median | 0.036 | 0.631 | 6.702 | 1.560 |
| | Min, Max | 0.01, 0.13 | 0.21, 2.65 | 2.07, 16.97 | 0.01, 16.97 |
| | n | 26 | 36 | 58 | 120 |
| Weight (kg) | Mean (SD) | 2.905 (0.879) | 7.625 (1.802) | 27.320 (20.140) | 16.122 (17.791) |
| | Median | 3.165 | 7.040 | 20.250 | 10.350 |
| | Min, Max | 1.12, 4.35 | 5.10, 11.90 | 9.98, 99.00 | 1.12, 99.00 |
| | n | 26 | 36 | 58 | 120 |
| Ethnicity, n (%) | White | 20 (76.9) | 23 (63.9) | 23 (39.7) | 66 (55.0) |
| | Black | 9 (25.0) | 9 (25.0) | 6 (10.3) | 15 (12.5) |
| | Asian | 1 (2.8) | 1 (2.8) | 1 (2.8) | 1 (0.8) |
| | American Indian | 0 (0.0) | 0 (0.0) | 0 (0.0) | 1 (0.8) |
| | Hispanic | 2 (5.6) | 2 (5.6) | 2 (5.6) | 32 (26.7) |
| | Other | 1 (3.8) | 1 (2.8) | 1 (2.8) | 5 (4.2) |
| Gender, n (%) | Male | 19 (73.1) | 20 (55.6) | 27 (46.6) | 66 (55.0) |
| | Female | 7 (26.9) | 16 (44.4) | 31 (53.4) | 54 (45.0) |

Overall, slightly more than one-half of the subjects were male (55%), with a median age of 1.56 years (range of 0.01 to 16.97 years) and a median weight of 10.35 kg (range of 1.12 to 99 kg). The majority of the subjects were Caucasian (55%). For the most part, the ranges of age and weight represented in the 3 studies comprise a continuum of maturation and size from very small infants to nearly adults with little or no overlap in these characteristics between studies. As shown in Table 47, the median alanine aminotransferase level was 21.0 U/L for the subjects overall, with a slightly higher median in the Example 5 subjects (24.0 U/L) compared to the median values in the Example 3 (19.0 U/L) and Example 1 (19.5 U/L) subjects. The median value for total bilirubin in the overall group was 0.5 mg/dL; although, total bilirubin levels were considerably higher in the Example 1 subjects (median total bilirubin level of 4.65 mg/dL).

TABLE 47

Summary of Laboratory Values, by Study

| Subject Characteristic | | Study Example 1 | Example 5 Study | Study Example 3 | Overall |
|---|---|---|---|---|---|
| Alanine aminotransferase (U/L) | Mean (SD) | 27.077 (22.337) | 25.917 (8.917) | 26.828 (21.881) | 26.608 (18.914) |
| | Median | 19.500 | 24.000 | 19.000 | 21.000 |
| | Min, Max | 7.00, 84.00 | 8.00, 52.00 | 9.00, 144.00 | 7.00, 144.00 |
| | n | 26 | 36 | 58 | 120 |
| Total bilirubin (mg/dL) | Mean (SD) | 4.871 (3.708) | 0.347 (0.146) | 0.591 (0.425) | 1.445 (2.503) |
| | Median | 4.650 | 0.300 | 0.500 | 0.500 |
| | Min, Max | 0.20, 14.60 | 0.10, 0.70 | 0.17, 2.20 | 0.10, 14.60 |
| | n | 27 | 36 | 58 | 120 |

Table 48 shows the summary statistics for cardiac status of the subjects (cardio-pulmonary bypass and heart ventricle physiology), administration of albumin infusion or medications known to be glucuronidation pathway inhibitors, and site of blood sampling for pharmacokinetics analysis of dexmedetomidine concentrations.

TABLE 48

Summary of Cardiac Status, Concomitant Medications, and Site of Pharmacokinetic Sampling

| Subject Characteristic | | Study Example 1 | Example 5 Study | Study Example 3 | Overall |
|---|---|---|---|---|---|
| Cardio-pulmonary bypass, n (%) | No | 21 (80.8) | 0 (0.0) | 17 (29.3) | 38 (31.7) |
| | Yes | 5 (19.2) | 36 (100.0) | 41 (70.7) | 82 (68.3) |
| Ventricle, n (%) | Single | 0 (0.0) | 19 (52.8) | 0 (0.0) | 19 (15.8) |
| | Double | 26 (100.0) | 17 (47.2) | 58 (100.0) | 101 (84.2) |
| Albumin infusion, n (%) | No | 19 (73.1) | 36 (100.0) | 46 (79.3) | 101 (84.2) |
| | Yes | 7 (26.9) | 0 (0.0) | 12 (20.7) | 19 (15.8) |
| Glucuronidation pathway inhibitors, n (%) | No | 6 (23.1) | 0 (0.0) | 7 (12.1) | 13 (10.8) |
| | Yes | 20 (76.9) | 36 (100.0) | 51 (87.9) | 107 (89.2) |
| Site of sampling[a] | Venous | 66 (38.2) | 443 (100.0) | 663 (100.0) | 1172 (91.6) |
| | Arterial | 95 (54.9) | 0 (0.0) | 0 (0.0) | 95 (7.4) |
| | Capillary | 12 (6.9) | 0 (0.0) | 0 (0.0) | 12 (0.9) |

All Example 5 subjects and most Example 3 subjects (70.7%) underwent cardio-pulmonary bypass, but relatively fewer subjects in the Example 1 study (19.2%) underwent this procedure. Subjects with single ventricle physiology were only present in the Example 5 study (52.8%). Overall, the majority of subjects (84.2%) did not receive an albumin infusion, and 89.2% of subjects received co-medications known to be glucuronidation pathway inhibitors 24 h prior to surgery, during surgery, or during dexmedetomidine treatment.

Plasma samples for the determination of dexmedetomidine concentrations were collected around the time of the loading dose, near the start and during the maintenance infusion, and after discontinuation of the maintenance infusion according to the pre-specified schedules for the studies in Examples 1, 3, and 5. The number of plasma dexmedetomidine concentrations contributed per individual subject ranged from 1 to 13 across studies with the most samples per subject in Example 5 (10 to 13, median of 13), a similar amount per subject in Example 3 (1 to 12, median of 12), and less from Example 1, as expected (5 to 7, median of 7 samples per subject). The overall range of dexmedetomidine doses for both the loading dose and maintenance infusion was large (56 ng to 140,000 ng and 357 ng to 828,800 ng, respectively). Summary statistics for the dexmedetomidine loading doses and maintenance infusion doses are shown in Tables 5A, 27A, and 37.

Looking across all of the treatment groups, the median total dexmedetomidine doses for the Example 1, 3, and 5 studies were 2184 ng, 36,011 ng, and 120,550 ng, respectively. The infusion durations for the loading dose (median of 0.167 h in almost all treatment groups) and maintenance doses (median ranged from approximately 6 h to 9 h in almost all treatment groups) were quite consistent across the studies.

FIGS. 16A-C present lineplots of plasma dexmedetomidine concentrations versus time since the start of the loading dose infusion for each treatment group in the 3 studies. In FIGS. 17A-C, lineplots of dexmedetomidine concentrations versus time since the end of the maintenance infusion are shown for each treatment group. Based on the concentrations measured after the end of the infusion, these plots suggest that a 2-compartment model would likely be adequate to describe these data. Although this finding is consistent with a previous report describing the population pharmacokinetics for dexmedetomidine in infants, other types of models were additionally examined.

FIGS. 18A-B show a semilogarithmic scatterplot of dose-normalized dexmedetomidine plasma concentrations versus time since the end of the maintenance infusion stratified by study, demonstrating that dexmedetomidine pharmacokinetics was generally similar across the treatment groups from the Example 3 and Example 5 studies. Smoothing splines are used in these plots to illustrate the trend over time within each treatment group. There appears to be a trend towards higher dose-normalized dexmedetomidine concentrations in the lowest dose group (0.05 mg/kg+0.05 mg/kg/h) from the Example 1 study, however, the pattern is less evident in the 0.10 mg/kg+0.10 mg/kg/h and 0.20 mg/kg+0.20 mg/kg/h dose groups.

The percent of BLQ samples within the Example 5 and Example 3 studies were quite similar (slightly less than 10% in each study and 3% and 5% overall, respectively), although the percent of samples that were BLQ was much higher in the Example 1 study (approximately 40% of the study and 5% overall). The BLQ samples were retained in the dataset and set to a value of one-half the LLOQ of the assay used to determine the dexmedetomidine concentration in the particular study.

The pooled data from Studies Example 3 and Example 5 were initially used for model development. Based on previous modeling efforts and the exploratory analysis results (in particular, the scatterplots of dexmedetomidine concentrations versus time), a 2-compartment model, as well as 1- and 3-compartment linear models, were fit to the data. (See Su et al.) A mammillary 2-compartment model best described the data, with IIV estimated on CL, Ve, Q, and volume of the Vp using exponential error models. Residual variability was estimated separately for each study using a combined additive and constant coefficient of variation error model.

Based on literature recommendations, fixed allometric exponents for scaling of body weight were included for the clearance and volume parameters (0.75 for CL and Q and 1.0 for Ve and Vp). These standard exponents predict a less than proportional increase in CL and Q with increasing body weight and a proportional increase in Vc and Vp with increasing body weight. A negative linear relationship between age and Vp, as well as a negative power function to relate age and Q, were also included in the base structural pharmacokinetic model describing the data from these 2 studies.

Pharmacokinetic parameter estimates and standard errors of the estimates for the fit of the 2-compartment model to these data are presented in Table 49.

Most parameters were estimated with reasonable precision (standard error of the mean expressed as a percentage [% SEM]<34%), with the exception of the IIV for Vp, which was estimated with slightly poorer precision (% SEM=56.7%). Diagnostic plots indicated a good fit to the data, with no apparent biases, except a slight degree of under-prediction of concentrations measured more than 10 h after the end of the infusion. This under-prediction may be due to the prediction of late samples at levels below the limit of quantitation of the assay, where the observed data were fixed to values of one-half the assay limit.

Model development was continued with the addition of the Example 1 data to the pooled Example 3 and Example 5 dataset. When the model developed using the Example 5 and Example 3 data was applied to the pooled dataset including Example 1, high correlations were initially observed between many of the parameters. Due to the difference in weight and age of the subjects from Example 1 as compared to the older subjects from the other two studies, the model including only the allometric functions of weight was evaluated next, removing the additional effects of age that were included in the previous model. After refining this model with the pooled dataset first, the effect of maturation on various pharmacokinetics parameters was then addressed.

In the evaluation of maturation effects on dexmedetomidine pharmacokinetics, shifts in the allometric exponents were tested for pre-term subjects (that is, those with gestational age≤28 weeks from Example 1), as well as neonates (that is, subjects less than 1 month of age, regardless of gestational age) as compared to all other subjects. Shifts in the allometric exponents for CL and Vc for neonates were asso-

TABLE 49

Parameter Estimates and Standard Errors From the Dexmedetomidine Pharmacokinetic Model Developed Using Example 5 and Example 3 Data Only

| Parameter | Final Parameter Estimate | | Magnitude of Interindividual Variability (% CV) | |
|---|---|---|---|---|
| | Population Mean | % SEM | Final Estimate | % SEM |
| CL (L/h)[a] | 18.5 | 3.5 | 30.76 | 18.3 |
| Vc (L)[b] | 18.9 | 8.9 | 68.26 | 17.0 |
| Intercompartmental CL (L/h)[c] | 35.9 | 15.8 | | |
| Exponent of power relationship between Q and age[c] | −0.509 | 33.6 | 117.05 | 24.9 |
| Vp (L)[d] | 19.1 | 9.3 | | |
| Slope of linear age effect on Vp (L/y)[d] | −1.43 | 15.3 | 27.15 | 56.7 |
| Ratio of additive to proportional RV: Example 5 | 11.8 | 14.7 | NA | NA |
| Ratio of additive to proportional RV: Example 3 | 42.1 | 15.5 | NA | NA |
| RV Example 5[e] | 0.0363 | 16.9 | NA | NA |
| RV Example 3[f] | 0.0712 | 19.1 | NA | NA |

Minimum value of the objective function = 9930.466
Abbreviations: CL, elimination clearance; IIV, interindividual variability; NA, not applicable; % CV, coefficient of variation expressed as a percentage; % SEM, standard error of the mean expressed as a percentage; Q, intercompartmental clearance; RV, residual variability; Vc, volume of the central compartment; Vp, volume of the peripheral compartment; WTKG, weight in kg.

[a] Typical $CL = 18.5 \times \left(\frac{WTKG}{19.8}\right)^{0.75}$

[b] Typical $Vc = 18.9 \times \left(\frac{WTKG}{19.8}\right)$

[c] Typical $Q = 35.9 \times \left(\frac{WTKG}{19.8}\right)^{0.75} \times \left(\frac{age}{4.8}\right)^{-0.509}$

[d] Typical $Vp = 19.1 \times \left(\frac{WTKG}{19.8}\right) - 1.43 \times (age - 4.8)$

[e] Residual variability estimate is expressed as a variance. The corresponding % CV for RV in Example 5 ranges from 108% CV at 2.12 ng/L (one-half the lower assay limit) to 19% CV at 700 ng/L.
[f] Residual variability estimate is expressed as a variance. The corresponding % CV for RV in Example 3 ranges from 79% CV at 15.12 ng/L (one-half the lower assay limit) to 27% CV at 2000 ng/L.

ciated with the largest reduction in the MVOF (approximately 48 points) and good precision of parameter estimates and were, therefore, retained in the model. Both Q and Vp were additionally found to be statistically significantly related to age. A power function was used to describe the negative relationships between these parameters and age (that is, both parameters decrease with increasing age).

The final base structural pharmacokinetics model for the pooled dataset of Examples 1, 3, and 5 was a 2-compartment model with IIV estimated on CL, Q, Vc, and Vp using exponential error models, separate additive and constant coefficient of variation RV models for each study, fixed allometric exponents (as stated above) on the clearance and volume parameters with an additional shift on the CL and Vc exponents for neonates, age effects on Q and Vp described by power functions (both decrease with increasing age), and covariance parameters for the IIVs on CL and Vp, and the IIVs on Q and Vc. The final base structural 2-compartment model and standard errors are presented in Table 50.

SEMs<40%). Goodness-of-fit plots are shown in FIGS. 19A-B for the base structural model for the pooled dataset of Examples 1, 3, and 5. Diagnostic plots indicate a good fit to the pooled data and a lack of substantial bias.

The following covariates were tested on CL and Vc: gender, ethnicity, cardio-pulmonary bypass use, albumin infusion (presence), and site of sampling (arterial versus venous versus capillary). The following covariates were tested on CL only: alanine aminotransferase, total bilirubin, glucuronidation pathway inhibitors (presence), and heart physiology (single versus double ventricle). The effect of ethnicity was modeled as Caucasian versus Hispanic versus all "other" race groups (Asian, black) that were combined due to the small sample sizes. Each continuous covariate effect was tested in NONMEM using a linear and power model. Categorical covariates were tested using additive shifts. Delta-parameter plots were generated to illustrate the possible relationships between the remaining unexplained ITV in CL or Vc and the covariates of interest. No obvious trends are apparent indi-

TABLE 50

Parameter Estimates and Standard Errors From the Dexmedetomidine Base Structural Model

| Parameter | Final Parameter Estimate | | Magnitude of Interindividual Variability (% CV) | |
|---|---|---|---|---|
| | Population Mean | % SEM | Final Estimate | % SEM |
| CL (L/h)$^a$ | 11.5 | 3.5 | | |
| Proportional shift in allometric exponent for CL for neonates$^a$ | 0.480 | 20.88 | 35.07 | 17.2 |
| Vc (L)$^b$ | 9.46 | 11.4 | | |
| Proportional shift in allometric exponent for Vc for neonates$^b$ | 0.513 | 56.7 | 53.48 | 21.6 |
| Intercompartmental CL (L/h)$^c$ | 71.0 | 41.4 | | |
| Exponent for power function effect of age on Q$^c$ | −0.286 | 37.8 | 164.32 | 34.3 |
| Vp (L)$^d$ | 15.2 | 8.8 | | |
| Exponent for power function effect of age on Vp$^d$ | −0.291 | 12.2 | 47.12 | 23.3 |
| Ratio of additive to proportional RV: Example 1 | 8.73 | 40.3 | NA | NA |
| Ratio of additive to proportional RV: Example 5 | 12.3 | 14.4 | NA | NA |
| Ratio of additive to proportional RV: Example 3 | 40.8 | 16.8 | NA | NA |
| cov (IIV in CL, IIV in Vp) | 0.124 | 21.5 | NA | NA |
| cov (IIV in Q, IIV in Vc) | 0.814 | 22.6 | NA | NA |
| RV Example 1$^e$ | 0.194 | 22.6 | NA | NA |
| RV Example 5$^f$ | 0.0359 | 16.4 | NA | NA |
| RV Example 3$^g$ | 0.0684 | 18.7 | NA | NA |

Minimum value of the objective function = 11069.294
Abbreviations: CL, elimination clearance; IIV, interindividual variability; NA, not applicable; NEO, indicator variable for neonates; % CV, coefficient of variation expressed as a percentage; % SEM, standard error of the mean expressed as a percentage; Q, intercompartmental clearance; RV, residual variability; Vc, volume of the central compartment; Vp, volume of the peripheral compartment; WTKG, weight in kg.

$^a$Typical CL $= 11.5 \times \left(\frac{WTKG}{10.35}\right)^{[0.75\times(1+0.480\times NEO)]}$ $^b$Typical Vc $= 9.46 \times \left(\frac{WTKG}{10.35}\right)^{[1+0.513\times NEO]}$ $^c$Typical Q $= 71.0 \times \left(\frac{WTKG}{10.35}\right)^{0.75} \times \left(\frac{age}{1.56}\right)^{-0.286}$ $^d$Typical Vp $= 15.2 \times \left(\frac{WTKG}{10.35}\right) \times \left(\frac{age}{1.56}\right)^{-0.291}$ $^e$Residual variability estimate is expressed as a variance. The corresponding % CV for RV in Example 1 study ranges from 51% CV at 14.97 ng/L (one-half the lower assay limit) to 44% CV at 200 ng/L.
$^f$Residual variability estimate is expressed as a variance. The corresponding % CV for RV in Example 5 study ranges from 112% CV at 2.12 ng/L (one-half the lower assay limit) to 19% CV at 700 ng/L.
$^g$Residual variability estimate is expressed as a variance. The corresponding % CV for RV in Example 3 study ranges from 75% CV at 15.12 ng/L (one-half the lower assay limit) to 26% CV at 3000 ng/L.

With the exception of the parameter for the proportional shift in the allometric exponent for Vc for neonates (% SEM of 56.7%), the other fixed and random effect model parameters were all estimated with reasonable precision (most % cating likely parameter-covariate relationships. Furthermore, the lack of trend in the plots for age and weight indicate that these factors are adequately accounted for in the base structural model, which includes allometric weight relationships and additional effects of maturation. Although the effect of several covariates (total bilirubin, albumin infusion, and alanine aminotransferase on CL) was statistically significant (P value<0.05 based on a reduction in the MVOF following their inclusion in the model), none of these covariate effects was also associated with a ≥5% reduction in ITV in CL.

As a result of the univariate forward selection results, no additional covariates were added to the base model. Therefore, the backward elimination step was not performed and this base model was next evaluated for further refinement and simplification. Next, the base structural model following forward selection was checked for possible simplifications in an effort to identify the most appropriate and parsimonious model which adequately characterized these data. Removal of the shift for the allometric exponent on Vc for neonates resulted in a non-statistically significant increase in the MVOF of 1.991 (P value>0.05) and was, therefore, removed from the model. Further simplification of the RV model for Example 1 to a constant coefficient of variation error model was also performed; this simplification was also associated with a non-statistically significant increase in the MVOF of 1.331 (P value>0.05) and was, therefore, implemented.

Goodness-of-fit diagnostic plots were examined for model misfit. Several alternative methods for handling of BLQ samples were also evaluated, including Beals M3 method and the exclusion of BLQ samples after the first one in a sequence, but these attempts did not minimize successfully or did not result in model improvement. A further assessment of the model including all outliers did not result in successful minimization; therefore, the observations identified as outliers during model development were permanently excluded. A simulation-based prediction-corrected VPC was performed using the final pharmacokinetics model, simulating 1000 replicates of the analysis dataset. This VPC method was used to improve the ability to diagnose possible model misspecification by removing the variability resulting from the broad range of doses and ages/weights of subjects. Therefore, for the purposes of the prediction correction, discrete bins based on time since the end of the infusion, dexmedetomidine treatment group, and age were defined.

FIG. 20 illustrates the 90% prediction interval, derived from the 1000 simulated datasets, overlaid on the observed dexmedetomidine concentrations versus time since the end of the maintenance infusion. Concentrations measured prior to the end of the maintenance infusion are presented with a negative value for the time since the end of the maintenance infusion. The majority of the observed data falls within the prediction interval. The percentage of the observed concentrations below the 5th percentile was 6.3% and the percentage above the 95th percentiles was 4.7%. The VPC indicates no apparent biases in the overall model fit by comparing the simulated data (based on the model) to the raw data.

FIG. 21 illustrates a comparison of the 5th, 50th, and 95th percentile of the prediction-corrected observed and model-based simulated data. This plot also confirms the high degree of concordance between the simulation-based data and the observed data, wherein the 50th percentiles of the observed and simulated data track very well across the entire range of time. For the purposes of the VPC, the simulated concentrations were treated in a manner identical to the observed concentrations, whereby values less than the assay limit for the study were set to one-half the appropriate limit.

The final population pharmacokinetics model was a 2-compartment model with IIV estimated on CL, Q, Vc, and Vp using exponential error models, fixed allometric exponents on the clearance (0.75 for CL and Q) and volume of distribution (1.0 for Vc and Vp) parameters, with an additional shift on the CL exponent for neonates, age effects on Q and Vp described by power functions (both decrease with increasing age), covariance terms for the IIVs on CL and Vp, and the IIVs on Q and Vc, separate additive plus constant coefficient of variation error models for Studies Example 3 and Example 5, and a constant coefficient of variation error model for the Example 1 study.

The parameter estimates for the final population pharmacokinetics model for dexmedetomidine are provided in Table 51.

TABLE 51

Parameter Estimates and Standard Errors From the Dexmedetomidine Final Population Pharmacokinetic Model

| Parameter | Final Parameter Estimate | | Magnitude of Interindividual Variability (% CV) | |
|---|---|---|---|---|
| | Population Mean | % SEM | Final Estimate | % SEM |
| CL (L/h)$^a$ | 11.4 | 3.5 | | 17.3 |
| Proportional shift in allometric exponent for CL for neonates$^a$ | 0.468 | 19.3 | 35.07 | |
| Vc (L)$^b$ | 9.20 | 11.6 | 54.13 | 21.6 |
| Intercompartmental CL (L/h)$^c$ | 70.5 | 43.7 | | 37.3 |
| Exponent for power function effect of age on Q$^c$ | −0.293 | 39.6 | 163.40 | |
| Vp (L)$^d$ | 15.2 | 8.8 | | 24.3 |
| Exponent for power function effect of age on Vp$^d$ | −0.282 | 12.9 | 47.33 | |
| Ratio of additive to proportional RV: Example 5 | 8.79 | 15.8 | NA | NA |
| Ratio of additive to proportional RV: Example 3 | 27.4 | 54.4 | NA | NA |
| cov (IIV in CL, IIV in Vp) | 0.124 | 22.8 | NA | NA |
| cov (IIV in Q, IIV in Vc) | 0.818 | 23.6 | NA | NA |
| RV Example 1$^e$ | 0.214 | 20.4 | NA | NA |

TABLE 51-continued

Parameter Estimates and Standard Errors From the Dexmedetomidine Final
Population Pharmacokinetic Model

| Parameter | Final Parameter Estimate | | Magnitude of Interindividual Variability (% CV) | |
|---|---|---|---|---|
| | Population Mean | % SEM | Final Estimate | % SEM |
| RV Example 5[f] | 0.0358 | 16.4 | NA | NA |
| RV Example 3[g] | 0.0682 | 18.8 | NA | NA |

Minimum value of the objective function = 11072.619

Abbreviations: CL, elimination clearance; IIV, interindividual variability; NA, not applicable; NEO, indicator variable for neonates; % CV, coefficient of variation expressed as a percentage; % SEM, standard error of the mean expressed as a percentage;
Q, intercompartmental clearance; RV, residual variability; Vc, volume of the central compartment;
Vp, volume of the peripheral compartment; WTKG, weight in kg.

[a] Typical $CL = 11.4 \times \left(\frac{WTKG}{10.35}\right)^{[0.75 \times (1+0.468 \times NEO)]}$

[b] Typical $CL = 9.20 \times \left(\frac{WTKG}{10.35}\right)$

[c] Typical $CL = 70.5 \times \left(\frac{WTKG}{10.35}\right)^{0.75} \times \left(\frac{age}{1.56}\right)^{-0.293}$

[d] Typical $Vp = 15.2 \times \left(\frac{WTKG}{10.35}\right) \times \left(\frac{age}{1.56}\right)^{-0.282}$

[e] Residual variability estimate is expressed as a variance. The corresponding % CV for RV in Example 1 is 46% CV.
[f] Residual variability estimate is expressed as a variance. The corresponding % CV for RV in Example 5 ranges from 111% CV at 2.12 ng/L (one-half the lower assay limit) to 19% CV at 700 ng/L.
[g] Residual variability estimate is expressed as a variance. The corresponding % CV for RV in Example 3 ranges from 75% CV at 15.12 ng/L (one-half the lower assay limit) to 26% CV at 3000 ng/L.

All fixed effect parameters were estimated with good precision (% SEMs<20%), with the exception of those associated with Q, which were estimated with slightly poorer precision (% SEMs of around 40%). Random effects were also estimated with good precision (most % SEMs<25%, except IIV in Q with % SEM=37%). Interindividual variability in CL, Vc, and Vp was moderate, ranging from 35% CV to 55% CV. Unexplained IIV in Q was very high at 163% CV. Overall, RV was the lowest in the Example 5 data (around 19% CV) and slightly higher in the Example 3 data (26% CV), but in both studies was considerably larger at low of variation RV model was found to adequately describe the data from Example 1, with a relatively higher estimate of 46% CV, regardless of concentration level.

The equations describing the relationships between the typical dexmedetomidine parameter values and the subject factors included in the model (that is, those relating to weight and age) are provided in Equation 1, Equation 2, Equation 3, and Equation 4.

$$\text{Typical } CL_j = 11.4 \times \left(\frac{WTKG_j}{10.35}\right)^{[0.75 \cdot (1-0.468 \times NEO_j)]} \quad (1)$$

$$\text{Typical } Vc_j = 9.20 \times \left(\frac{WTKG_j}{10.35}\right) \quad (2)$$

$$\text{Typical } Q_j = 70.5 \times \left(\frac{WTKG_j}{10.35}\right)^{0.75} \times \left(\frac{age_j}{1.56}\right)^{-0.293} \quad (3)$$

$$\text{Typical } Vp_j = 15.2 \times \left(\frac{WTKG_j}{10.35}\right) \times \left(\frac{age_j}{1.56}\right)^{-0.282} \quad (4)$$

Where:

$CL_j$ is the typical value of dexmedetomidine clearance in the jth subject predicted by the model, $Vc_j$ is the typical value of dexmedetomidine volume of the central compartment in the jth subject predicted by the model, $Q_j$ is the typical value of dexmedetomidine intercompartmental clearance in the jth subject predicted by the model, $Vp_j$ is the typical value of dexmedetomidine volume of the peripheral compartment in the jth subject predicted by the model, $age_j$ is the age, in years, of the jth subject, $WTKG_j$ is the weight, in kg, of the jth subject, and $NEO_j$ is an indicator variable with a value of 1 for neonate subjects and 0 otherwise.

Goodness-of-fit plots for this model are provided in FIGS. 22A-D for the entire population. At the level of the overall dataset, these diagnostic plots indicate a reasonably unbiased fit of the model to the dataset, with a slight underprediction of the samples collected more than 10 h after the end of the infusion. This is apparent in the grouping of points that are associated with positive weighted residuals after 10 h in the plot of weighted residuals versus time since end of the infusion. In addition, these plots provide support for the selected models for RV based on the lack of trend or pattern in the plots of individual weighted residuals versus individual predicted concentrations. To further illustrate the appropriateness of the model across the treatment groups and age range of the subjects, additional goodness-of-fit plots were prepared stratified by treatment group and by age group. Although some treatment and age groups represent very small sample sizes, these plots indicated no substantial persistent trends of misfit or bias across the range of doses or age levels. Calculations of the shrinkage of the empirical Bayesian estimate distributions indicate no concern over excessive shrinkage for any of the pharmacokinetics parameters as the estimates are all indicative of low shrinkage (that is, 3.5% for CL, 13.7% for Vc, 13.7% for Q, and 12.6% for Vp).

Pairwise scatterplots of these terms are provided in FIG. 25. These plots demonstrate the modeled correlations between the IIV in CL and Vp and between the ITV in Q and Vc, as well as a lack of substantial relationship between other pairs of terms.

The final base structural pharmacokinetics model for dexmedetomidine using the pooled data from the 3 studies was a 2-compartment model with fixed allometric exponents on the clearance and volume parameters, an additional shift on the CL and Vc exponents for neonates, and age effects on Q and Vp. The allometric weight adjustments using the fixed coefficients of 0.75 for CL and 1 for volume terms were based on a well-described scientific framework that can be related to basic physiologic functions, and have been used frequently in pediatric pharmacokinetics analyses. Because the allometric coefficients were fixed for maturation based on age could be delineated from the effect of size. With the inclusion of the Example 1 study data in the analysis, the shifts on CL and Vc were included for the neonate group to correct for maturation only in these youngest subjects. In addition, the age effects on Q and Vp (decrease with increasing age) were included in the model for all subjects, and are consistent with known age-dependent changes in proportions of body water and fat which influence the distribution of drugs. Overall, this covariate approach avoided problems with co-linearity between size and age by first addressing size as a fixed allometric exponent, and then using age to describe maturation, as has been previously suggested in the literature.

Additional covariate effects were tested on dexmedetomidine CL and Vc based on clinical interest and physiologic plausibility; however, no effect met the pre-specified criteria for inclusion in the model. In a previously developed 2-compartment population pharmacokinetics model of dexmedetomidine in infants (aged 1 to 24 months) after open heart surgery, significant covariate effects included total bypass time on CL and Vc and ventricular physiology (1- or 2-ventricle) on CL, in addition to fixed allometric effects of weight on CL, Q, Vc, and Vp. There are several factors that may contribute to the difference in findings between the 2 analyses.

Su et al. used a full model approach for covariate selection while the current analysis used step-wise hypothesis testing, with fairly stringent criteria that required achievement of both statistical significance as well as a 5% reduction in IIV. (See Anesth Analg. 2010; 110(5):1383-1392.) The data available for covariate assessment also differed from Su et al., where total bypass time was determined to be a significant covariate as a continuous variable; the current analysis was limited to evaluation of CPB use as a dichotomous variable indicating occurrence or lack of occurrence.

Since no additional covariates were found to be significant, the final pharmacokinetics model was structurally similar to the base model with the exception of 2 model refinements consisting of the removal of the allometric exponent on Vc for neonates and simplification of the RV model for the Example 1 study to a constant coefficient of variation error model. The degree of RV was relatively higher in the Example 1 study data (46% CV) compared to the Study Example 3 (26% CV) and Example 5 data (19% CV). Different levels of enzyme maturation in the subjects in the Example 1 study are a likely contributing factor to the increased variability. In addition, comparatively more data was collected after low dexmedetomidine doses in the Example 1 study resulting in an increased frequency of plasma concentrations in the lower range of the assay where variability tends to be greater.

Overall, all fixed effect parameters were precisely estimated except for those associated with Q (% SEMs approximately 40%). The estimate of Q was considerably higher (70.5 L/h) and the unexplained IIV in Q was also quite high (163% CV) compared to an initial model based on data from only Studies Example 3 and Example 5 (Q=35.9 L/h, IIV in Q=117% CV). This finding may be related to the sparser nature of the data added from the Example 1 study and, as a result, the plasma sampling for dexmedetomidine concentrations was less informative to the 2-compartment model parameters in the neonates.

The final pharmacokinetics model for dexmedetomidine was a 2-compartment model as has been previously described in other investigations of pediatric subjects. Given the remaining slight bias towards underprediction of concentrations obtained at later sampling times after the end of the maintenance infusion seen in the goodness-of-fit plots (FIGS. 22A-D), a 3-compartment model was also evaluated using the concentration data from Studies Example 3 and Example 5. However, the 3-compartment model fit was essentially identical to the 2-compartment model, and the underprediction bias (FIG. 18) was not corrected. A 3-compartment model was not attempted with the addition of the Example 1 study data since the sparser data from neonates would be even less informative at the later sampling times.

Comparison of fixed effect parameters from the 2-compartment model published by Su et al. (based on only 35 subjects from the Example 5 study ranging in age from 1 to 24 months) for a subject aged 7.7 months, weighing 7 kg, and with the median value for total bypass time (57 minutes) with those from the final pharmacokinetics model developed herein (based on 115 subjects ranging in age from less than 1 week to 17 y) revealed fairly similar estimates, except for Q. Values for CL, Ve, Q, and Vp were 7.26 L/h, 8.4 L, 24.1 L/h, and 10.2 L from the Su et al. model compared to 8.5 L/h, 6.22 L, 68.21 L/h, and 13.21 L from the current analysis. Estimates of the initial distribution ($\alpha$) and terminal elimination ($\beta$) half-lives in the current analysis were 3.2 minutes and 1.6 h for a pediatric subject with the median age and weight of 1.56 y and 10.35 kg, respectively, and 7.5 minutes and 1.8 h for a 17 year old, 70-kg subject. These results are generally similar to the ranges of initial distribution half-life (4.08 minutes to 9 minutes) and terminal elimination half-life (1.6 h to 2.65 h), previously reported for dexmedetomidine given as 1 µg/kg for 5 minutes or 10 minutes, or 0.2 µg/kg/h to 0.7 µg/kg/h infusion. (See Diaz et al., Pediatr Crit. Care Med. 2007; 8:419-424; Petroz et al., Anesthesiology. 2006; 105:1098-1110; and Vilo et al., Br J. Anaesthesia. 2008; 100:697-700).

It is also of interest to compare CL and volume of distribution (Vc+Vp) across the age range of the 6 pediatric age groups represented in the 3 studies of dexmedetomidine contributing to the pharmacokinetics model (28 weeks to <1 month, 1 month to <6 months, 6 months to <12 months, 12 months to <24 months, 2 years to <6 years, and 6 years to <17 years). FIG. 23 and FIG. 24 (upper panels) provide the geometric means and 95% confidence intervals for the individual Bayesian estimates of dexmedetomidine CL and volume of distribution plotted at the midpoint of each age group, with the corresponding weight-adjusted estimates for the pharmacokinetics parameter depicted similarly in the lower panels. A line for the population model-based typical value of each parameter versus age is overlaid in each plot.

Table 52 and Table 53 provide summary statistics for the individual Bayesian parameter estimates and the model-predicted typical value estimates by age group for dexmedetomidine CL, weight-adjusted CL, volume of distribution, and weight-adjusted volume of distribution, respectively.

TABLE 52

Summary Statistics for the Individual Bayesian Estimates and Model-Predicted Typical Values of Dexmedetomidine Clearance and Weight-Adjusted Clearance by Age Group

| Age Group | Median Weight (kg) (min, max) | Median Age (y) (min, max) | CL (L/h) | | Weight-Adjusted CL (L/h/kg) | |
|---|---|---|---|---|---|---|
| | | | Geo. Mean (95% CI) | Predicted Typical Value | Geo. Mean (95% CI) | Predicted Typical Value |
| 28 weeks GA - <1 month (n = 22) | 3.12 (1.19, 3.80) | 0.029 (0.008, 0.077) | 2.71 (2.03, 3.61) | 3.04 | 0.991 (0.810, 1.212) | 0.976 |
| 1 month - <6 months (n = 14) | 5.99 (3.15, 7.00) | 0.332 (0.099, 0.484) | 6.95 (5.52, 8.75) | 7.56 | 1.213 (0.998, 1.475) | 1.263 |
| 6 months - <12 months (n = 16) | 7.28 (5.10, 9.34) | 0.657 (0.521, 0.896) | 8.15 (7.05, 9.43) | 8.75 | 1.110 (0.945, 1.302) | 1.203 |
| 12 months - <24 months (n = 8) | 10.20 (8.87, 11.90) | 1.493 (0.973, 1.651) | 11.34 (9.13, 14.07) | 11.28 | 1.118 (0.908, 1.375) | 1.105 |
| 2 y-<6 y (n = 26) | 13.75 (9.98, 23.59) | 3.548 (2.070, 5.761) | 15.88 (14.06, 17.95) | 14.11 | 1.108 (1.000, 1.228) | 1.026 |
| 6 y-<17 y (n = 29) | 30.20 (13.60, 99.00) | 9.887 (6.032, 16.967) | 24.46 (19.50, 30.67) | 25.45 | 0.796 (0.695, 0.911) | 0.843 |

TABLE 53

Summary Statistics for the Individual Bayesian Estimates and Model-Predicted Typical Values of Dexmedetomidine Volume of Distribution and Weight-Adjusted Volume of Distribution by Age Group

| Age Group | Median Weight (kg) (min, max) | Median Age (y) (min, max) | Volume of Distribution (L) | | Weight-Adjusted V (L/kg) | |
|---|---|---|---|---|---|---|
| | | | Geo. Mean (95% CI) | Predicted Typical Value | Geo. Mean (95% CI) | Predicted Typical Value |
| 28 weeks GA - <1 month (n = 22) | 3.12 (1.19, 3.80) | 0.029 (0.008, 0.077) | 15.38 (11.67, 20.28) | 16.90 | 5.634 (4.456, 7.124) | 5.418 |
| 1 month - <6 months (n = 14) | 5.99 (3.15, 7.00) | 0.332 (0.099, 0.484) | 17.26 (14.84, 20.07) | 18.91 | 3.012 (2.498, 3.632) | 3.160 |
| 6 months - <12 months (n = 16) | 7.28 (5.10, 9.34) | 0.657 (0.521, 0.896) | 21.27 (18.26, 24.77) | 20.10 | 2.895 (2.438, 3.438) | 2.763 |
| 12 months - <24 months (n = 8) | 10.20 (8.87, 11.90) | 1.493 (0.973, 1.651) | 25.29 (19.84, 32.24) | 24.23 | 2.493 (1.963, 3.167) | 2.376 |
| 2 y-<6 y (n = 26) | 13.75 (9.98, 23.59) | 3.548 (2.070, 5.761) | 33.51 (28.94, 38.80) | 28.24 | 2.338 (2.052, 2.665) | 2.054 |
| 6 y-<17 y (n = 29) | 30.20 (13.60, 99.00) | 9.887 (6.032, 16.967) | 51.51 (39.84, 66.61) | 53.19 | 1.677 (1.402, 2.005) | 1.761 |

In FIG. 23 (upper panel), the steeper slope of the profile exhibited at the youngest age levels results from the additional maturation covariate effect on the CL exponent for neonates, with a shallower increase in CL evident with increasing age greater than 1 year. The weight-adjusted CL shown in the lower panel of FIG. 23 also increases between the 2 youngest age groups, but then continues to decrease across the remaining groups. The overall slope of the profile exhibited for volume of distribution in the upper panel of FIG. 24 represents the net effect of increasing Vc and Vp with increasing weight and decreasing Vp with increasing age.

Likewise, the pronounced reduction in weight-adjusted volume of distribution with increasing age in the youngest age groups (FIG. 24, lower panel) is most likely attributable to the negative effect of age on Vp (power function), while Vc remains more constant with increasing age. This pediatric pharmacokinetics model can be further used to extrapolate values for pediatric pharmacokinetics parameters to values expected at usual adult ages and weights, for comparison to typical pharmacokinetics parameter values obtained from the previously developed adult population pharmacokinetics model for dexmedetomidine. Based on a hypothetical pediatric subject at the upper end of the ranges for age and weight (that is, 17 years and 70 kg), the dexmedetomidine CL and volume of distribution are predicted to be 47.8 L/h and 114.6 L, compared to corresponding values of 39 L/h (mean body weight associated with this CL was 72 kg) and 118 L as reported in the product label for Precedex.

Similarly, dexmedetomidine CL and volume of distribution were 35.8 L/h and 112.7 L22 in the typical subject from the adult population pharmacokinetics analysis of long-term (>24 h) dexmedetomidine use, and 39.4 L/h and 152 L, respectively, from the noncompartmental analysis of this data. These extrapolated results based on a 70-kg subject are also consistent with estimates of CL and volume of distribution standardized to a 70-kg adult of 42.1 L/h and 125.3 L from a population pharmacokinetics analysis of pooled data from 4 studies of dexmedetomidine in pediatric intensive care (subjects aged 1 week to 14 years given 1 μg/kg/h to 6 μg/kg/h infusion). 24 Overall, this model provides a robust characterization of the pharmacokinetics of dexmedetomidine in pediatrics.

The model evaluation results provide evidence that the model is able to predict well over the entire range of dexmedetomidine concentrations occurring during the maintenance infusion, as well as after discontinuation. In addition, this population model is based on the largest population of pediatric subjects, and broadest range of ages (neonate to 17 years), maintenance doses, and infusion durations reported to date.

The conclusions of the analysis are as follows. A linear 2-compartment model was found to best characterize the pooled dexmedetomidine concentration data collected from pediatric subjects enrolled in three studies after a range of dexmedetomidine doses were administered as a short intravenous infusion, followed by a maintenance infusion of varying duration. • Fixed allometric functions were used to account for the influence of body weight on all pharmacokinetic parameters in this pediatric population. The allometric exponent for dexmedetomidine clearance was additionally adjusted in neonate subjects. • The intercompartmental clearance and the volume of the peripheral compartment for dexmedetomidine were both found to be related to maturation, as described by age, according to a power function (both decrease with increasing age).

The effects of ethnicity, gender, alanine aminotransferase, total bilirubin, heart physiology (single- versus double-ventricle), use of concomitant glucuronidation pathway inhibitors, albumin infusion, use of cardio-pulmonary bypass, and site of sampling were not identified as statistically significant predictors of dexmedetomidine pharmacokinetic variability.

Clearance estimates from this model increase with increasing age and weight-adjusted clearance estimates decrease with increasing age, approaching values expected in adults. Volume of distribution estimates from this model increase with increasing age and weight-adjusted volume of distribution estimates decrease with increasing age, approaching values expected in adults. The model evaluation supports the robustness of the model to predict well over the entire range of concentrations.

Example 7

Pharmacokinetics of Dexmedetomidine in Pediatric Patients Aged 12 Months to 24 Months A 5-subject, randomized, open-label, single-center study of dexmedetomidine was conducted on subjects aged 12 months to weeks to <24 months of age. The study population consisted of initially intubated and mechanically ventilated pediatric subjects that required sedation in an intensive care setting for a minimum of 6 hours but did not exceed 24 hours.

Subjects were randomized into one of two dose levels: dose level 1 consisted of a 0.7 μg/kg loading dose immediately followed by a 0.5 μg/kg/hr maintenance infusion; dose level 2 consisted of a 1 μg/kg loading dose immediately followed by a 0.75 μg/kg/hr maintenance infusion. A total of five subjects were randomized at one site in the United States. Two subjects were randomized to dose level 1 and three subjects to dose level 2. All five subjects who were enrolled in the trial received dexmedetomidine and completed the treatment. No subjects prematurely discontinued the study.

The dose levels are outlined in Table 54 below.

TABLE 54

Dosing Levels

| Dose Level | Loading Dose (μg/kg) | Maintenance Dose (μg/kg/hr, as a continuous infusion) |
|---|---|---|
| 1 | 0.7 | 0.5 |
| 2 | 1 | 0.75 |

The dexmedetomidine was administered as a 10-minute loading dose infusion of dexmedetomidine immediately followed by a continuous fixed maintenance dose infusion of dexmedetomidine across two dose levels so that the duration of infusion was a minimum of 6 and up to 24 hours postoperatively (loading dose+maintenance dose combined). Dexmedetomidine was administered at the site of insertion of the IV catheter to avoid flushing the drug. No other medications were to be administered through the IV line designated for dexmedetomidine.[a]

The dexmedetomidine administered was Precedex® (dexmedetomidine hydrochloric acid injection, 100 μg/mL, base). The dexmedetomidine solution was diluted to 4 μg/mL in 0.9% sodium chloride or dextrose 5% in water. The dexmedetomidine solution was not to be refrigerated.

A subject was allowed to be extubated at any time after dexmedetomidine administration began. The dexmedetomidine was infused using a controlled infusion device. Manually controlled microdrippers, macrodrippers, or other non-automated infusion devices were not permitted.

Dexmedetomidine could not be given as a bolus dose. In order to ensure proper infusion, dexmedetomidine was not administered directly into the pulmonary artery.

The level of sedation was assessed using the University of Michigan Sedation Scale. Pain was assessed using the Faces, Legs, Activity, Cry and Consolability (FLACC) scale. Following completion of screening procedures, the dexmedetomidine infusion began after discontinuation of all other sedative agents and after the subject had attained a UMSS≤4. Sedation dosages were calculated using the subject's most recently measured weight (considered baseline weight).

Subjects who remained intubated or were reintubated during the post-infusion period or required sedation for other reasons during the post-infusion period were treated according to standard of care at the study site. However, this did not include dexmedetomidine until all post-infusion pharmacokinetics samples had been obtained. When applicable, open-label dexmedetomidine could resume 24 hours from study drug discontinuation.

For subjects to be considered evaluable, they must have received at least 5 hours of continuous dexmedetomidine administration. The dexmedetomidine infusion could not have extended beyond 24 hours. Once dexmedetomidine was discontinued (no weaning of dexmedetomidine allowed), post-infusion procedures began and continued for 24 hours. During the dexmedetomidine administration period, the dexmedetomidine infusion rate could not be titrated.

A schematic of the overall study design is provided below in Table 55 below.

TABLE 55

Study Schematic

| Screening Period | DEX Infusion Period | Post-DEX Observation Period |
|---|---|---|
| Dose Level 1 (n = 3) | DEX Load 0.7 µg/kg UMSS with rescue MDZ PK sampling FLACC with rescue Fentanyl | DEX Maintenance 0.5 µg/kg/hr <br><br> FLACC with rescue Fentanyl |
| Dose Level 2 (n = 3) | DEX Load 1 µg/kg UMSS with rescue MDZ PK sampling FLACC with rescue Fentanyl 10 minutes 6 to 24 hours | DEX Maintenance 0.75 µg/kg/hr <br><br> FLACC with rescue Fentanyl <br><br> 24 hours |

DEX = dexmedetomidine;
FLACC = Faces, Legs, Activity, Cry and Consolability;
MDZ = midazolam;
PK = pharmacokinetic;
UMSS = University of Michigan Sedation Scale Adequacy of sedation was assessed using the UMSS throughout the study, with the target level of sedation a UMSS score between 2 and 4. Prior to the start of dexmedetomidine infusion, a baseline score using the UMSS was obtained. The UMSS score was measured according to the following schedule: just prior to loading dose, and then at 5 and 10 minutes during loading dose; at the start of maintenance of infusion, and at 5, 10, 15, 30, and 60 minutes for the first hour; every 4 hours thereafter during the remainder of the maintenance infusion; and within 5 minutes of obtaining each pharmacokinetics sample.

If a subject was not at the desired target level of sedation (i.e., UMSS<2), rescue medication could be administered for sedation. The rescue medication was midazolam. Repeated rescue with midazolam (0.05 to 0.1 mg/kg) at a recommended frequency of every 2 to 3 minutes per dose or at a frequency based on investigator judgment could be provided until the subject had reached the desired sedation level. A UMSS was obtained within 5 minutes prior to and within 5 minutes following administration of rescue midazolam along with the dose of rescue midazolam administered.

Pain was assessed using the FLACC scale. Rescue opiate analgesia, consisting of IV fentanyl was administered, based on the judgment of the investigator, or when the FLACC score was >4. The fentanyl was administered either as an intermittent bolus or as a continuous IV infusion.

If fentanyl was given as a bolus, a FLACC score was recorded within 5 minutes prior to and within 5 minutes following fentanyl bolus administration together along with the dose of rescue fentanyl administered. If fentanyl was given as a continuous infusion, FLACC scores were obtained with the scheduled vital signs every 4 hours. If the infusion was titrated, pain assessments were collected within 5 minutes prior to and within 5 minutes following each titration. The recommended dosage for fentanyl administration was an IV bolus of 1 to 4 µg/kg/dose every 2 to 4 hours as needed and a continuous IV infusion of 1 to 3 µg/kg/hr.

Following the discontinuation of dexmedetomidine, further sedation and analgesia were allowed to be provided per standard of care; however, dexmedetomidine could not be restarted until after completion of the 24-hour post-dexmedetomidine observation period.

Midazolam or fentanyl was used in instances where severe anxiety/agitation or pain was anticipated (e.g., prior to a painful procedure, such as suctioning or chest tube removal). The date, time, and type of any painful procedure (e.g., suctioning, chest tube removal) were recorded. In addition, the date and time of any non-pharmacologic intervention (e.g., swaddling, cuddling, and rocking) were documented, and a UMSS and/or FLACC score were recorded within 5 minutes prior to and within 5 minutes following the intervention.

At any time clinically indicated (e.g., subject discomfort despite maximum doses of rescue), or at the discretion of the investigator, the subject could have been converted to an alternative sedative or analgesic therapy that was not permitted within this protocol. This did not occur in this study.

Thirteen (13) 1 mL venous blood samples (~2½ tsp) were collected via a peripheral venous, central venous, or peripherally-inserted central catheter line into heparinized vacuum tubes at each of the following time points for pharmacokinetics analysis: no more than 30 minutes prior to start of the loading dose; within 5 minutes before finishing the loading dose; 30 minutes, 1, 2, and 4-6 hours after start of maintenance infusion; within 30 minutes prior to end of maintenance infusion (must be within 24 hours of start of maintenance infusion); 10 minutes after end of maintenance infusion; and 30 minutes, 1, 2, 4, and 10 hours after end of maintenance infusion.

For pharmacokinetics analyses, venous blood samples (1 mL) were collected in heparinized tubes at a site opposite from the site of infusion (e.g., left arm versus right arm). Samples were not drawn from the second lumen of a multi-lumen catheter through which dexmedetomidine was being administered.

The pharmacodynamics measurements were conducted no more than 5 minutes prior to the scheduled blood draws. Pharmacodynamic measurements included: sedation scores from UMSS; pain scores from FLACC; use of rescue medication (midazolam or fentanyl); and vital signs, i.e., HR, SBP, DBP, mean arterial pressure, respiratory rate, and oxygen saturation by pulse oximetry.

An adverse event was defined as any untoward medical occurrence associated with the use of a drug in humans, whether or not considered drug-related. An adverse event could therefore be any unfavorable and unintended sign (e.g., an abnormal laboratory finding), symptom, or disease temporally-associated with the use of a medicinal (investigational) product, whether or not the event was considered causally-related to the use of the product.

Such an event can result from use of the drug as stipulated in the protocol or labeling, from any use of the drug (e.g., off-label, use in combination with another drug) and from any route of administration, formulation, or dose as well as from accidental or intentional overdose, drug abuse, or drug withdrawal. Any worsening of a pre-existing condition or illness was considered an adverse event. Clinically significant abnormalities were to be followed to resolution (i.e., become stable, return to normal, return to baseline, or become explainable). Laboratory abnormalities and changes in vital signs were considered adverse events only if they resulted in discontinuation from the study, necessitated therapeutic medical intervention, met protocol-specific criteria, and/or if the Investigator considered them to be adverse events.

An elective surgery/procedure scheduled to occur during the study was not considered an adverse event if the surgery/procedure was performed for a pre-existing condition and the surgery/procedure had been planned prior to study entry. However, if the pre-existing condition deteriorated unexpectedly during the study (i.e., surgery performed earlier than planned), then the deterioration of the condition for which the elective surgery/procedure was being done was to be considered an adverse event.

Common post-operative sequelae specifically related to surgery were not reported as adverse events. The following sequelae at the surgical wound site were considered common surgically-related events and were not reported as adverse events: bleeding, bruising, itching, redness, swelling, numbness, tingling, burning, pain, infection, and wound dehiscence.

For the period immediately following discontinuation of dexmedetomidine and up to 7 days following the start of dexmedetomidine or hospital discharge (whichever came first), subjects were followed for the onset of adverse events. Special attention was made to follow the adverse events including but not limited to rebound tachycardia or hypertension, signs of withdrawal, agitation/rage, and pulmonary system complications (i.e., acute respiratory distress syndrome). The occurrence of comorbidities of prematurity, such as intraventricular hemorrhage, necrotizing enterocolitis, sepsis and persistent ductus arteriosus were also assessed. No serious adverse events occurred during this study.

All non-serious adverse events that occurred from the start of dexmedetomidine administration until 7 days following the start of dexmedetomidine were collected, whether elicited or spontaneously reported by the subject. In addition, serious adverse events were collected from the time the subject's legal representative signed the study-specific informed consent form until 7 days following the start of dexmedetomidine administration.

Laboratory evaluations were drawn at three time points: pre-dose; 4 to 6 hours after start of maintenance infusion; and 10 hours after end of maintenance infusion. All blood samples were collected in appropriately labeled tubes and sent for analysis. Whenever possible, in order to avoid extra blood draws, the laboratory blood samples were drawn simultaneously with 1 of the scheduled pharmacokinetics samples. The clinical laboratory tests performed are given in Table 56 below.

TABLE 56

Clinical Laboratory Tests

| Hematology | Blood Chemistry | Urinalysis |
| --- | --- | --- |
| Hematocrit | Blood Urea Nitrogen (BUN) | Specific gravity |
| Hemoglobin | | Ketones |
| Red blood cell (RBC) count | Creatinine | pH |
| White blood cell (WBC) count | Total bilirubin | Protein |
| | Serum glutamic-pyruvic transaminase (SGPT/ALT) | Blood |
| Neutrophils | | Glucose |
| Bands | Serum glutamic-oxaloacetic transaminase (SGOT/AST) | |
| Lymphocytes | | |
| Monocytes | Alkaline phosphatase | |
| Basophils | Sodium | |
| Eosinophils | Potassium | |
| Platelet count (estimate not acceptable) | Magnesium | |
| | Calcium | |
| | Phosphorus | |
| | Uric acid | |
| | Total protein | |
| | Glucose | |
| | Albumin | |

Core body temperature (i.e., tympanic, rectal, or via indwelling device) was monitored. Abnormal body temperatures were to be recorded as adverse events according to the clinical judgment of the investigator. Subjects with body temperature fluctuations below 35.6° C. (96° F.) or above 38.6° C. (101.5° F.) were evaluated for the presence of an adverse event.

A physical examination was performed during the screening period to establish baseline values for evaluations and in close proximity to 24 hours after the discontinuation of the dexmedetomidine infusion or on the day of discharge, whichever came first. All input/output fluid volumes were captured during the dexmedetomidine infusion period.

Electrocardiograms were obtained at the following times: pre-dose; 4 to 6 hours after start of maintenance infusion; and 10 hours after end of maintenance infusion. A clinically significant abnormality was grounds for excluding a subject from entry into the study. All subjects underwent continuous cardiac monitoring throughout the dexmedetomidine infusion period. The interpretation of the ECG was recorded as either normal, abnormal not clinically significant, or abnormal clinically significant by the investigator or physician.

Pharmacokinetic assessments of clearance, exposure, distribution, and elimination were appropriate for this study. The pharmacodynamic assessments using the UMSS (sedation) and FLACC (pain) have been established as validated and reliable. The safety measures used in this study were considered standard and suitable.

The primary evaluation was the assessment of dexmedetomidine pharmacokinetics. Data from all fully evaluable subjects (i.e., those receiving at least 5 hours of dexmedetomidine infusion) were included in the analyses. Pharmacodynamic measurements were conducted within 5 minutes prior to scheduled blood draws. Standard pharmacokinetics parameters were estimated by non-compartmental methods and/or population pharmacokinetics methods. Parameters of dexmedetomidine that were calculated included: area under the concentration-time curve; observed peak plasma concentration; steady state concentration; plasma clearance; terminal-phase elimination rate constant; observed time to reach maximum plasma concentration, expressed in hours; terminal elimination half-life; volume of distribution; and volume of distribution at steady state. Additional parameters, including pharmacokinetics parameters adjusted for weight and/or dose may have been determined as deemed appropriate (e.g., plasma clearance, weight adjusted [CL$_w$]).

Pharmacodynamic variables included: sedation scores from UMSS; pain scores from FLACC; use of rescue medication (midazolam or fentanyl); and vital signs, i.e., SBP, DBP, MAP, HR, RR, SpO$_2$.

Analysis of safety variables were based on the incidence of adverse events, clinical laboratory tests, changes from screening/baseline in vital signs, ECGs, and input/output fluid balance. The following variables were also assessed: use of rescue regimens to support vital signs, use of concomitant medications, and incidence of signs of withdrawal (changes in blood pressure or HR) after discontinuing dexmedetomidine infusion.

The statistical analyses were performed using SAS, version 9.1. For continuous variables, N, mean, median, standard deviation (SD), minimum, Q1, Q3, and maximum are presented. The mean and median are displayed to 1 decimal place more than the raw value. The SD is displayed to 2 decimal places more than the raw value. For categorical variables, N and percent are shown. All percentages are reported to 1 decimal place.

Descriptive statistics (N, mean, SD, median, min, Q1, Q3, max, and CV [%]) were used to summarize the pharmacokinetics parameters for each of the dose groups, and where pharmacokinetically appropriate, across all dose groups. Standard pharmacokinetics parameters were estimated by non-compartmental methods and/or population pharmacokinetics methods. Normalization of parameters based on administered dose could have been done as appropriate.

The following pharmacodynamic variables were evaluated: the percentage of subjects that required rescue midazolam for sedation during dexmedetomidine infusion; the incidence of rescue medication use for analgesia during dexmedetomidine infusion; the (a) total amount and (b) the weight adjusted total amount (per kg) of rescue medication midazolam or fentanyl given for sedation and analgesia during dexmedetomidine infusion; the time to first dose of rescue medication for sedation and analgesia were summarized with Kaplan Meier estimates; the absolute time and percentage of time on dexmedetomidine infusion that the subject had UMSS 2-4 and UMSS<2 was summarized for each dose level with descriptive statistics; descriptive statistics for FLACC scores while on study drug were summarized using all FLACC scores for a subject; and the time to successful extubation in subjects was summarized with Kaplan-Meier estimates.

The time on dexmedetomidine was summarized descriptively for each dose level, and also the number and percentage of subjects exposed to dexmedetomidine during the treatment period was summarized (N and percent) by time of exposure for the following time periods (<6 hour, <12 hour, <24 hours) and (>0-<6 hours, ≥6-<12 hours, ≥12-<24 hours, and ≥24 hours) by dose level.

Loading dose was summarized using the parameters total dose and duration of dose. Maintenance dose was summarized descriptively for each dose level and age group by total dose infused (μg/kg), average dose (μg/kg/hr), and duration of hours dosed. Total dose infused equaled infusion rate (μg/kg/hr) times duration of infusion (hour). The total dose of dexmedetomidine infused (μg/kg), total dose (μg), and the length of infusion (hours) was summarized descriptively by dose level.

Prior and concomitant medications were summarized according to the WHO DRUG Dictionary. The number and percentage of subjects who used prior medications (by preferred term) were tabulated for each dose level. The number and percentage of subjects who used concomitant medications were similarly tabulated.

Only treatment-emergent adverse events were analyzed. The number and percentage of subjects with treatment-emergent adverse events was summarized for each dose level according to the Medical Dictionary for Regulatory Activities (MedDRA) system organ class (SOC) and preferred term. Category of adverse event severity and category of adverse event relationship to dexmedetomidine were similarly summarized. For each subject with multiple adverse events, only the most severe category and the closest relationship to dexmedetomidine were counted once.

Additionally, separate tabulations were created for treatment-emergent serious adverse events, treatment-emergent adverse events leading to discontinuation, treatment-emergent adverse events related to dexmedetomidine, and treatment-emergent adverse events by severity.

For summaries by severity, if a subject had multiple events occurring in the same SOC or same preferred term, the event with the highest severity was summarized. Any adverse event with a missing severity was to be summarized as severe. Relationship to dexmedetomidine was summarized as follows: elated (included definitely related, probably related, and possibly related) or not related (included probably not related and not related).

All laboratory values outside the normal range were flagged in the data listings and clinically significant abnormal laboratory values were recorded. The number and percentage of subjects with clinically significant abnormal laboratory values at the baseline, during dexmedetomidine infusion, and during the post-dexmedetomidine period were summarized for each age group overall and by dose level. Descriptive statistics for clinical laboratory tests and change from baseline were summarized.

The mean, minimum, and maximum of the post-baseline vital signs HR, SBP, DBP, MAP, RR, and SpO$_2$. measured during the dexmedetomidine infusion period and during the 24-hour follow-up were determined for each subject. The absolute value and change from baseline was summarized descriptively for each of the mean, minimum, and maximum value by dose level. The incidence of abnormal ECG findings at baseline, during dexmedetomidine infusion, and during the post-dexmedetomidine period was tabulated by dose level.

The total amount of input (mL) and the total amount of output (mL) measured during the dexmedetomidine infusion period and post-dexmedetomidine infusion were calculated for each subject, and descriptively summarized by dose level.

Two subjects received sedatives or analgesics during dexmedetomidine infusion which were protocol violations. These were two dose level 2 subjection, one of whom received morphine and sufentanil for pain and the other subject received propofol for tracheostomy tube placement. These deviations were not believed to have had an impact on the safety of the subjects.

The most common medical history included cardiovascular and respiratory disease in all five subjects. Four of the five subjects had gastrointestinal conditions. All subjects were post-surgery.

All five subjects received prior medication before entering this study and concomitant medication during the study. The most common prior or concomitant drug classes were categorized in the blood and blood forming organs class (IV fluids and blood products in particular) or drugs for the nervous system. All subjects received at least one post-dexmedetomidine infusion medication; the most common drugs were for the nervous system The mean plasma pharmacokinetics parameters of dexmedetomidine following a loading dose and a continuous maintenance dose are given in Table 57 below.

TABLE 57

Mean Plasma Pharmacokinetic Parameters

| Pharmacokinetic Parameter (units) | Dose Level 1 DEX LD = 0.7 µg/kg MD = 0.5 µg/kg/hr (N = 2) Mean (% CV) | Dose Level 2 DEX LD = 1 µg/kg MD = 0.75 µg/kg/hr (N = 3) Mean (% CV) |
|---|---|---|
| CL (L/hr) | 12.192 (78.55) | 5.836 (50.30) |
| $CL_w$ (L/hr/kg) | 1.292 (87.48) | 0.617 (61.79) |
| AUC (0-Infinity) [(pg/mL)hr] | 4639.170 (87.48) | 14203.544 (91.89) |
| AUC (0-Infinity)$_{Dose}$ [(pg/mL)hr/µg] | 118.610 (78.55) | 221.131 (67.92) |
| $C_{max}$ (pg/mL) | 4499.925 (129.49) | 11737.387 (30.24) |
| $V_d$ (L) | 31.845 (64.17) | 15.780 (22.47) |
| $V_{dw}$ (L/kg) | 3.343 (74.52) | 1.590 (39.01) |
| $t_{1/2}$ (hr) | 1.958 (19.22) | 2.260 (53.99) |

CV = coefficient of variation;
LD = Loading dose;
MD = maintenance dosing $T_{max}$ was generally 0.08 hrs before the end of the loading dose, and was fairly constant across all subjects and both dose levels. The one exception (Subject 01-0007, dose level 2) had a $T_{max}$ of 0.68 hrs after the start of the maintenance infusion.

Exposure to dexmedetomidine, measured as $C_{max}$ or AUC, appeared to be dose-related, although highly variable. Mean $C_{max}$ increased from 4500 pg/mL in dose level 1 to 11737 pg/mL in dose level 2, while dose-adjusted $C_{max}$ was fairly constant. Likewise, AUC (0-Infinity) increased from 4639 (pg/mL)hr in dose level 1 to 14204 (pg/mL)hr in dose level 2, whereas dose-adjusted AUC (0-Infinity) was fairly constant. This high variability in exposure was mainly attributable to one outlier (Subject 01-0003, dose level 1). Also since dose level 1 and dose level 2 contain 2 and 3 subjects, respectively, pharmacokinetics data should be interpreted cautiously (especially in the presence of a possible outlier).

Dexmedetomidine half-life was about 2 hrs in all subjects and was independent of dose. With the exception of one outlier (Subject 01-0003, dose level 1), both CL and $CL_w$ were fairly constant across both dose levels. Clearance was about 5.7 L/hr (2.5 to 8.2 L/hr) whereas weight adjusted CL was about 0.6 L/hr/kg (0.2 to 0.9 L/hr/kg). $V_d$ was also fairly constant across both dose levels. Again with the exclusion of one outlier (Subject 01-0003, dose level 1), $V_d$ was about 16.2 L (13.4 to 19.9 L) whereas weight adjusted $V_d$ was about 1.6 L/kg (0.99 to 2.23 L/kg).

The mean total amount of midazolam received was 0.50 mg (0.06 mg/kg) in Subject 01-0003 (dose level 1) and 3.70 mg (0.42 mg/kg) in Subject 01-0001 (dose level 2) who required rescue midazolam. The mean total amount of rescue fentanyl received was 60 µg (6.62 µg/kg) in 1 subject in dose level 1 (Subject 01-0003) and 49.56 µg (5.50 µg/kg) in 2 subjects in dose level 2 (Subjects 01-0001 and 01-0004).

The mean total amount of midazolam received was 0.50 mg (0.06 mg/kg) in Subject 01-0003 (dose level 1) and 3.70 mg (0.42 mg/kg) in Subject 01-0001 (dose level 2) who required rescue midazolam. The mean total amount of rescue fentanyl received was 60 µg (6.62 µg/kg) in 1 subject in dose level 1 (Subject 01-0003) and 49.56 µg (5.50 µg/kg) in 2 subjects in dose level 2 (Subjects 01-0001 and 01-0004).

For dose level 1, Subject 01-0003 required rescue midazolam and fentanyl. This subject required multiple IV boluses of fentanyl for pain beginning 1.43 hours after the start of dexmedetomidine infusion. This subject also required one dose of rescue midazolam at 5.27 hours after the start of dexmedetomidine infusion for agitation/surgically related pain. Relevant ongoing medical history included hypoplastic left heart syndrome and was post-surgery (cardiac catheterization, left pulmonary artery stenosis with balloon dilatation and aortopulmonary collaterals that required coil embolization). The other dose level one subject, Subject 01-0006, did not require rescue midazolam or fentanyl. However, this subject was on lorazepam 1 mg every 6 hours per gastric tube for seizures and could have received chloral hydrate for agitation as needed during dexmedetomidine infusion. It was determined the subject did not receive chloral hydrate during dexmedetomidine infusion. This subject was post-surgery for a recurrent rectal prolapse with surgical repair.

For dose level 2, Subject 01-0001 required rescue midazolam and fentanyl. Rescue midazolam was given in several doses for agitation/surgically related pain between 1.2 to 5.57 hours after the dexmedetomidine infusion started. Rescue fentanyl was given between 1.62 to 6.18 hours after the start of dexmedetomidine infusion for pain in the form of several boluses and also continuous infusions. This subject continued to receive fentanyl after the dexmedetomidine infusion ended. Relevant medical history included transposition of the great arteries, pulmonary stenosis, and ventricular septal defect and was postoperative for open heart surgery for correction of these problems (Nikaidoh operation). This subject also received sufentanil IV and IV morphine, both one time each for pain during dexmedetomidine infusion which were protocol violations.

Another dose level 2 subject, Subject 01-0004, did not require rescue midazolam, but did require rescue fentanyl given in the form of several boluses between 0.67 hours and 5.1 hours after the start of dexmedetomidine infusion. This subject had a history of congenital heart disease (congenital defect of the aortopulmonary trunk with tracheal compression and bronchial malacia) and was post-surgery from correction of these problems (aorotopexy).

The third dose level 2 subject, Subject 01-0007, did not require rescue midazolam or fentanyl but received propofol during dexmedetomidine infusion for tracheostomy tube placement (also a protocol violation). This subject had an ongoing medical history of hypoplastic right lung and was tracheostomy/ventilator dependent. The subject had an imperforated anus and was post-surgery for colostomy and anorectoplasty and colostomy reversal.

The maintenance infusion doses of dexmedetomidine used in this trial, 0.5 µg/kg/hr (dose level 1) and 0.75 µg/kg/hr (dose level 2), were moderately effective at sedating and keeping subjects comfortable. The use of concomitant sedatives and analgesics confounded the interpretation of the pharmacodynamic results.

Since the subject numbers were so small, the statistical results for the time to first dose of rescue medication were not statistically or clinically meaningful and are not discussed further.

For rescue midazolam, Subject 01-0003 (dose level 1) received rescue midazolam at 5.27 hours and Subject 01-0001 (dose level 2) beginning at 1.2 hours after the start of dexmedetomidine infusion. For rescue fentanyl, Subject 01-0003 (dose level 1) received rescue fentanyl beginning at 1.43 hours, Subject 01-0001 (dose level 2) beginning at 1.62 hours, and Subject 01-0004 (dose level 2) beginning at 0.67 hours after the start of dexmedetomidine infusion.

The target UMSS score was between 2 to 4. For dose levels 1 and 2, the median absolute time spent in this target range was 3.6 hours (58.9% of the time) and 5.9 hours (95.1% of the time), respectively. The median absolute time spent with a total UMSS score<2 for dose levels 1 and 2 was 2.5 hours (41.1% of the time) and 0.3 hours (4.9%), respectively. The results observed are confounded by the receipt of concomitant sedative/analgesic drugs during dexmedetomidine infusion.

One of the criteria used for judging whether to give rescue fentanyl was if the total FLACC score was >4. The median total FLACC score was 1.6 in dose level 1 and 4.4 in dose level 2, and 3.2 for both dose levels combined. The results observed are confounded by the receipt of concomitant sedative/analgesic drugs during dexmedetomidine infusion. Compared to dose level 2 subjects, subjects in dose level 1 spent considerably less time in the target UMSS range of 2 to 4, but had lower total FLACC scores.

Generally, trends in mean change from baseline in vital signs were not clinically meaningful. There were no treatment-emergent adverse events pertaining to HR, SBP, DBP, MAP, RR, or $SpO_2$.

Two of the five subjects were able to be extubated by the end of the study. These subjects were Subjects 01-0006 (dose level 1), extubated at 17.7 hours from the start time of study drug, and Subject 01-0007 (dose level 2) extubated at 26.27 hours from the start time of study drug.

The median dose and duration of dexmedetomidine exposure is given in Table 58 below.

TABLE 58

Median Dose and Duration of Dexmedetomidine Exposure

| Median Parameter | Dose Level 1 (N = 2) | Dose Level 2 (N = 3) | Total (N = 5) |
|---|---|---|---|
| Loading dose | | | |
| N | 2 | 3 | 5 |
| Total loading dose (μg) | 7.02 | 9.11 | 8.90 |
| Duration (min) | 10.0 | 10.0 | 10.0 |
| Maintenance dose | | | |
| N | 2 | 3 | 5 |
| Total maintenance dose (μg) | 30.11 | 41.00 | 41.00 |
| Duration (min) | 360.0 | 360.0 | 360.0 |

Only one of the five subjects (20.0%) experienced treatment-emergent adverse events. These events were mild pyrexia and mild atelectasis in a dose level 2 subject; both events were assessed as not related to dexmedetomidine. There were no treatment-emergent serious adverse events leading to death, no other treatment-emergent serious adverse events, and no treatment-emergent adverse events that led to dexmedetomidine discontinuation.

There was variability between subjects in hematology tests. In general, no evidence of systematic change for most hematologic variables was found. However, subjects in both dose levels had large mean decreases in the percent of lymphocytes during and post-dexmedetomidine administration. Subjects in both dose levels had large mean increases in the percent of neutrophils during and post-dexmedetomidine administration. Also, dose level 2 subjects had larger mean decreases in platelets during dexmedetomidine administration compared to baseline than subjects in dose level 1. Post-dexmedetomidine administration, dose level 2 subjects had a large mean decrease in platelets while dose level 1 subjects had a slight mean increase in platelets.

There was variability between subjects in chemistry tests. In general, no evidence of systematic change for most chemistry variables was found. However, during and post-dexmedetomidine administration, dose level 2 subjects had a large mean increase in aspartate aminotransferase (AST) compared to baseline. Both dose levels had large mean increases in uric acid crystals. In general, no evidence of systematic change for these urinalysis variables was found. No subjects had abnormal hematology, chemistry, or urinalysis results assessed as clinically significant during or post-dexmedetomidine administration. No abnormal clinically significant ECG findings were present in any of the 5 study subjects at screening or during or post-dexmedetomidine administration. There were no treatment-emergent adverse events pertaining to hematology, chemistry, urinalysis results, HR, SBP, DBP, MAP, RR, or $SpO_2$. The most common abnormal findings at screening and post-dexmedetomidine administration were in the cardiopulmonary system.

Dexmedetomidine was safe and well tolerated at both dose levels. The maintenance infusion doses of dexmedetomidine used in this trial, 0.5 μg/kg/hr (dose level 1) and 0.75 μg/kg/hr (dose level 2), were moderately effective at sedating and keeping subjects comfortable.

Example 8

Pooled Pharmacokinetic Data of Dexmedetomidine in Pediatric Patients

A population pharmacokinetic evaluation of dexmedetomidine in pediatric subjects was completed, as described in Example 6. Example 6 combines the populations described in Examples 1, 3 and 5. The ages enrolled in each of the studies were 1 month to <24 months (Example 5), 2 years to <17 years (Example 3) and ≥28 weeks gestational age to <1 month (Example 1).

In this study, an additional 11 subjects were included in the modeling described by Example 6. The additional subjects included 6 neonatal subjects aged≥28 weeks gestational age to <36 weeks gestational age group treated at the second dose level from the additional cohort of Example 1 (0.1 μg/kg load 10.1 μg/kg/hr Maintenance); and the five subjects in the age group 12 months to <24, as described in Example 7. The model parameters were determined as described above in Example 6. Results of the updated model are described in FIGS. 26-33.

Population pharmacokinetic modeling was performed using the nonlinear mixed effects modeling (NONMEM®) computer program, Version 6.0, Level 2.0 on an Intel cluster with the Linux operating system.

The first-order conditional estimation (FOCE) with interaction method was used at all stages of model development. The effects of both weight and age were included in the model considered the base structural model, given the range of weights and ages in this pediatric population and their likely impact on pharmacokinetic. Evaluation of the influence of other covariates (gender, ethnicity, cardio-pulmonary bypass use, albumin infusion, and site of sampling on elimination clearance (CL) and volume of the central compartment (Vc), alanine aminotransferase (ALT), total bilirubin, concomitant glucuronidation pathway inhibitors, and heart physiology (single versus double ventricle) on CL) was performed using a forward selection ($\alpha$=0.05 plus at least a 5% reduction in interindividual variability (IIV) in the parameter of interest) followed by a backward elimination ($\alpha$=0.001) procedure.

Following any necessary refinements, the adequacy of the final model was evaluated using a simulation-based prediction-corrected visual predictive check method. Conditional on the final model point estimates, 1000 replicates of the analysis dataset were simulated using NONMEM, and the 5th, 50th (median), and 95th percentiles of the distributions of the simulated concentrations were calculated. Prediction correction was performed for discrete bins based on the time since the end of the infusion, treatment group, and age category. Concordance between the prediction interval based on the simulations and the observed data and corresponding percentiles of the observed data was assessed visually and numerically, by calculating the percentage of observed data points above and below the prediction interval bounds.

The population pharmacokinetic analysis results were as follows. The base structural model for the pooled dataset of Example 1, Example 3, and Example 5 was a 2-compartment model with fixed allometric exponents for weight effects on clearance and volume parameters (0.75 for CL and inter-compartmental clearance (Q) and 1.0 for Vc and volume of the peripheral compartment (Vp)), an additional shift in the CL and Vc exponents for neonates, and age effects on Q and Vp described by power functions (both decrease with increasing age). (See Example 6).

As a result of forward selection, no additional covariate effects were added to the model as none met the pre-specified criteria of a statistically significant reduction in the MVOF and at least a 5% decrease in IIV. During subsequent model refinement, the shift in the Vc allometric exponent for neonates was found to be non-statistically significant and was thus removed from the model.

The final base structural pharmacokinetic model was a 2-compartment model with IIV estimated on CL, Q, Vc, and Vp using exponential error models, fixed allometric exponents on the clearance (0.75 for CL and Q) and volume of distribution (1.0 for Vc and Vp) parameters, with an additional shift on the CL exponent for neonates, age effects on Q and Vp described by power functions (both decrease with increasing age), covariance terms for the IIVs on CL and Vp, and the IIVs on Q and Vc, separate additive plus constant coefficient of variation error models for Example 3 and Example 5, and a constant coefficient of variation error model for Example 1.

The parameter estimates for the final population pharmacokinetic model for dexmedetomidine from the original analysis as described in Example 6 are provided in Table 51.

All fixed effect parameters were estimated with good precision (% SEMs<20%), with the exception of those associated with Q, which were estimated with slightly poorer precision (% SEMs of around 40%). Random effects were also estimated with good precision (most % SEMs<25%, except IIV in Q with % SEM=37%). Interindividual variability in CL, Vc, and Vp was moderate, ranging from 35% CV to 55% CV. Unexplained IIV in Q was very high at 163% CV. Overall, RV was the lowest in the Example 5 data (around 19% CV) and slightly higher in the Example 3 data (26% CV), but in both studies was considerably larger at low concentration values, especially near the lower limit of the assay. A constant coefficient of variation RV model was found to adequately describe the data from Example 1, with a relatively higher estimate of 46% CV, regardless of concentration level.

The prediction-corrected visual predictive check results indicate that the model-based simulated concentrations were in close agreement with the observed data from the 3 studies with 6.3% of observations and 4.7% of observations below and above the bounds of the 90% prediction interval, respectively. Furthermore, the median of the simulated concentration data corresponded consistently with the median of the observed data.

The additional cohort of Example 1, consisting of six neonatal subjects in the ≥28 weeks gestational age to <36 weeks gestational age at the second dose level (0.1 μg/kg Load/0.1 μg/kg/hr Maintenance), have been completed. The five subjects from example 7 for age group 12 months to <24 months have also been completed. These subjects were added to the population pharmacokinetic model described in Example 6, and the model parameters were determined as described above for the original analysis (i.e., Example 6). There was very little change in the model parameters and the resulting clearance and volume of distribution point estimates and associated 95% confidence intervals compared to the original analysis.

The parameter estimates for the final population pharmacokinetic model for dexmedetomidine including the additional 11 subjects completed since the original analysis are provided in Table 59.

TABLE 59

Parameter Estimates and Standard Errors From the Dexmedetomidine Final Population Pharmacokinetic Model (Studies Example 5, Example 3, Example 1, and Example 7)

| Parameter | Final Parameter Estimate | | Magnitude of Interindividual Variability (% CV) | |
|---|---|---|---|---|
| | Population Mean | % SEM | Final Estimate | % SEM |
| CL (L/h)[a] | 10.7 | 3.4 | 37.01 | 17.0 |
| Proportional shift in allometric exponent for CL for neonates[a] | 0.531 | 17.2 | | |
| Vc (L)[b] | 8.49 | 10.5 | 53.76 | 20.8 |
| Inter-compartmental CL (L/h)[c] | 63.5 | 23.8 | 161.25 | 23.7 |
| Exponent for power function effect of age on Q[c] | −0.342 | 27.9 | | |
| Vp (L)[d] | 14.7 | 7.2 | 51.19 | 20.6 |
| Exponent for power function effect of age on Vp[d] | −0.280 | 10.6 | | |
| Ratio of additive to proportional RV: Example 5 | 12.3 | 15.0 | NA | NA |
| Ratio of additive to proportional RV: Example 3 | 40.4 | 26.0 | NA | NA |
| cov (IIV in CL, IIV in Vp) | 0.145 | 20.8 | NA | NA |
| cov (IIV in Q, IIV in Vc) | 0.796 | 19.6 | NA | NA |

TABLE 59-continued

Parameter Estimates and Standard Errors From the Dexmedetomidine Final Population Pharmacokinetic Model (Studies Example 5, Example 3, Example 1, and Example 7)

| Parameter | Final Parameter Estimate | | Magnitude of Interindividual Variability (% CV) | |
|---|---|---|---|---|
|  | Population Mean | % SEM | Final Estimate | % SEM |
| RV Example 1[e] | 0.189 | 18.6 | NA | NA |
| RV Example 5[f] | 0.0358 | 16.5 | NA | NA |
| RV Example 3[g] | 0.0685 | 20.6 | NA | NA |
| RV Example 7[h] | 0.0935 | 29.8 | NA | NA |

Minimum value of the objective function = 11885.512

Abbreviations: CL, elimination clearance; IIV, interindividual variability; NA, not applicable; NEO, indicator variable for neonates; % CV, coefficient of variation expressed as a percentage; % SEM, standard error of the mean expressed as a percentage; Q, inter-compartmental clearance; RV, residual variability; Vc, volume of the central compartment; Vp, volume of the peripheral compartment; WTKG, weight in kg.

[a] Typical $CL = 10.7 \times \left(\frac{WTKG}{9.6}\right)^{[0.75 \times (1 + 0.531 \times NEO)]}$

[b] Typical $Vc = 8.49 \times \left(\frac{WTKG}{9.6}\right)$

[c] Typical $Q = 63.5 \times \left(\frac{WTKG}{9.6}\right)^{0.75} \times \left(\frac{age}{1.31}\right)^{-0.342}$

[d] Typical $Vp = 14.7 \times \left(\frac{WTKG}{9.6}\right) \times \left(\frac{age}{1.31}\right)^{-0.280}$

[e] Residual variability estimate is expressed as a variance. The corresponding % CV for RV in Example 1 is 43% CV.
[f] Residual variability estimate is expressed as a variance. The corresponding % CV for RV in Example 5 ranges from 111% CV at 2.12 ng/L (one-half the lower assay limit) to 19% CV at 700 ng/L.
[g] Residual variability estimate is expressed as a variance. The corresponding % CV for RV in Example 3 ranges from 75% CV at 15.12 ng/L (one-half the lower assay limit) to 26% CV at 3000 ng/L.
[h] Residual variability estimate is expressed as a variance. The corresponding % CV for RV in Example 7 is 31% CV.

Table 60 provides summary statistics for the individual Bayesian parameter estimates and the model-predicted typical value estimates by age group for dexmedetomidine weight-adjusted CL and weight-adjusted volume of distribution for the original (Example 6) and updated analyses.

TABLE 60

Summary Statistics for the Weight-Adjusted Clearance and Weight-Adjusted Volume of Distribution by Age Group

|  | Weight-Adjusted CL (L/h/kg) Geometric Mean (95% CI as Percent of Geo. Mean) | | Weight-Adjusted $V_d$ (L/kg) Geometric Mean (95% CI as Percent of Geo. Mean) | |
|---|---|---|---|---|
| Age Group | Initial Model | Including Additional 11 Subjects | Initial Model | Including Additional 11 Subjects |
| 28 weeks GA-<1 month | 0.991 | 0.929 | 5.634 | 5.741 |
|  | (81.7-122.3) | (82.45-121.4) | (79.1-126.4) | (80.87-123.7) |
|  | (n = 22) | (n = 28) | (n = 22) | (n = 28) |
| 1 month-<6 months | 1.213 | 1.211 | 3.012 | 3.016 |
|  | (82.3-121.6) | (82.16-121.7) | (82.9-120.6) | (82.66-121.0) |
|  | (n = 14) | (n = 14) | (n = 14) | (n = 14) |
| 6 months-<12 months | 1.110 | 1.109 | 2.895 | 2.893 |
|  | (85.1-117.3) | (85.21-117.4) | (84.2-118.8) | (84.17-118.8) |
|  | (n = 16) | (n = 16) | (n = 16) | (n = 16) |
| 12 months-<24 months | 1.118 | 1.060 | 2.493 | 2.353 |
|  | (81.2-123.0) | (82.45-121.3) | (78.7-127.0) | (77.31-129.4) |
|  | (n = 8) | (n = 13) | (n = 16) | (n = 13) |
| 2 y-<6 y | 1.108 | 1.109 | 2.338 | 2.352 |
|  | (90.3-110.8) | (90.17-110.8) | (87.8-114.0) | (87.63-114.1) |
|  | (n = 26) | (n = 26) | (n = 26) | (n = 26) |

TABLE 60-continued

Summary Statistics for the Weight-Adjusted Clearance and Weight-Adjusted Volume of Distribution by Age Group

| | Weight-Adjusted CL (L/h/kg) Geometric Mean (95% CI as Percent of Geo. Mean) | | Weight-Adjusted $V_d$ (L/kg) Geometric Mean (95% CI as Percent of Geo. Mean) | |
|---|---|---|---|---|
| Age Group | Initial Model | Including Additional 11 Subjects | Initial Model | Including Additional 11 Subjects |
| 6 y-<17 y | 0.796 (87.3-114.4) (n = 29) | 0.796 (87.31-114.6) (n = 29) | 1.677 (83.6-119.6) (n = 29) | 1.681 (83.58-119.6) (n = 29) |

Abbreviations:
CI, confidence interval;
CL, clearance;
GA, gestational age;
Geo., geometric;
max, maximum;
min, minimum;
n, number of subjects;
y, years.

Tables 61 and 62 provide summary statistics for the individual Bayesian estimates and model-predicted typical values of dexmedetomidine clearance and weight-adjusted clearance by age group (Table 61) and of dexmedetomidine clearance and weight-adjusted clearance by age group estimates by age group for dexmedetomidine volume of distribution and weight-adjusted volume of distribution by age group (Table 62).

TABLE 61

Summary Statistics for the Individual Bayesian Estimates and Model-Predicted Typical Values of Dexmedetomidine Clearance and Weight-Adjusted Clearance by Age Group

| | | | CL (L/h) | | Weight-Adjusted CL (L/h/kg) | |
|---|---|---|---|---|---|---|
| Age Group | Median Weight (kg) (min, max) | Median Age (y) (min, max) | Geo. Mean (95% CI) | Predicted Typical Value | Geo. Mean (95% CI) | Predicted Typical Value |
| 28 weeks GA - <1 month (n = 28) | 2.89 (1.09, 3.80) | 0.023 (0.005, 0.077) | 2.28 (1.73, 3.02) | 2.69 | 0.929 (0.766, 1.128) | 0.933 |
| 1 month-<6 months (n = 14) | 5.99 (3.15, 7.00) | 0.332 (0.099, 0.484) | 6.94 (5.50, 8.74) | 7.51 | 1.211 (0.995, 1.474) | 1.254 |
| 6 months-<12 months (n = 16) | 7.28 (5.10, 9.34) | 0.657 (0.521, 0.896) | 8.15 (7.04, 9.42) | 8.69 | 1.109 (0.945, 1.302) | 1.195 |
| 12 months-<24 months (n = 13) | 10.10 (8.87, 13.50) | 1.491 (0.973, 1.766) | 10.76 (9.14, 12.67) | 11.12 | 1.060 (0.874, 1.286) | 1.101 |
| 2 y-<6 y (n = 26) | 13.75 (9.98, 23.59) | 3.548 (2.070, 5.761) | 15.89 (14.06, 17.96) | 14.01 | 1.109 (1.000, 1.229) | 1.019 |
| 6 y-<17 y (n = 29) | 30.20 (13.60, 99.00) | 9.887 (6.032, 16.967) | 24.45 (19.49, 30.68) | 25.27 | 0.796 (0.695, 0.912) | 0.837 |

Abbreviations:
CI, confidence interval;
CL, clearance;
GA, gestational age;
Geo., geometric;
max, maximum;
min, minimum;
n, number of subjects;
y, years

TABLE 62

Summary Statistics for the Individual Bayesian Estimates and Model-Predicted Typical Values of Dexmedetomidine Volume of Distribution and Weight-Adjusted Volume of Distribution by Age Group

| Age Group | Median Weight (kg) (min, max) | Median Age (y) (min, max) | Volume of Distribution (L) | | Weight-Adjusted V (L/kg) | |
|---|---|---|---|---|---|---|
| | | | Geo. Mean (95% CI) | Predicted Typical Value | Geo. Mean (95% CI) | Predicted Typical Value |
| 28 weeks GA - <1 month (n = 28) | 2.89 (1.09, 3.80) | 0.023 (0.005, 0.077) | 14.11 (10.95, 18.18) | 16.21 | 5.741 (4.643, 7.100) | 5.618 |
| 1 month-<6 months (n = 14) | 5.99 (3.15, 7.00) | 0.332 (0.099, 0.484) | 17.28 (14.83, 20.13) | 18.75 | 3.016 (2.493, 3.649) | 3.133 |
| 6 months-<12 months (n = 16) | 7.28 (5.10, 9.34) | 0.657 (0.521, 0.896) | 21.25 (18.23, 24.76) | 19.95 | 2.893 (2.435, 3.436) | 2.742 |
| 12 months-<24 months (n = 13) | 10.10 (8.87, 13.50) | 1.491 (0.973, 1.766) | 23.90 (18.66, 30.61) | 23.85 | 2.353 (1.819, 3.044) | 2.361 |
| 2 y-<6 y (n = 26) | 13.75 (9.98, 23.59) | 3.548 (2.070, 5.761) | 33.70 (29.07, 39.07) | 28.09 | 2.352 (2.061, 2.684) | 2.043 |
| 6 y-<17 y (n = 29) | 30.20 (13.60, 99.00) | 9.887 (6.032, 16.967) | 51.65 (39.96, 66.77) | 52.97 | 1.681 (1.405, 2.011) | 1.754 |

Abbreviations:
CI, confidence interval;
CL, clearance;
GA, gestational age;
Geo., geometric;
max, maximum;
min, minimum;
n, number of subjects;
y, years FIG. 26 and FIG. 27 provide the 95% confidence intervals for the individual Bayesian estimates expressed as the percent of the geometric mean of dexmedetomidine weight-adjusted CL and weight-adjusted volume of distribution for each age group as determined from the original analysis.

FIG. 28 and FIG. 29 provide the 95% confidence intervals for the individual Bayesian estimates expressed as the percent of the geometric mean of dexmedetomidine weight-adjusted CL and weight-adjusted volume of distribution for each age group as determined from the updated analysis.

FIGS. 30A-H show goodness-of-fit plots for the final population pharmacokinetic model for dexmedetomidine of the present study. FIGS. 31A-B show the prediction-corrected visual predictive check results. Prediction interval overlaid on the observed data is shown in FIG. 31A, and percentiles of the observed data is shown in FIG. 31B. FIG. 32 shows the geometric means and 95% confidence intervals for the Bayesian estimates of dexmedetomidine clearance and weight-adjusted clearance in specified age groups with the population model-based typical values of clearance and weight-adjusted clearance overlaid. FIG. 33 shows the geometric means and 95% confidence intervals for the Bayesian estimates of dexmedetomidine volume distribution and weight-adjusted volume of distribution in specified age groups, with the population model-based typical values of volume of distribution and weight-adjusted volume of distribution overlaid.

There was very little difference in the pharmacokinetic model parameters from the original analysis and the updated analysis which included the additional 11 subjects. The final model fully characterizes the pharmacokinetic of dexmedetomidine in pediatric subjects ages 28 weeks GA to <17 years. The results for all age groups from both analyses show that the 95% confidence intervals are completely contained within 60% and 140% of the point estimate.

\* \* \*

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications publications product descriptions, and protocols are cited throughout this application the disclosures of which are incorporated herein by reference in their entireties for all purposes.

What is claimed is:

1. A method of providing sedation or analgesia to a pediatric patient in need thereof, wherein the method comprises administering a ready to use liquid pharmaceutical premix composition comprising dexmedetomidine or a pharmaceutically acceptable salt thereof disposed within a sealed glass container at a concentration of about 0.005 to about 50 µg/mL to the pediatric patient;
   wherein the dexmedetomidine or pharmaceutically acceptable salt thereof is administered as a first loading dose at a concentration of between 0.2 to 1.5 µg/kg prior to a second maintenance dose at a concentration of between 0.005 to 1.5 µg/kg/hr;
   wherein the pediatric patient is 1 month to less than 17 years of age; and
   wherein the dexmedetomidine is administered as a continuous infusion for a period of time of less than about 36 hours.

2. The method of claim 1, wherein the dexmedetomidine is parenterally administered.

3. The method of claim 1, wherein the dexmedetomidine is administered by an intravenous infusion.

4. The method of claim 1, wherein the dexmedetomidine is administered before or after surgery.

5. The method of claim 1, wherein the pediatric patient is intubated.

6. The method of claim 1, wherein the dexmedetomidine is administered to the pediatric patient in an intensive care unit.

7. The method of claim 4, wherein the dexmedetomidine is administered after cardiopulmonary bypass.

* * * * *